United States Patent
Banker et al.

(10) Patent No.: US 7,449,468 B2
(45) Date of Patent: *Nov. 11, 2008

(54) THIAZOLE AND OXAZOLE DERIVATIVES AS ACTIVATORS OF HUMAN PEROXISOME PROLIFERATOR ACTIVATED RECEPTORS

(75) Inventors: Pierette Banker, Durham, NC (US); Rodolfo Cadilla, Durham, NC (US); Millard Hurst Lambert, III, Durham, NC (US); Stephen William Rafferty, Durham, NC (US); Daniel David Sternbach, Durham, NC (US); Marcos Luis Sznaidman, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/753,848

(22) Filed: May 25, 2007

(65) Prior Publication Data

US 2007/0225294 A1      Sep. 27, 2007

Related U.S. Application Data

(63) Continuation of application No. 11/550,060, filed on Oct. 17, 2006, now Pat. No. 7,229,998, which is a continuation of application No. 10/451,295, filed as application No. PCT/US01/51056 on Dec. 19, 2001, now abandoned.

(30) Foreign Application Priority Data

Dec. 20, 2000  (GB)  .................................. 0031103.5

(51) Int. Cl.
| | |
|---|---|
| C07D 277/26 | (2006.01) |
| C07D 277/28 | (2006.01) |
| A61K 31/496 | (2006.01) |
| A61K 31/426 | (2006.01) |
| A61K 31/427 | (2006.01) |

(52) U.S. Cl. .................. 514/254.02; 514/365; 544/369; 544/357; 548/204; 548/236

(58) Field of Classification Search .................. None
See application file for complete search history.

(56) References Cited

U.S. PATENT DOCUMENTS

| 5,972,881 | A | 10/1999 | Heyman et al. | |
|---|---|---|---|---|
| 6,518,290 | B1 * | 2/2003 | Sierra ......................... | 514/365 |
| 6,710,063 | B1 * | 3/2004 | Chao et al. .................. | 514/365 |
| 6,723,740 | B2 * | 4/2004 | Chao et al. .................. | 514/365 |
| 7,153,878 | B2 * | 12/2006 | Conner et al. ............... | 514/365 |
| 7,259,175 | B2 * | 8/2007 | Conner et al. ............... | 514/342 |
| 2004/0077659 | A1 | 4/2004 | Oliver | |

FOREIGN PATENT DOCUMENTS

| WO | 0008002 | 2/2000 |
|---|---|---|
| WO | 0100603 | 1/2001 |
| WO | 01/40207 | * 6/2001 |
| WO | 0140207 | 6/2001 |
| WO | 01/00603 | * 12/2001 |
| WO | 0250048 | 6/2002 |
| WO | 0262774 | 8/2002 |

OTHER PUBLICATIONS

Berger et al.; "The Mechanisms of Action of PPARs"; Annu. Rev. Med.; 2002; vol. 53; pp. 409-435.

Bishop-Bailey; "Peroxisome Proliferator Activated Receptors in the Cardiovascular System"; British Journal of Pharmacology; 2000; vol. 129, No. 5; pp. 823-834.

Ellis et al.; "Troglitazone Improves Psoriasis and Normalizes Models of Proliferative Skin Disease"; Arch. Dermatol.; 2000; vol. 136; pp. 609-616.

Lehmann et al.; "An Antidiabetic Thiazolidinedione is a High Affinity Ligand for Peroxisome Proliferator-Activated Receptor Gamma"; Journal of Biological Chemistry; 1995; vol. 270, No. 22; pp. 12953-12956.

Mae et al.; "A Licorice Ethanolic Extract with Peroxisome Proliferator-Activated Receptory Ligand-Binding Activity Affects Diabetes in KK-A[y] Mice, Abdominal Obesity in Diet-Induced Obese C57BL Mica and Hypertension in Spontaneously Hypertensive Rats"; Journal of Nutrition; 2003; vol. 133, No. 11; pp. 3369-3377.

Miyachi et al.; "Nucleophilic Group Transfer Reactivity for Fibric Acid Derived Drug Molecules"; Expert Opin. Ther. Patents; 2004; vol. 14, pp. 607-618.

Mukherjee et al.; "Nuclear Receptors in Metabolic Diseases"; Emerging Therapeutic Targets; 2000; vol. 4; pp. 377-396.

(Continued)

Primary Examiner—Emily Bernhardt
(74) Attorney, Agent, or Firm—Robert H. Brink

(57) ABSTRACT

The present invention provides a compound of formula (I):

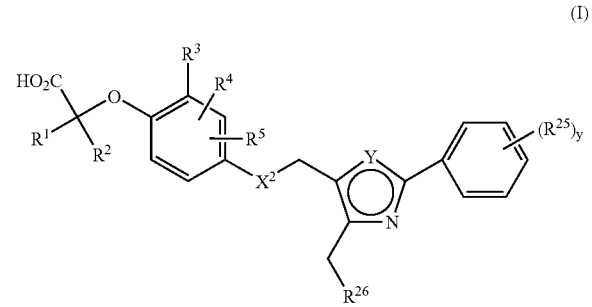

(I)

wherein $R^1$-$R^5$, $R^{25}$, $R^{26}$, Y, y, and $X^2$ are as defined herein. The compounds activate human peroxisome proliferater activated receptors (hPPARs) and are useful for the treatment of associated disorders such as dyslipidemia, syndrome X, hypercholesteremia, type II diabetes mellitus, type I diabetes, insulin resistance, hyperlipidemia, and obesity.

9 Claims, No Drawings

OTHER PUBLICATIONS

Oliver et al.; "A Selective Peroxisome Proliferator-Activated Receptor Delta Agonist Promotes Reverse Cholesterol Transport"; Proceedings of the National Academy of Sciences of the USA; 2001; vol. 98, No. 9; pp. 5306-5311.

Rami et al.; "Synthetic Ligands for PPAR: Review of Patent Literature 1994-1999"; Exp. Opin. Ther. Patents; 2000; vol. 10; pp. 623-634.

Vippagunta et al.; "Crystalline Solids"; Advanced Drug Delivery Reviews; 2001; vol. 48; pp. 3-26.

\* cited by examiner

THIAZOLE AND OXAZOLE DERIVATIVES AS ACTIVATORS OF HUMAN PEROXISOME PROLIFERATOR ACTIVATED RECEPTORS

CROSS-REFERENCE TO RELATED APPLICATIONS

This application is a Continuation of Ser. No. 11/550,060 filed Oct. 17, 2006 now U.S. Pat. No. 7,229,998; which is a Continuation of Ser. No. 10/451,295 filed Oct. 31, 2003, now abandoned; which is a 371 application of PCT/US01/51056 filed Dec. 19, 2001; which claims priority to GB 0031103.5 filed Dec. 20, 2000. All four applications are incorporated herein by reference in their entirety.

FIELD OF THE INVENTION

The present invention relates to certain novel compounds. In particular, the present invention relates to compounds that activate human peroxisome proliferator activated receptors ("hPPARs"). The present invention also relates to methods for preparing the compounds, their use in medicine, pharmaceutical compositions containing them and methods for the prevention or treatment of PPAR mediated diseases or conditions.

BACKGROUND OF THE INVENTION

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been successfully addressed by drug therapy (i.e. currently there are no drugs on the market that are useful for raising HDL-c). (Bisgaier, C. L.; Pape, M. E. Curr. Pharm. Des. 1998, 4, 53-70).

Syndrome X (including metabolic syndrome) is loosely defined as a collection of abnormalities including hyperinsulinemia, obesity, elevated levels of triglycerides, uric acid, fibrinogen, small dense LDL particles, and plasminogen activator inhibitor 1(PAI-1), and decreased levels of HDL-c.

NIDDM is described as insulin resistance which in turn causes anomalous glucose output and a decrease in glucose uptake by skeletal muscle. These factors eventually lead to impaired glucose tolerance (IGT) and hyperinsulinemia.

Peroxisome Proliferator Activated Receptors (PPARs) are ophan receptors belonging to the steroid/retinoid receptor superfamily of ligand-activated transcription factors. See, for example Willson T. M. and Wahli, W., Curr. Opin. Chem. Biol.(1997) Vol. 1, pp. 235-241and Willson T. M. et al., J. Med. Chem (2000) Vol. 43, pp. 527-549. The binding of agonist ligands to the receptor results in changes in the expression level of mRNA's encoded by PPAR target genes.

Three mammalian Peroxisome Proliferator-Activated Receptors have been isolated and termed PPAR-alpha, PPAR-gamma, and PPAR-delta (also known as NUC1or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, Trends Endocrin. Met 291-296, 4(1993)).

It has now been reported that thiazolidinediones are potent and selective activators of PPAR-gamma and bind directly to the PPAR-gamma receptor (J. M. Lehmann et al., J. Biol. Chem. 12953-12956, 270(1995)), providing evidence that PPAR-gamma is a possible target for the therapeutic actions of the thiazolidinediones.

Activators of the nuclear receptor PPARγ, for example troglitazone, have been shown in the clinic to enhance insulin-action, reduce serum glucose and have small but significant effects on reducing serum triglyceride levels in patients with Type 2diabetes. See, for example, D. E. Kelly et al., Curr. Opin. Endocrinol. Diabetes, 90-96, 5(2), (1998); M. D. Johnson et al., Ann. Pharmacother., 337-348, 32(3), (1997); and M. Leutenegger et al., Curr. Ther. Res., 403-416, 58(7), (1997).

The mechanism for this triglyceride lowering effect appears to be predominantly increased clearance of very low density lipoproteins (VLDL) through induction of lipoprotein lipase (LPL) gene expression. See, for example, B. Staels et al., Arterioscler. Thromb., Vasc. Biol., 1756-1764, 17(9), (1997).

Fibrates are a class of drugs which may lower serum triglycerides 20-50%, lower LDLc 10-15%, shift the LDL particle size from the more atherogenic small dense to normal dense LDL, and increase HDLc 10-15%. Experimental evidence indicates that the effects of fibrates on serum lipids are mediated through activation of PPARα. See, for example, B. Staels et al., Curr. Pharm. Des., 1-14, 3(1), (1997). Activation of PPARα results in transcription of enzymes that increase fatty acid catabolism and decrease de-novo fatty acid synthesis in the liver resulting in decreased triglyceride synthesis and VLDL production/secretion. In addition, PPARα activation decreases production of apoC-III. Reduction in apoC-III, an inhibitor of LPL activity, increases clearance of VLDL. See, for example, J. Auwerx et al., Atherosclerosis, (Shannon, Irel.), S29-S37, 124(Suppl), (1996).

Certain compounds that activate or otherwise interact with one or more of the PPARs have been implicated in the regulation of triglyceride and cholesterol levels in animal models. See, for example, U.S. Pat. No. 5,847,008(Doebber et al.) and U.S. Pat No. 5,859,051(Adams et al.) and PCT publications WO 97/28149(Leibowitz et al.) and WO99/04815 (Shimokawa et al.). In a recent report (Berger et al., J. Biol. Chem. 1999), Vol. 274, pp. 6718-6725) it was stated that PPARδ activation does not appear to modulate glucose or triglyceride levels.

SUMMARY OF THE INVENTION

In one aspect, the present invention provides compounds of formula (I) and pharmaceutically acceptable salts, solvates, and hydrolysable esters thereof wherein;

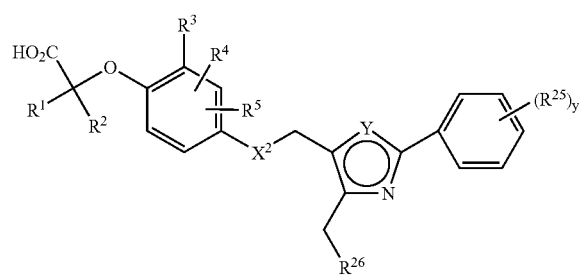

(I)

$R^1$ and $R^2$ are independently hydrogen or $C_{1-3}$alkyl;
$X^2$ is O, S, or $CH_2$;

$R^3$, $R^4$, and $R^5$ are independently H, $C_{1-3}$alkyl, $OCH_3$, $CF_3$, $OCF_3$, allyl, CN, or halogen;

Y is S or O;

each $R^{25}$ is independently $CH_3$, $OCH_3$, $OCF_3$, $CF_3$, or halogen;

y is 0, 1, 2, 3, 4 or 5; and $R^{26}$ is selected from the group consisting of the moieties A through K depicted below:

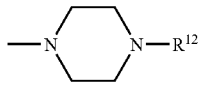
A wherein $R^{12}$ is selected from the group consisting of $C_{1-6}$alkyl, $C_{1-6}$alkylenearyl, and the moieties depicted below in Group II, Group II

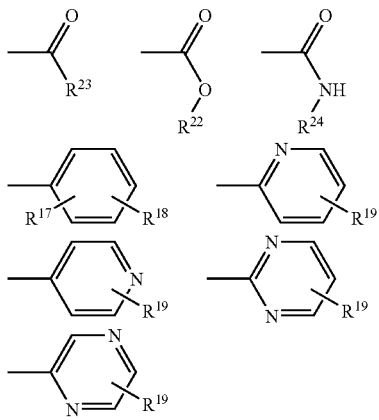

wherein $R^{17}$ and $R^{18}$ are independently hydrogen, halogen, hydroxy, —CN, $C_{1-6}$alkyl, $C_{1-6}$perfluoroalkyl, $C_{1-6}$acyl, —$OC_{1-6}$alkyl, perfluoro$OC_{1-6}$alkyl, or $C_{1-6}$hydroxyalkyl;

$R^{19}$ is hydrogen or $C_{1-6}$alkyl;

$R^{21}$ is $C_{1-6}$alkyl, —$C_{1-6}$-alkylenearyl, aryl, or -aryl-heteroaryl;

$R^{22}$ is $C_{1-6}$alkyl, aryl, or —$C_{1-6}$alkylenearyl;

$R^{23}$ is $C_{1-6}$alkyl, $C_{3-6}$cycloalkyl, or aryl;

$R^{24}$ is $C_{1-6}$alkyl, —$C_{1-6}$alkylenearyl, $C_{3-6}$-cycloalkyl, or aryl;

B wherein Z is O, N or S (note that when Z is N, the depicted bond can be attached to the nitrogen in the ring as well as any of the carbons in the ring);

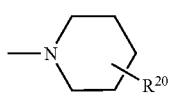
C wherein $R^{20}$ is $C_{1-6}$alkyl, aryl, —$OC_{1-6}$alkyl, hydroxy, $C_{1-6}$hydroxyalkyl, or 1-alkoxy$C_{1-6}$alkyl;

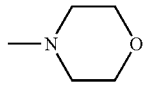
D

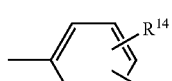
E wherein $R^{13}$ and $R^{14}$ are independently hydrogen, halogen, CN, perfluoro$C_{1-6}$alkyl, perfluoro$OC_{1-6}$alkyl, $C_{1-6}$alkyl, —$OC_{1-6}$alkyl, —$C_{1-6}$alkylene$OC_{1-6}$alkyl, —$SC_{1-6}$alkyl, or aryl;

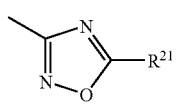
F wherein $R^{21}$ is independently as defined above;

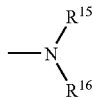
G wherein $R^{15}$ and $R^{16}$ are independently hydrogen, $C_{1-6}$alkyl, $C_{3-6}$cycloalkyl optionally substituted with 1 or 2 $C_{1-3}$ alkyl groups, or $R^{12}$ as defined above;

H

I

—(CH$_2$)nPh wherein n is 1-3

J

—O—$R^{21}$ wherein $R^{21}$ is independently as defined above; and

K

—S—$R^{21}$ wherein $R^{21}$ is independently as defined above. As used herein "aryl" or in any phrase or term including "aryl" such as "—$C_{1-6}$alkylenearyl", the "aryl" means a phenyl group or a 5 or 6 membered heteroaryl group. As used herein "heteroaryl" means a 5 or 6 membered heteroaryl group. As used herein any such "aryl" or "heteroaryl" group may optionally be substituted with one or two substituents selected from the group consisting of halogen, CN, dimethylamino, perfluoro$C_{1-6}$alkyl, perfluoro$OC_{1-6}$alkyl, $C_{1-6}$alkyl, —$OC_{1-6}$-alkyl, —$C_{1-6}$-alkylene$OC_1$-alkyl, and —$SC_{1-6}$alkyl.

In another aspect, the present invention discloses a method for prevention or treatment of a disease or condition mediated by one or more human PPAR alpha, gamma or delta ("hPPARs") comprising administration of a therapeutically effective amount of a compound of this invention. hPPAR mediated diseases or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, type II diabetes mellitus, type I diabetes, insulin resistance, hyperlipidemia, inflammation, epithelial hyperproliferative diseases including eczema and psoriasis and conditions associated with the lung and gut and regulation of appetite and food intake in subjects suffering from disorders such as obesity, anorexia bulimia, and anorexia nervosa. In particular, the compounds of this invention are useful in the treatment and prevention of diabetes and cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR mediated disease or condition.

As used herein, "a compound of the invention" means a compound of formula (I) or a pharmaceutically acceptable hydrolyzable ester or, solvate, thereof.

While hydrolyzable esters are included in the scope of this invention, the acids are preferred because the data suggests that while the esters are useful compounds, it may actually be the acids to which they hydrolyze that are the active compounds. Esters that hydrolyze readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$alkyl esters wherein the alkyl group may be straight chain or branched chain. Methyl or ethyl esters are more preferred.

Preferably $R^1$ and $R^2$ are independently H or $CH_3$. Most preferably $R^1$ and $R^2$ are either both H or both $CH_3$.

Preferably $X^2$ is O or S. More preferably $X^2$ is S;

Preferably $R^3$ is $CH_3$ or H;

Preferably $R^4$ and $R^5$ are H.

Preferably Y is S.

Preferably y is 1or 2. When y is 2, preferably one $R^{25}$ is halogen; more preferably one is halogen and the other is $CF_3$. When y is 1, preferably the $R^{25}$ is in the para position on the ring and is more preferably $CF_3$.

Preferably $R^{26}$ is selected from the moieties shown below in Group III.

Group III

Preferably $R^{12}$ is selected from the moieties shown below in Group IV.

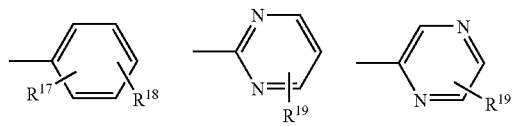

Group IV

Preferably $R^{13}$ or $R^{14}$ are independently fluorine, bromine, phenyl, thienyl, $CF_3$, $OCF_3$, $OCH_3$, $SCH_3$, or t-butyl. Most preferably $R^{14}$ is thienyl, $OCH_3$, $OCF_3$, $CF_3$, or fluorine. Most preferably $R^{14}$ is substituted para to the depicted open valence. Most preferably $R^{13}$ is hydrogen or fluorine.

Preferably $R^{17}$ and $R^{18}$ are independently hydrogen, OH, $OC_{1-3}$alkyl, CN, halogen, $CF_3$, $COCH_3$, $CH(OH)CH_3$, or $OCF_3$. Most preferably $R^{17}$ is fluorine, chlorine, $OC_{1-3}$alkyl, or $COCH_3$ and $R^{18}$ is $OCH_3$ or hydrogen. Most preferably $R^{17}$ is substituted para to the depicted open valence.

Preferably $R^{20}$ is phenyl, methyl, $OCH_3$, OH, or $CH_2OH$.

Preferably $R^{21}$ is —$C_{1-3}$alkylenephenyl, phenyl-5-methyl-1,2,4-oxadiazol-3-yl, or phenyl optionally substituted by methyl or CN.

Preferably $R^{22}$ is $C_{1-6}$alkyl, phenyl, or benzyl.

Preferably $R^{23}$ is $C_{1-6}$alkyl, furanyl, thienyl, methoxymethyl, $C_{3-6}$cyclalkyl, or phenyl optionally substituted by a halogen a methoxy or a dimethylamino group.

Preferably $R^{24}$ is H, $C_{1-6}$alkyl, cyclohexyl, m-methoxyphenyl, p-fluorophenyl, or —$CH_2CH_2$phenyl.

Preferably $R^{19}$ is hydrogen.

Particularly preferred compounds will be those is which most or all of the variables are selected from the preferred or most preferred groups for each variable.

While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred, more preferred, and most preferred groups.

Suitable compounds of formula (1) include:

2-[4-({[4-{[4-(4-acetylphenyl)-1-piperazinyl]methyl}-2-(4-fluorophenyl)-1,3-thiazol-5-yl]methyl}sulfanyl)-2-methylphenoxy]-2-methylpropanoic acid, 2-methyl-2-{2-methyl-4-[({4-[4-(methylsulfanyl)benzyl]-2-[4-(trifluoromethyl)phenyl]-1,3-thiazol-5-yl}methyl)sulfanyl]phenoxy}propanoic acid, {2-methyl-4-[({4-(3-thienylmethyl)-2-[4-(trifluoromethyl)phenyl]-1,3-thiazol-5-ylmethyl}sulfanyl]phenoxy}acetic acid, {4-[({4-benzyl-2-[4-(trifluoromethyl)phenyl]-1,3-thiazol-5-yl}methyl)sulfanyl]-2,5-dimethylphenoxy}acetic acid, 2-{4-[({4-{[4-(4-acetylphenyl)-1-piperazinyl]methyl}-2-[4-(trifluoromethyl)phenyl]-1,3-thiazol-5-yl}methyl)sulfanyl]-2-methylphenoxy}propanoic acid, 2-{4-[({4-{[4-(4-acetylphenyl)-1-piperazinyl]methyl}-2-[4-(trifluoromethyl)phenyl]-1,3-thiazol-5-yl}methyl)sulfanyl]-2-ethylphenoxy}propanoic acid, 2-{2-methyl-4-[({4-(2-thienylmethyl)-2-[4-(trifluoromethyl)phenyl]-1,3-thiazol-5-yl}methyl)sulfanyl]phenoxy}propanoic acid, 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}propanoic acid, 2-{4-[({4-{[4-(4-ethoxyphenyl)-1-piperazinyl]methyl}-2-[4-(trifluoromethyl)phenyl]-1,3-thiazol-5-yl}methyl)sulfanyl]-2-methylphenoxy}propanoic acid, 2-methyl-2-{2-methyl-4-[({4-{[4-(phenoxycarbonyl)-1-piperazinyl]methyl}-2-[4-(trifluoromethyl)phenyl]-1,3-thiazol-5-yl}methyl)sulfanyl]phenoxy}propanoic acid, 2-{4-[({4-{[4-(4-acetylphenyl)-1-piperazinyl]methyl}-2-[4-(trifluoromethyl)phenyl]-1,3-thiazol-5-yl}methyl)sulfanyl]-2-propylphenoxy}propanoic acid, {2-methyl-4-[({4-[4-(3-thienyl)benzyl]-2-[4-(trifluoromethyl)phenyl]-1,3-thiazol-5-yl}methyl)sulfanyl]phenoxy}acetic acid, 2-(4-{[(2-{4-fluorophenyl)-4-{[4-(4-methoxyphenyl)-1-piperazinyl]methyl}-1,3-thiazol-5-yl}methyl]sulfanyl}-2-methylphenoxy)-2-methylpropanoic acid, 2-{4-[({4-{[4-(4-acetylphenyl)-1-piperazinyl]methyl}-2-[4-(trifluoromethyl)phenyl]-1,3-thiazol-5-yl}methyl)sulfanyl]phenoxy}-2-methylpropanoic acid, 2-{4-[({4-{[4-(2,4-dimethoxyphenyl)-1-piperazinyl]methyl}-2-[4-(trifluoromethyl)phenyl]-1,3-thiazol-5-yl}methyl)sulfanyl]-2-methylphenoxy}propanoic acid, {2-isopropyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetic acid, 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-propylphenoxy}propanoic acid, 2-{4-[({4-benzyl-2-[4-(trifluoromethyl)phenyl]-1,3-thiazol-5-yl}methyl)sulfanyl]-2-methylphenoxy}propanoic acid, 2-{2-ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}propanoic acid, 2-methyl-2-{2-methyl-4-[({4-[4-trifluoromethyl)benzyl]-2-[4-(trifluoromethyl)phenyl]-1,3-thiazol-5-yl}methyl)sulfanyl]phenoxy}propanoic acid, 2-{4-[({4-{[4-(4-fluorophenyl)-1-piperazinyl]methyl}-2-[4-(trifluoromethyl)phenyl]-1,3-thiazol-5-yl}methyl)sulfanyl]-2-methylphenoxy}-2-methylpropanoic acid, {4-[({4-{[4-(4-acetylphenyl)-1-piperazinyl]methyl}-2-[4-(trifluoromethyl)phenyl]-1,3-thiazol-5-yl}methyl)sulfanyl]-2-propylphenoxy}acetic acid, {4-[({4-([1,1'-biphenyl]-4-ylmethyl)-2-[4-(trifluoromethyl)phenyl]-1,3-thiazol-5-yl}methyl)sulfanyl]-2-methylphenoxy}acetic acid, 2-{4-[({4-{[4-(4-fluorophenyl)-1-piperazinyl]methyl}-2-[4-(trifluoromethyl)phenyl]-1,3-thiazol-5-yl}methyl)sulfanyl]-2-methylphenoxy}propanoic acid, {4-[({4-{[4-(3-methoxyphenyl)-1-piperazinyl]methyl}-2-[4-(trifluoromethyl)phenyl]-1,3-thiazol-5-yl}methyl)sulfanyl]-2-methylphenoxy}acetic acid, 2-{2-methyl-4-[({4-(3-thienylmethyl)-2-[4-(trifluoromethyl)phenyl]-1,3-thiazol-5-yl}methyl)sulfanyl]phenoxy}propanoic acid, {4-[({4-{[4-(2-methoxyphenyl)-1-piperazinyl]methyl}-2-[4-(trifluoromethyl)phenyl]-1,3-thiazol-5-yl}methyl)sulfanyl]-2-methylphenoxy}acetic acid, 2-{2-isopropyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}propanoic acid, 2-{4-[({4-(4-tert-butylbenzyl)-2-[4-(trifluoromethyl)phenyl]-1,3-thiazol-5-yl}methyl)sulfanyl]-2-methylphenoxy}-2-methylpropanoic acid, 2-{4-[({4-{[4-(3-methoxyphenyl)-1-piperazinyl]methyl}-2-[4-(trifluoromethyl)phenyl]-1,3-thiazol-5-yl}methyl)sulfanyl]-2-methylphenoxy}propanoic acid, 2-{4-[({4-benzyl-2-[4-(trifluoromethyl)phenyl]-1,3-thiazol-5-yl}methyl)sulfanyl]-2,3-dimethylphenoxy}propanoic acid, 2-{4-[({4-{[4-(4-chlorophenyl)-1-piperazinyl]methyl}-2-[4-(trifluoromethyl)phenyl]-1,3-thiazol-5-yl}methyl)sulfanyl]-2-methylphenoxy}propanoic acid, 2-{4-[({4-benzyl-2-[4-(trifluoromethyl)phenyl]-1,3-thiazol-5-yl}methyl)sulfanyl]-2-fluorophenoxy}propanoic acid, 2-{4-[({4-{[4-(2,4-difluorophenyl)-1-piperazinyl]methyl}-2-[4-(trifluoromethyl)phenyl]-1,3-thiazol-5-yl}methyl)sulfanyl]-2-methylphenoxy}propanoic acid, {4-[({4-(2,4-difluorobenzyl)-2-[4-(trifluoromethyl)phenyl]-1,3-thiazol-5-yl}methyl)sulfanyl]-2-methylphenoxy}acetic acid, 2-{4-[({4-{[4-(4-acetylphenyl)-1-piperazinyl]methyl}-2-[4-(trifluoromethyl)phenyl]-1,3-thiazol-5-yl}methyl)sulfanyl]-2-methylphenoxy}-2-methylpropanoic acid, 2-methyl-2-{2-methyl-4-[({4-(3-thienylmethyl)-2-[4-(trifluoromethyl)phenyl]-1,3-thiazol-5-yl}methyl)sulfanyl]phenoxy}propanoic acid, 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}propanoic acid, {2-ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetic acid, 2-{4-[({4-(4-methoxybenzyl)-2-[4-(trifluoromethyl)phenyl]-1,3-thiazol-5-yl}methyl)sulfanyl]-2-methylphenoxy}-2-methylpropanoic acid, 2-methyl-2-{4-[({4-{[4-(2-pyrazinyl)-1-piperazinyl]methyl}-2-[4-(trifluoromethyl)phenyl]-1,3-thiazol-5-yl}methyl)sulfanyl]phenoxy}propanoic acid, 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}-2-methylpropanoic acid, 2-{4-[({4-{[4-(4-methoxyphenyl)-1-piperazinyl]methyl}-2-[4-(trifluoromethyl)phenyl]-1,3-thiazol-5-yl}methyl)sulfanyl]phenoxy}-2-methylpropanoic acid, 2-methyl-2-{2-methyl-4-[({4-[4-(trifluoromethoxy-benzyl]-2-[4-(trifluoromethyl)phenyl]-1,3-thiazol-5-yl}methyl)sulfanyl]phenoxy}propanoic acid, 2-{4-[({4-{[4-(4-isopropoxyphenyl)-1-piperazinyl]methyl}-2-[4-(trifluoromethyl)phenyl]-1,3-thiazol-5-yl}methyl)sulfanyl]-2-methylphenoxy}propanoic acid, 2-{2-methyl-4-[({4-{[4-(2-pyrimidinyl)-1-piperazinyl]methyl}-2-[4-(trifluoromethyl)phenyl]-1,3-thiazol-5-yl}methyl)sulfanyl]phenoxy}propanoic acid, {2-methyl-4-[({4-(3-phenylpropyl)-2-[4-(trifluoromethyl)phenyl]-1,3-thiazol-5-yl}methyl)sulfanyl]phenoxy}acetic acid,

[4-[({4-benzyl-2-[4-(trifluoromethyl)phenyl]-1,3-thiazol-5-yl}methyl)sulfanyl]-2-(trifluoromethyl)phenoxy]acetic acid, {2-methyl-4-[({4-{[4-(5-methyl-1,2,4-oxadiazol-3-yl)phenoxy]methyl}-2-[4-(trifluoromethyl)phenyl]-1,3-thiazol-5-yl}methyl)sulfanyl]phenoxy}acetic acid, {4-[({4-benzyl-2-[4-(trifluoromethyl)phenyl]-1,3-thiazol-5-yl}methyl)sulfanyl]-5-chloro-2-methylphenoxy}acetic acid, {4-[({4-benzyl-2-[4-(trifluoromethyl)phenyl]-1,3-thiazol-5-yl}methyl)sulfanyl]-2-methylphenoxy}acetic acid, {4-[({4-(4-methoxybenzyl)-2-[4-(trifluoromethyl)phenyl]-1,3-thiazol-5-yl}methyl)sulfanyl]-2-methylphenoxy}acetic acid, {2,5-dimethyl-4-[({4-(3-thienylmethyl)-2-[4-(trifluoromethyl)phenyl]-1,3-thiazol-5-yl}methyl)sulfanyl]phenoxy}acetic acid, {2-methyl-4-[({4-{[4-(2-pyrazinyl)-1-piperazinyl]methyl}-2-[4-(trifluoromethyl)phenyl]-1,3-thiazol-5-yl}methyl)sulfanyl]phenoxy}acetic acid, {4-[({4-benzyl-2-[4-(trifluoromethyl)phenyl]-1,3-thiazol-5-yl}methyl)sulfanyl]-2,3-dimethylphenoxy}acetic acid,

[4-({[2-(4-chlorophenyl)-4-methyl-1,3-thiazol-5-yl]methyl}sulfanyl)-2-methylphenoxy]acetic acid, {2-methyl-4-[({4-[(4-methyl-2-thienyl)methyl]-2-[4-(trifluoromethyl)phenyl]-1,3-thiazol-5-yl}methyl)sulfanyl]phenoxy}acetic acid, {4-[({4-benzyl-2-[4-(trifluoromethyl)phenyl]-1,3-thiazol-5-yl}methyl)sulfanyl]-2-bromophenoxy}acetic acid, {2-methyl-4-[({4-[(2-phenylethoxy)methyl]-2-[4-(trifluoromethyl)phenyl]-1,3-thiazol-5-yl}methyl)sulfanyl]phenoxy}acetic acid, {2-methyl-4-[({4-(2-phenylethyl)-2-[4-(trifluoromethyl)phenyl]-1,3-thiazol-5-yl}methyl)sulfanyl]phenoxy}acetic acid, and pharmaceutically acceptable salts, solvates, and hydrolyzable esters thereof.

More preferred compounds of formula (1) include:

2-methyl-2-{2-methyl-4-[({4-(3-thienylmethyl)-2-[4-(trifluoromethyl)phenyl]-1,3-thiazol-5-yl}methyl)sulfanyl]phenoxy}propanoic acid, 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}propanoic acid, {2-ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetic acid, 2-{4-[({4-(4-methoxybenzyl)-2-[4-(trifluoromethyl)phenyl]-1,3-thiazol-5-yl}methyl)sulfanyl]-2-methylphenoxy}-2-methylpropanoic acid, 2-methyl-2-{4-[({4-{[4-(2-pyrazinyl)-1-piperazinyl]methyl}-2-[4-(trifluoromethyl)phenyl]-1,3-thiazol-5-yl}methyl)sulfanyl]phenoxy}propanoic acid, 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}-2-methylpropanoic acid, 2-{4-[({4-{[4-(4-methoxyphenyl)-1-piperazinyl]methyl}-2-[4-(trifluoromethyl)phenyl]-1,3-thiazol-5-yl}methyl)sulfanyl]phenoxy}-2-methylpropanoic acid, 2-methyl-2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoic acid, 2-{4-[({4-{[4-(4-isopropoxyphenyl)-1-piperazinyl]methyl}-2-[4-(trifluoromethyl)phenyl]-1,3-thiazol-5-yl}methyl)sulfanyl]-2-methylphenoxy}propanoic acid, 2-{2-methyl-4-[({4-{[4-(2-pyrimidinyl)-1-piperazinyl]methyl}-2-[4-(trifluoromethyl)phenyl]-1,3-thiazol-5-yl}methyl)sulfanyl]phenoxy}propanoic acid, and pharmaceutically acceptable salts, solvates, and hydrolyzable esters thereof.

DETAILED DESCRIPTION OF THE INVENTION

Preferably, the compounds of formula (I) are hPPAR agonists. The hPPAR agonists of formula (I) may be agonists of only one type ("selective agonists"), agonists for two PPAR subtypes ("dual agonists"), or agonists for all three subtypes ("pan agonists"). As used herein, by "agonist", or "activating compound", or "activator", or the like, is meant those compounds which have a pKi of at least 5.0 preferably at least 6.0 to the relevant PPAR, for example hPPARδ in the binding assay described below, and which achieve at least 30% activation of the relevant PPAR relative to the appropriate indicated positive control in the transfection assay described below at concentrations of $10^{-5}$M or less. More preferably, the compounds of this invention achieve 30% activation of at least one human PPAR in the relevant transfection assay at concentrations of $10^{-6}$M or less. More preferably the compounds of the invention achieve 30% activation of at least one human PPAR in the relevant transfection assay at concentrations of $10^{-7}$M or less.

Preferably the compounds of formula (1) are hPPARδ agonists. More preferably they are also agonists of at least one of PPARγ or PPARα. Most preferably they are pan hPPAR agonists.

It will also be appreciated by those skilled in the art that the compounds of the present invention may also be utilized in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of formula (I) are within the scope of the invention. References hereinafter to a compound according to the invention include both compounds of formula (I) and their pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (I) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02-5000mg per day, preferably 1-1500mg per day. The desired dose may conveniently be presented in a single dose or as divided doses administered at appropriate intervals, for example as two, three, four or more sub-doses per day. The formulations according to the invention may contain between 0.1-99% of the active ingredient, conveniently from 30-95% for tablets and capsules and 3-50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR gamma, PPAR alpha or PPAR alpha/gamma agonists (for example thiazotidinediones such as e.g. Pioglitazone and Rosiglitazone). The compounds may also be used in combination with antihypertensive agents such as angistensin antagonists e.g. telmisartan, calcium channel antagonists e.g. lacidipine and ACE inhibitors e.g. enalapril. The invention thus provides in a further aspect the use of a combination comprising a compound of formula (I) with a further therapeutic agent in the treatment of a hPPAR mediated disease.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same hPPAR mediated disease, the dose of each compound may differ from that when the compound is used alone. Appropriate doses will be readily appreciated by those skilled in the art.

There is further provided processes for the preparation of compounds of 1. Unless otherwise indicated all definitions are as above.

In general when $X^2$ is O or S the compounds could be assembled by coupling through an alkylation step such as that shown below.

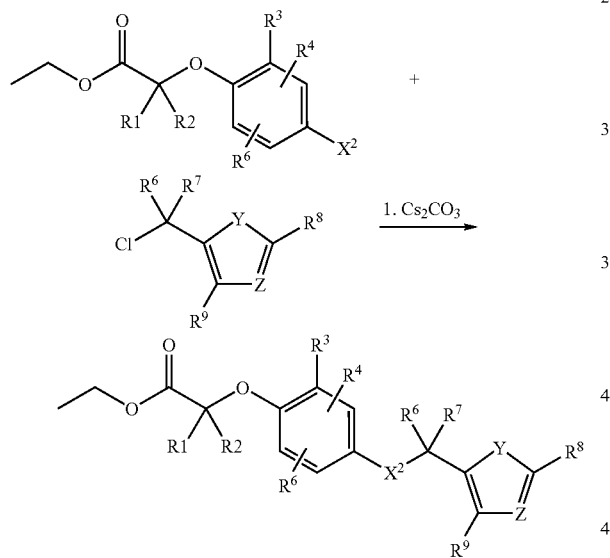

The esters are commercially available or made by the following general route when $X^2$ is S.

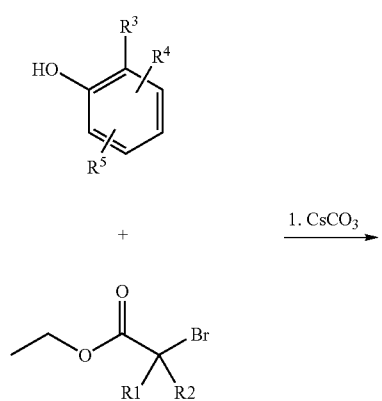

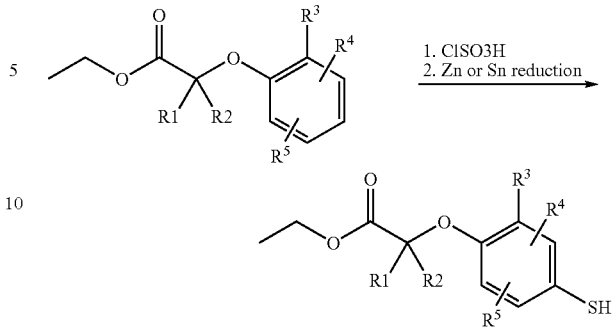

The heterocycle when Y is O or S and Z is N was generally made as shown below from an appropriate amide or thioamide:

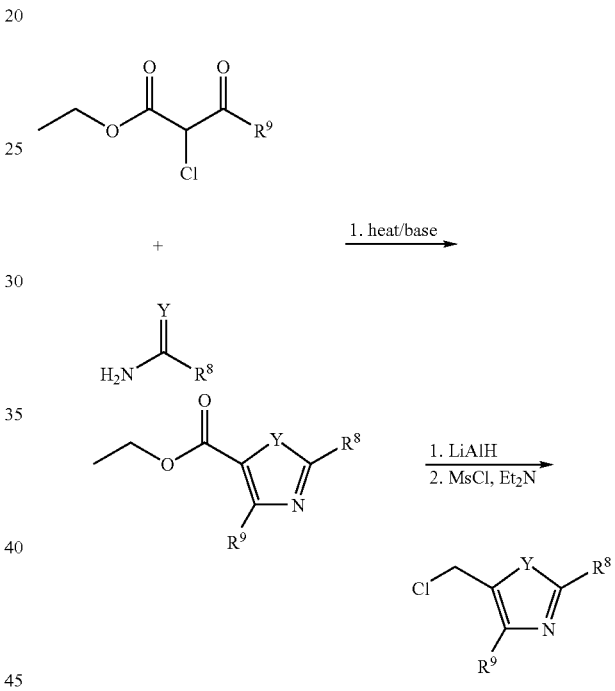

In specific cases the overall coupling step could be carried out directly after chlorosulfonation of the ester component without the need for formation of the chloride of the heterocyclic moiety, as shown below:

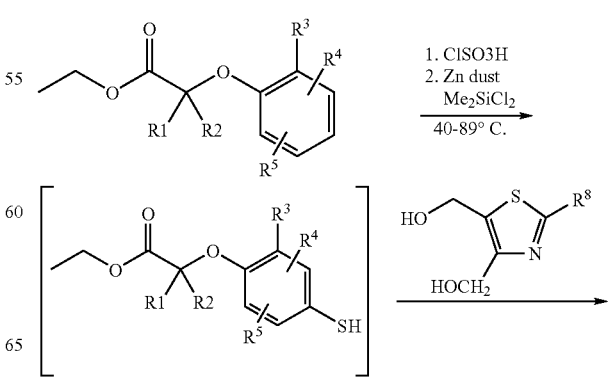

-continued

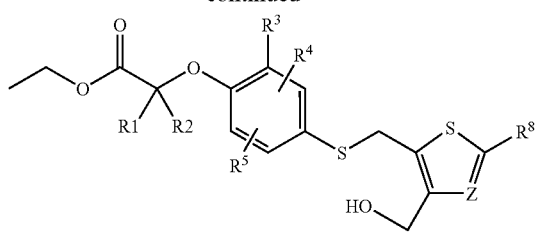

In some cases R⁹ was further elaborated through palladium coupling at the ester stage as shown below:

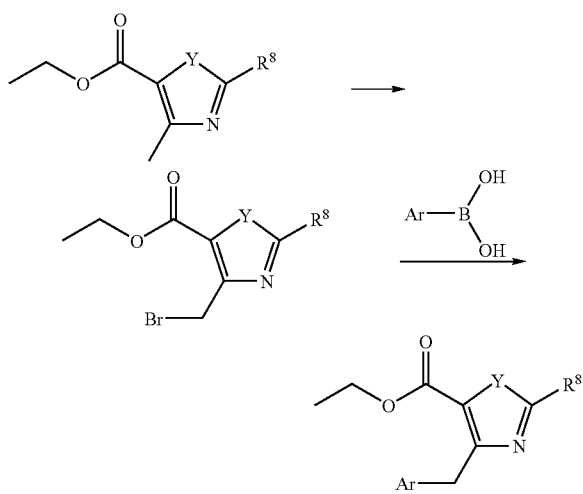

Alternatively R⁹ was elaborated after the coupling reaction by nucleophilic displacement of a mesylate shown below:

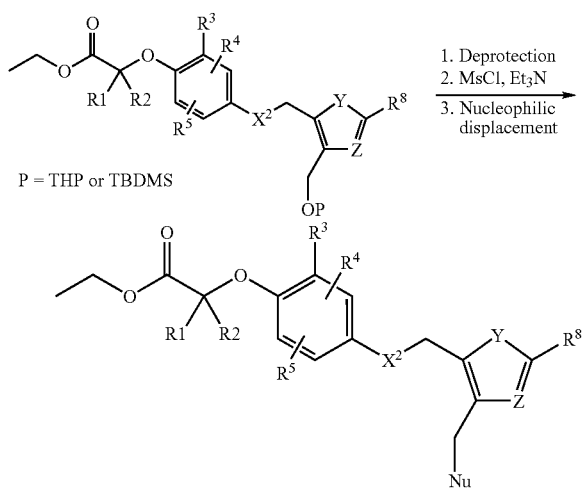

EXAMPLES

The invention is further illustrated by the following Examples which should not be construed as constituting a limitation thereto.

Ethyl 4-(bromomethyl)-2-[4-(trifluoromethyl)phenyl]-1,3-thiazole-5-carboxylate To a 2-L round-bottom flask equipped with an mechanical overhead stirrer, a reflux condenser and a $N_2$ inlet was added ethyl 4-methyl-2-[4-(trifluoromethyl)phenyl]-1,3-thiazole-5-carboxylate (85g, 0.27moles, 1.0eq) and dry carbon tetrachloride (750ml, 0.38M). Freshly recrystallized N-bromo succinimide (52.72g, 1.1eq) was added as a solid, Benzoyl peroxide (6.5g, 10mol %) was added at room temperature all at once as a solid, and the reaction mixture was refluxed for 5hrs. The reaction was monitored by $^1H$ NMR and was determined to be composed of a 9:1mixture of mono-bromination product (i.e. desired product) and di-bromination product with a 90% conversion. After cooling to 0° C. (to precipitate out the succinimide) the reaction was filtered through Celite and the solvent was removed under reduced pressure to yield a brown oil. The oil was crystallized using hexanes to yield 100g (94%) of an off-white product of 90% purity.

$^1H$ NMR (CDCl$_3$) 400MHz δ 8.10(d, 2H, J=8.20Hz), 7.72 (d, 2H, J=8.20Hz), 4.99(s, 2H), 4.40(q, 2H, J=7.18Hz), 1.41 (t, 3H, J=7.18Hz),

TLC(15% EtOAc/Hexanes) R$_f$=0.55

Ethyl 4-(bromomethyl)-2-phenyl-1,3-thiazole-5-carboxylate

The title compound was made using the same procedure as above.

$^1H$ NMR (CDCl$_3$) 400MHz δ 7.98(dd, 2H, J=7.86, 1.54Hz), 7.47(m, 3H), 4.99(s, 2H), 4.39(q, 2H, J=7.12Hz), 1.40(t, 3H, J=7.12Hz),

TLC(15% EtOAc/Hexanes) R$_f$=0.50

Ethyl 4-(hydroxymethyl)-2-[4-(trifluoromethyl)phenyl]-1,3-thiazole-5-carboxylate To a stirred solution of ethyl 4-(bromomethyl)-2-[4-(trifluoromethyl)phenyl]-1,3-thiazole-5-carboxylate (50g, 0.127moles, 1eq) in dry DMF (300ml) under a positive $N_2$ flow was added silver trifluoroacetate (42.02g, 0.191moles, 1.5eq) all at once as a solid. This was stirred at room temperature for 3.5hrs. The reaction was partitioned between ethyl ether (1.5L) and water (500ml). The phases were separated and the organic phase washed twice with water (500ml). After separation of the phases, the organic fraction was dried with Na$_2$SO$_4$, filtered and concentrated in vacuo. The crude trifluoroacetate product was used without characterization. Ethanol (300ml) was added and the reaction was refluxed for 10hrs. After cooling to room temperature the ethanol was removed in vacuo to yield 42g (100%) of the title compound. The product was used without purification.

1H NMR (CDCl3) 400MHz δ 8.09(d, 2H, J=8.20Hz), 7.73 (d, 2H, J=8.20Hz), 5.09(s, 2H), 4.41(q, 2H, J=7.12Hz), 1.40 (t, 3H, J=7.12Hz),

Ethyl 4-(hydroxymethyl)-2-phenyl-1,3-thiazole-5-carboxylate

The title compound was made using the same procedure as above.

$^1H$ NMR (CDCl$_3$) 400MHz δ 7.95(m, 2H), 7.48(m, 3H), 5.09(s, 2H), 4.40(q, 2H, J=7.12Hz), 1.41(t, 3H, J=7.12Hz),

Ethyl 4-[(tetrahydro-2H-pyran-2-yloxy)methyl]-2-[4-(trifluoromethyl)phenyl]-1,3-thiazole-5-carboxylate To a 1-L round-bottom flask equipped with a magnetic stir-bar and a $N_2$ inlet was added Ethyl 4-(hydroxymethyl)-2-[4-(trifluoromethyl)phenyl]-1,3-thiazole-5-carboxylate (42g, 0.127moles, 1eq) and dry $CH_2Cl_2$ (300ml) at room temperature. This was followed by the addition of 3,4-dihydro-2H-pyran (14ml, 0.152moles, 1.2eq) as a neat liquid and pyridinium p-toluenesulfonate (6.4g, 25.4mmoles, 20mol %). The reaction mixture was stirred at room temperature overnight (10hrs). The volatiles were then removed in vacuo and the residue was purified by flash silica gel chromatography (10% EtOAc/Hexanes to 30% EtOAc/Hexanes) to yield 34g (64%) of pure title compound.

$^1$H NMR (CDCl$_3$) 400MHz δ 8.10(d, 2H, J=8.20Hz), 7.72 (d, 2H, J=8.20Hz), 4.99(s, 2H), 4.40(q, 2H, J=7.18Hz), 1.41 (t, 3H, J=7.18Hz),
TLC(15% EtOAc/Hexanes) R$_f$=0.55

Ethyl 4-bromomethyl)-2-phenyl-1,3-thiazole-5-carboxylate

The title compound was made using the same procedure as above.
$^1$H NMR (CDCl$_3$) 400MHz δ 7.98(dd, 2H, J=7.86, 1.54Hz), 7.47(m, 3H), 4.99(s, 2H), 4.39(q, 2H, J=7.12Hz), 1.40(t, 3H, J=7.12Hz),
TLC(15% EtOAc/Hexanes) R$_f$=0.50

Ethyl 4-(hydroxymethyl)-2-[4-(trifluoromethyl)phenyl]-1,3-thiazole-6-carboxylate To a stirred solution of ethyl 4-(bromomethyl)-2-[4-(trifluoromethyl)phenyl]-1,3-thiazole-5-carboxylate (50g, 0.127moles, 1eq) in dry DMF (300ml) under a positive $N_2$ flow was added silver trifluoroacetate (42.02g, 0.191moles, 1.5eq) all at once as a solid. This was stirred at room temperature for 3.5hrs. The reaction was partitioned between ethyl ether (1.5L) and water (500ml). The phases were separated and the organic phase washed twice with water (500ml). After separation of the phases, the organic fraction was dried with $Na_2SO_4$, filtered and concentrated in vacuo. The crude trifluoroacetate product was used without characterization. Ethanol (300ml) was added and the reaction was refluxed for 10hrs. After cooling to room temperature the ethanol was removed in vacuo to yield 42g (100%) of the title compound. The product was used without purification.

1H NMR (CDCl3) 400MHz δ 8.09(d, 2H, J=8.20Hz), 7.73 (d, 2H, J=8.20Hz), 5.09(s, 2H), 4.41(q, 2H, J=7.12Hz), 1.40 (t, 3H, J=7.12Hz),

Ethyl 4-(hydroxymethyl)-2-phenyl-1,3-thiazole-5-carboxylate

The title compound was made using the same procedure as above.
$^1$H NMR (CDCl$_3$) 400MHz δ 7.95(m, 2H), 7.48(m, 3H), 5.09(s, 2H), 4.40(q, 2H, J=7.12Hz), 1.41(t, 3H, J=7.12Hz),

Ethyl 4-[(tetrahydro-2H-pyran-2-yloxy)methyl]-2-[4-(trifluoromethyl)phenyl]-1,3-thiazole-5-carboxylate To a 1-L round-bottom flask equipped with a magnetic stir-bar and a $N_2$ inlet was added Ethyl 4-(hydroxymethyl)-2-[4-(trifluoromethyl)phenyl]-1,3-thiazole-5-carboxylate (42g, 0.127moles, 1eq) and dry $CH_2Cl_2$(300ml) at room temperature. This was followed by the addition of 3,4-dihydro-2H-pyran (14ml, 0.1S2moles, 1.2eq) as a neat liquid and pyridinium p-toluenesulfonate (6.4g, 25.4mmoles, 20mol %). The reaction mixture was stirred at room temperature overnight (10hrs). The volatiles were then removed in vacuo and the residue was purified by flash silica gel chromatography (10% EtOAc/Hexanes to 30% EtOAc/Hexanes) to yield 34g (64%) of pure title compound.

Ethyl 4-[4-methoxybenzyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.25g, 0.63mmol), ethyl 4-[4-methoxybenzyl]-2-[4-(trifluoromethyl)phenyl]-1,3-thiazole-5-carboxylate (0.16g, 63%) was obtained as a yellow semi-solid.

$^1$H NMR (CDCl$_3$): δ 8.18(d, 2H), 7.70(d, 2H), 7.40(d, 2H), 6.80(d, 2H), 4.57(s, 2H), 4.40(q, 2H), 3.80(s, 3H), 1.40(t, 3H); MS m/z 422(M+1).

Ethyl 4-[4-(methylsulfanyl)benzyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.4g, 1.01mmol), ethyl 4-[4-(methylsulfanyl)benzyl]-2-[4-(trifluoromethyl)phenyl]-1,3-thiazole-5-carboxylate (0.44g, 100%) was obtained as a light yellow solid.

$^1$H NMR (CDCl$_3$): δ 8.11(d, 2H), 7.71(d, 2H), 7.38(d, 2H), 7.21(d, 2H), 4.52(s, 2H), 4.38(q, 2H), 2.49(s, 3H), 1.40(t, 3H); MS m/z 438(M+1).

Ethyl 4-[4-tert-butylbenzyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.4g, 1.01mmol), ethyl 4-[4-tert-butylbenzyl]-2-[4-(trifluoromethyl)phenyl]-1,3-thiazole-5-carboxylate (0.24g, 54%) was obtained as a white solid.

$^1$H NMR (CDCl$_3$): δ 8.11(d, 2H), 7.73(d, 2H), 7.56(d, 1H), 7.49(d, 1H), 7.34(m, 2H), 4.58(s, 2H), 4.40(q, 2H), 1.40(t, 3H), 1.27(s, 9H); MS m/z 448(M+1).

Ethyl 4-[3-thienylmethyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.4g, 1.01mmol), ethyl 4-[3-thienylmethyl]-2-[4-(trifluoromethyl)phenyl]-1,3-thiazole-5-carboxylate (0.4g 100%) was obtained as a yellow solid.

$^1$H NMR (CDCl$_3$): δ 8.12(d, 2H), 7.77(d, 2H), 7.40(d, 1H), 7.28(d, 1H), 7.20(s, 1H), 4.61(s, 2H), 4.41(q, 2H), 1.40(t, 3H); MS m/z 398(M+1).

Ethyl 4-[2-furylmethyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.4g, 1.01mmol), ethyl 4-[2-furylmethyl]-2-[4-(trifluoromethyl)phenyl]-1,3-thiazole-5-carboxylate (0.204g, 53%) was obtained as a white solid.

MS m/z 382(M+1); HPLC RT 4.072(C18 4.2×100mm, 0-100% ACN/H$_2$O (0.1% TFA), 6min @ 2ml/min @254/220nm).

Ethyl 4-[3-furylmethyl]-2-[4-trifluoromethyl)phenyl]-1,3-thiazole-5-carboxylate From ethyl 4-(bromomethyl)-2-[4-(trifluoromethyl)phenyl]-1,3-thiazole-5-carboxylate (0.4g, 1.01mmol), ethyl 4-[3-furylmethyl]-2-[4-(trifluoromethyl)phenyl]-1,3-thiazole-5-carboxylate (0.217g, 56%) was obtained as a white solid.

MS m/z 382(M+1); HPLC RT 4.091(C18 4.2×100mm, 0-100% ACN/H$_2$O (0.1% TFA), 6min @ 2ml/min @254/220nm).

Ethyl 4-[2-thienylmethyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.4g, 1.01mmol), ethyl 4-[2-thienylmethyl]-2-[4-(trifluoromethyl)phenyl]-1,3-thiazole-5-carboxylate (0.248g, 62%) was obtained as a yellow solid.

MS m/z 398(M+1); HPLC RT 4.224(C18 4.2×100mm, 0-100% ACN/H$_2$O (0.1% TFA), 6min @ 2ml/min @254/220nm).

Ethyl 4-[(4-methyl-2-thienyl)methyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.6g, 1.52mmol), ethyl 4-[(4-methyl-2-thienyl)methyl]-2-[4-(trifluoromethyl)phenyl]-1,3-thiazole-5-carboxylate (0.5g, 81%) was obtained as a yellow solid.

MS m/z 412(M+1); HPLC RT 4.682(C18 4.2×100mm, 0-100% ACN/H$_2$O (0.1% TFA), 6min @ 2ml/min @254/220nm).

Ethyl 4-[2,4-difluorobenzyl]-2-[4-(trifluoromethyl)phenyl]-1,3-thiazole-5-carboxylate From ethyl 4-(bromomethyl)-2-[4-(trifluoromethyl)phenyl]-1,3-thiazole-5-carboxylate (0.6g, 1.52mmol), ethyl 4-[2,4-difluorobenzyl]-2-[4-(trifluoromethyl)phenyl]-1,3-thiazole-5-carboxylate (0.222g, 35%) was obtained as a white solid.

MS m/z 428(M+1); HPLC RT 4.618(C18 4.2×100mm, 0-100% ACN/H$_2$O (0.1% TFA), 6min @ 2ml/min @254/220nm).

4-[(Tetrahydro-2H-pyran-2-yloxy)methyl]-2-[4-(trifluoromethyl)phenyl]-1,3-thiazol-5-yl}methanol To a stirred solution of lithium aluminum hydride (95%, 3.3g, 81.84mmoles, 1eq) in dry ethyl ether (300ml) at 0° C. was added ethyl 4-[(tetrahydro-2H-pyran-2-yloxy)methyl]-2-[4-(trifluoromethyl)phenyl]-1,3-thiazole-5-carboxylate (34g, 81.84mmoles, 1eq) in dry ethyl ether (50ml) dropwise via an addition funnel maintaining the internal reaction temperature below 5° C. This was stirred at 0° C. for 1hr. At 0° C. 3.5ml water was added dropwise very carefully and was then allowed to warm to room temperature. This was followed by the addition 3.5ml 5N NaOH and 10ml water. The mixture was stirred at room temperature for 2hrs. At this point a fine white precipitate formed. The reaction was filtered through Celite and the resulting aluminum salts were washed with 500ml EtOAc. The ether/EtOAc solution was concentrated in vacuo to 30.6g (100%) of titled alcohol.

$^1$H NMR (CDCl$_3$) 400MHz δ 8.07(d, 2H, J=8.20Hz), 7.72 (d, 2H, J=8.20Hz), 4.93(m, 4H), 4.78(t, 1H, J=3.32Hz), 3.90 (m, 1H), 3.61(m, 1H), 1.73(m, 6H),

TLC(30% EtOAc/Hexanes)=0.20

The following intermediates were reduced as above for 4-[(Tetrahydro-2H-pyran-2-yloxy)methyl]-2-[4-(trifluoromethyl)phenyl]-1,3-thiazol-5-yl}methanol.

{4-[(Tetrahydro-2H-pyran-2-yloxy)methyl]-2-[4-(trifluoromethyl)phenyl]-1,3-thiazol-5-yl}methanol $^1$H NMR (CDCl$_3$) 400MHz δ 8.07(d, 2H, J=8.20Hz), 7.72 (d, 2H, J=8.20Hz), 4.93(m, 4H), 4.78(t, 1H, J=3.32Hz), 3.90 (m, 1H), 3.61(m, 1H), 1.73(m, 6H), TLC(30% EtOAc/Hexanes)=0.20

{2-(4-Fluorophenyl)-4-[(tetrahydro-2H-pyran-2-yloxy)methyl]-1,3-thiazol-5-yl}methanol $^1$H NMR (CDCl$_3$) 400MHz δ 7.89(m, 2H), 7.09(m, 2H), 4.81(m, 5H), 3.84(m, 1H), 3.55(m, 1H), 1.67(m, 6H),

{2-Phenyl-4-[(tetrahydro-2H-pyran-2-yloxy)methyl]-1,3-thiazol-5-yl}methanol

1H NMR (CDCl3) 400MHz δ 7.96(m, 2H), 7.47(m, 3H), 4.92(m, 4H), 4.79(t, 1H, J=3.45Hz), 3.91(m, 1H), 3.60(m, 1H), 1.73(m, 6H),

{2-(4-{trifluoromethyl}phenyl)-4-[(2-phenylethoxy)methyl]-1,3-thiazol-5-yl}methanol $^1$H(CDCl$_3$) 300MHz δ 7.99(d, 2H, J=8.79Hz), 7.67(d, 2H, J=8.79Hz), 7.26(m, 5H), 4.78(s, 2H), 4.71(s, 2H), 3.84(t, 2H, J=6.94Hz), 2.95(t, 2H, J=6.94Hz), 2.63(s, 1H),

[2-(4-{trifluoromethyl}phenyl)-4-(3-phenylpropyl)-1,3-thiazol-5-yl]methanol $^1$H NMR (CDCl$_3$) 300MHz δ 8.02(d, 2H, J=8.79Hz), 7.67 (d, 2H, J=8.79Hz), 7.23(m, 4H), 4.76(s, 2H), 2.84(t, 2H, 7.28Hz), 2.67(t, 2H, 7.28Hz), 2.12(m, 2H),

[4-benzyl-2-(4-{trifluoromethyl}phenyl)-1,3-thiazol-5-yl]methanol $^1$H (CDCl$_3$) 300MHz δ 8.01(d, 2H, J=8.79Hz), 7.65(d, 2H, J=8.79Hz), 7.26(m, 5H), 4.78(s, 2H), 4.15(s, 2H), TLC(20% EtOAc/Hexanes) R$_f$=0.18

MS(ES$^+$) M+H=350

[2-(4-{trifluoromethyl}phenyl)-4-(2-phenylethyl)-1,3-thiazol-5-yl]methanol $^1$H (CDCl$_3$) 300MHz δ 8.06(d, 2H, J=9.61Hz), 7.70(d, 1H, J=9.48Hz), 7.23(m, 4H), 7.06(m, 2H), 4.40(d, 2H, J=5.63Hz), 3.07(s, 4H), 1.08(s, 1H), TLC(20% EtOAc/Hexanes) R$_f$=0.18

MS(ES$^+$) M+H=364

[4-[(Benzyloxy)methyl]-2-(4-{trifluoromethyl}phenyl)-1,3-thiazol-5-yl]methanol ¹H (CDCl₃) 300MHz δ 8.02(d, 2H, J=8.79Hz), 7.68(d, 2H, J=8.79Hz), 7.35(m, 5H), 4.82(m, 4H), 4.68(s, 2H), TLC(20% EtOAc/Hexanes) R_f=0.14

[4-(4-Bromobenzyl)-2-(4-{trifluoromethyl}phenyl)-1,3-thiazol-5-yl]methanol

¹H NMR (CDCl₃) 300MHz δ 7.99(d, 2H, J=8.10Hz), 7.66 (d, 2H, J=8.10Hz), 7.40(d, 2H, J=8.38Hz), 7.15(d, 2H, J=8.38Hz), 4.81(s, 2H), 4.10(s, 2H), TLC(20% EtOAc/Hexanes) R_f=0.14

{4-[4-(trifluoromethyl)benzyl]-2-[4-(trifluoromethyl)phenyl]-1,3-thiazol-5-yl}methanol From ethyl 4-[4-(trifluoromethyl)benzyl]-2-[4-(trifluoromethyl)phenyl]-1,3-thiazole-5-carboxylate (0.096g, 0.21mmol), {4-[4-(trifluoromethyl)benzyl]-2-[4-(trifluoromethyl)phenyl]-1,3-thiazol-5-yl}methanol (0.09g, 100%) was obtained as a white solid.
¹H NMR (CDCl₃); δ 8.16(d, 2H), 7.73(d, 2H), 7.59(d, 2H), 7.44(d, 2H), 4.90(d, 2H), 4.26(t, 2H); MS m/z 418(M+1).

{4-[4-(trifluoromethoxy)benzyl]-2-[4-(trifluoromethyl)phenyl]-1,3-thiazol-5-yl}methanol From ethyl 4-[4-(trifluoromethoxy)benzyl]-2-[4-(trifluoromethyl)phenyl]-1,3-thiazole-5-carboxylate (0.123g 0.26mmol), {4-[4-(trifluoromethoxy)benzyl]-2-[4-(trifluoromethyl)phenyl]-1,3-thiazol-5-yl}methanol (0.13g, 99%) was obtained as a white solid.
¹H NMR (CDCl₃): δ 8.07(d, 2H), 7.71(d, 2H), 7.38(d, 2H), 7.18(d, 2H), 4.80(d, 2H), 4.20(s, 2H); MS m/z 434(M+1).

{4-(4-methoxybenzyl)-2-[4-(trifluoromethyl)phenyl]-1,3-thiazol-5-yl}methanol From ethyl 4-[4-methoxybenzyl]-2-[4-(trifluoromethyl)phenyl]-1,3-thiazole-5-carboxylate 0.16g, 0.38mmol), {4-(4-methoxybenzyl)-2-[4-(trifluoromethyl)phenyl]-1,3-thiazol-5-yl}methanol (0.06g, 40%) was obtained as a white solid.
MS m/z 380(M+1); HPLC RT 3.552(C18 4.2×100mm, 0-100% ACN/H₂O (0.1% TFA), 6min @ 2ml/min @254/220nm).

{4-[4-(methylsulfanyl)benzyl]-2-[4-(trifluoromethyl)phenyl]-1,3-thiazol-5-yl}methanol From ethyl 4-[4-(methylsulfanyl)benzyl]-2-[4-(trifluoromethyl)phenyl]-1,3-thiazole-5-carboxylate (0.44g, 1.0mmol), {4-[4-(methylsulfanyl)benzyl]-2-[4-(trifluoromethyl)phenyl]-1,3-thiazol-5-yl}methanol (0.3g, 76%) was obtained as a white solid.
MS m/z 396(M+1); HPLC RT 3.699(C18 4.2×100mm, 0-100% ACN/H₂O (0.1% TFA), 6min @ 2ml/min @254/220nm).

{4-(4-tert-butylbenzyl)-2-[4-(trifluoromethyl)phenyl]-1,3-thiazol-5-yl}methanol From ethyl 4-[4-tert-butylbenzyl-2-[4-(trifluoromethyl)phenyl]-1,3-thiazole-5-carboxylate (0.24g, 0.54mmol), {4-(4-tert-butylbenzyl)-2-[4-(trifluoromethyl)phenyl]-1,3-thiazol-5-yl}methanol (0.13g, 64%) was obtained as a white solid.
MS m/z 406(M+1); HPLC RT 4.002(C18 4.2×100mm, 0-100% ACN/H₂O (0.1% TFA), 6min @ 2ml/min @254/220nm).

{4-(3-thienylmethyl)-2-[4-trifluoromethyl)phenyl]-1,3-thiazol-5-yl}methanol

From ethyl 4-[3-thienylmethyl]-2-[4-(trifluoromethyl)phenyl]-1,3-thiazole-5-carboxylate (0.44g, 1.11mmol), {4-(3-thienylmethyl)-2-[4-(trifluoromethyl)phenyl]-1,3-thiazol-5-yl}methanol (0.098g, 25%) was obtained as a yellow solid.
MS m/z 356(M+1); HPLC RT 3.513(C18 4.2×100mm, 0-100% ACN/H₂O (0.1% TFA), 6min @ 2ml/min @254/220nm).

{4-(2-furylmethyl)-2-[4-(trifluoromethyl)phenyl]-1,3-thiazol-5-yl}methanol

From ethyl 4-[2-furylmethyl]-2-[4-(trifluoromethyl)phenyl]-1,3-thiazole-5-carboxylate (0.204g, 0.53mmol), {4-(2-furylmethyl)-2-[4-(trifluoromethyl)phenyl]-1,3-thiazol-5-yl}methanol (0.162g, 89%) was obtained as a white solid.
MS m/z 340(M+1); HPLC RT 3.382(C18 4.2×100mm, 0-100% ACN/H₂O (0.1% TFA), 6min @ 2ml/min @254/220nm).

{4-(3-furylmethyl)-2-[4-(trifluoromethyl)phenyl]-1,3-thiazol-5-yl}methanol

From ethyl 4-[3-furylmethyl]-2-[4-(trifluoromethyl)phenyl]-1,3-thiazole-5-carboxylate (0.217g 0.57mmol), {4-(3-furylmethyl)-2-[4-(trifluoromethyl)phenyl]-1,3-thiazol-5-yl}methanol (0.180g, 88%) was obtained as a white solid.
MS m/z 340(M+1); HPLC RT 3.385(C18 4.2×100mm, 0-100% ACN/H₂O (0.1% TFA), 6min @ 2ml/min @254/220nm).

{4-(2-thienylmethyl)-2-[4-(trifluoromethyl)phenyl]-1,3-thiazol-5-yl}methanol From ethyl 4-[2-thienylmethyl]-2-[4-(trifluoromethyl)phenyl]-1,3-thiazole-5-carboxylate (0.248g, 0.62mmol), {4-(2-thienylmethyl)-2-[4-(trifluoromethyl)phenyl]-1,3-thiazol-5-yl}methanol (0.186g, 87%) was obtained as a yellow solid.
MS m/z 356(M+1); HPLC RT 3.528(C18 4.2×100mm, 0-100% ACN/H₂O (0.1% TFA), 6min @ 2ml/min @254/220nm).

{4-[(4-Methyll-2-thienyl)methyl]-2-[4-(trifluoromethyl)phenyl]-1,3-thiazol-6-yl}methanol From ethyl 4-[(4-methyl-2-thienyl)methyl]-2-[4-(trifluoromethyl)phenyl]-1,3-thiazole-5-carboxylate (0.5g, 1.22mmol), {4-[(4-methyl-2-thienyl)methyl]-2-[4-(trifluoromethyl)phenyl]-1,3-thiazol-5-yl}methanol (0.084g, 19%) was obtained as a yellow solid.
MS m/z 370(M+1); HPLC RT 3.913(C18 4.2×100mm, 0-100% ACN/H₂O (0.1% TFA), 6min @ 2ml/min @254/220nm).

{4-(2,4-difluorobenzyl)-2-[4-(trifluoromethyl)phenyl]-1,3-thiazol-5-yl}methanol

From ethyl 4-[2,4-difluorobenzyl]-2-[4-(trifluoromethyl)phenyl]-1,3-thiazole-5-carboxylate (0.46g, 1.08mmol), {4-(2,4-difluorobenzyl)-2-[4-(trifluoromethyl)phenyl]-1,3-thiazol-5-yl}methanol (0.222g, 54%) was obtained as a white solid.

MS m/z 386(M+1); HPLC RT 3.900(C18 4.2×100mm, 0-100% ACN/H$_2$O (0.1% TFA), 6min @ 2ml/min @254/220nm).

5-(Chloromethyl)-4-[(tetrahydro-2H-pyran-2-yloxy)methyl]-2-[4-(trifluoromethyl)phenyl]-1,3-thiazole To a 500-ml round-bottom flask equipped with a magnetic stir-bar, an addition funnel and a N$_2$inlet was added 4-[(Tetrahydro-2H-pyran-2-yloxy)methyl]-2-[4-(trifluoromethyl)phenyl]-1,3-thiazol-5-yl}methanol (15g, 40.17mmoles, 1eq) and dry CH$_2$Cl$_2$(150ml, 0.27M). Methanesulfonyl chloride (3.73ml, 48.20mmoles, 1.2eq) was added neat all at once followed by the dropwise addition of triethylamine (8.44ml, 60.26mmoles, 1.5eq) over 10minutes. This solution was stirred at room temperature for 1hr. The reaction was transferred to a separatory funnel and washed with water and brine. After the phases were separated the CH$_2$Cl$_2$ fraction was dried over Na$_2$SO$_4$ and the solvent was removed in vacuo. This yielded 15.74g (100%) of a brown oil. The crude product was used as is and required no purification.

$^1$H NMR (CDCl$_3$) 300MHz δ 8.08(d, 2H, J=8.20Hz), 7.73 (d, 2H, J=8.20Hz), 5.00(m, 3H), 4.80(m, 2H), 3.97(m, 1H), 3.64(m, 1H), 1.77(m, 6H),

TLC(25% EtOAc/Hexanes) R$_f$=0.64

The following intermediates were also prepared using the above mesylation/chloride displacement procedure:

5-(Chloromethyl)-2-(4-fluorophenyl)-4-[(tetrahydro-2H-pyran-2-yloxy)methyl]-1,3-thiazole $^1$H NMR (CDCl$_3$) 400MHz δ 7.90(m, 2H), 7.11(m, 2H), 4.94(s, 2H), 4.91(d, 1H, J=45Hz), 4.76(t, 1H, J=3.39Hz), 4.72(d, 1H, J=45Hz), 3.92(m, 1H), 3.58(m, 1H), 1.69(m, 6H),

[5-(Chloromethyl)-2-phenyl-1,3-thiazol-4-yl]methyl tetrahydro-2H-pyran-2-yl ether $^1$H NMR (CDCl$_3$) 300MHz δ 7.95(m, 2H), 7.47(m, 3H), 4.98(m, 3H), 4.80(m, 2H), 3.98(m, 1H), 3.63(m, 1H), 1.73(m, 6H), TLC(25% EtOAc/Hexanes) R$_f$=0.57

5-(Chloromethyl)-2-(4-{trifluoromethyl}phenyl)-4-[4-3-thienyl)benzyl]-1,3-thiazole $^1$H NMR (CDCl$_3$) 300MHz δ 8.06(d, 2H, J=8.23Hz), 7.71 (d, 2H, J=8.23Hz), 7.58(d, 2H, J=8.23Hz), 7.41(m, 5H), 4.84 (s, 2H), 4.26(s, 2H), TLC(20% EtOAc/Hexanes) R$_f$=0.66

4-[(Benzyloxy)methyl]-5-(chloromethyl)-2-[4-(trifluoromethyl)phenyl]-1,3-thiazole $^1$H NMR (CDCl$_3$) 300MHz δ 8.03(d, 2H, J=8.79Hz), 7.69 (d, 2H, J=8.79Hz), 7.37(m, 5H), 4.90(s, 2H), 4.77(s, 2H), 4.66(s, 2H)

4-Benzyl-5-(chloromethyl)-2-(4-{trifluoromethyl}phenyl)-1,3-thiazole $^1$H (CDCl$_3$) 300MHz δ 8.02(d, 2H, J=8.79Hz), 7.67(d, 2H, J=8.79Hz), 7.26(m, 5H), 4.77(s, 2H), 4.21(s, 2H), TLC(20% EtOAc/Hexanes) R$_f$=0.66

5-Chloromethyl)-2-(4-{trifluoromethyl}phenyl)-4-(2-phenylethyl)-1,3-thiazole $^1$H (CDCl$_3$) 300MHz δ 8.05(d, 2H, J=8.79Hz), 7.70(d, 2H, J=8.79Hz), 7.22(m, 5H), 4.46(s, 2H), 3.09(s, 4H), TLC(20% EtOAc/Hexanes) R$_f$=0.67

5-(Chloromethyl)-2-4-{trifluoromethyl}phenyl)-4-[(2-phenylethoxy)methyl]-1,3-thiazole $^1$H NMR (CDCl$_3$) 300MHz δ 8.01(d, 2H, J=8.79Hz), 7.68 (d, 2H, J=8.79Hz), 7.26(m, 5H), 4.76(s, 2H), 4.74(s, 2H), 3.78(t, 2H, J=6.94Hz), 2.94(t, 2H, J=6.94Hz), TLC(20% EtOAc/Hexanes) R$_f$0.56

5-(Chloromethyl)-2-(4-{trifluoromethyl}phenyl)-4-(3-phenylpropyl)-1,3-thiazole

TLC(20% EtOAc/Hexanes) R$_f$=0.63

4-(4-Bromobenzyl)-5-(chloromethyl)-2-(4-{trifluoromethyl}phenyl)-1,3-thiazole $^1$H NMR (CDCl$_3$) 300MHz δ 8.00(d, 2H, J=8.10Hz), 7.67 (d, 2H, J=8.10Hz), 7.42(d, 2H, J=8.38Hz), 7.18(d, 2H, J=8.38Hz), 4.77(s, 2H), 4.14(s, 2H), TLC(20% EtOAc/Hexanes) R$_f$0.66

4-([1,1'-Biphenyl]-4-ylmethyl)-5-(chloromethyl)-2-(4-{trifluoromethyl}phenyl)-1,3-thiazole $^1$H NMR (CDCl$_3$) 300MHz δ 8.07(d, 2H, J=8.23Hz), 7.72 (d, 2H, J=8.23Hz), 7.57(m, 4H), 7.39(m, 5H), 4.85(s, 2H), 4.28(s, 2H), TLC(20% EtOAc/Hexanes) R$_f$=0.69

5-(chloromethyl)-4-[4-(trifluoromethyl)benzyl]-2-[4-(trifluoromethyl)phenyl]-1,3-thiazole From {4-[4-(trifluoromethyl)benzyl]-2-[4-(trifluoromethyl)phenyl]-1,3-thiazol-5-yl}methanol (0.09g, 0.216mmol), 5-(chloromethyl)-4-[4-(trifluoromethyl)benzyl]-2-[4-(trifluoromethyl)phenyl]-1,3-thiazole (0.087g, 93%) was obtained as a yellow oil and immediately taken on without purification.

5-(chloromethyl)-4-[4-(trifluoromethoxy)benzyl]-2-[4-(trifluoromethyl)phenyl]-1,3-thiazole From {4-[4-(trifluoromethoxy)benzyl]-2-[4-(trifluoromethyl)phenyl]-1,3-thiazol-5-yl}methanol (0.13g, 0.3mmol), 5-(chloromethyl)-4-[4-(trifluoromethoxy)benzyl]-2-[4-(trifluoromethyl)phenyl]-1,3-thiazole (0.135g, 100%) was obtained as a yellow oil and immediately taken on without purification.

5-(chloromethyl)-4-(4-methoxybenzyl)-2-[4-(trifluoromethyl)phenyl]-1,3-thiazole From {4-(4-methoxybenzyl)-2-[4-(trifluoromethyl)phenyl]-1,3-thiazol-5-yl}methanol (0.06g, 0.158mmol), 5-(chloromethyl)-4-(4-methoxybenzyl)-2-[4-(trifluoromethyl)phenyl]-1,3-thiazole (0.08g, 100%) was obtained as a yellow oil and immediately taken on without purification.

5-(chloromethyl)-4-[4-methylsulfanyl)benzyl]-2-[4-(trifluoromethyl)phenyl]-1,3-thiazole From {4-[4-(methylsulfanyl)benzyl]-2-[4-(trifluoromethyl)phenyl]-1,3-thiazol-5-yl}methanol (0.3g, 0.76mmol), 5-(chloromethyl)-4-[4-(methylsulfanyl)benzyl]-2-[4-(trifluoromethyl)phenyl]-1,3-thiazole (0.33g, 100%) was obtained as a yellow oil and immediately taken on without purification.
MS m/z 414(M+1).

4-(4-tert-butylbenzyl)-5-(chloromethyl)-2-[4-(trifluoromethyl)phenyl]-1,3-thiazole From {4-(4-tert-butylbenzyl)-2-[4-(trifluoromethyl)phenyl]-1,3-thiazol-5-yl}methanol (0.13g, 0.32mmol), 4-(4-tert-butylbenzyl)-5-(chloromethyl)-2-[4-(trifluoromethyl)phenyl]-1,3-thiazole (0.151g, 100%) was obtained as a yellow oil and immediately taken on without purification.
MS m/z 424(M+1).

5-(chloromethyl)-4-(3-thienylmethyl)-2-[4-(trifluoromethyl)phenyl]-1,3-thiazole From {4-(3-thienylmethyl)-2-[4-(trifluoromethyl)phenyl]-1,3-thiazol-5-yl}methanol (0.098g, 0.28mmol), 5-(chloromethyl)-4-(3-thienylmethyl)-2-[4-(trifluoromethyl)phenyl]-1,3-thiazole (0.105g, 100%) was obtained as a yellow oil and immediately taken on without purification.
MS m/z 374(M+1).

5-(chloromethyl)-4-(2-furylmethyl)-2-[4-(trifluoromethyl)phenyl]-1,3-thiazole From {4-(2-furylmethyl)-2-[4-(trifluoromethyl)phenyl]-1,3-thiazol-5-yl}methanol (0.162g, 0.48mmol), 5-(chloromethyl)-4-(2-furylmethyl)-2-[4-(trifluoromethyl)phenyl]-1,3-thiazole (0.097g, 57%) was obtained as a yellow oil and immediately taken on without purification.
MS m/z 358(M+1).

5-(chloromethyl)-4-(3-furylmethyl)-2-[4-(trifluoromethyl)phenyl]-1,3-thiazole From {4-(3-furylmethyl)-2-[4-(trifluoromethyl)phenyl]-1,3-thiazol-5-yl}methanol (0.18g, 0.53mmol), 5-(chloromethyl)-4-(3-furylmethyl)-2-[4-(trifluoromethyl)phenyl]-1,3-thiazole (0.172g, 91%) was obtained as a yellow oil and immediately taken on without purification.
MS m/z 358(M+1).

5-(chloromethyl)-4-(2-thienylmethyl)-2-[4-(trifluoromethyl)phenyl]-1,3-thiazole From {4-(2-thienylmethyl)-2-[4-(trifluoromethyl)phenyl]-1,3-thiazol-5-yl}methanol (0.186g, 0.52mmol), 5-(chloromethyl)-4-(2-thienylmethyl)-2-[4-(trifluoromethyl)phenyl]-1,3-thiazole (0.185g, 95%) was obtained as a yellow oil and immediately taken on without purification.
MS m/z 374(M+1).

5-(chloromethyl)-4-[(4-methyl-2-thienyl)methyl]-2-[4-(trifluoromethyl)phenyl]-1,3-thiazole From {4-[(4-methyl-2-thienyl)methyl]-2-[4-(trifluoromethyl)phenyl]-1,3-thiazol-5-yl}methanol (0.084g, 0.23mmol), 5-(chloromethyl)-4-[(4-methyl-2-thienyl)methyl]-2-[4-(trifluoromethyl)phenyl]-1,3-thiazole (0.123g, 100%) was obtained as a yellow oil and immediately taken on without purification.

5-chloromethyl)-4-(2,4-difluorobenzyl)-2-[4-(trifluoromethyl)phenyl]-1,3-thiazole From {4-(2,4-difluorobenzyl)-2-[4-(trifluoromethyl)phenyl]-1,3-thiazol-5-yl}methanol (0.222g, 0.58mmol), 5-(chloromethyl)-4-(2,4-difluorobenzyl)-2-[4-(trifluoromethyl)phenyl]-1,3-thiazole (0.279g, 100%) was obtained as a yellow oil and immediately taken on without purification.

Ethyl 2-methyl-2-phenoxypropanoate

To a solution of potassium t-butoxide (1M in THF, 531ml, 0.531moles, 1eq) precooled to 0° C. (ice bath) was added phenol (50g, 0.531moles, 1eq) in dry THF (50ml) dropwise via an addition funnel over 20minutes maintaining the internal temperature of the reaction below 5degrees centigrade. Ethyl-2-bromoisobutyrate (70.14ml, 0.9eq, 0.478moles) in dry THF (20ml) was added dropwise over 10minutes maintaining the internal reaction temperature below 5° C. After the addition was complete, the ice bath was removed and the reaction was allowed to warm to room temperature. The reaction was brought to reflux and maintained at this reflux temperature for 8hours. Following the cooling of the reaction to 0° C. the volatiles were removed in vacuo. The residue was then partitioned between EtOAc and 1N NaOH. The phases were separated and the organic phase washed with 1N NaOH, $H_2O$, brine and dried over $Na_2SO_4$. After filtration the solution was concentrated under reduced pressure to yield 83g (75%) of clean title compound.
$^1$H NMR ($CDCl_3$) 400MHz δ 7.21(m, 2H), 6.95(t, 1H, J=7.41Hz), 6.82(m, 2H), 4.21(q, 2H, J=7.13Hz), 1.57(s, 6H), 1.22(t, 3H, J=7.13Hz),

Ethyl (2-ethylphenoxy)acetate

To a stirred solution of 2-ethylphenol (5ml, 42.4mmoles, 1eq) in dry DMF (120ml, 0.35M) was added potassium carbonate (6.45g, 46.6mmoles, 1.1eq) and ethylbromoacetate (4.7ml, 42.2mmoles, 1eq) and heated to 60° C. overnight. After cooling to room temperature the reaction mixture was partitioned between ethyl ether and 1N NaOH. The phases were separated and the organic portion washed twice with 1N NaOH, twice with $H_2O$, brine, dried over $Na_2SO_4$, filtered and concentrated in vacuo to yield 7.2g (82%) of product.
$^1$H NMR ($CDCl_3$) 400MHz δ 7.14(m, 2H), 6.92(t, 1H, J=8.24Hz), 6.70(d, 1H, J=8.24Hz), 4.62(s, 2H), 4.24(q, 2H, J=7.14Hz), 2.70(q, 2H, J=7.51Hz), 1.27(t, 3H, J=7.14Hz), 1.21(t, 3H, J=7.51Hz), The following were compounds were made using the same alkylation procedure:

Ethyl (2-isopropylphenoxy)acetate $^1$H NMR (CDCl$_3$) 400MHz δ 7.23(d, 1H, J=7.69Hz), 7.11 (t, 1H, J=7.69Hz), 6.96(t, 1H, J=7.69Hz), 6.70(d, 1H, J=7.69Hz), 4.62(s, 2H), 4.25(q, 2H, J=7.14Hz), 3.41(m, 1H), 1.26(m, 9H),

Ethyl (2-propylphenoxy)acetate $^1$H NMR (CDCl$_3$) 400MHz δ 7.12(m, 2H), 6.90(t, 1H, J=8.24Hz), 6.69(d, 1H, J=8.24Hz), 4.61(s, 2H), 4.24(q, 2H, J=7.14Hz), 2.64(t, 2H, J=7.33Hz), 1.64(m, 2H), 1.27(t, 3H, J=7.14Hz), 0.94(t, 3H, J=7.33Hz),

Ethyl [4-(chlorosulfonyl)-2-ethylphenoxy]acetate

To a 250ml round-bottom flask containing chlorosulfonic acid (30ml) cooled to 0° C. was added ethyl (2-ethylphenoxy) acetate (7.2g, 34.6mmoles) dropwise. Once the addition was complete the ice-bath was removed and the reaction was allowed to warm to room temperature at which the reaction was stirred for 3hours. The reaction was then slowly added to ice and, once the excess chlorosulfonic acid was quenched, the mixture was diluted with CH$_2$Cl$_2$(200ml). The phases were separated and the aqueous fraction washed with CH$_2$Cl$_2$twice. The combined organic fractions were dried over Na$_2$SO$_4$and filtered and concentrated in vacuo to yield 7.2g (70%) of crude product. The crude product was used with no purification.

$^1$H NMR (CDCl$_3$) 400MHz δ 7.84(m, 2H), 6.79(d, 1H, J=8.24Hz), 4.75(s, 2H), 4.26(q, 2H, J=7.14Hz), 2.77(q, 2H, J=7.51Hz), 1.26(m, 6H),

The following were compounds were made using the same chlorosulfonation procedure:

Ethyl [4-(chlorosulfonyl)-2-methylphenoxy]acetate $^1$H NMR (d6-DMSO) 300MHz δ 7.41(m, 2H), 6.79(d, 1H, J=8.23Hz), 4.82(s, 2H), 4.16(q, 2H, J=7.17Hz), 2.21(s, 3H), 1.21(t, 3H, J=7.17Hz),

Ethyl 2-[4-chlorosulfonyl)-2-methylphenoxy]propanoate $^1$H NMR (d6-DMSO) 300MHz δ 7.44(m, 1H), 7.39(dd, 1H, J=8.23, 2.39Hz), 6.74(d, 1H, J=8.23Hz), 4.96(q, 1H, J=6.81Hz), 4.13(q, 2H, J=7.08Hz), 2.20(s, 3H), 1.54(d, 3H, J=6.81Hz), 1.18(t, 3H, J=7.08Hz),

Ethyl 2-[4-(chlorosulfonyl)-2-isopropylphenoxy]propanoate $^1$H NMR (CDCl$_3$) 400MHz δ 7.81(m, 2H), 6.76(d, 1H, J=8.42Hz), 4.87(q, 1H, J=6.78Hz), 4.21(q, 2H, J=7.14Hz), 3.40(m, 1H), 1.65(d, 3H, J=6.78Hz), 1.24(m, 9H),

Ethyl [4-(chlorosulfonyl)-2-isopropylphenoxy]acetate $^1$H NMR (CDCl$_3$) 400MHz δ 7.84(m, 2H), 6.80(d, 1H, J=8.42Hz), 4.75(s, 2H), 4.26(q, 2H, J=7.14Hz), 3.42(m, 1H), 1.27(m, 9H),

Ethyl 2-[4-(chlorosulfonyl)-2-propylphenoxy]propanoate $^1$H NMR (CDCl$_3$) 400MHz δ 7.80(m, 2H), 6.75(d, 1H, J=8.42Hz), 4.85(q, 1H, J=6.78Hz), 4.21(q, 2H, J=7.14Hz), 2.69(t, 2H, J=7.51Hz), 1.66(m, 5H), 1.23(t, 3H, J=7.14Hz), 0.95(t, 3H, J=7.51Hz),

Ethyl [4-(chlorosulfonyl)-2-propylphenoxy]acetate $^1$H NMR (CDCl$_3$) 400MHz δ 7.83(m, 2H), 6.79(d, 1H, J=8.42Hz), 4.73(s, 2H), 4.26(q, 2H, J=7.14Hz), 2.70(t, 2H, J=7.51Hz), 1.67(m, 2H), 1.29(t, 3H, J=7.14Hz), 0.95(t, 3H, J=7.51Hz),

Ethyl 2-[4-chlorosulfonyl)-2-ethylphenoxy]propanoate $^1$H NMR (CDCl$_3$) 400MHz δ 7.81(m, 2H), 6.75(d, 1H, J=8.42Hz), 4.86(q, 1H, J=6.78Hz), 4.21(q, 2H, J=7.08Hz), 2.75(m, 2H), 1.68(d, 3H, J=6.78Hz), 1.23(m, 6H),

Ethyl 2-[4chlorosulfonyl)phenoxy]-2-methylpropanoate

To a 3-L three-neck round-bottom flask equipped with a magnetic stir-bar, low temperature thermometer with thermometer adapter, addition funnel and a N$_2$inlet was added ethyl 2-methyl-2-phenoxypropanoate (83g, 0.399moles, 1eq) and dry CH$_2$Cl$_2$(1L, 0.4M). After cooling the reaction to 0° C. (ice bath) chlorosulfonic acid (26.5ml, 0.399moles, 1eq) in dry CH$_2$Cl$_2$(50ml) was added dropwise over 30minutes via addition funnel maintaining the internal temperature below 5° C. Following this dropwise addition the reaction was allowed to stir at O C for 3hours. The reaction was monitored by HPLC and after 3hours complete conversion was observed [(C-18, 3μm) 0%-95% Acetonitrile/Water over 8minutes R$_t$=2.96minutes]. At this point dry DMF (124ml, 4eq) was added slowly maintaining the internal temperature below 5° C. This was followed by the dropwise addition of thionyl chloride (43.77ml, 0.599moles, 1.5eq) in dry CH$_2$Cl$_2$(50ml) over 25minutes maintaining the internal temperature below 5° C. After stirring at 0° C. for 1.5hours and monitoring by HPLC [(C-18, 3μm) 0%-95% Acetonitrile/Water over 8minutes R$_t$=5.97minutes] the reaction was allowed to warm to room temperature. The reaction mixture was then washed with 0.1N HCl and the phases were separated, with discarding the aqueous fraction. The organic fraction washed with 0.1N HCl, H$_2$O, brine and dried over Na$_2$SO$_4$. The solution was filtered and concentrated in vacuo to yield 119.95g (98%) of pure sulfonyl chloride.

$^1$H NMR (CDCl$_3$) 400MHz δ 7.89(d, 2H, J=9.31Hz), 6.89 (d, 2H, J=9.31Hz), 4.21(q, 2H, J=7.16Hz), 1.66(s, 6H), 1.20 (t, 3H, J=7.16Hz),

HPLC(C-18, 3μm) 0%-95% Acetonitrile/Water over 8minutes R$_t$=5.97minutes

Ethyl 2-methyl-2-(4-sulfanylphenoxy)propanoate

To a 3-L three-neck round-bottom flask equipped with an overhead mechanical stirrer, addition funnel and a N$_2$inlet was added ethyl 2-[4-(chlorosulfonyl)phenoxy]-2-methylpropanoate (53g, 0.173moles, 1eq) and absolute EtOH (500ml). Tin powder (325mesh, 123.06g, 1.04moles, 6eq) was added as a solid. The overhead stirrer was adjusted so that the rotor is as close as possible to the bottom of the round-bottom flask and stirring speed was accelerated to a very high setting before adding the HCl to prevent the clumping of the tin metal. Hydrogen chloride (4N in dioxane, 300ml) was added dropwise over the course of 1hour. The reaction mixture was refluxed for 4hours at which point the hot ethanolic solution was poured into a 2-L Erlenmeyer flask containing $CH_2Cl_2$(1L) and ice. After stirring for 10minutes the biphasic mixture was filtered through Celite. After transferring to a separatory funnel the phases were separated and the aqueous fraction washed with $CH_2Cl_2$(2×100ml). The combined organic fractions were dried over $Na_2SO_4$, filtered and concentrated in vacuo. A bright yellow oil with a white precipitate suspended resulted. This yellow mixture was dissolved in a minimum amount of $CH_2Cl_2$ and filtered once again through Celite to yield 30g (75%) of a bright yellow oil.

$^1$H NMR (CD$_3$OD) 300MHz δ 7.18(m, 2H), 6.73(d, 2H, J=8.00Hz), 4.23(q, 2H, J=7.17Hz), 3.69(s, 1H), 1.59(s, 6H), 1.26(t, 3H, J=7.17Hz),

The following were compounds were made using the same reduction procedure:

Ethyl (2-methyl-4-sulfanylphenoxy)acetate $^1$H NMR (CDCl$_3$) 400MHz δ 7.15(m, 2H), 6.63(d, 1H, J=8.23Hz), 4.64(s, 2H), 4.29(q, 2H, J=7.17Hz), 3.36(s, 1H), 2.29(s, 3H), 1.33(t, 3H, J=7.17Hz), Ethyl 2-(2-methyl-4-sulfanylphenoxy)propanoate $^1$H NMR (CDCl$_3$) 400MHz δ 7.12(d, 1H, J=2.39Hz), 7.04 (dd, 1H, J=8.37, 2.39Hz), 6.56(d, 1H, J=8.37Hz), 4.67(q, 1H, J=6.72Hz), 4.19(q, 2H, J=7.12Hz), 3.31(s, 1H), 2.22(s, 3H), 1.61(d, 3H, J=6.72Hz), 1.23(t, 3H, J=7.12Hz), TLC(20% EtOAc/Hexanes) R$_f$=0.60

Ethyl (2-ethyl-4-sulfanylphenoxy)acetate $^1$H NMR (CDCl$_3$) 400MHz δ 7.13(d, 1H, J=2.20Hz), 7.08 (dd, 1H, J=8.42, 2.38Hz), 6.58(d, 1H, J=8.42Hz), 4.59(s, 2H), 4.24(q, 2H, J=7.14Hz), 3.33(s, 1H), 2.64(q, 2H, J=7.51Hz), 1.28(t, 3H, J=7.14Hz), 1.18(t, 3H, J=7.51Hz), Ethyl 2-(2-ethyl-4-sulfanylphenoxy)propanoate $^1$H NMR (CDCl$_3$) 400MHz δ 7.15(d, 1H, J=2.20Hz), 7.07 (dd, 1H, J=8.42, 2.20Hz), 6.55(d, 1H, J=8.42Hz), 4.74(q, 1H, J=6.78Hz), 4.17(m, 2H), 3.32(s, 1H), 2.61(q, 2H, J=7.51Hz), 1.61(d, 3H, J=6.59Hz), 1.19(m, 6H), The following four compounds were made in the same way and used without further purification.

Ethyl (2-propyl)--4-sulfanylphenoxy)acetate

Ethyl 2-(2-propyl-4-sulfanylphenoxy)propanoate

Ethyl (2-isopropyl-4-sulfanylphenoxy)acetate

Ethyl 2-(2-isopropyl-4-sulfanylphenoxy)propanoate

Ethyl 2-methyl-2-{4-[({4-[(tetrahydro-2H-pyran-2-yloxy)methyl]-2-[4-(trifluoromethyl)phenyl]-1,3-thiazol-5-yl}methyl)sulfanyl]phenoxy}propanoate To a 250ml round-bottom flask equipped with a magnetic stir-bar and N$_2$ inlet was added 5-(chloromethyl)-4-[(tetrahydro-2H-pyran-2-yloxy)methyl]-2-[4-(trifluoromethyl)phenyl]-1,3-thiazole (7.87g, 20.09mmoles, 1eq) and dry CH$_3$CN (100ml, 0.27M). Solid cesium carbonate (16.4g, 50.22mmoles, 2.5eq) was added all at once followed by the quick addition of ethyl 2-methyl-2-(4-sulfanylphenoxy)propanoate (5.79g, 24.11mmoles, 1.2eq) in dry CH$_3$CN (10ml). The reaction was allowed to stir at room temperature for 2hours at which point the solvent was removed under reduced pressure. The resulting residue was partitioned between EtOAc and 1N NaOH. After the phases were separated the organic fraction washed with H$_2$O, brine and dried over Na$_2$SO$_4$. After filtration the volatiles were removed in vacuo to yield the titled compound in >100% yield. Sometimes because of the difficult separation between the thiophenol and the product, the crude product was carried forward without purification.

The following compounds were made using the same alkylation procedure. Where selectivity was an issue the alkylations were carried out below room temperature:

Ethyl 2-{2-methyl-4-[({2-phenyl-4-[(tetrahydro-2H-pyran-2-yloxy)methyl]-1,3-thiazol-5-yl}methyl)sulfanyl]phenoxy}propanoate $^1$H NMR (CDCl$_3$) 300MHz δ 7.93(m, 2H), 7.44(m, 3H), 7.28(d, 1H, J=2.39Hz), 7.15(dd, 1H, J=8.23, 2.39Hz), 6.61(d, 1H, J=8.23Hz), 4.72(m, 3H), 4.50(d, 1H, J=21Hz), 4.32(s, 2H), 4.23(q, 2H, J=7.08Hz), 3.93(m, 1H), 3.59(m, 1H), 2.26 (s, 3H), 1.71(m, 9H), 1.28(t, 3H, J=7.08Hz), Ethyl 2-{2-methyl-4-[({4-[(tetrahydro-2H-pyran-2-yloxy)methyl]-2-[4-(trifluoromethyl)phenyl]-1,3-thiazol-5-yl}methyl)sulfanyl]phenoxy}propanoate $^1$H NMR (CDCl$_3$) 300MHz δ 8.04(d, 2H, J=8.23Hz), 7.70 (d, 2H, J=8.23Hz), 7.27(d, 1H, J=2.39Hz), 7.15(dd, 1H, J=8.49, 2.39Hz), 6.60(d, 1H, J=8.49Hz), 4.73(m, 3H), 4.51 (d, 1H, J=21Hz), 4.32(s, 2H), 4.20(q, 2H, J=7.17Hz), 3.93(m, 1H), 3.60(m, 1H), 2.27(m, 3H), 1.71(m, 9H), 1.27(t, 3H, J=7.17Hz), TLC(30% EtOAc/Hexanes)=0.73

Ethyl 2-{4-[({2-(4-fluorophenyl)-4-[(tetrahydro-2H-pyran-2-yloxy)methyl]-1,3-thiazol-5-yl}methyl)sulfanyl]-2-methylphenoxy}propanoate $^1$H NMR (CDCl$_3$) 400MHz δ 7.88(m, 2H), 7.19(d, 1H, J=2.24Hz), 7.08(m, 3H), 6.54(d, 1H, J=8.45Hz), 4.65(m, 3H), 4.44(m, 1H), 4.24(s, 2H), 4.16(q, 2H, J=7.13Hz), 3.86 (m, 1H), 3.53(m, 1H), 2.21(s, 3H), 1.66(m, 9H), 1.20(t, 3H, J=7.13Hz), Ethyl {2-ethyl-4-[({4-[(tetrahydro-2H-pyran-2-yloxy)methyl]-2-[4-(trifluoromethyl)phenyl]-1,3-thiazol-5-yl}methyl)sulfanyl]phenoxy}acetate $^1$H NMR (CDCl$_3$) 400MHz δ 7.98(d, 2H, J=8.24Hz), 7.64 (d, 2H, J=8.24Hz), 7.20(d, 1H, J=2.20Hz), 7.15(dd, 1H, J=8.42, 2.20Hz), 6.60(d, 1H, J=8.42Hz), 4.63(m, 4H), 4.42 (d, 1H, J=27Hz), 4.24(m, 4H), 3.87(m, 1H), 3.54(m, 1H), 2.64(q, 2H, J=7.51Hz), 1.66(m, 6H), 1.26(t, 3H, J=7.14Hz), 1.15(t, 3H, J=7.51Hz), Ethyl 2-{2-ethyl-4-[({4-[(tetrahydro-2H-pyran-2-yloxy)methyl]-2-[4-(trifluoromethyl)phenyl]-1,3-thiazol-5-yl}methyl)sulfanyl]phenoxy}propanoate $^1$H NMR (CDCl$_3$) 400MHz δ 7.98(d, 2H, J=8.24Hz), 7.64 (d, 2H, J=8.24Hz), 7.17(d, 1H, J=2.38Hz), 7.11(dd, 1H, J=8.42, 2.38Hz), 6.56(d, 1H, J=8.42Hz), 4.71(q, 1H, J=6.78Hz), 4.66(t, 1H, J=3.39Hz), 4.60(d, 1H, J=27Hz), 4.41 (d, 1H, J=27Hz), 4.26(s, 2H), 4.16(q, 2H, J=7.14Hz), 3.87(m, 1H), 3.54(m, 1H), 2.62(q, 2H, J=7.51Hz), 1.60(m, 9H), 1.20 (t, 3H, J=7.14Hz), 1.15(t, 3H, J=7.51Hz), Ethyl {2-propyl-4-[({4-[(tetrahydro-2H-pyran-2-yloxy)methyl]-2-[4-(trifluoromethyl)phenyl]-1,3-thiazol-5-yl}methyl)sulfanyl]phenoxy}acetate $^1$H NMR (CDCl$_3$) 400MHz δ 7.97(d, 2H, J=8.20Hz), 7.64 (d, 2H, J=8.20Hz), 7.16(m, 2H), 6.59(d, 1H, J=8.24Hz), 4.66 (m, 1H), 4.61(m, 3H), 4.43(d, 1H, J=27Hz), 4.23(m, 4H), 3.88(m, 1H), 3.54(m, 1H), 2.57(t, 2H, J=7.33Hz), 1.68(m, 8H), 1.26(t, 3H, J=7.14Hz), 0.88(t, 3H, J=7.33Hz), Ethyl 2-{2-propyl-4-[({4-[(tetrahydro-2H-pyran-2-yloxy)methyl]-2-[4-(trifluoromethyl)phenyl]-1,3-thiazol-5-yl}methyl)sulfanyl]phenoxy}propanoate $^1$H NMR (CDCl$_3$) 400MHz δ 7.97(d, 2H, J=8.24Hz), 7.64 (d, 2H, J=8.24Hz), 7.17(d, 1H, J=2.38Hz), 7.11(dd, 1H, J=8.42, 2.38Hz), 6.55(d, 1H, J=8.42Hz), 4.70(q, 1H, J=6.78Hz), 4.66(t, 1H, J=3.39Hz), 4.62(d, 1H, J=27Hz), 4.43 (d, 1H, J=27Hz), 4.25(s, 2H), 4.15(q, 2H, J=7.14Hz), 3.88(m, 1H), 3.54(m, 1H), 2.56(t, 2H, J=7.33Hz), 1.60(m, 1H), 1.21(t, 3H, J=7.14Hz), 0.88(t, 3H, J=7.33Hz), Ethyl {2-isopropyl-4-[({4-[(tetrahydro-2H-pyran-2-yloxy)methyl]-2-[4-(trifluoromethyl)phenyl]-1,3-thiazol-5-yl}methyl)sulfanyl]phenoxy}acetate $^1$H NMR (CDCl$_3$) 400MHz δ 7.98(d, 2H, J=8.24Hz), 7.64 (d, 2H, J=8.24Hz), 7.20(d, 1H, J=2.38Hz), 7.15(dd, 1H, J=8.42, 2.38Hz), 6.60(d, 1H, J=8.42Hz), 4.65(t, 1H, J=3.48Hz), 4.60(s, 2H), 4.56(d, 1H, J=09Hz), 4.38(d, 1H, J=09Hz), 4.23(m, 4H), 3.87(m, 1H), 3.53(m, 1H), 3.32(m, 1H), 1.66(m, 6H), 1.26(t, 3H, J=7.14Hz), 1.15(d, 6H, J=6.96Hz), Ethyl 2-{4-[({4-(2-furylmethyl)-2-[4-(trifluoromethyl)phenyl]-1,3-thiazol-5-yl}methyl)sulfanyl]-2-methylphenoxy}propanoate From 5-(chloromethyl)-4-(2-furylmethyl)-2-[4-(trifluoromethyl)phenyl]-1,3-thiazole (0.097g, 0.27mmol), ethyl 2-{4-[({4-(2-furylmethyl)-2-[4-(trifluoromethyl)phenyl]-1,3-thiazol-5-yl}methyl)sulfanyl]-2-methylphenoxy}propanoate (0.091g, 60%) was obtained as a white solid.

$^1$H NMR (CDCl$_3$): δ 8.00(d, 2H), 7.68(d, 2H), 7.23(m, 2H), 6.62(m 2H), 6.30(s, 1H), 6.02(s, 1H), 4.76(q, 1H), 4.21 (q, 2H), 4.17(s, 2H), 3.98(s, 2H), 2.29(s, 3H), 1.63(s, 3H), 1.24(t, 3H); MS m/z 562(M+1).

Ethyl 2-{4-[({4-(3-furylmethyl)-2-[4-(trifluoromethyl)phenyl]-1,3-thiazol-5-yl}methyl)sulfanyl]-2-methylphenoxy}Propanoate From 5-(chloromethyl)-4-(3-furylmethyl)-2-[4-(trifluoromethyl)phenyl]-1,3-thiazole (0.172g, 0.48mmol), ethyl 2-{4-[({4-(3-furylmethyl)-2-[4-(trifluoromethyl)phenyl]-1,3-thiazol-5-yl}methyl)sulfanyl]-2-methylphenoxy}propanoate (0.177g, 65%) was obtained as a white solid.

$^1$H NMR (CDCl$_3$): δ 8.00(d, 2H), 7.70(d, 2H), 7.28(m, 2H), 7.16, (d, 1H), 6.61(m, 2H), 6.31(s, 1H), 4.78(q, 1H), 4.27(q, 2H), 4.18(s, 2H), 3.68(s, 2H), 2.22(s, 3H), 1.68(s, 3H), 1.30(t, 3H); MS m/z 578(M+1).

Ethyl 2-{4-[({4-(2-thienylmethyl)-2-[4-(trifluoromethyl)phenyl]-1,3-thiazol-5-yl}methyl)sulfanyl]-2-methylphenoxy}propanoate From 5-(chloromethyl)-4-(3-furylmethyl)-2-[4-(trifluoromethyl)phenyl]-1,3-thiazole (0.185g, 0.50mmol), ethyl 2-{4-[({4-(2-thienylmethyl)-2-[4-(trifluoromethyl)phenyl]-1,3-thiazol-5-yl}methyl)sulfanyl]-2-methylphenoxy}propanoate (0.21g, 73%) was obtained as a yellow solid.

$^1$H NMR (CDCl$_3$): δ 8.01(d, 2H), 7.70(d, 2H), 7.20(s, 1H), 7.17(m, 1H), 6.93(m, 1H), 6.80(s 1H), 6.60(m, 2H), 4.74(q, 1H), 4.20(q, 2H), 4.19(s, 2H), 4.17(s, 2H), 2.29(s, 3H), 1.67 (s, 3H), 1.30(t, 3H); MS m/z 578(M+1).

Ethyl 2-methyl-2-{4-[({4-[4-(trifluoromethoxy)benzyl]-2-[4-(trifluoromethyl)phenyl]-1,3-thiazol-5-yl}methyl)sulfanyl]phenoxy}propanoate From 5-(chloromethyl)-4-[4-(trifluoromethoxy)benzyl]-2-[4-(trifluoromethyl)phenyl]-1,3-thiazole (0.166g, 0.37mmol) (prepared as in U16097-118-2), ethyl 2-methyl-2-{4-[({4-[4-(trifluoromethoxy)benzyl]-2-[4-(trifluoromethyl)phenyl]-1,3-thiazol-5-yl}methyl)sulfanyl] phenoxy}propanoate (0.210g, 87%) was obtained as a white solid.

MS m/z 656(M+1); HPLC RT 4.862(C18 4.2×100mm, 0-100% ACN/H$_2$O (0.1% TFA), 6min @ 2ml/min @254/220nm).

Ethyl 2-methyl-2-{4-[({4-[(4-methyl-2-thienyl)methyl]-2-[4-(trifluoromethyl)phenyl]-1,3-thiazol-5-yl}methyl)sulfanyl]phenoxy}propanoate From 5-(chloromethyl)-4-(2-thienylmethyl)-2-[4-(trifluoromethyl)phenyl]-1,3-thiazole (0.062g, 0.16mmol), ethyl 2-methyl-2-{4-[({4-[(4-methyl-2-thienyl)methyl]-2-[4-(trifluoromethyl)phenyl]-1,3-thiazol-5-yl}methyl)sulfanyl] phenoxy}propanoate (0.17g, 100%) was obtained as a yellow oil.

MS m/z 592(M+1); HPLC RT 4.534(C18 4.2×100mm, 0-100% ACN/H$_2$O (0.1% TFA), 6min @ 2ml/min @254/220nm).

Ethyl {2-methyl-4-[({4-[(4-methyl-2-thienyl)methyl]-2-[4-(trifluoromethyl)phenyl]-1,3-thiazol-5-yl}methyl)sulfanyl]phenoxy}acetate From 5-(chloromethyl)-4-(2-thienylmethyl)-2-[4-(trifluoromethyl)phenyl]-1,3-thiazole (0.062g, 0.16mmol), ethyl {2-methyl-4-[({4-[(4-methyl-2-thienyl)methyl]-2-[4-(trifluoromethyl)phenyl]-1,3-thiazol-5-yl}methyl)sulfanyl] phenoxy}acetate (0.13g, 100%) was obtained as a yellow oil.

MS m/z 578(M+1); HPLC RT 4.338(C18 4.2×100mm, 0-100% ACN/H$_2$O (0.1% TFA), 6min @ 2ml/min @254/220nm).

Ethyl {4-[({4-(2,4-difluorobenzyl)-2-[4-(trifluoromethyl)phenyl]-1,3-thiazol-5-yl}methyl)sulfanyl]-2-methylphenoxy}acetate From 5-(chloromethyl)-4-(2,4-difluorobenzyl)-2-[4-(trifluoromethyl)phenyl]-1,3-thiazole (0.139g, 0.34mmol), ethyl {4-[({4-(2,4-difluorobenzyl)-2-[4-(trifluoromethyl)phenyl]-

1,3-thiazol-5-yl}methyl)sulfanyl]-2-methylphenoxy}acetate, (0.1g, 49%) was obtained as a white solid.

MS m/z 594(M+1); HPLC RT 4.337(C18 4.2×100mm, 0-100% ACN/H$_2$O (0.1% TFA), 6min @ 2ml/min @254/220nm).

Ethyl {4-[({4-(4-methoxybenzyl)-2-[4-(trifluoromethyl)phenyl]-1,3-thiazol-5-yl}methyl)sulfanyl]-2-methylphenoxy}acetate From 5-(chloromethyl)-4-(4-methoxybenzyl)-2-[4-(trifluoromethyl)phenyl]-1,3-thiazole (0.09g, 0.4mmol) (prepared as in U17097-118-3), ethyl {4-[({4-(4-methoxybenzyl)-2-[4-(trifluoromethyl)phenyl]-1,3-thiazol-5-yl}methyl)sulfanyl]-2-methylphenoxy}acetate (0.160g, 68%) was obtained as a white solid.

MS m/z 588(M+1); HPLC RT 4.631(C18 4.2×100mm, 0-100% ACN/H$_2$O (0.1% TFA), 6min @ 2ml/min @254/220nm).

2-Methyl-4-[({4-[(tetrahydro-2H-pyran-2-yloxy)methyl]-2-[4-(trifluoromethyl)phenyl]-1,3-thiazol-5-yl}methyl)sulfanyl]phenol $^1$H NMR (CDCl$_3$) 400MHz δ 7.97(d, 2H, J=8.10Hz), 7.63 (d, 2H, J=8.10Hz), 7.16(d, 1H, J=2.24Hz), 7.06(dd, 1H, J=8.28, 2.24Hz), 6.63(d, 1H, J=8.28Hz), 4.64(t, 1H, J=3.53Hz), 4.59(d, 1H, J=24Hz), 4.40(d, 1H, J=24Hz), 4.23 (s, 2H), 3.86(m, 1H), 3.53(m, 1H), 2.16(s, 3H), 1.66(m, 6H),

2-Methyl-4-[({4-(4-trifluoromethyl)benzyl)-2-[4-(trifluoromethyl)phenyl]-1,3-thiazol-5-yl}methyl)sulfanyl]phenol From 5-(chloromethyl)-4-[4-(trifluoromethyl)benzyl]-2-[4-(trifluoromethyl)phenyl]-1,3-thiazole (0.82g, 0.19mmol), 2-methyl-4-[({4-(4-trifluoromethyl)benzyl)-2-[4-(trifluoromethyl)phenyl]-1,3-thiazol-5-yl}methyl)sulfanyl]phenol (0.021g, 21%) was obtained as a white solid.

$^1$H NMR (CDCl$_3$): δ 8.00(d, 2H), 7.69(d, 2H), 7.52(d, 2H), 7.29(d, 2H), 7.18(s, 1H), 7.16(d 1H), 6.70(d, 1H), 4.15(s, 2H), 4.00(s, 2H), 2.20(s, 3H); MS m/z 540(M+1).

2-Methyl 4-[({4-(4-trifluoromethoxy)benzyl)-2-[4-(trifluoromethyl)phenyl]-1,3-thiazol-5-yl}methyl)sulfanyl]phenol From 5-(chloromethyl)-4-[4-(trifluoromethoxy)benzyl]-2-[4-(trifluoromethyl)phenyl]-1,3-thiazole (0.147g, 0.33mmol), 2-methyl-4-[({4-(4- trifluoromethoxy)benzyl]-2-[4-(trifluoromethyl)phenyl]-1,3-thiazol-5-yl}methyl)sulfanyl]phenol (0.048g, 27%) was obtained as a white solid.

$^1$H NMR (CDCl$_3$): δ 8.01(d, 2H), 7.71(d, 2H), 7.13(m, 6H), 6.69(d, 1H), 4.18(s, 2H), 3.96(s, 2H), 2.22(s, 3H); MS m/z 556(M+1).

4-[({4-(4-methoxybenzyl)-2-[4-(trifluoromethyl)phenyl]-1,3-thiazol-5-yl}methyl)sulfanyl]-2-methylphenol From 5-(chloromethyl)-4-(4-methoxybenzyl)-2-[4-(trifluoromethyl)phenyl]-1,3-thiazole (0.063g, 0.16mmol), 4-[({4-(4-methoxybenzyl)-2-[4-(trifluoromethyl)phenyl]-1,3-thiazol-5-yl}methyl)sulfanyl]-2-methylphenol (0.022g, 28%) was obtained as a white solid.

$^1$H NMR (CDCl$_3$): δ 8.00(d, 2H), 7.68(d, 2H), 7.19(s, 1H), 7.09(m, 3H) 6.82(d, 2H), 6.70(d, 1H), 4.14(s, 2H), 3.90(s, 2H), 2.20(s, 3H); MS m/z 502(M+1).

2-Methyl-4-[({4-(4-methylsulfanyl)benzyl)-2-[4-(trifluoromethyl)phenyl]-1,3-thiazol-5-yl}methyl)sulfanyl]phenol From 5-(chloromethyl)-4-[4-(methylsulfanyl)benzyl]-2-[4-(trifluoromethyl)phenyl]-1,3-thiazole (0.33g, 0.78mmol), 2-methyl-4-[({4-(4-methylsulfanyl)benzyl)-2-[4-(trifluoromethyl)phenyl]-1,3-thiazol-5-yl}methyl)sulfanyl]phenol (0.296g, 72%) was obtained as a white solid.

MS m/z 518(M+1).

4-[({4-(4-(4-tert-butylbenzyl)-2-[4-(trifluoromethyl)phenyl]-1,3-thiazol-5-yl}methyl)sulfanyl]-2-methylphenol From 4-(4-tert-butylbenzyl)-5-(chloromethyl)-2-[4-(trifluoromethyl)phenyl]-1,3-thiazole (0.151g, 0.36mmol), 4-[({4-(4-tert-butylbenzyl)-2-[4-(trifluoromethyl)phenyl]-1,3-thiazol-5-yl}methyl)sulfanyl]-2-methylphenol (0.113g, 60%) was obtained as a white solid. MS m/z 528(M+1).

2-Methyl-4-[({4-(3-thienylmethyl)-2-[4-(trifluoromethyl)phenyl]-1,3-thiazol-5-yl}methyl)sulfanyl]phenol From 5-(chloromethyl)-4-(3-thienylmethyl)-2-[4-(trifluoromethyl)phenyl]-1,3-thiazole (0.105g, 0.28mmol), 2-methyl-4-[({4-(3-thienylmethyl)-2-[4-(trifluoromethyl)phenyl]-1,3-thiazol-5-yl}methyl)sulfanyl]phenol (0.072g, 54%) was obtained as a yellow oil. MS m/z 478(M+1).

The following three compounds were also prepared by the same route but were carried on without purification:

Ethyl 2-{2-isopropyl-4-[({4-[(tetrahydro-2H-pyran-2-yloxy)methyl]-2-[4-(trifluoromethyl)phenyl]-1,3-thiazol-5-yl}methyl)sulfanyl]phenoxy}propanoate

4-[({4-[(Tetrahydro-2H-pyran-2-yloxy)methyl]-2-[4-(trifluoromethyl)phenyl]-1,3-thiazol-5-yl}methyl)sulfanyl]phenol

4-[({2-(4-Fluorophenyl)-4-[(tetrahydro-2H-pyran-2-yloxy)methyl]-1,3-thiazol-5-yl}methyl)sulfanyl]-2-methylphenol

Ethyl 2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoate From 2-methyl-4-[({4-(4-trifluoromethoxy)benzyl]-2-[4-(trifluoromethyl)phenyl]-1,3-thiazol-5-yl}methyl)sulfanyl] phenol (0.17g, 0.31mmol), ethyl 2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoate (0.17g, 83%) was obtained as a white solid.

MS m/z 656(M+1); HPLC RT 4.553(C18 4.2×100mm, 0-100% ACN/H$_2$O (0.1% TFA), 6min @ 2ml/min @254/220nm).

Methyl {2-methyl-4-[({4-[4-(trifluoromethoxy)benzyl]-2-[4-(trifluoromethyl)phenyl]-1,3-thiazol-5-yl}methyl)sulfanyl]phenoxy}acetate From 2-methyl-4-[({4-(4-trifluoromethoxy)benzyl]-2-[4-(trifluoromethyl)phenyl]-1,3-thiazol-5-yl}methyl)sulfanyl]phenol (0.17g, 0.31mmol), methyl {2-methyl-4-[({4-[4-(trifluoromethoxy)benzyl]-2-[4-(trifluoromethyl)phenyl]-1,3-thiazol-5-yl}methyl)sulfanyl]phenoxy}acetate (0.15g, 80%) was obtained as a white solid. MS m/z 628(M+1); HPLC RT 4.398(C18 4.2×100mm, 0-100% ACN/H$_2$O (0.1% TFA), 6min @ 2ml/min @254/220nm).

Ethyl 2-{2-methyl-4-[({4-(3-thienylmethyl)-2-[4-(trifluoromethyl)phenyl]-1,3-thiazol-5-yl}methyl)sulfanyl]phenoxy}propanoate From 2-methyl-4-[({4-(3-thienylmethyl)-2-[4-(trifluoromethyl)phenyl]-1,3-thiazol-5-yl}methyl)sulfanyl]phenol, ethyl 2-{2-methyl-4-[({4-(3-thienylmethyl)-2-[4-(trifluoromethyl)phenyl]-1,3-thiazol-5-yl}methyl)sulfanyl]phenoxy}propanoate (0.225g, 0.47mmol), (0.255g, 91%) was obtained as a yellow oil.

MS m/z 578(M+1); HPLC RT 4.412(C18 4.2×100mm, 0-100% ACN/H$_2$O (0.1% TFA), 6min @ 2ml/min @254/220nm).

Methyl {2-methyl-4-[({4-(3-thienylmethyl)-2-[4-(trifluoromethyl)phenyl]-1,3-thiazol-5-yl}methyl)sulfanyl]phenoxy}acetate From 2-methyl-4-[({4-(3-thienylmethyl)-2-[4-(trifluoromethyl)phenyl]-1,3-thiazol-5-yl}methyl)sulfanyl]phenol, methyl {2-methyl-4-[({4-(3-thienylmethyl)-2-[4-(trifluoromethyl)phenyl]-1,3-thiazol-5-yl}methyl)sulfanyl]phenoxy}acetate (0.225g, 0.47mmol), (0.259g, 94%) was obtained as a yellow oil.

MS m/z 550(M+1); HPLC RT 4.243(C18 4.2×100mm, 0-100% ACN/H$_2$O (0.1% TFA), 6min @ 2ml/min @254/220nm).

Ethyl 2-{4-[({4-(hydroxymethyl)-2-[4-(trifluoromethyl)phenyl]-1,3-thiazol-5-yl}methyl)sulfanyl]phenoxy}-2-methylpropanoate To a stirred solution of crude ethyl {2-methyl-4-[({4-[(tetrahydro-2H-pyran-2-yloxy)methyl]-2-[4-(trifluoromethyl)phenyl]-1,3-thiazol-5-yl}methyl)sulfanyl]phenoxy}acetate (11.98g, 20.09mmoles, 1eq) in MeOH (100ml, 0.20M) was added as a solid p-toluenesulfonic acid (800mg, 25mol %) at room temperature. The reaction mixture was stirred at room temperature for 3hours. The MeOH was removed in vacuo and the residue was purified by silica gel chromatography (15% EtOAc/Hexanes to 30% EtOAc/Hexanes) to yield 8g (78%) of pure titled alcohol.

$^1$H NMR (CDCl$_3$) 400MHz δ 7.96(d, 2H, J=8.06Hz), 7.65 (d, 2H, J=8.06Hz), 7.23(d, 2H, J=8.79Hz), 6.73(d, 2H, J=8.79Hz), 4.44(s, 2H), 4.17(m, 4H), 2.33(br s, 1H), 1.56(s, 6H), 1.21(t, 3H, J=7.14Hz),

TLC(30% EtOAc/Hexanes) R$_f$=0.32

4-[({4-(Hydroxymethyl)-2-[4-(trifluoromethyl)phenyl]-1,3-thiazol-5-yl}methyl)sulfanyl]-2-methylphenol $^1$H NMR (CDCl$_3$) 400MHz δ 7.95(d, 2H, J=7.93Hz), 7.64 (d, 2H, J=7.93Hz), 7.15(d, 1H, J=2.07Hz), 6.98(dd, 1H, J=8.10, 2.07Hz), 6.62(d, 1H, J=8.10Hz), 4.39(s, 2H), 4.11(s, 2H), 2.14(s, 3H),

Ethyl 2-{4-[({4-(hydroxymethyl)-2-[4-(trifluoromethyl)phenyl]-1,3-thiazol-5-yl}methyl)sulfanyl]-2-propylphenoxy}propanoate $^1$H NMR (CDCl$_3$) 400MHz δ 7.97(d, 2H, J=8.06Hz), 7.66 (d, 2H, J=8.06Hz), 7.13(d, 1H, J=2.38Hz), 7.10(dd, 1H, J=8.24, 2.38Hz), 6.55(d, 1H, J=8.24Hz), 4.70(q, 1H, J=6.78Hz), 4.43(s, 2H), 4.14(m, 4H), 2.55(t, 2H, J=7.33Hz), 2.19(br s, 1H), 1.55(m, 5H), 1.21(t, 3H, J=7.14Hz), 0.85(t, 3H, J=7.33Hz),

Methyl {4-[({4-hydroxymethyl)-2-[4-(trifluoromethyl)phenyl]-1,3-thiazol-5-yl}methyl)sulfanyl]-2-isopropylphenoxy}acetate $^1$H NMR (CDCl$_3$) 400MHz δ 7.97(d, 2H, J=8.42Hz), 7.66 (d, 2H, J=8.42Hz), 7.15(m, 2H), 6.60(d, 1H, J=8.79Hz), 4.64 (s, 2H), 4.38(s, 2H), 4.15(s, 2H), 3.77(s, 3H), 3.31(m, 1H), 2.03(br s, 1H), 1.12(d, 6H, J=6.96Hz),

Ethyl 2-{4-[({4-hydroxymethyl)-2-[4-(trifluoromethyl)phenyl]-1,3-thiazol-5-yl}methyl)sulfanyl]-2-isopropylphenoxy}propanoate $^1$H NMR (CDCl$_3$) 400MHz δ 7.97(d, 2H, J=8.24Hz), 7.66 (d, 2H, J=8.24Hz), 7.15(d, 1H, J=2.38Hz), 7.11(dd, 1H, J=8.42, 2.38Hz), 6.56(d, 1H, J=8.42Hz), 4.73(q, 1H, J=6.78Hz), 4.38(s, 2H), 4.14(m, 4H), 3.30(m, 1H), 1.60(d, 3H, J=6.78Hz), 1.17(m, 9H),

Ethyl 2-{4-[({4-(hydroxymethyl)-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.00(d, 2H, J=8.23Hz), 7.69 (d, 2H, J=8.23Hz), 7.22(d, 1H, J=2.39Hz), 7.12(dd, 1H, J=8.23, 2.39Hz), 6.59(d, 1H, J=8.23Hz), 4.74(q, 1H, J=6.77Hz), 4.51(s, 2H), 4.19(m, 4H), 3.68(br s, 1H), 2.26(s, 3H), 1.65(d, 3H, J=6.77Hz), 1.26(t, 3H, J=7.17Hz), TLC(50% EtOAc/Hexanes) R$_f$=0.40

The following four compounds were deprotected as above but used without further purification;

Ethyl 2-[4-({[2-(4-fluorophenyl)-4-(hydroxymethyl)-1,3-thiazol-5-yl]methyl}sulfanyl)-2-methylphenoxy]propanoate

Ethyl {2-ethyl-4-[({4-(hydroxymethyl)-2-[4-(trifluoromethyl)phenyl]-1,3-thiazol-5-yl}methyl)sulfanyl]phenoxy}acetate

Ethyl 2-{2-ethyl-4-[({4-(hydroxymethyl)-2-[4-(trifluoromethyl)phenyl]-1,3-thiazol-5-yl}methyl)sulfanyl]phenoxy}propanoate Ethyl {4-[({4-(hydroxymethyl)-2-[4-(trifluoromethyl)phenyl]-1,3-thiazol-5-yl}methyl)sulfanyl]-2-propylphenoxy}acetate

Ethyl {[tert-butyl(diphenyl)silyl]oxy}acetate

To a 500ml round-bottom flask equipped with a magnetic stir-bar, $N_2$ inlet was added ethyl glycolate (10g, 96.0mmoles, 1eq) and dry $CH_2Cl_2$ (200ml, 0.5M). This was followed by the addition of triethylamine (40ml, 0.288moles, 3eq) and DMAP (1.17g, 9.6mmoles, 10mol %) followed by the dropwise addition of TBDPSCl (27.5ml, 0.106moles, 1.1eq) in dry $CH_2Cl_2$ (20ml). The reaction mixture was allowed to stir at room temperature overnight at which time the reaction mixture was diluted with $CH_2Cl_2$ and washed with 1N HCl, saturated sodium bicarbonate, $H_2O$ and dried over $Na_2SO_4$. After filtration the volatiles were removed in vacuo to yield 30g (91%) of titled compound.

$^1$H NMR (CDCl$_3$) 300MHz δ 7.69(m, 4H), 7.39(m, 6H), 4.23(s, 2H), 4.14(q, 2H, J=7.14Hz), 1.22(t, 3H, J=7.14Hz), 1.08(m, 9H),
TLC(20% EtOAc/Hexanes) R$_f$=0.67

{[tert-Butyl(diphenyl)silyl]oxy}acetic acid

To a stirred solution of ethyl {[tert-butyl(diphenyl)silyl]oxy}acetate (20g, 58.4mmoles, 1eq) in THF (100ml, 0.58M) was added 1N NaOH (6ml, 0.117moles, 2eq) and was allowed to stir at room temperature overnight. The THF was removed in vacuo and the residue was partitioned between $CH_2Cl_2$ and 1N HCl until a pH of 2 was reached. The phases were separated and the aqueous phase washed twice with $CH_2Cl_2$. The combined organic fractions were dried over $Na_2SO_4$, filtered and concentrated in vacuo to yield 17g (90%) of product.

$^1$H NMR (CDCl$_3$) 300MHz δ 7.68(m, 4H), 7.41(m, 6H), 4.22(s, 2H), 1.11(s, 9H),
TLC(5% MeOH/CH$_2$Cl$_2$) R$_f$=0.37

{[tert-Butyl(diphenyl)silyl]oxy}acetyl chloride

In a 500ml round-bottom flask was mixed {[tert-butyl(diphenyl)silyl]oxy}acetic acid (17g, 54.0mmoles, 1eq), thionyl chloride (11.7g, 0.162moles, 3eq) and dry $CH_2Cl_2$ (120ml, 0.45M). This mixture was refluxed for 5hours. After cooling to room temperature the volatiles were removed in vacuo. The resulting residue washed twice with toluene and the toluene was subsequently removed in vacuo to remove excess thionyl chloride. This resulted in 18g (100%) of titled compound.

$^1$H NMR (CDCl$_3$) 300MHz δ 7.72(m, 4H), 7.44(m, 6H), 4.54(s, 2H), 1.11(m, 9H),

Ethyl 4-{[tert-butyl(diphenyl)silyl]oxy}-3-oxobutanoate

To a 1-L round-bottom flask equipped with a magnetic stir-bar, addition funnel, low temperature thermometer with thermometer adapter and a $N_2$ inlet was added monoethyl malonate (14.53g, 0.11moles, 2eq) in dry THF (150ml, 0.73M) and 20mg of 2,2'-dipyridyl. After cooling the reaction mixture to −78° C. (dry ice/acetone), n-BuLi (2.5M in Hexanes, 88ml, 0.22moles, 4eq) was added at a rate to maintain the internal temperature below −10° C. Once the addition was complete the reaction was allowed to warm to −10° C. by removal of the cold bath. The reaction remained a light pink color; this designates that there was ample amount of n-BuLi to deprotonate the monoethyl malonate. (If the color had turned yellow the reaction would have had to have been re-cooled to −78° C. and additional n-BuLi would have had to have been added followed be re-warming to −10° C.) At this point the reaction mixture was cooled to −78° C. followed by the dropwise addition of neat {[tert-Butyl(diphenyl)silyl]oxy}acetyl chloride (18g, 54mmoles, 1eq) over a period of 15minutes maintaining the internal reaction temperature below 60° C. This was allowed to stir at −78° C. for 10minutes at which point the reaction was transferred to a separatory funnel containing diethyl ether (900ml) and 1N HCl (450ml). This was agitated and vented until further gas evolution ceased after which the phases were separated and the organic phase washed with saturated sodium bicarbonate, brine and dried over $Na_2SO_4$. This was then filtered, concentrated in vacuo and purified by silica gel chromatography (5% EtOAc/Hexanes to 20% EtOAc/Hexanes) to yield 12.2g (60%) of product.

$^1$H NMR (CDCl$_3$) 300MHz δ 7.63(m, 4H), 7.41(m, 6H), 4.19(m, 4H), 3.63(s, 2H), 1.27(t, 3H, J=7.14Hz), 1.08(s, 9H),
TLC(20% EtOAc/Hexanes) R$_f$=0.53

The following compounds were made according to W. Wierenga (J. Org. Chem. 1979vol 44p 310):

Ethyl 4-(4-bromophenyl)-3-oxobutanoate $^1$H NMR (CDCl$_3$) 300MHz δ 7.45(d, 2H, J=8.38Hz), 7.10 (d, 2H, J=8.38Hz), 4.17(q, 2H, J=7.14Hz), 3.79(s, 2H), 3.45 (s, 2H), 1.26(t, 3H, J=7.14Hz),

Ethyl 3-oxo-4-(2-phenylethoxy)butanoate $^1$H NMR (CDCl$_3$) 300MHz δ 7.26(m, 5H), 4.15(q, 4H, J=7.14Hz), 3.71(t, 2H, J=6.94Hz), 3.46(s, 2H), 2.92(t, 2H, J=6.94Hz), 1.27(t, 3H, J=7.14Hz),

Ethyl 3-oxo-6-phenylhexanoate $^1$H NMR (CDCl$_3$) 300MHz δ 7.22(m, 5H), 4.18(q, 2H, J=7.14Hz), 3.39(s, 2H), 2.62(t, 2H, J=7.28Hz), 2.53(t, 2H, J=7.28Hz), 1.92(m, 2H), 1.25(t, 3H, J=7.14Hz),

Ethyl 3-oxo-4-phenylbutanoate $^1$H (CDCl$_3$) 300MHz 7.29(m, 5H), 4.18(q, 2H, J=7.14Hz), 3.83(s, 2H), 3.44(s, 2H), 1.26(t, 3H, J=7.14Hz),
TLC(20% EtOAc/Hexanes) R$_f$=0.36

Ethyl 4-(benzyloxy)-3-oxobutanoate $^1$H (CDCl$_3$) 300MHz 7.36(m, 5H), 4.59(s, 2H), 4.16(q, 4H, J=7.14Hz), 3.53(s, 2H), 1.26(t, 3H, J=7.14Hz),

Ethyl 3-oxo-5-phenylpentanoate $^1$H NMR (CDCl$_3$) 300MHz 7.24(m, 5H), 4.18(q, 2H, J=7.14Hz), 3.42(s, 2H), 2.90(m, 4H), 1.27(t, 3H, J=7.14Hz)

Ethyl 4-{[tert-butyl(diphenyl)silyl]oxy}-2-chloro-3-oxobutanoate

To a 100ml round-bottom flask equipped with a magnetic stir-bar and a $N_2$ inlet was added ethyl 4-{[tert-butyl(diphenyl)silyl]oxy}-3-oxobutanoate (4g, 10.4mmoles, 1eq) and dry $CH_2Cl_2$(25ml, 0.42M) at room temperature. This was followed by the addition of neat sulfuryl chloride (0.833ml, 10.4mmoles, 1eq) and the reaction was allowed to stir overnight at room temperature. After dilution with CH$_2$Cl$_2$(50ml) the reaction mixture was treated with saturated sodium bicarbonate until bubbling ceased. The phases were separated and the organic fraction washed with sat. NaHCO$_3$, brine and dried over Na$_2$SO$_4$. After filtration and concentration in vacuo was yielded 4.2g (96%) of crude chloride. This crude product was used without purification.

$^1$H NMR (CDCl$_3$) 400MHz δ 7.62(m, 4H), 7.41(m, 6H), 5.26(s, 1H), 4.40(m, 2H), 4.25(m, 2H), 1.28(t, 3H, J=7.14Hz), 1.09(s, 9H),

The following intermediates were made by the same procedure as that used for Ethyl 4-{[tert-butyl(diphenyl)silyl]oxy}-2-chloro-3-oxobutanoate;

Ethyl 4-(benzyloxy)-2-chloro-3-oxobutanoate $^1$H (CDCl$_3$) 300MHz δ 7.36(m, 5H), 5.10(s, 1H), 4.59(s, 2H), 4.32(s, 2H), 4.23(q, 2H, J=7.23Hz), 1.28(t, 3H, J=7.14Hz),

Ethyl 2-chloro-3-oxo-6-phenylhexanoate $^1$H (CDCl$_3$) 300MHz δ 7.23(m, 5H), 4.75(s, 1H), 4.27(q, 2H, J=7.14Hz), 2.72(t, 2H, J=7.28Hz), 2.63(t, 2H, J=7.28Hz), 1.97(m, 2H, J=7.28Hz), 1.28(t, 3H, J=7.14Hz),

Ethyl 2-chloro-3-oxo-4-(2-phenylethoxy)butanoate $^1$H NMR (CDCl$_3$) 300MHz δ 7.25(m, 5H), 5.03(s, 1H), 4.29(m, 2H), 4.24(q, 2H, J=7.14Hz), 3.73(t, 2H, J=7.00Hz), 2.91(t, 2H, J=7.00Hz), 1.29(t, 3H, J=7.14Hz),

Ethyl 2-chloro-3-oxo-4-phenylbutanoate $^1$H (CDCl$_3$) 300MHz δ 7.29(m, 5H), 4.87(s, 1H), 4.23(m, 2H, J=7.14, 7.00, 7.14, 1.10, 1.24, 1.24, 0.82Hz), 4.02(d, 2H, J=4.53Hz), 1.31(t, 3H, J=7.14Hz),
TLC(20% EtOAc/Hexanes) R$_f$=0.51

Ethyl 2-chloro-3-oxo-5-phenylpentanoate $^1$H (CDCl$_3$) 300MHz δ 7.25(m, 5H), 4.76(s, 1H), 4.25(q, 2H, J=7.14Hz), 2.99(m, 4H), 1.31(t, 3H, J=7.14Hz),
TLC(20% EtOAc/Hexanes) R$_f$=0.46

Ethyl 4-(4-bromophenyl)-2-chloro-3-oxobutanoate $^1$H NMR (CDCl$_3$) 300MHz δ 7.48(d, 2H, J=8.51Hz), 7.10 (d, 2H, J=8.51Hz), 4.84(s, 1H), 4.25(q, 2H, J=7.14Hz), 3.97(s, 2H), 1.29(t, 3H, J=7.14Hz),
TLC(20% EtOAc/Hexanes) R$_f$=0.58

Ethyl 4-({[tert-butyl(diphenyl)silyl]oxy}methyl)-2-(4-{trifluoromethyl}phenyl)-1,3-thiazole-5-carboxylate To a 500ml round-bottom flask equipped with a magnetic stir-bar was mixed ethyl 4-{[tert-butyl(diphenyl)silyl]oxy}-2-chloro-3-oxobutanoate (20.4g, 52.88mmoles, 1eq), 4-trifluoromethylthiobenzamide (12.2g, 59.5mmoles, 1.1eq), 1,2-dichloroethane (150ml, 0.44M) and H$_2$O (3ml). This mixture was refluxed for 12hrs. After cooling to room temperature, the reaction mixture was diluted with CH$_2$Cl$_2$(100ml) and washed with sat. NaHCO$_3$. Once the phases were separated, the organic phase washed with water, brine and dried over Na$_2$SO$_4$. This was then filtered, concentrated in vacuo and purified via silica gel chromatography (5% EtOAc/Hexanes to 20% EtOAc/Hexanes) to yield 20.3g (76%) of the titled compound.

$^1$H NMR (CDCl$_3$) 400MHz δ 8.07(d, 2H, J=8.37Hz), 7.76 (m, 4H), 7.71(d, 2H, J=8.37Hz), 7.37(m, 6H), 5.24(s, 2H), 4.26(q, 2H, J=7.18Hz), 1.29(t, 3H, J=7.18Hz), 1.11(s, 9H),
TLC(20% EtOAc/Hexanes) R$_f$=0.72

Ethyl 4-({[tert-butyl(diphenyl)silyl]oxy}methyl)-2-phenyl-1,3-thiazole-5-carboxylate Analogous procedure to that used for ethyl 4-({[tert-butyl(diphenyl)silyl]oxy}methyl)-2-(4-{trifluoromethyl}phenyl)-1,3-thiazole-5-carboxylate except thiobenzamide is the starting material.

$^1$H NMR (CDCl$_3$) 400MHz δ 7.98(m, 2H), 7.76(m, 4H), 7.40(m, 9H), 5.21(s, 2H), 4.23(q, 2H, J=7.12Hz), 1.28(t, 3H, J=7.12Hz), 1.08(s, 9H),
TLC(20% EtOAc/Hexanes) R$_f$=0.67

The following intermediates were made using the same procedure as Ethyl 4-({[tert-butyl(diphenyl)silyl]oxy}methyl)-2-(4-{trifluoromethyl}phenyl)-1,3-thiazole-5-carboxylate:

Ethyl 2-(4-{trifluoromethyl}phenyl)-4-[(2-phenylethoxy)methyl]-1,3-thiazole-5-carboxylate $^1$H (CDCl$_3$) 300MHz δ 8.10(d, 2H, J=8.79Hz), 7.71(d, 2H, J=8.79Hz), 7.23(m, 5H), 5.02(s, 2H), 4.37(q, 2H, J=7.14Hz), 3.86(t, 2H, J=7.42Hz), 2.99(t, 2H, J=7.42Hz), 1.41(t, 3H, J=7.14Hz),

Ethyl 2-(4-{trifluoromethyl}phenyl)-4-(3-phenylpropyl)-1,3-thiazole-5-carboxylate $^1$H (CDCl$_3$) 300MHz δ 8.08(d, 2H, J=8.24Hz), 7.71(d, 2H, J=8.24Hz), 7.23(m, 5H), 4.34(q, 2H, J=7.14Hz), 3.25(t, 2H, J=7.69Hz), 2.71(t, 2H, J=7.69Hz), 2.13(m, 2H), 1.35(t, 3H, J=7.14Hz),

Ethyl 4-[(benzyloxy)methyl]-2-(4-{trifluoromethyl}phenyl)-1,3-thiazole-5-carboxylate $^1$H (CDCl$_3$) 300MHz δ 8.12(d, 2H, J=8.79Hz), 7.72(d, 2H, J=8.79Hz), 7.35(m, 5H), 5.04(s, 2H), 4.74(s, 2H), 4.36(q, 2H, J=7.10Hz), 1.38(t, 3H, J=7.14Hz),
TLC(20% EtOAc/Hexanes) R$_f$=0.49

Ethyl 4-(4-bromobenzyl)-2-(4-{trifluoromethyl}phenyl)-1,3-thiazole-5-carboxylate $^1$H NMR (CDCl$_3$) 300MHz δ 8.07(d, 2H, J=8.79Hz), 7.69 (d, 2H, J=8.79Hz), 7.43(d, 2H, J=8.51Hz), 7.28(d, 2H, J=8.51Hz), 4.51(s, 2H), 4.38(q, 2H, J=7.14Hz), 1.39(t, 3H, J=7.14Hz),
TLC(20% EtOAc/Hexanes) R$_f$=0.66

Ethyl 4-(2-phenylethyl)-2-[4-{trifluoromethyl}phenyl]-1,3-thiazole-5-carboxylate $^1$H (CDCl$_3$) 300MHz δ 8.10(d, 2H, J=8.79Hz), 7.72(d, 2H, J=8.79Hz), 7.24(m, 5H), 4.37(q, 2H, J=7.14Hz), 3.51(m, 2H), 3.10(m, 2H), 1.40(t, 3H, J=7.14Hz),
MS(ES$^+$) M+H=405.99

Ethyl 4-benzyl-2-[4-(trifluoromethyl)phenyl]-1,3-thiazole-5-carboxylate $^1$H (CDCl$_3$) 300MHz δ 8.08(d, 2H, J=8.79Hz), 7.70(d, 2H, J=8.79Hz), 7.42(d, 2H, J=9.61Hz), 7.23(m, 3H), 4.58(s, 2H), 4.38(q, 2H, J=7.14Hz), 1.39(t, 3H, J=7.14Hz),
TLC(20% EtOAc/Hexanes) R$_f$=0.57
MS(ES$^+$) M+H=391.9

{4-({[tert-Butyl(diphenyl)silyl]oxy}methyl)-2-[4-(trifluoromethyl)phenyl]-1,3-thiazol-5-yl}methanol Analogous reduction as in the synthesis of 4-[(tetrahydro-2H-pyran-2-yloxy)methyl]-2-[4-(trifluoromethyl)phenyl]-1,3-thiazol-5-yl}methanol.
$^1$H NMR (CDCl$_3$) 400MHz δ 7.97(d, 2H, J=8.03Hz), 7.68 (m, 6H), 7.41(m, 6H), 4.97(s, 2H), 4.84(s, 2H), 1.08(s, 9H),

[4-({[tert-Butyl(diphenyl)silyl]oxy}methyl)-2-phenyl-1,3-thiazol-6-yl]methanol Analogous reduction as in the synthesis of 4-[(tetrahydro-2H-pyran-2-yloxy)methyl]-2-[4-(trifluoromethyl)phenyl]-1,3-thiazol-5-yl}methanol.
$^1$H NMR (CDCl$_3$) 300MHz δ 7.90(m, 2H), 7.75(m, 4H), 7.45(m, 9H), 5.00(s, 2H), 4.86(s, 2H), 1.13(s, 9H), The following compounds were all made by the general alkylation procedure with the appropriate thiols made above and the alkyl halides made from either {4-({[tert-Butyl(diphenyl)silyl]oxy}methyl)-2-[4-(trifluoromethyl)phenyl]-1,3-thiazol-5-yl}methanol or {4-({[tert-Butyl(diphenyl)silyl]oxy}methyl)-2-[4-(trifluoromethyl)phenyl]-1,3-thiazol-5-yl}methanol via the chlorides as described above.

Ethyl [4-({[4-({[tert-butyl(diphenyl)silyl]oxy}methyl)-2-phenyl-1,3-thiazol-5-yl]methyl}sulfanyl)-2-methylphenoxy]acetate $^1$H NMR (CDCl$_3$) 400MHz δ 7.85(m, 2H), 7.68(m, 4H), 7.39(m, 9H), 7.12(d, 1H, J=2.39Hz), 7.03(dd, 1H, J=8.37, 2.39Hz), 6.50(d, 1H, J=8.37Hz), 4.61(s, 2H), 4.55(s, 2H), 4.24(q, 2H, J=7.12Hz), 4.10(s, 2H), 2.18(s, 3H), 1.26(t, 3H, J=7.12Hz), 1.05(s, 9H),
TLC(20% EtOAc/Hexanes) R$_f$=0.43

Ethyl 2-{4-[({4-({[tert-butyl(diphenyl)silyl]oxy}(methyl)-2-[4-(trifluoromethyl)phenyl]-1,3-thiazol-5-yl}methyl)sulfanyl]-2-methylphenoxy}propanoate $^1$H NMR (CDCl$_3$) 400MHz δ 7.94(d, 2H, J=8.20Hz), 7.67 (m, 6H), 7.39(m, 6H), 7.11(d, 1H, J=2.39Hz), 7.00(dd, 1H, J=8.37, 2.39Hz), 6.49(d, 1H, J=8.37Hz), 4.65(m, 2H), 4.17 (q, 2H, J=7.18Hz), 4.09(s, 2H), 2.17(s, 3H), 1.60(d, 3H, J=6.84Hz), 1.21(t, 3H, J=7.18Hz), 1.05(s, 9H),
TLC(20% EtOAc/Hexanes) R$_f$=0.57

Ethyl 2-[4-({[4-({[tert-butyl(diphenyl)silyl]oxy}methyl)-2-phenyl-1,3-thiazol-5-yl]methyl}sulfanyl)-2-methylphenoxy]propanoate $^1$H NMR (CDCl$_3$) 400MHz δ 7.85(m, 2H), 7.68(m, 4H), 7.38(m, 9H), 7.11(d, 1H, J=2.39Hz), 6.99(dd, 1H, J=8.55, 2.39Hz), 6.49(d, 1H, J=8.55Hz), 4.64(m, 3H), 4.16(q, 2H, J=7.12Hz), 4.07(s, 2H), 2.17(s, 3H), 1.59(d, 3H, J=6.84Hz), 1.20(t, 3H, J=7.12Hz), 1.05(m, 9H),
TLC(20% EtOAc/Hexanes) R$_f$=0.48

Ethyl (4-[({3-({[tert-butyl(diphenyl)silyl]oxy)methyl)-5-[4-(trifluoromethyl)phenyl]-2-thienyl}methyl)sulfanyl]-2-methylphenoxy}acetate $^1$H NMR (CDCl$_3$) 400MHz δ 7.94(d, 2H, J=8.20Hz), 7.66 (m, 6H), 7.38(m, 6H), 7.11(d, 1H, J=2.22Hz), 7.03(dd, 1H, J=8.37, 2.22Hz), 6.50(d, 1H, J=8.37Hz), 4.63(s, 2H), 4.56(s, 2H), 4.23(q, 2H, J=7.12Hz), 4.10(s, 2H), 2.18(s, 3H), 1.27(t, 3H, J=7.12Hz), 1.04(s, 9H),
TLC(20% EtOAc/Hexanes) R$_f$=0.50

Ethyl [4-({[4-(hydroxymethyl)-2-(4-{trifluoromethyl}phenyl)-1,3-thiazol-5-yl]methyl}sulfanyl)-2-methylphenoxy]acetate $^1$H NMR (CDCl$_3$) 300MHz δ 7.97(d, 2H, J=8.23Hz), 7.67 (d, 2H, J=8.23Hz), 7.22(d, 1H, J=2.39Hz), 7.14(dd, 1H, J=8.23, 2.39Hz), 6.61(d, 1H, J=8.23Hz), 4.63(s, 2H), 4.50(s, 2H), 4.26(q, 2H, J=7.17Hz), 4.18(s, 2H), 2.83(s, 1H), 2.25(s, 3H), 1.29(t, 3H, J=7.17Hz),
TLC(50% EtOAc/Hexanes) R$_f$=0.51

(4-Bromophenyl)acetyl chloride

To a stirred solution of 4-bromophenylacetic acid (10g, 46.5mmoles, 1eq) in dry CH$_2$Cl$_2$(100ml, 0.47M) was added thionyl chloride (20.2ml, 0.280moles, 6eq) and refluxed for 36hours. After cooling to room temperature the reaction was concentrated in vacuo to yield 10.86g (100%) of acid chloride.
$^1$H (CDCl$_3$) 300MHz δ 7.50(d, 2H, J=8.38Hz), 7.14(d, 2H, J=8.38Hz), 4.09(s, 2H),

4-Phenylbutanoyl chloride $^1$H NMR (CDCl$_3$) 300MHz δ 7.25(m, 5H), 2.90(t, 2H, J=7.28Hz), 2.69(t, 2H, J=7.28Hz), 2.05(m, 2H),

(2-Phenylethoxy)acetyl chloride $^1$H NMR (CDCl$_3$) 300MHz δ 7.26(m, 5H), 4.39(s, 2H), 3.80(t, 2H, J=6.94Hz), 2.93(t, 2H, J=6.94Hz)

[4-([1,1'-Biphenyl]-4-ylmethyl)-2-(4-{trifluoromethyl}phenyl)-1,3-thiazol-5-yl]methanol To a stirred solution of [4-(4-Bromobenzyl)-2-(4-{trifluoromethyl}phenyl)-1,3-thiazol-5-yl]methanol (0.33g, 0.78mmoles, 1eq) in dry 1,2-dimethoxyethane (5ml, 0.16M) was added tetrakis(triphenylphosphino) palladium I (0.45g, 0.39mmoles, 0.5eq) and stirred for 5minutes at room temperature. Phenylboronic acid (0.143g, 1.2mmoles, 1.5eq) was then added followed by the addition of sodium carbonate (2M aqueous solution, 2.3ml, 4.68mmoles, 6eq). The reaction mixture was heated at 100degrees centigrade for 13hours at which point, after cooling to room temperature, the reaction was partitioned between EtOAc and water. After separation of the phases the organic phase washed with brine, dried over anhydrous sodium sulfate, filtered, concentrated in vacuo to yield after purification by silica gel chromatography (CH$_2$Cl$_2$ to 2% MeOH/CH$_2$Cl$_2$) 268mg (80%) of product.
$^1$H NMR (CDCl$_3$) 400MHz δ 8.03(d, 2H, J=8.20Hz), 7.67 (d, 2H, J=8.20Hz), 7.54(m, 4H), 7.36(m, 5H), 4.85(s, 2H), 4.22(s, 2H), The following intermediate was prepared in using the same procedure:

{2-4-{trifluoromethyl}phenyl)-4-[4-(3-thienyl)benzyl]-1,3-thiazol-5-yl}methanol

¹H NMR (CDCl₃) 400MHz δ 8.03(d, 2H, J=8.20Hz), 7.67 (d, 2H, J=8.20Hz), 7.52(d, 2H, J=8.37Hz), 7.35(m, 5H), 4.84 (s, 2H), 4.20(s, 2H),

The following compounds were made by the same procedure for phenol alkylation:

Ethyl {2-methyl-4-[({4-[(tetrahydro-2H-pyran-2-yloxy)methyl]-2-[4-trifluoromethyl)phenyl]-1,3-thiazol-5-yl}methyl)sulfanyl]phenoxy}acetate To a 250ml round-bottom flask equipped with a magnetic stir-bar and N₂inlet was added 5-(chloromethyl)-4-[(tetrahydro-2H-pyran-2-yloxy)methyl]-2-[4-(trifluoromethyl)phenyl]-1,3-thiazole (7.87g, 20.09mmoles, 1eq) and dry CH₃CN (100ml, 0.27M). Solid cesium carbonate (16.4g, 50.22mmoles, 2.5eq) was added all at once followed by the quick addition of ethyl 2-methyl-2-(4-sulfanylphenoxy)propanoate (5.79g, 24.11mmoles, 1.2eq) in dry CH₃CN (10ml). The reaction was allowed to stir at room temperature for 2hours at which point the solvent was removed under reduced pressure. The resulting residue was partitioned between EtOAc and 1N NaOH. After the phases were separated the organic fraction washed with H₂O, brine and dried over Na₂SO₄. After filtration the volatiles were removed in vacuo to yield the titled compound in >100% yield. Because of the difficult separation between the thiophenol and the product, the crude product was carried forward without purification.

4-[({4-(Bromomethyl)-2-[4-(trifluoromethyl)phenyl]-1,3-thiazol-5-yl}methyl)sulfanyl]-2-methylphenol ¹H NMR (CDCl₃) 400MHz δ 8.01(d, 2H, J=8.10Hz), 7.68 (d, 2H, J=8.10Hz), 7.17(d, 1H, J=2.41Hz), 7.08(dd, 1H, J=8.10, 2.41Hz), 6.67(d, 1H, J=8.10Hz), 4.63(s, 2H), 4.14(s, 2H), Ethyl 2-{4-[({4-{[4-(4-(methoxyphenyl)-1-piperazinyl]methyl}-2-[4-(trifluoromethyl)phenyl]-1,3-thiazol-5-yl}methyl)sulfanyl]phenoxy}-2-methylpropanoate To a 500ml 3-neck round-bottom flask equipped with a magnetic stir-bar, low temperature thermometer with thermometer adapter, addition funnel and N₂inlet was added ethyl 2-{4-[({4-(hydroxymethyl)-2-[4-(trifluoromethyl)phenyl]-1,3-thiazol-5-yl}methyl)sulfanyl]phenoxy}-2-methylpropanoate (16g, 31.28mmoles, 1eq) and dry CH₂Cl₂(120ml, 0.26M) and cooled to 0° C. Methanesulfonyl chloride (2.91ml, 37.54mmoles, 1.2eq) was added neat all at once. Triethylamine (6.6ml, 46.92mmoles, 1.5eq) was added dropwise over 20minutes maintaining the internal temperature below 5° C. and was stirred at 0° C. for 30minutes. The reaction mixture was transferred to a separatory funnel and washed with H₂O, brine and the organic fraction was dried over Na₂SO₄. After filtration the solvent was removed under reduced pressure to yield the corresponding mesylate in quantitative yield. Because of the unstable nature of the mesylate, the product was not characterized and was progressed onto the next stage without purification.

To the crude mesylate dissolved in dry THF (200ml, 0.16M) was added 4-methoxyphenyl piperazine (13g, 62.56mmoles, 2eq) and the reaction mixture was refluxed for 5hours. After cooling to room temperature the solvent was removed in vacuo to yield a yellow solid residue. The residue washed with a minimal amount of EtOAc and filtered through Celite to remove the 4-methoxyphenyl piperazine hydrochloride salt. The EtOAc was removed in vacuo and the resulting solid was filtered through a "plug" of silica gel using 30% EtOAc/Hexanes to yield 20.37g (95%)of a light-yellow solid.

¹H NMR (CDCl₃) 400MHz δ 7.96(d, 2H, J=8.24Hz), 7.63 (d, 2H, J=8.24Hz), 7.27(d, 2H, J=8.79Hz), 6.87(d, 2H, J=9.16Hz), 6.80(d, 2H, J=9.16Hz), 6.74(d, 2H, J=8.79Hz), 4.32(s, 2H), 4.17(q, 2H, J=7.14Hz), 3.73(s, 3H), 3.56(s, 2H), 3.06(br s, 4H), 2.59(br s, 4H), 1.55(s, 6H), 1.21(t, 3H, J=7.14Hz),

HPLC(C-18, 3μm) 0%-95% Acetonitrile/Water over 8minutes R$_t$=6.06minutes

The follow intermediates were made using the same alkylation conditions:

4-[({4-{[4-(4-Methoxyphenyl)-1-piperazinyl]methyl}-2-[4-(trifluoromethyl)phenyl]-1,3-thiazol-5-yl}methyl)sulfanyl]-2-methylphenol ¹H NMR (CDCl₃) 400MHz δ 7.94(d, 2H, J=8.10Hz), 7.64 (d, 2H, J=8.10Hz), 7.16(d, 1H, J=2.07Hz), 7.07(dd, 1H, J=8.10, 2.07Hz), 6.86(m, 2H), 6.80(d, 2H, J=8.97Hz), 6.66 (d, 1H, J=8.10Hz), 4.27(s, 2H), 3.73(s, 3H), 3.59(s, 2H), 3.15(br s, 4H), 2.67(br s, 4H), 2.16(s, 3H), Ethyl [2-methyl-4-({[2-(4-{trifluoromethyl}phenyl)-4-(4-morpholinylmethyl)-1,3-thiazol-5-yl]methyl}sulfanyl)phenoxy]acetate ¹H NMR (CDCl₃) 300MHz δ 8.02(d, 2H, J=8.23Hz), 7.69 (d, 2H, J=8.23Hz), 7.27(m, 1H), 7.17(dd, 1H, J=8.23, 2.39Hz), 6.62(d, 1H, J=8.23Hz), 4.64(s, 2H), 4.36(s, 2H), 4.25(q, 2H, J=7.17Hz), 3.72(t, 4H, J=4.51Hz), 3.53(s, 2H), 2.48(t, 4H, J=4.51Hz), 2.27(s, 3H), 1.32(t, 3H, J=7.17Hz), TLC(50% EtOAc/Hexanes) R$_f$=0.26

Ethyl [4-({[4-[(4-benzyl-1-piperazinyl)methyl]-2-(4-{trifluoromethyl}phenyl)-1,3-thiazol-5-yl]methyl}sulfanyl)-2-methylphenoxy]acetate ¹H NMR (CDCl₃) 300MHz δ 8.02(d, 2H, J=8.76Hz), 7.68 (d, 2H, J=8.76Hz), 7.31(m, 6H), 7.16(dd, 1H, J=8.49, 2.39Hz), 6.62(d, 1H, J=8.49Hz), 4.63(s, 2H), 4.35(s, 2H), 4.27(q, 2H, J=7.17Hz), 3.54(m, 4H), 2.51(br s, 8H), 2.27(s, 3H), 1.32(t, 3H, J=7.17Hz), TLC(50% EtOAc/Hexanes)=0.19

Ethyl 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 400MHz δ7.99(d, 2H, J=8.20Hz), 7.66 (d, 2H, J=8.20Hz), 7.23(d, 1H, J=2.39Hz), 7.13(dd, 1H, J=8.37, 2.39Hz), 6.89(d, 2H, J=9.23Hz), 6.83(d, 2H, J=9.23Hz), 6.57(d, 1H, J=8.37Hz), 4.70(q, 1H, J=6.84Hz), 4.34(s, 2H), 4.17(q, 2H, J=7.18Hz), 3.76(s, 3H), 3.58(s, 2H), 3.09(m, 4H), 2.63(m, 4H), 2.24(s, 3H), 1.62(d, 3H, J=6.84Hz), 1.21(t, 3H, J=7.18Hz), TLC(30% EtOAc/Hexanes)=0.29

Ethyl {2-methyl-4-[({2-(4-{trifluoromethyl}phenyl)-4-[(4-phenyl-1-piperazinyl)methyl]-1,3-thiazol-5-yl}methyl)sulfanyl]phenoxy}acetate $^1$H NMR (CDCl$_3$) 300MHz δ 8.04(d, 2H, J=8.23Hz), 7.70 (d, 2H, J=8.23Hz), 7.29(m, 3H), 7.21(dd, 1H, J=8.23, 2.39Hz), 6.92(m, 3H), 6.63(d, 1H, J=8.23Hz), 4.64(s, 2H), 4.38(s, 2H), 4.27(q, 2H, J=7.17Hz), 3.63(s, 2H), 3.21(m, 4H), 2.66(m, 4H), 2.28(s, 3H), 1.32(t, 3H, J=7.17Hz),
TLC(50% EtOAc/Hexanes) R$_f$=0.52

Ethyl 4-{[5-({[4-(2-ethoxy-2-oxoethoxy)-3-methylphenyl]sulfanyl}methyl)-2-(4-{trifluoromethyl}phenyl)-1,3-thiazol-4-yl]methyl}-1-piperazinecarboxylate $^1$H NMR (CDCl$_3$) 300MHz δ 7.99(d, 2H, J=8.23Hz), 7.68 (d, 2H, J=8.23Hz), 7.25(m, 1H), 7.17(dd, 1H, J=8.49, 2.12Hz), 6.61(d, 1H, J=8.49Hz), 4.64(s, 2H), 4.28(m, 4H), 4.14(t, 2H, J=7.17Hz), 3.50(m, 6H), 2.44(br s, 4H), 2.26(s, 3H), 1.29(t, 3H, J=7.17Hz),
TLC(50% EtOAc/Hexanes) R$_f$=0.17

Ethyl {2-methyl-4-[({2-(4-(trifluoromethyl}phenyl)-4-[(4-phenyl-1-piperidinyl)methyl]-1,3-thiazol-5-ylmethyl)sulfanyl]phenoxy}acetate $^1$H NMR (CDCl$_3$) 300MHz δ 8.04(d, 2H, J=8.23Hz), 7.70 (d, 2H, J=8.23Hz), 7.27(m, 7H), 6.64(d, 1H, J=8.49Hz), 4.64 (s, 2H), 4.41(s, 2H), 4.28(q, 2H, J=7.17Hz), 3.60(s, 2H), 3.02(m, 2H), 2.53(m, 1H), 2.30(s, 3H), 2.18(m, 2H), 1.84(m, 4H), 1.32(t, 3H, J=7.17Hz),
TLC(50% EtOAc/Hexanes) R$_f$=0.48

Ethyl {2-methyl-4-[({2-(4-{trifluoromethyl}phenyl)-4-[(4-methyl-1-piperidinyl)methyl]-1,3-thiazol-5-yl}methyl)sulfanyl]phenoxy}acetate $^1$H NMR (CDCl$_3$) 300MHz δ 8.02(d, 2H, J=8.23Hz), 7.68 (d, 2H, J=8.23Hz), 7.28(d, 1H, J=2.39Hz), 7.19(dd, 1H, J=8.49, 2.39Hz), 6.62(d, 1H, J=8.49Hz), 4.64(s, 2H), 4.38(s, 2H), 4.28(q, 2H, J=7.17Hz), 3.51(s, 2H), 2.84(m, 4H), 2.28(s, 3H), 2.02(m, 4H), 1.61(m, 4H), 1.30(m, 8H), 0.94(d, 3H, J=6.11Hz),
TLC(50% EtOAc/Hexanes) R$_f$=0.36

Ethyl (2-methyl-4-{[(2-(4-{trifluoromethyl}phenyl)-4-{[4-(2-methylphenyl)-1-piperazinyl]-methyl}-1,3-thiazol-5-yl)methyl]sulfanyl}phenoxy)acetate $^1$H (CDCl$_3$) 400MHz δ 7.99(d, 2H, J=8.20Hz), 7.66(d, 2H, J=8.20Hz), 7.25(m, 1H), 7.16(m, 3H), 6.98(m, 2H), 6.60(d, 1H, J=8.55Hz), 4.60(s, 2H), 4.37(s, 2H), 4.23(q, 2H, J=7.12Hz), 3.59(s, 2H), 2.93(s, 4H), 2.63(s, 4H), 2.29(s, 3H), 2.24(s, 3H), 1.27(t, 5H, J=7.12Hz),
TLC(50% EtOAc/Hexanes) R$_f$=0.73

Ethyl [4-({[4-{4-(4-methoxyphenyl)-1-piperazinyl]methyl}-2-(4-trifluoromethyl)phenyl)-1,3-thiazol-5-yl]methyl}sulfanyl)-2-methyl phenoxy]acetate $^1$H (CDCl$_3$) 400MHz δ 7.99(d, 2H, J=8.20Hz), 7.65(d, 2H, J=8.20Hz), 7.24(dd, 1H, J=2.39Hz), 7.16(dd, 1H, J=8.37, 2.39Hz), 6.84(m, 4H), 6.58(d, 1H, J=8.37Hz), 4.59(s, 2H), 4.33(s, 2H), 4.23(q, 2H, J=7.18Hz), 3.75(s, 3K), 3.57(s, 2H), 3.07(m, 4H), 2.62(s, 4H), 2.24(s, 3H), 1.27(t, 3H, J=7.18Hz),
TLC(50% EtOAc/Hexanes) R$_f$=0.44

Ethyl (2-methyl-4-{[(2-(4-{trifluoromethyl}phenyl)-4-{[4-3-methylphenyl)-1-piperazinyl]methyl}-1,3-thiazol-5-yl)methyl]sulfanyl}phenoxy)acetate $^1$H (CDCl$_3$) 400MHz δ 7.99(d, 2H, J=8.20Hz), 7.66(d, 2H, J=8.20Hz), 7.24(m, 1H), 7.14(m, 2H), 6.70(s, 3H), 6.59(d, 1H, J=8.55Hz), 4.60(s, 2H), 4.33(s, 2H), 4.23(q, 2H, J=7.12Hz), 3.57(s, 2H), 3.16(br s, 4H), 2.62(br s, 4H), 2.30(s, 3H), 2.24(s, 3H), 1.26(t, 3H, J=7.12Hz),
TLC(50% EtOAc/Hexanes) R$_f$=0.64

Ethyl (2-methyl-4-{[(2-(4-{trifluoromethyl}phenyl)-4-{[4-(4-methylphenyl)-1-piperazinyl]methyl}-1,3-thiazol-5-yl)methyl]sulfanyl}phenoxy)acetate $^1$H (CDCl$_3$) 400MHz δ 7.99(d, 2H, J=8.20Hz), 7.65(d, 2H, J=8.20Hz), 7.24(d, 1H, J=2.39Hz), 7.15(dd, 1H, J=8.37, 2.39Hz), 7.04(d, 2H, J=8.55Hz), 6.82(d, 2H, J=8.55Hz), 6.58 (d, 1H, J=8.37Hz), 4.60(s, 2H), 4.32(s, 2H), 4.23(q, 2H, J=7.12Hz), 3.57(s, 2H), 3.10(s, 4H), 2.60(s, 4H), 2.26(s, 3H), 2.23(s, 3H), 1.26(t, 3H, J=7.12Hz),
TLC(50% EtOAc/Hexanes) R$_f$=0.64

Ethyl [4-({[4-{4-(2-furoyl)-1-piperazinyl]methyl}-2-(4-{trifluoromethyl}phenyl)-1,3-thiazol-5-yl]methyl}sulfanyl)-2-methylphenoxy]acetate $^1$H (CDCl$_3$) 400MHz δ 7.98(d, 2H, J=8.20Hz), 7.65(d, 2H, J=8.20Hz), 7.46(m, 1H), 7.22(d, 1H, J=2.39Hz), 7.13(dd, 1H, J=8.37, 2.39Hz), 6.96(d, 1H, J=3.42Hz), 6.59(d, 1H, J=8.37Hz), 6.46(m, 1H), 4.62(s, 2H), 4.29(s, 2H), 4.21(q, 2H, J=7.12Hz), 3.80(s, 4H), 3.50(s, 2H), 2.53(s, 4H), 2.23(s, 3H), 1.26(t, 3H, J=7.18Hz),
TLC(50% EtOAc/Hexanes) R$_f$=0.06

Ethyl (2-methyl-4-{[2-(4-{trifluoromethyl}phenyl)-4-{[4-(2-pyridinyl)-1-piperazinyl]methyl}-1,3-thiazol-5-yl)methyl]sulfanyl}phenoxy)acetate $^1$H (CDCl$_3$) 400MHz δ 8.16(m, 1H), 7.98(d, 2H, J=8.20Hz), 7.63(d, 2H, J=8.20Hz), 7.45(s, 1H), 7.25(d, 1H, J=2.22Hz), 7.15(dd, 1H, J=8.37, 2.22Hz), 6.56(m, 3H), 4.60 (s, 2H), 4.33(s, 2H), 4.21(q, 2H, J=7.12Hz), 3.53(m, 6H), 2.57(s, 4H), 2.23(s, 3H), 1.27(t, 3H, J=7.12Hz),
TLC(50% EtOAc/Hexanes) R$_f$=0.25

Ethyl [4-({[4-{4-(4-chlorobenzyl)-1-piperazinyl]methyl}-2-(4-{trifluoromethyl}phenyl)-1,3-thiazol-5-yl]methyl}sulfanyl)-2-methylphenoxy]acetate $^1$H (CDCl$_3$) 400MHz δ 7.96(d, 2H, J=8.20Hz), 7.64(d, 2H, J=8.20Hz), 7.25(m, 5H), 7.13(dd, 1H, J=8.37, 2.39Hz), 6.58 (d, 1H, J=8.37Hz), 4.59(s, 2H), 4.31(s, 2H), 4.22(q, 2H, J=7.18Hz), 3.52(s, 2H), 3.42(s, 2H), 2.48(br s, 8H), 2.20(s, 3H), 1.26(t, 3H, J=7.18Hz),
TLC(50% EtOAc/Hexanes) R$_f$=0.23

Ethyl [4-({[4-{4-(4-acetylphenyl)-1-piperazinyl]methyl}-2-(4-{trifluoromethyl}phenyl)-1,3-thiazol-5-yl]methyl}sulfanyl)-2-methylphenoxy]acetate $^1$H (CDCl$_3$) 400MHz δ 7.98(d, 2H, J=8.20Hz), 7.85(d, 2H, J=9.06Hz), 7.66(d, 2H, J=8.20Hz), 7.24(d, 1H, J=2.39Hz), 7.16(dd, 1H, J=8.20, 2.39Hz), 6.84(d, 2H, J=9.06Hz), 6.58(d, 1H, J=8.20Hz), 4.61(s, 2H), 4.31(s, 2H), 4.22(q, 2H, J=7.18Hz), 3.58(s, 2H), 3.33(br s, 4H), 2.60(br s, 4H), 2.50 (m, 3H), 2.24(s, 3H), 1.27(t, 3H, J=7.18Hz),
TLC(50% EtOAc/Hexanes) R$_f$=0.23

Ethyl [4-({[4-{[4-(2-hydroxyethyl)-1-piperazinyl]methyl}-2-(4-{trifluoromethyl}phenyl)-1,3-thiazol-5-yl]methyl}sulfanyl)-2-methylphenoxy]acetate ¹H (CDCl₃) 400MHz δ 7.97(d, 2H, J=8.20Hz), 7.64(d, 2H, J=8.20Hz), 7.23(d, 1H, J=2.22Hz), 7.14(dd, 1H, J=8.37, 2.22Hz), 6.58(d, 1H, J=8.37Hz), 4.60(s, 2H), 4.30(s, 2H), 4.22(q, 2H, J=7.12Hz), 3.60(m, 2H), 3.50(s, 2H), 2.94(s, 1H), 2.53(m, 10H), 2.23(s, 3H), 1.26(t, 3H, J=7.12Hz),

Ethyl (2-methyl-4-{[(2-(4-{trifluoromethyl}phenyl)-4-{[(3-pyridinylmethyl)amino]methyl]-1,3-thiazol-5-yl)methyl]sulfanyl}phenoxy)acetate ¹H (CDCl₃) 400MHz δ 8.55(m, 1H), 8.50(m, 1H), 7.98(d, 2H, J=8.20Hz), 7.71(m, 1H), 7.65(m, 2H), 7.24(m, 1H), 7.17(m, 1H), 7.10(m, 1H), 6.55(d, 1H, J=8.37Hz), 4.58(s, 2H), 4.22(q, 2H, J=7.12Hz), 4.12(s, 2H), 3.77(s, 2H), 3.63(s, 2H), 2.64(br s, 1H), 2.21(s, 3H), 1.27(t, 3H, J=7.12Hz),

Ethyl (4-{[(4-{[4-(4-methoxyphenyl)-1-piperazinyl]methyl}-2-phenyl-1,3-thiazol-5-yl)methyl]sulfanyl}-2-methylphenoxy)acetate ¹H NMR (CDCl₃) 400MHz δ 7.88(m, 2H), 7.40(m, 3H), 7.25(d, 1H, J=2.39Hz), 7.17(dd, 1H, J=8.37, 2.39Hz), 6.89(d, 2H, J=9.06Hz), 6.81(d, 2H, J=9.06Hz), 6.58(d, 1H, J=8.37Hz), 4.59(s, 2H), 4.32(s, 2H), 4.23(q, 2H, J=7.12Hz), 3.74(s, 3H), 3.56(s, 2H), 3.06(m, 4H), 2.62(m, 4H), 2.24(s, 3H), 1.27(t, 3H, J=7.12Hz),

Ethyl 2-(4-{[(4-{[4-(4-methoxyphenyl)-1-piperazinyl]methyl}-2-phenyl-1,3-thiazol-5-yl)methyl]sulfanyl}-2-methylphenoxy)propanoate ¹H NMR (CDCl₃) 400MHz δ 7.88(m, 2H), 7.40(m, 3H), 7.25(d, 1H, J=2.39Hz), 7.14(dd, 1H, J=8.37, 2.39Hz), 6.89(d, 2H, J=9.40Hz), 6.82(d, 2H, J=9.40Hz), 6.57(d, 1H, J=8.37Hz), 4.70(q, 1H, J=6.84Hz), 4.32(s, 2H), 4.17(q, 2H, J=7.18Hz), 3.76(s, 3H), 3.56(s, 2H), 3.08(m, 4H), 2.63(m, 4H), 2.23(m, 3H), 1.61(d, 3H, J=6.84Hz), 1.25(t, 3H, J=7.18Hz),

Ethyl {2-methyl-4-[({2-(4-{trifluoromethyl}phenyl)-4-[(pentylamino)methyl]-1,3-thiazol-5-yl}methyl)sulfanyl]phenoxy}acetate ¹H (CDCl₃) 400MHz δ 7.97(d, 2H, J=8.20Hz), 7.65(d, 2H, J=8.20Hz), 7.20(d, 1H, J=2.39Hz), 7.12(dd, 1H, J=8.37, 2.39Hz), 6.58(d, 1H, J=8.37Hz), 4.60(s, 2H), 4.23(q, 2H, J=7.18Hz), 4.18(s, 2H), 3.64(s, 2H), 2.58(t, 2H, J=6.92Hz), 2.22(s, 3H), 1.50(m, 2H), 1.28(m, 7H), 0.87(t, 3H, J=6.92Hz),

Ethyl 2-{4-[({4-{[4-(4-hydroxyphenyl)-1-piperazinyl]methyl}-2-[4-(trifluoromethyl)phenyl]-1,3-thiazol-4-yl}methyl)sulfanyl]-2-methylphenoxy}propanoate ¹H NMR (CDCl₃) 300MHz δ 8.08(d, 2H, J=8.28Hz), 7.75(d, 2H, J=8.28Hz), 7.27(d, 1H, J=2.21Hz), 7.17(dd, 1H, J=8.28, 2.21Hz), 6.87(d, 2H, J=8.83Hz), 6.73(d, 2H, J=8.83Hz), 6.66(d, 1H, J=8.28Hz), 4.83(q, 1H, J=6.81Hz), 4.34(s, 2H), 4.15(q, 2H, J=7.08Hz), 3.47(s, 2H), 3.00(t, 4H, J=4.83Hz), 2.57(t, 4H, J=4.83Hz), 2.20(s, 3H), 1.57(d, 3H, J=6.81Hz), 1.20(t, 3H, J=7.08Hz),

Ethyl 2-[4-[({4-{[4-(3,4-dimethoxyphenyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 300MHz δ 8.06(d, 2H, J=8.28Hz), 7.72(d, 2H, J=8.28Hz), 7.26(d, 1H, J=2.21Hz), 7.16(dd, 1H, J=8.55, 2.21Hz), 6.82(d, 1H, J=8.55Hz), 6.64(m, 2H), 6.47(dd, 1H, J=8.55, 2.21Hz), 4.81(q, 1H, J=6.99Hz), 4.34(s, 2H), 4.14(q, 2H, J=7.17Hz), 3.82(s, 3H), 3.77(s, 3H), 3.52(s, 2H), 3.07(t, 4H, J=4.55Hz), 2.63(t, 4H, J=4.55Hz), 2.20(s, 3H), 1.57(d, 3H, J=6.99Hz), 1.18(t, 3H, J=7.17Hz),

Ethyl 2-(4-{[(4-{[4-(4-methoxyphenyl)-1-piperazinyl]methyl}-2-phenyl-1,3-thiazol-5-yl)methyl]sulfanyl}phenoxy)-2-methylpropanoate ¹H NMR (CDCl₃) 400MHz δ 7.87(m, 2H), 7.40(m, 3H), 7.28(d, 2H, J=8.89Hz), 6.89(d, 2H, J=9.23Hz), 6.82(d, 2H, J=9.23Hz), 6.75(d, 2H, J=8.89Hz), 4.33(s, 2H), 4.19(q, 2H, J=7.18Hz), 3.76(s, 3H), 3.56(s, 2H), 3.09(br s, 4H), 2.65(br s, 4H), 1.58(s, 6H), 1.20(t, 3H, J=7.18Hz),

Ethyl {4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetate ¹H NMR (CDCl₃) 400MHz δ 7.99(d, 2H, J=8.20Hz), 7.66(d, 2H, J=8.20Hz), 7.35(d, 2H, J=8.89Hz), 6.88(d, 2H, J=9.40Hz), 6.83(m, 4H), 4.58(s, 2H), 4.34(s, 2H), 4.24(q, 2H, J=7.18Hz), 3.76(s, 3H), 3.57(s, 2H), 3.08(m, 4H), 2.63(m, 4H), 1.27(t, 3H, J=7.18Hz),

Ethyl 2-{4-{({4-{[4-(4-methoxyphenyl)-1-piperazinyl]methyl}-2-[4-(trifluoromethyl)phenyl]-1,3-thiazol-5-yl}methyl)sulfanyl]phenoxy}propanoate ¹H NMR (CDCl₃) 400MHz δ 7.99(d, 2H, J=8.20Hz), 7.66(d, 2H, J=8.20Hz), 7.32(d, 2H, J=8.89Hz), 6.89(d, 2H, J=9.23Hz), 6.83(d, 2H, J=9.23Hz), 6.79(d, 2H, J=8.89Hz), 4.70(q, 1H, J=6.78Hz), 4.33(s, 2H), 4.16(q, 2H, J=7.09Hz), 3.75(s, 3H), 3.57(s, 2H), 3.08(m, 4H), 2.63(m, 4H), 1.60(d, 3H, J=6.78Hz), 1.24(t, 3H, J=7.09Hz),

Ethyl 2-(4-{[(4-{[4-4-methoxyphenyl)-1-piperazinyl]methyl}-2-phenyl-1,3-thiazol-5-yl)methyl]sulfanyl}phenoxy)propanoate ¹H NMR (CDCl₃) 400MHz δ 7.87(m, 2H), 7.39(m, 3H), 7.32(d, 2H, J=8.85Hz), 6.87(d, 2H, J=9.06Hz), 6.82(d, 2H, J=9.06Hz), 6.77(d, 2H, J=8.85Hz), 4.69(q, 1H, J=6.78Hz), 4.31(s, 2H), 4.18(q, 2H, J=7.12Hz), 3.75(s, 3H), 3.54(s, 2H), 3.08(m, 4H), 2.62(m, 4H), 1.59(d, 3H, J=6.78Hz), 1.20(t, 3H, J=7.12Hz),

Ethyl 2-{4-[({4-{[4-(3-methoxyphenyl)-1-piperazinyl]methyl}-2-[4-(trifluoromethyl)phenyl]-1,3-thiazol-5-yl}methyl)sulfanyl]-2-methylphenoxy}-2-methylpropanoate ¹H NMR (CDCl₃) 400MHz δ 7.96(d, 2H, J=8.28Hz), 7.63(d, 2H, J=8.28Hz), 7.21(d, 1H, J=2.41Hz), 7.13(t, 1H, J=8.10Hz), 7.07(dd, 1H, J=8.45, 2.41Hz), 6.53(m, 2H), 6.43(t, 1H, J=2.24Hz), 6.38(dd, 1H, J=8.10, 2.24Hz), 4.31(s, 2H), 4.18(q, 2H, J=7.16Hz), 3.75(s, 3H), 3.55(s, 2H), 3.16(t, 4H, J=4.83Hz), 2.58(t, 4H, J=4.83Hz), 2.17(s, 3H), 1.57(s, 6H), 1.22(t, 3H, J=7.16Hz), Ethyl 2-{4-[({4-{[4-(4-fluorophenyl)-1-piperazinyl]methyl}-2-[4-(trifluoromethyl)phenyl]-1,3-thiazol-5-yl}methyl)sulfanyl]-2-methylphenoxy}-2-methylpropanoate $^1$H NMR (CDCl$_3$) 400MHz δ 7.96(d, 2H, J=8.28Hz), 7.62 (d, 2H, J=8.28Hz), 7.21(d, 1H, J=2.41Hz), 7.06(dd, 1H, J=8.45, 2.41Hz), 6.91(m, 2H), 6.83(m, 2H), 6.53(d, 1H, J=8.45Hz), 4.30(s, 2H), 4.13(q, 2H, J=7.16Hz), 3.55(s, 2H), 3.06(t, 4H, J=4.66Hz), 2.57(t, 4H, J=4.66Hz), 2.15(s, 3H), 1.55(s, 6H), 1.21(t, 3H, J=7.16Hz), Ethyl 2-{4-[({4-{[4-methoxyphenyl)-1-piperazinyl]methyl}-2-[4-(trifluoromethyl)phenyl]-1,3-thiazol-5-yl}methyl)sulfanyl]phenoxy}-2-methylpropanoate $^1$H NMR (CDCl$_3$) 400MHz δ 7.96(d, 2H, J=8.10Hz), 7.63 (d, 2H, J=8.10Hz), 7.26(d, 2H, J=8.79Hz), 7.14(t, 1H, J=8.28Hz), 6.74(d, 2H, J=8.79Hz), 6.51(dd, 1H, J=8.28, 2.24Hz), 6.43(t, 1H, J=2.24Hz), 6.39(dd, 1H, J=8.28, 2.24Hz), 4.31(s, 2H), 4.16(q, 2H, J=7.07Hz), 3.74(s, 3H), 3.54(s, 2H), 3.17(t, 4H, J=4.66Hz), 2.58(t, 4H, J=4.66Hz), 1.56(s, 6H), 1.20(t, 3H, J=7.07Hz), Ethyl 2-{4-[({4-{[4-(4-chlorophenyl)-1-piperazinyl]methyl}-2-[4-(trifluoromethyl)phenyl]-1,3-thiazol-5-yl}methyl)sulfanyl]phenoxy}-2-methylpropanoate $^1$H NMR (CDCl$_3$) 400MHz δ 7.96(d, 2H, J=8.10Hz), 7.63 (d, 2H, J=8.10Hz), 7.27(d, 2H, J=8.79Hz), 7.15(d, 2H, J=9.14Hz), 6.80(d, 2H, J=9.14Hz), 6.73(d, 2H, J=8.79Hz), 4.30(s, 2H), 4.17(q, 2H, J=7.16Hz), 3.54(s, 2H), 3.12(t, 4H, J=4.74Hz), 2.57(m, 4H), 1.55(s, 6H), 1.17(t, 3H, J=7.16Hz), Ethyl 2-{4-[({4-{[4-(4-acetylphenyl)-1-piperazinyl]methyl}-2-[4-(trifluoromethyl)phenyl]-1,3-thiazol-5-yl}methyl)sulfanyl]phenoxy}-2-methylpropanoate $^1$H NMR (CDCl$_3$) 400MHz δ 7.95(d, 2H, J=8.28Hz), 7.83 (d, 2H, J=9.14Hz), 7.62(d, 2H, J=8.28Hz), 7.26(d, 2H, J=8.62Hz), 6.82(d, 2H, J=9.14Hz), 6.73(d, 2H, J=8.62Hz), 4.29(s, 2H), 4.17(q, 2H, J=7.07Hz), 3.53(s, 2H), 3.32(t, 4H, J=4.66Hz), 2.57(br s, 4H), 2.48(s, 3H), 1.55(s, 6H), 1.17(t, 3H, J=7.07Hz), Ethyl 2-{4-[({4-{[4-(4-methoxyphenyl)-1-piperazinyl]methyl}-2-[4-(trifluoromethyl)phenyl]-1,3-thiazol-5-yl}methyl)sulfanyl]phenoxy}-2-methylpropanoate $^1$H NMR (CDCl$_3$) 400MHz δ 7.96(d, 2H, J=8.28Hz), 7.63 (d, 2H, J=8.28Hz), 7.26(d, 2H, J=8.79Hz), 6.87(d, 2H, J=9.14Hz), 6.81(d, 2H, J=9.14Hz), 6.73(d, 1H, J=8.79Hz), 4.32(s, 2H), 4.17(q, 2H, J=7.16Hz), 3.73(s, 3H), 3.54(s, 2H), 3.06(t, 4H, J=4.83Hz), 2.60(br s, 4H), 1.55(s, 6H), 1.20(t, 3H, J=7.16Hz), Ethyl 2-(4-{[(2-(4-fluorophenyl)-4-{[4-(4-methoxyphenyl)-1-piperazinyl]methyl}-1,3-thiazol-5yl)methyl]sulfanyl}-2-methylphenoxy)-2-methylpropanoate $^1$H NMR (CDCl$_3$) 400MHz δ 7.84(m, 2H), 7.20(d, 1H, J=2.20Hz), 7.07(m, 3H), 6.87(d, 2H, J=9.16Hz), 6.81(d, 2H, J=9.16Hz), 6.54(d, 1H, J=8.42Hz), 4.29(s, 2H), 4.19(q, 2H, J=7.14Hz), 3.75(s, 3H), 3.54(s, 2H), 3.07(t, 4H, J=4.76Hz), 2.61(br s, 4H), 2.15(s, 3H), 1.54(s, 6H), 1.21(t, 3H, J=7.14Hz), Ethyl 2-[4-({[4-{[4-(4-acetylphenyl)-1-piperazinyl]methyl}-2-(4-fluorophenyl)-1,3-thiazol-5-yl]methyl}sulfanyl)-2-methylphenoxy]-2-methylpropanoate $^1$H NMR (CDCl$_3$) 400MHz δ 7.84(m, 4H), 7.20(d, 1H, J=2.38Hz), 7.07(m, 3H), 6.83(d, 2H, J=9.16Hz), 6.53(d, 1H, J=8.42Hz), 4.28(s, 2H), 4.18(q, 2H, J=7.14Hz), 3.53(s, 2H), 3.33(t, 4H, J=4.58Hz), 2.58(br s, 4H), 2.48(s, 3H), 2.16(s, 3H), 1.58(s, 6H), 1.23(t, 3H, J=7.14Hz), Ethyl 2-(4-{[(2-(4-fluorophenyl)-4-{[4-(3-methoxyphenyl)-1-piperazinyl]methyl}-1,3-thiazol-5-yl)methyl]sulfanyl}-2-methylphenoxy)-2-methylpropanoate $^1$H NMR (CDCl$_3$) 400MHz δ 7.85(m, 2H), 7.20(d, 1H, J=2.38), 7.14(t, 1H, J=8.24Hz), 7.07(m, 3H), 6.53(m, 2H), 6.44(t, 1H, J=2.29Hz), 6.39(dd, 1H, J=8.06, 2.38Hz), 4.29(s, 2H), 4.19(q, 2H, J=7.14Hz), 3.76(s, 3H), 3.53(s, 2H), 3.17(t, 4H, J=4.67Hz), 2.59(br s, 4H), 2.16(s, 3H), 1.55(s, 6H), 1.21 (t, 3H, J=7.14Hz), Ethyl 4-{[5-({[4-(2-ethoxy-1,1-dimethyl-2-oxoethoxy)-3-methylphenyl]sulfanyl}methyl)-2-(4-fluorophenyl)-1,3-thiazol-4-yl]methyl}-1-piperazinecarboxylate $^1$H NMR (CDCl$_3$) 400MHz δ 7.82(m, 2H), 7.18(d, 1H, J=2.38Hz), 7.06(m, 3H), 6.53(d, 1H, J=8.61Hz), 4.25(s, 2H), 4.19(q, 2H, J=7.14Hz), 4.10(q, 2H, J=7.08Hz), 3.45(m, 6H), 2.40(br s, 4H), 2.16(s, 3H), 1.55(s, 6H), 1.21(m, 6H), Ethyl 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}-2-methylpropanoate $^1$H NMR (CDCl$_3$) 400MHz δ 7.96(d, 2H, J=8.28Hz), 7.63 (d, 2H, J=8.28Hz), 7.21(d, 1H, J=2.24Hz), 7.07(dd, 1H, J=8.45, 2.24Hz), 6.86(d, 2H, J=9.14Hz), 6.80(d, 2H, J=9.14Hz), 6.53(d, 1H, J=8.45Hz), 4.31(s, 2H), 4.17(q, 2H, J=7.16Hz), 3.72(s, 3H), 3.55(s, 2H), 3.05(t, 4H, J=4.66Hz), 2.59(t, 4H, J=4.66Hz), 2.16(s, 3H), 1.55(s, 6H), 1.20(t, 3K, J=7.16Hz), Ethyl 2-{4-[({4-{[4-(4-acetylphenyl)-1-piperazinyl]methyl}-2-[4-(trifluoromethyl)phenyl]-1,3-thiazol-5-yl}methyl)sulfanyl]-2-methylphenoxy}-2-methylpropanoate $^1$H NMR (CDCl$_3$) 400MHz δ 7.95(d, 2H, J=8.10Hz), 7.82 (d, 2H, J=8.97Hz), 7.62(d, 2H, J=8.10Hz), 7.19(d, 1H, J=2.41Hz), 7.06(dd, 1H, J=8.45, 2.41Hz), 6.82(d, 2H, J=8.97Hz), 6.52(d, 1H, J=8.45Hz), 4.27(s, 2H), 4.16(q, 2H, J=7.07Hz), 3.53(s, 2H), 3.29(t, 4H, J=4.66Hz), 2.54(t, 4H, J=4.66Hz), 2.47(s, 3H), 2.14(s, 3H), 1.55(s, 6H), 1.18(t, 3H, J=7.07Hz), Ethyl 2-{4-[({4-[(4-acetyl-1-piperazinyl)methyl]-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.00(d, 2H, J=8.23Hz), 7.68 (d, 2H, J=8.23Hz), 7.27(d, 1H, J=2.39Hz), 7.14(dd, 1H, J=8.23, 2.39Hz), 6.59(d, 1H, J=8.23Hz), 4.73(q, 1H, J=6.72Hz), 4.30(s, 2H), 4.20(q, 2H, J=7.17Hz), 3.65(t, 2H, J=4.65Hz), 3.54(s, 2H), 3.45(t, 2H, J=4.05Hz), 2.48(t, 4H, J=4.65Hz), 2.26(s, 3H), 2.09(s, 3H), 1.65(d, 3H, J=6.72Hz), 1.25(dd, 3H, J=7.17Hz), 2-Methyl-2-{4-[({4-{[4-(phenoxycarbonyl)-1-piperazinyl]methyl}-2-[4-(trifluoromethyl)phenyl]-1,3-thiazol-5-yl}methyl)sulfanyl]phenoxy}propanoic acid ¹H NMR (CDCl₃) 400MHz δ 7.95(d, 2H, J=8.28Hz), 7.65 (d, 2H, J=8.28Hz), 7.33(m, 2H), 7.26(d, 2H, J=8.79Hz), 7.17 (t, 1H, J=7.59Hz), 7.06(d, 2H, J=7.59Hz), 6.74(d, 2H, J=8.79Hz), 4.32(s, 2H), 4.18(q, 2H, J=7.07Hz), 3.61(m, 6H), 2.51(br s, 4H), 1.57(s, 6H), 1.20(t, 3H, J=7.07Hz), tert-Butyl 4-({5-({[4-ethoxy-1,1-dimethyl-2-oxoethoxy)phenyl]sulfanyl}methyl)-2-[4-(trifluoromethyl)phenyl]-1,3-thiazol-4-yl}methyl)-1-Piperazinecarboxylate ¹H NMR (CDCl₃) 400MHz δ 7.94(d, 2H, J=8.28Hz), 7.63 (d, 2H, J=8.28Hz), 7.24(d, 2H, J=8.79Hz), 6.72(d, 2H, J=8.79Hz), 4.29(s, 2H), 4.18(q, 2H, J=7.07Hz), 3.44(m, 6H), 2.43(br s, 4H), 1.56(s, 6H), 1.42(s, 9H), 1.19(t, 3H, J=7.07Hz), Ethyl 2-methyl-2-{4-[({4-{[4-(2-pyrazinyl)-1-piperazinyl]methyl}-2-[4-(trifluoromethyl)phenyl]-1,3-thiazol-5-yl}methyl)sulfanyl]phenoxy}propanoate ¹H NMR (CDCl₃) 400MHz δ 8.12(s, 1H), 8.04(s, 1H), 7.94(d, 2H, J=8.28Hz), 7.83(s, 1H), 7.65(d, 2H, J=8.28Hz), 7.26(d, 2H, J=8.79Hz), 6.73(d, 2H, J=8.79Hz), 4.32(s, 2H), 4.17(q, 2H, J=7.07Hz), 3.62(m, 6H), 2.64(br s, 4H), 1.56(s, 6H), 1.18(t, 3H, J=7.07Hz), Ethyl 2-{4-[({4-{[4-(2-methoxyphenyl)-1-piperazinyl]methyl}-2-[4-4-(trifluoromethyl)phenyl]-1,3-thiazol-5-yl}methyl)sulfanyl]phenoxy}-2-methylpropanoate ¹H NMR (CDCl₃) 400MHz δ 7.96(d, 2H, J=8.28Hz), 7.64 (d, 2H, J=8.28Hz), 7.27(d, 2H, J=8.97Hz), 6.98(m, 1H), 6.90 (m, 2H), 6.83(m, 1H), 6.73(d, 2H, J=8.97Hz), 4.35(s, 2H), 4.17(q, 2H, J=7.07Hz), 3.83(s, 3H), 3.60(s, 2H), 3.11(br s, 4H), 2.72(br s, 4H), 1.58(s, 6H), 1.18(t, 3H, J=7.07Hz), tert-Butyl 4-({5-({[4-(2-methoxy-2-oxoethoxy)-3-methylphenyl]sulfanyl}methyl)-2-[4-(trifluoromethyl)phenyl]-1,3-thiazol-4-yl}methyl)-1-piperazinecarboxylate ¹H NMR (CDCl₃) 400MHz δ 7.90(d, 2H, J=8.28Hz), 7.58 (d, 2H, J=8.28Hz), 7.16(d, 1H, J=2.24Hz), 7.08(dd, 1H, J=8.45, 2.24Hz), 6.52(d, 1H, J=8.45Hz), 4.56(s, 2H), 4.20(s, 2H), 3.70(s, 3H), 3.44(s, 2H), 3.36(t, 4H, J=4.48Hz), 2.32(br s, 4H), 2.17(s, 3H), 1.38(s, 9H), Ethyl 2-{2-methyl-4-[({4-{[4-(4-pyridinyl)-1-piperazinyl]methyl}-2-[4-(trifluoromethyl)phenyl]-1,3-thiazol-5-yl}methyl)sulfanyl]phenoxy}propanoate ¹H NMR (CDCl₃) 300MHz δ 8.28(d, 2H, J=6.37Hz), 8.02 (d, 2H, J=8.23Hz), 7.69(d, 2H, J=8.23Hz), 7.28(d, 1H, J=2.39Hz), 7.16(dd, 1H, J=8.49, 2.39Hz), 6.68(d, 2H, J=6.37Hz), 6.60(d, 1H, J=8.49Hz), 4.73(q, 1H, J=6.72Hz), 4.32(s, 2H), 4.20(q, 2H, J=7.08Hz), 3.59(s, 2H), 3.34(t, 4H, J=5.04Hz), 2.58(t, 4H, J=5.04Hz), 2.26(s, 3H), 1.65(d, 3H, J=6.72Hz), 1.25(t, 3H, J=7.08Hz), Ethyl 2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 400MHz δ 7.99(d, 2H, J=8.20Hz), 7.66 (d, 2H, J=8.20Hz), 7.23(d, 1H, J=2.39Hz), 7.13(dd, 1H, J=8.37, 2.39Hz), 6.89(d, 2H, J=9.23Hz), 6.83(d, 2H, J=9.23Hz), 6.57(d, 1H, J=8.37Hz), 4.70(q, 1H, J=6.84Hz), 4.34(s, 2H), 4.17(q, 2H, J=7.18Hz), 3.76(s, 3H), 3.58(s, 2H), 3.09(m, 4H), 2.63(m, 4H), 2.24(s, 3H), 1.62(d, 3H, J=6.84Hz), 1.21(t, 3H, J=7.18Hz), TLC(30% EtOAc/Hexanes)=0.29

Ethyl 2-{4-[({4-{[4-4(2,4-difluorophenyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 300MHz δ 8.03(d, 2H, J=8.28Hz), 7.69 (d, 2H, J=8.28Hz), 7.27(d, 1H, J=2.21Hz), 7.17(dd, 1H, J=8.28, 2.21Hz), 6.86(m, 3H), 6.61(d, 1H, J=8.28Hz), 4.73 (q, 1H, J=6.71Hz), 4.36(s, 2H), 4.21(q, 2H, J=7.17Hz), 3.62 (s, 2H), 3.06(t, 4H, J=4.55Hz), 2.67(t, 4H, J=4.55Hz), 2.27(s, 3H), 1.65(d, 3H, J=6.71Hz), 1.26(t, 3H, J=7.17Hz), Ethyl 2-{2-methyl-4-[({4-({4-[4-(trifluoromethoxy)phenyl]-1-piperazinyl}methyl)-2-[4-(trifluoromethyl)phenyl]-1,3-thiazol-5-yl}methyl)sulfanyl]phenoxy}propanoate ¹H NMR (CD₃OD) 400MHz δ 7.97(d, 2H, J=8.24Hz), 7.63(d, 2H, J=8.24Hz), 7.19(s, 1H), 7.10(dd, 1H, J=8.42, 2,20Hz), 7.03(d, 2H, J=9.16Hz), 6.85(d, 2H, J=9.16Hz), 6.57 (d, 1H, J=8.42Hz), 4.73(q, 1H, J=6.78Hz), 4.27(s, 2H), 4.07 (m, 2H), 3.41(s, 2H), 3.03(br s, 4H), 2.48(br s, 4H), 2.13(s, 3H), 1.51(d, 3H, J=6.78Hz), 1.11(t, 3H, J=7.14Hz), Ethyl 2-{4-[({4-{[4-(4-ethoxyphenyl)-1-piperazinyl]methyl}-2-[4-(trifluoromethyl)phenyl]-1,3-thiazol-5-yl}methyl)sulfanyl]-2-methylphenoxy}propanoate ¹H NMR (CD₃OD) 400MHz δ 8.01(d, 2H, J=8.28Hz), 7.70(d, 2H, J=8.28Hz), 7.21(d, 1H, J=2.24Hz), 7.11(dd, 1H, J=8.45, 2.24Hz), 6.86(d, 2H, J=9.14Hz), 6.76(d, 2H, J=9.14Hz), 6.61(d, 1H, J=8.45Hz), 4.77(q, 1H, J=6.72Hz), 4.29(s, 2H), 4.10(q, 2H, J=7.16Hz), 3.91(q, 2H, J=6.98Hz), 3.40(s, 2H), 2.96(t, 4H, J=4.83Hz), 2.50(t, 4H, J=4.83Hz), 2.14(s, 3H), 1.52(d, 3H, J=6.72Hz), 1.30(t, 3H, J=6.98Hz), 1.14(t, 3H, J=7.16Hz), Ethyl 2-{2-methyl-4-[({4-{[4-4-(4-propoxyphenyl)-1-piperazinyl]methyl}-2-[4-(trifluoromethyl)phenyl]-1,3-thiazol-5-yl}methyl)sulfanyl]phenoxy}propanoate ¹H NMR (CD₃OD) 400MHz δ 7.96(d, 2H, J=8.10Hz), 7.63(d, 2H, J=8.10Hz), 7.18(s, 1H), 7.09(d, 1H, J=8.45Hz), 6.81(d, 2H, J=8.97Hz), 6.73(d, 2H, J=8.97Hz), 6.56(d, 1H, J=8.45Hz), 4.71(q, 1H, J=7.07Hz), 4.25(s, 2H), 4.06(q, 2H, J=7.07Hz), 3.76(t, 2H, J=7.41Hz), 3.39(s, 2H), 2.92(br s, 4H), 2.48(br s, 4H), 2.12(s, 3H), 1.67(m, 2H), 1.49(d, 3H, J=6.47Hz), 1.11(t, 3H, J=7.07Hz), 0.94(t, 3H, J=7.41Hz),

Ethyl 2-{4-[({4-{[4-(4-isopropoxyphenyl)-1-piperazinyl]methyl}-2-[4-(trifluoromethyl)phenyl]-1,3-thiazol-5-yl}methyl)sulfanyl]-2-methylphenoxy}propanoate $^1$H NMR (CD$_3$OD) 400MHz δ 7.96(d, 2H, J=8.28Hz), 7.64(d, 2H, J=8.28Hz), 7.18(d, 1H, J=2.24Hz), 7.09(dd, 1H, J=8.45, 2.24Hz), 6.81(d, 2H, J=9.14Hz), 6.73(d, 2H, J=9.14Hz), 6.57(d, 1H, J=8.45Hz), 4.71(q, 1H, J=6.78Hz), 4.36(m, 1H), 4.24(s, 2H), 4.06(q, 2H, J=7.16Hz), 3.39(s, 2H), 2.92(t, 4H, J=4.57Hz), 2.47(t, 4H, J=4.57Hz), 2.11(s, 3H), 1.48(d, 3H, J=6.78Hz), 1.19(d, 6H, J=6.21Hz), 1.11(t, 3H, J=7.16Hz),

Ethyl 4-({5-({[4-(2-ethoxy-1,1-dimethyl-2-oxoethoxy)phenyl]sulfanyl}methyl)-2-[4-(trifluoromethyl)phenyl]-1,3-thiazol-4-yl}methyl)-1-piperazinecarboxylate $^1$H NMR (CDCl$_3$) 400MHz δ 7.94(d, 2H, J=8.28Hz), 7.63(d, 2H, J=8.28Hz), 7.24(m, 2H), 6.72(d, 2H, J=8.79Hz), 4.30(s, 2H), 4.18(q, 2H, J=7.07Hz), 4.10(q, 2H, J=7.13Hz), 3.49(m, 6H), 2.46(br s, 4H), 1.58(s, 6H), 1.21(m, 6H),

Ethyl 4-({5-({[4-(2-methoxy-2-oxoethoxy)-3-methylphenyl]sulfanyl}methyl)-2-[4-(trifluoromethyl)phenyl]-1,3-thiazol-4-yl}methyl)-1-piperazinecarboxylate $^1$H NMR (CDCl$_3$) 400MHz δ 7.95(d, 2H, J=8.10Hz), 7.64(d, 2H, J=8.10Hz), 7.20(d, 1H, J=2.21Hz), 7.13(dd, 1H, J=8.45, 2.21Hz), 6.57(d, 1H, J=8.45Hz), 4.62(s, 2H), 4.30(s, 2H), 4.10(q, 2H, J=7.16Hz), 3.77(s, 3H), 3.49(m, 6H), 2.45(br s, 4H), 2.21(s, 3H), 1.23(t, 3H, J=7.16Hz),

Methyl {4-[({4-{[4-(3-methoxyphenyl)-1-piperazinyl]methyl}-2-[4-(trifluoromethyl)phenyl]-1,3-thiazol-5-yl}methyl)sulfanyl]-2-methylphenoxy}acetate $^1$H NMR (CDCl$_3$) 400MHz δ 7.97(d, 2H, J=8.28Hz), 7.64(d, 2H, J=8.28Hz), 7.21(d, 1H, J=2.24Hz), 7.14(m, 2H), 6.57(d, 1H, J=8.45Hz), 6.49(dd, 1H, J=8.10, 2.20Hz), 6.40(s, 2H), 4.60(s, 2H), 4.33(s, 2H), 3.76(s, 6H), 3.59(s, 2H), 3.21(br s, 4H), 2.68(br s, 4H), 2.21(s, 3H),

Methyl {4-[({4-{[4-(4-acetylphenyl)-1-piperazinyl]methyl}-2-[4-(trifluoromethyl)phenyl]-1,3-thiazol-5-yl}methyl)sulfanyl]-2-methylphenoxy}acetate $^1$H NMR (CDCl$_3$) 400MHz δ 7.93(d, 2H, J=8.28Hz), 7.82(d, 2H, J=8.97Hz), 7.61(d, 2H, J=8.28Hz), 7.20(d, 1H, J=2.24Hz), 7.13(dd, 1H, J=8.45, 2.24Hz), 6.80(d, 2H, J=8.97Hz), 6.55(d, 1H, J=8.45Hz), 4.57(s, 2H), 4.27(s, 2H), 3.73(s, 3H), 3.52(s, 2H), 3.27(t, 4H, J=4.83Hz), 2.54(t, 4H, J=4.83Hz), 2.45(s, 3H), 2.20(s, 3H),

Methyl {4-[({4-{[4-(2-methoxyphenyl)-1-piperazinyl]methyl}-2-[4-(trifluoromethyl)phenyl]-1,3-thiazol-5-yl}methyl)sulfanyl]-2-methylphenoxy}acetate $^1$H NMR (CDCl$_3$) 400MHz δ 7.97(d, 2H, J=8.10Hz), 7.66(d, 2H, J=8.10Hz), 7.21(m, 1H), 7.15(dd, 1H, J=8.45, 2.07Hz), 6.98(br s, 1H), 6.89(m, 2H), 6.83(d, 1H, J=7.41Hz), 6.57(d, 1H, J=8.45Hz), 4.61(s, 2H), 4.35(s, 2H), 3.83(s, 3H), 3.75(s, 3H), 3.61(s, 2H), 3.11(br s, 4H), 2.70(br s, 4H), 2.22(s, 3H),

Methyl (2-methyl-4-[({4-{[4-(2-pyrazinyl)-1-piperazinyl]methyl}-2-[4-(trifluoromethyl)phenyl]-1,3-thiazol-5-yl}methyl)sulfanyl]phenoxy)acetate $^1$H NMR (CDCl$_3$) 400MHz δ 8.07(s, 1H), 7.99(m, 1H), 7.94(d, 2H, J=8.10Hz), 7.77(d, 1H, J=2.59Hz), 7.60(d, 2H, J=8.10Hz), 7.20(d, 1H, J=2.24Hz), 7.12(dd, 1H, J=8.45, 2.24Hz), 6.54(d, 1H, J=8.45Hz), 4.58(s, 2H), 4.26(s, 2H), 3.73(s, 3H), 3.52(m, 6H), 2.52(t, 4H, J=4.83Hz), 2.19(s, 3H),

Ethyl (4-{[(4-{[4-(4-methoxyphenyl)-1-piperazinyl]methyl}-2-phenyl-1,3-thiazol-5-yl)methyl]sulfanyl}-2-methylphenoxy)acetate $^1$H NMR (CDCl$_3$) 400MHz δ 7.88(m, 2H), 7.40(m, 3H), 7.25(d, 1H, J=2.39Hz), 7.17(dd, 1H, J=8.37, 2.39Hz), 6.89(d, 2H, J=9.06Hz), 6.81(d, 2H, J=9.06Hz), 6.58(d, 1H, J=8.37Hz), 4.59(s, 2H), 4.32(s, 2H), 4.23(q, 2H, J=7.12Hz), 3.74(s, 3H), 3.56(s, 2H), 3.06(m, 4H), 2.62(m, 4H), 2.24(s, 3H), 1.27(t, 3H, J=7.12Hz),

Ethyl 2-(4-{[(4-{[4-(4-methoxyphenyl)-1-piperazinyl]methyl}-2-phenyl-1,3-thiazol-5-yl)methyl]sulfanyl}-2-methylphenoxy)propanoate $^1$H NMR (CDCl$_3$) 400MHz δ 7.88(m, 2H), 7.40(m, 3H), 7.25(d, 1H, J=2.39Hz), 7.14(dd, 1H, J=8.37, 2.39Hz), 6.89(d, 2H, J=9.40Hz), 6.82(d, 2H, J=9.40Hz), 6.57(d, 1H, J=8.37Hz), 4.70(q, 1H, J=6.84Hz), 4.32(s, 2H), 4.17(q, 2H, J=7.18Hz), 3.76(s, 3H), 3.56(s, 2H), 3.08(m, 4H), 2.63(m, 4H), 2.23(m, 3H), 1.61(d, 3H, J=6.84Hz), 1.25(t, 3H, J=7.18Hz),

Ethyl 2-(4-{[(4-{[4-(4-methoxyphenyl)-1-piperazinyl]methyl}-2-phenyl-1,3-thiazol-5-yl)methyl]sulfanyl}phenoxy)-2-methylpropanoate $^1$H NMR (CDCl$_3$) 400MHz δ 7.87(m, 2H), 7.40(m, 3H), 7.28(d, 2H, J=8.89Hz), 6.89(d, 2H, J=9.23Hz), 6.82(d, 2H, J=9.23Hz), 6.75(d, 2H, J=8.89Hz), 4.33(s, 2H), 4.19(q, 2H, J=7.18Hz), 3.76(s, 3H), 3.56(s, 2H), 3.09(br s, 4H), 2.65(br s, 4H), 1.58(s, 6H), 1.20(t, 3H, J=7.18Hz),

Ethyl 2-{4-[({4-{[4-(2-methoxyphenyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.03(d, 2H, J=8.28Hz), 7.69(d, 2H, J=8.28Hz), 7.28(d, 1H, J=2.21Hz), 7.17(dd, 1H, J=8.28, 2.21Hz), 7.00(m, 3H), 6.88(d, 1H, J=7.73Hz), 6.61(d, 1H, J=8.28Hz), 4.74(q, 1H, J=6.81Hz), 4.39(s, 2H), 4.21(q, 2H, J=7.17Hz), 3.89(s, 3H), 3.63(s, 2H), 3.12(br s, 4H), 2.72(br s, 4H), 2.27(s, 3H), 1.65(d, 3H, J=6.81Hz), 1.26(t, 3H, J=7.17Hz),

Ethyl 2-[2-methyl-4-({[2-[4-(trifluoromethyl)phenyl]-4-({4-[3-(trifluoromethyl)phenyl]-1-piperazinyl}methyl)-1,3-thiazol-5-yl]methyl}sulfanyl)phenoxy]propanoate $^1$H NMR (CDCl$_3$) 300MHz δ 8.03(d, 2H, J=8.28Hz), 7.70(d, 2H, J=8.28Hz), 7.36(t, 1H, J=8.00Hz), 7.29(d, 1H, J=2.21Hz), 7.13(m, 4H), 6.61(d, 1H, J=8.28Hz), 4.74(q, 1H, J=6.90Hz), 4.36(s, 2H), 4.18(q, 2H, J=7.08Hz), 3.62(s, 2H), 3.26(t, 4H, J=4.83Hz), 2.65(t, 4H, J=4.83Hz), 2.26(s, 3H), 1.65(d, 3H, J=6.90Hz), 1.27(t, 3H, J=7.08Hz), Ethyl 2-{2-methyl-4-[({4-({4-[2-oxo-2-(1-pyrrolidinyl)ethyl]-1-piperazinyl}methyl)-2-[4-(trifluoromethyl)phenyl]-1,3-thiazol-5-yl}methyl)sulfanyl]phenoxy}propanoate $^1$H NMR (CDCl$_3$) 300MHz δ 7.96(d, 2H, J=8.28Hz), 7.63 (d, 2H, J=8.28Hz), 7.20(d, 1H, J=2.21Hz), 7.10(dd, 1H, J=8.28, 2.21Hz), 6.56(d, 1H, J=8.28Hz), 4.69(q, 1H, J=6.71Hz), 4.30(s, 2H), 4.16(q, 2H, J=7.08Hz), 3.47(m, 8H), 3.10(s, 2H), 2.54(m, 6H), 2.20(s, 3H), 1.85(m, 4H), 1.60(d, 3H, J=6.71Hz), 1.20(t, 3H, J=7.08Hz), Ethyl 2-{2-methyl-4-[({4-{[4-(2-pyrimidinyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 300MHz δ 8.31(d, 2H, J=4.69Hz), 8.01 (d, 2H, J=8.28Hz), 7.68(d, 2H, J=8.28Hz), 7.27(d, 1H, J=2.21Hz), 7.16(dd, 1H, J=8.28, 2.21Hz), 6.60(d, 1H, J=8.28Hz), 6.48(t, 1H, J=4.69Hz), 4.74(q, 1H, J=6.71Hz), 4.35(s, 2H), 4.20(q, 2H, J=7.08Hz), 3.85(t, 4H, J=4.97Hz), 3.57(s, 2H), 2.54(t, 4H, J=4.97Hz), 2.24(s, 3H), 1.64(d, 3H, J=6.71Hz), 1.24(t, 3H, J=7.08Hz), Ethyl 2-{2-methyl-4-[({4-{[4-(2-pyrazinyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 300MHz δ 8.14(m, 1H), 8.06(m, 1H), 8.01(d, 2H, J=8.28Hz), 7.85(d, 1H, J=2.48Hz), 7.67(d, 2H, J=8.28Hz), 7.27(d, 1H, J=2.21Hz), 7.15(dd, 1H, J=8.28, 2.21Hz), 6.59(d, 1H, J=8.28Hz), 4.73(q, 1H, J=6.71Hz), 4.33 (s, 2H), 4.16(q, 2H, J=7.17Hz), 3.60(m, 6H), 2.58(t, 4H, J=4.83Hz), 2.25(s, 3H), 1.64(d, 3H, J=6.71Hz), 1.25(t, 3H, J=7.17Hz), Ethyl 2-[2-methyl-4-({[2-[4-(trifluoromethyl)phenyl]-4-({4-[4-(trifluoromethyl)phenyl]-1-piperazinyl}methyl)-1,34-thiazol-5-yl]methyl}sulfanyl)phenoxy]propanoate $^1$H NMR (CDCl$_3$) 300MHz δ 8.03(d, 2H, J=8.28Hz), 7.70 (d, 2H, J=8.28Hz), 7.51(d, 2H, J=8.55Hz), 7.28(d, 1H, J=2.21Hz), 7.18(dd, 1H, J=8.28, 2.21Hz), 6.94(d, 2H, J=8.55Hz), 6.61(d, 1H, J=8.28Hz), 4.74(q, 1H, J=6.71Hz), 4.35(s, 2H), 4.21(q, 2H, J=7.17Hz), 3.62(s, 2H), 3.33(t, 4H, J=4.55Hz), 2.66(t, 4H, J=4.55Hz), 2.27(s, 3H), 1.66(d, 3H, J=6.71Hz), 1.26(t, 3H, J=7.17Hz), Ethyl 2-{4-[({4-[(4-acetyl-1-piperazinyl)methyl]-2-[4-(trifluoromethyl)phenyl]-1,3-thiazol-5-yl}methyl)sulfanyl]-2-isopropylphenoxy}propanoate $^1$H NMR (CDCl$_3$) 400MHz δ 7.94(d, 2H, J=8.10Hz), 7.64 (d, 2H, J=8.10Hz), 7.17(d, 1H, J=2.24Hz), 7.11(dd, 1H, J=8.45, 2.24Hz), 6.54(d, 1H, J=8.45Hz), 4.72(q, 1H, J=6.78Hz), 4.23(s, 2H), 4.14(q, 2H, J=7.13Hz), 3.59(s, 2H), 3.42(br s, 4H), 3.30(m, 1H), 2.42(br s, 4H), 2.04(s, 3H), 1.59(d, 3H, J=6.78Hz), 1.17(m, 9H), Ethyl 2-{4-[({4-{[4-(4-fluorophenyl)-1-piperazinyl]methyl}-2-[4-(trifluoromethyl)phenyl]-1,3-thiazol-5-yl}methyl)sulfanyl]-2-isopropylphenoxy}propanoate $^1$H NMR (CDCl$_3$) 400MHz δ 7.97(d, 2H, J=8.28Hz), 7.64 (d, 2H, J=8.28Hz), 7.20(d, 1H, J=2.24Hz), 7.13(dd, 1H, J=8.45, 2.24Hz), 6.92(m, 2H), 6.83(m, 2H), 6.55(d, 1H, J=8.45Hz), 4.71(q, 1H, J=6.78Hz), 4.28(s, 2H) 4.14(q, 2H, J=7.18Hz), 3.48(s, 2H), 3.31(m, 1H), 3.07(t, 4H, J=4.83Hz), 2.59(br s, 4H), 1.59(d, 3H, J=6.78Hz), 1.15(m, 9H), Ethyl 2-{2-isopropyl-4-[({4-(4-morpholinylmethyl)-2-[4-(trifluoromethyl)phenyl]-1,3-thiazol-5-yl}methyl)sulfanyl]phenoxy}propanoate $^1$H NMR (CDCl$_3$) 400MHz δ 7.95(d, 2H, J=8.28Hz), 7.63 (d, 2H, J=8.28Hz), 7.19(d, 1H, J=2.24Hz), 7.12(dd, 1H, J=8.45, 2.24Hz), 6.55(d, 1H, J=8.45Hz), 4.71(q, 1H, J=6.78Hz), 4.26(s, 2H), 4.14(q, 2H, J=7.13Hz), 3.67(m, 4H), 3.41(s, 2H), 3.30(m, 1H), 2.42(br s, 4H), 1.59(d, 3H, J=6.78Hz), 1.16(m, 9H), Ethyl 2-{2-methyl-4-[({4-(1-piperazinylmethyl)-2-[4-(trifluoromethyl)phenyl]-1,3-thiazol-5-yl}methyl)sulfanyl]phenoxy}propanoate $^1$H NMR (CDCl$_3$) 300MHz δ 8.01(d, 2H, J=8.23Hz), 7.67 (d, 2H, J=8.23Hz), 7.27(d, 1H, J=2.39Hz), 7.15(dd, 1H, J=8.23, 2.39Hz), 6.59(d, 1H, J=8.23Hz), 4.73(q, 1H, J=6.64Hz), 4.34(s, 2H), 4.20(q, 2H, J=7.08Hz), 3.52(s, 2H), 2.91(t, 4H, J=4.91Hz), 2.46(m, 4H), 2.33(br s, 1H), 2.26(s, 3H), 1.64(d, 3H, J=6.64Hz), 1.25(t, 3H, J=7.08Hz), tert-Butyl 4-({5-({[4-(2-ethoxy-1-methyl-2-oxoethoxy)-3-methylphenyl]sulfanyl}methyl)-2-[4-(trifluoromethyl)phenyl]-1,3-thiazol-4-yl}methyl)-1-piperazinecarboxylate $^1$H NMR (CDCl$_3$) 300MHz δ 8.01(d, 2H, J=8.23Hz), 7.68 (d, 2H, J=8.23Hz), 7.27(d, 1H, J=2.39Hz), 7.15(dd, 1H, J=8.49, 2.39Hz), 6.60(d, 1H, J=8.49Hz), 4.74(q, 1H, J=6.72Hz), 4.33(s, 2H), 4.22(q, 2H, J=7.08Hz), 3.54(s, 2H), 3.46(m, 4H), 2.44(m, 4H), 2.27(s, 3H), 1.65(d, 3H, J=6.72Hz), 1.48(s, 9H), 1.26(t, 3H, J=7.08Hz), Ethyl 2-{4-[({4-{[4-(4-chlorophenyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.03(d, 2H, J=8.23Hz), 7.70 (d, 2H, J=8.23Hz), 7.22(m, 4H), 6.86(d, 2H, J=9.03Hz), 6.61 (d, 1H, J=8.49Hz), 4.73(q, 1H, J=6.81Hz), 4.36(s, 2H), 4.18 (q, 2H, J=7.08Hz), 3.61(s, 2H), 3.17(m, 4H), 2.64(m, 4H), 2.27(s, 3H), 1.65(d, 3H, J=6.84Hz), 1.27(t, 3H, J=7.08Hz), Ethyl 2-{4-[({4-[({4-[(3,5-dimethyl-1-piperazinyl)methyl]-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.01(d, 2H, J=8.23Hz), 7.68 (d, 2H, J=8.23Hz), 7.27(d, 1H, J=2.39Hz), 7.15(dd, 1H, J=8.49, 2.39Hz), 6.60(d, 1H, J=8.49Hz), 4.74(q, 1H, J=6.72Hz), 4.35(s, 2H), 4.21(q, 2H, J=7.08Hz), 3.53(s, 2H), 2.96(m, 2H), 2.78(m, 2H), 2.26(s, 3H), 1.73(m, 2H), 1.65(d, 3H, J=6.72Hz), 1.26(t, 3H, J=7.08Hz), 1.09(d, 6H, J=6.37Hz), Ethyl 2-{4-[({4-{[4-(4-fluorophenyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.03(d, 2H, J=8.49Hz), 7.70 (d, 2H, J=8.49Hz), 7.28(d, 1H, J=2.39Hz), 7.18(dd, 1H, J=8.23, 2.39Hz), 6.94(m, 4H), 6.62(d, 1H, J=8.23Hz), 4.74

(q, 1H, J=6.72Hz), 4.37(s, 2H), 4.21(q, 2H, J=7.08Hz), 3.63 (s, 2H), 3.14(t, 4H, J=4.51Hz), 2.67(t, 4H, J=4.51Hz), 2.28(s, 3H), 1.65(d, 3H, J=6.72Hz), 1.26(t, 3H, J=7.08Hz),

Ethyl 2-{4-[({4-{[4-(4-acetylphenyl)-1-piperazinyl] methyl}-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.02(d, 2H, J=8.23Hz), 7.89 (d, 2H, J=8.76Hz), 7.69(d, 2H, J=8.23Hz), 7.28(br s, 1H), 7.17(dd, 1H, J=8.23, 2.39Hz), 6.88(d, 2H, J=8.76Hz), 6.60(d, 1H, J=8.23Hz), 4.73(q, 1H, J=6.81Hz), 4.34(s, 2H), 4.18(q, 2H, J=7.17Hz), 3.60(s, 2H), 3.37(m, 4H), 2.63(m, 4H), 2.54 (s, 3H), 2.26(s, 3H), 1.65(d, 3H, J=6.81Hz), 1.27(t, 3H, J=7.17Hz), Ethyl 4-({5-({[4-(2-ethoxy-1-methyl-2-oxoethoxy)-3-methylphenyl]sulfanyl}methyl)-2-[4-(trifluoromethyl)phenyl]-1,3-thiazol-4-yl}methyl)-1-piperazinecarboxylate $^1$H NMR (CDCl$_3$) 300MHz δ 8.00(d, 2H, J=8.23Hz), 7.68 (d, 2H, J=8.23Hz), 7.27(d, 1H, J=2.39Hz), 7.14(dd, 1H, J=8.23, 2.39Hz), 6.60(d, 1H, J=8.23Hz), 4.73(q, 1H, J=6.81Hz), 4.31(s, 2H), 4.18(m, 4H), 3.50(m, 6H), 2.44(m, 4H), 2.26(s, 3H), 1.65(d, 3H, J=6.81Hz), 1.26(m, 6H), Ethyl 2-{2-methyl-4-[({4-(4-morpholinylmethyl)-2-[4-(trifluoromethyl)phenyl]-1,3-thiazol-5-yl}methyl)sulfanyl]phenoxy}propanoate $^1$H NMR (CDCl$_3$) 300MHz δ 8.01(d, 2H, J=8.23Hz), 7.68 (d, 2H, J=8.23Hz), 7.27(d, 1H, J=2.39Hz), 7.16(dd, 1H, J=8.49, 2.39Hz), 6.60(d, 1H, J=8.49Hz), 4.73(q, 1H, J=6.72Hz), 4.34(s, 2H), 4.21(q, 2H, J=7.08Hz), 3.73(t, 4H, J=4.51Hz), 3.54(s, 2H), 2.49(t, 4H, J=4.51Hz), 2.26(s, 3H), 1.85(d, 3H, J=6.72Hz), 1.26(t, 3H, J=7.08Hz), Ethyl 2-{4-[({4-{[4-(3-methoxyphenyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.04(d, 2H, J=8.23Hz), 7.70 (d, 2H, J=8.23Hz), 7.28(m, 1H), 7.18(m, 2H), 6.62(d, 1H, J=8.23Hz), 6.56(dd, 1H, J=8.23, 2.39Hz), 6.50(t, 1H, J=2.26Hz), 6.45(dd, 1H, J=8.23, 2.39Hz), 4.74(q, 1H, J=6.81Hz), 4.37(s, 2H), 4.21(q, 2H, J=7.08Hz), 3.82(s, 3H), 3.61(s, 2H), 3.22(t, 4H, J=4.65Hz), 2.65(t, 4H, J=4.65Hz), 2.28(s, 3H), 1.66(d, 3H, J=6.81Hz), 1.26(t, 3H, J=7.08Hz), Ethyl 2-{4-[({4-[(4-acetyl-1-piperazinyl)methyl]-2-[4-trifluoromethyl)phenyl]-1,3-thiazol-5-yl}methyl)sulfanyl]-2-propylphenoxy}propanoate $^1$H NMR (CDCl$_3$) 400MHz δ 7.95(d, 2H, J=8.06Hz), 7.63 (d, 2H, J=8.06Hz), 7.16(d, 1H, J=2.38Hz), 7.11(dd, 1H, J=8.24, 2.38Hz), 6.55(d, 1H, J=8.24Hz), 4.70(q, 1H, J=6.84Hz), 4.23(s, 2H), 4.13(q, 2H, J=7.14Hz), 3.59(br s, 2H), 3.47(s, 2H), 3.40(t, 2H, J=4.58Hz), 2.55(t, 2H, J=7.33Hz), 2.40(m, 4H), 2.05(s, 3H), 1.56(m, 5H), 1.20(t, 3H, J=7.14Hz), 0.86(t, 3H, J=7.33Hz), Ethyl 2-{4-[({4-{[4-(4-fluorophenyl)-1-piperazinyl] methyl}-2-[4-(trifluoromethyl)phenyl]-1,3-thiazol-5-yl}methyl)sulfanyl]-2-propylphenoxy}propanoate $^1$H NMR (CDCl$_3$) 400MHz δ 7.97(d, 2H, J=8.24Hz), 7.64 (d, 2H, J=8.24Hz), 7.19(d, 1H, J=2.38Hz), 7.14(dd, 1H, J=8.42, 2.38Hz), 6.93(m, 2H), 6.84(m, 2H), 6.56(d, 1H, J=8.42Hz), 4.69(q, 1H, J=6.78Hz), 4.30(s, 2H), 4.14(q, 2H, J=7.14Hz), 3.54(s, 2H), 3.07(t, 4H, J=4.58Hz), 2.58(m, 6H), 1.57(m, 5H), 1.22(t, 3H, J=7.14Hz), 0.86(t, 3H, J=7.33Hz), Ethyl 2-{4-[({4-(4-morpholinylmethyl)-2-[4-(trifluoromethyl)phenyl]-1,3-thiazol-5-yl}methyl)sulfanyl]-2-propylphenoxy}propanoate $^1$H NMR (CDCl$_3$) 400MHz δ 7.95(d, 2H, J=8.24Hz), 7.63 (d, 2H, J=8.24Hz), 7.17(d, 1H, J=2.38Hz), 7.12(dd, 1H, J=8.42, 2.38Hz), 6.55(d, 1H, J=8.42Hz), 4.69(q, 1H, J=6.78Hz), 4.27(s, 2H), 4.14(q, 2H, J=7.14Hz), 3.66(t, 4H, J=4.67Hz), 3.45(s, 2H), 2.56(t, 2H, J=7.33Hz), 2.42(m, 4H), 1.56(m, 5H), 1.21(t, 3H, J=7.14Hz), 0.86(t, 3H, J=7.33Hz), Methyl {4-[({4-[(4-acetyl-1-piperazinyl)methyl]-2-[4-(trifluoromethyl)phenyl]-1,3-thiazol-5-yl}methyl)sulfanyl]-2-isopropylphenoxy}acetate $^1$H NMR (CDCl$_3$) 400MHz δ 7.95(d, 2H, J=8.61Hz), 7.64 (d, 2H, J=8.61Hz), 7.20(d, 1H, J=2.20Hz), 7.15(dd, 1H, J=8.42, 2.20Hz), 6.59(d, 1H, J=8.42Hz), 4.63(s, 2H), 4.25(s, 2H), 3.76(s, 3H), 3.56(s, 2H), 3.41(m, 4H), 3.31(m, 1H), 2.38(m, 4H), 2.05(s, 3H), 1.11(d, 6H, J=6.78Hz), Methyl {4-[({4-{[4-(4-fluorophenyl)-1-piperazinyl] methyl}-2-[4-(trifluoromethyl)phenyl]-1,3-thiazol-5-yl}methyl)sulfanyl]-2-isopropylphenoxy}acetate $^1$H NMR (CDCl$_3$) 400MHz δ 7.98(d, 2H, J=8.24Hz), 7.65 (d, 2H, J=8.24Hz), 7.23(d, 1H, J=2.20Hz), 7.18(dd, 1H, J=8.42, 2.20Hz), 6.94(m, 2H), 6.83(m, 2H), 6.60(d, 1H, J=8.42Hz), 4.61(s, 2H), 4.30(s, 2H), 3.76(s, 3H), 3.49(s, 2H), 3.34(m, 1H), 3.07(t, 4H, J=4.58Hz), 2.59(m, 4H), 1.13(d, 6H, J=6.96Hz), Methyl {2-isopropyl-4-[({4-(4-morpholinylmethyl)-2-[4-(trifluoromethyl)phenyl]-1,3-thiazol-5-yl}methyl)sulfanyl]phenoxy}acetate $^1$H NMR (CDCl$_3$) 400MHz δ 7.96(d, 2H, J=8.24Hz), 7.64 (d, 2H, J=8.24Hz), 7.21(d, 1H, J=2.38Hz), 7.16(dd, 1H, J=8.42, 2.38Hz), 6.59(d, 1H, J=8.42Hz), 4.62(s, 2H), 4.28(s, 2H), 3.76(s, 3H), 3.66(t, 4H, J=4.58Hz), 3.41(s, 2H), 3.32(m, 1H), 2.42(m, 4H), 1.15(d, 6H, J=6.96Hz), Methyl {2-isopropyl-4-[({4-{[4-(4-methoxyphenyl)-1-piperazinyl]methyl}-2-[4-(trifluoromethyl)phenyl]-1,3-thiazol-5-yl}methyl)sulfanyl] phenoxy}acetate $^1$H NMR (CDCl$_3$) 400MHz δ 7.98(d, 2H, J=8.24Hz), 7.65 (d, 2H, J=8.24Hz), 7.23(d, 1H, J=2.20Hz), 7.18(dd, 1H, J=8.42, 2.20Hz), 6.87(d, 2H, J=9.16Hz), 6.81(d, 2H, J=9.16Hz), 6.60(d, 1H, J=8.42Hz), 4.61(m, 2H), 4.31(s, 2H), 3.77(s, 3H), 3.74(s, 3H), 3.50(s, 2H), 3.33(m, 1H), 3.05(m, 4H), 2.60(br s, 4H), 1.15(d, 6H, J=6.96Hz), Methyl {4-[({4-{[4-(4-acetylphenyl)-1-piperazinyl] methyl}-2-[4-(trifluoromethyl)phenyl]-1,3-thiazol-5yl}methyl)sulfanyl]-2-isopropylphenoxy}acetate $^1$H NMR (CDCl$_3$) 400MHz δ 7.95(d, 2H, J=8.28Hz), 7.84 (d, 2H, J=9.14Hz), 7.62(d, 2H, J=8.28Hz), 7.21(d, 1H, J=2.24Hz), 7.16(dd, 1H, J=8.45, 2.24Hz), 6.80(d, 2H, J=9.14Hz), 6.58(d, 1H, J=8.45Hz), 4.59(s, 2H), 4.27(s, 2H), 3.73(s, 3H), 3.46(s, 2H), 3.30(m, 5H), 2.54(t, 4H, J=4.57Hz), 2.47(s, 3H), 1.12(d, 6H, J=6.90Hz), Methyl {2-isopropyl-4-[({4-{[4-(3-methoxyphenyl)-1-piperazinyl]methyl}-2-[4-(trifluoromethyl)phenyl]-1,3-thiazol-5-yl}methyl)sulfanyl]phenoxy}acetate $^1$H NMR (CDCl$_3$) 400MHz δ 7.98(d, 2H, J=8.28Hz), 7.65 (d, 2H, J=8.28Hz), 7.24(d, 1H, J=2.38Hz), 7.19(dd, 1H, J=8.42, 2.38Hz), 7.14(t, 1H, J=8.24Hz), 6.60(d, 1H, J=8.42Hz), 6.51(dd, 1H, J=8.24, 2.38Hz), 6.44(t, 1H, J=2.29Hz), 6.39(dd, 1H, J=8.24, 2.38Hz), 4.62(s, 2H), 4.30 (s, 2H), 3.75(m, 6H), 3.48(s, 2H), 3.34(m, 1H), 3.16(t, 4H, J=4.67Hz), 2.57(t, 4H, J=4.67Hz), 1.14(d, 6H, J=6.78Hz), Ethyl 2-{2-isopropyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 400MHz δ 8.04(d, 2H, J=8.24Hz), 7.71 (d, 2H, J=8.24Hz), 7.16(m, 2H), 6.87(d, 2H, J=9.16Hz), 6.78 (d, 2H, J=9.16Hz), 6.64(d, 1H, J=8.42Hz), 4.81(q, 1H, J=6.71Hz), 4.27(s, 2H), 4.11(q, 2H, J=7.08Hz), 3.69(s, 3H), 3.28(m, 3H), 2.96(t, 4H, J=4.94Hz), 2.51(t, 4H, J=4.94Hz), 1.54(d, 3H, J=6.71Hz), 1.12(m, 9H), Ethyl 2-{4-[({4-{[4-(4-acetylphenyl)-1-piperazinyl]methyl}-2-[4-trifluoromethyl)phenyl]-1,3-thiazol-5-yl}methyl)sulfanyl]-2-isopropylphenoxy}propanoate $^1$H NMR (CDCl$_3$) 400MHz δ 7.96(d, 2H, J=8.28Hz), 7.83 (d, 2H, J=9.14Hz), 7.64(d, 2H, J=8.28Hz), 7.19(d, 1H, J=2.24Hz), 7.12(dd, 1H, J=8.45, 2.24Hz), 6.81(d, 2H, J=9.14Hz), 6.55(d, 1H, J=8.45Hz), 4.71(q, 1H, J=6.78Hz), 4.26(s, 2H), 4.12(q, 2H, J=7.16Hz), 3.47(s, 2H), 3.29(m, 5H), 2.56(br s, 4H), 2.48(s, 3H), 1.58(d, 3H, J=6.78Hz), 1.15(m, 9H), Ethyl 2-{2-isopropyl-4-[({4-{[4-(3-methoxyphenyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 400MHz δ 7.98(d, 2H, J=8.24Hz), 7.65 (d, 2H, J=8.24Hz), 7.21(d, 1H, J=2.38Hz), 7.14(m, 2H), 6.58 (d, 1H, J=8.61Hz), 6.51(dd, 1H, J=8.24, 2.20Hz), 6.43(t, 1H, J=2.29Hz), 6.39(dd, 1H, J=8.24, 2.20Hz), 4.72(q, 1H, J=6.78Hz), 4.29(s, 2H), 4.15(q, 2H, J=7.14Hz), 3.76(s, 3H), 3.48(s, 2H), 3.33(m, 1H), 3.16(br s, 4H), 2.59(br s, 4H), 1.60(d, 3H, J=6.78Hz), 1.16(m, 9H), Ethyl {4-[({4-(4-morpholinylmethyl)-2-[4-(trifluoromethyl)phenyl]-1,3-thiazol-5-yl}methyl)sulfanyl]-2-propylphenoxy}acetate $^1$H NMR (CDCl$_3$) 400MHz δ 7.95(d, 2H, J=8.24Hz), 7.63 (d, 2H, J=8.24Hz), 7.19(m, 2H), 6.58(d, 1H, J=8.24Hz), 4.59 (s, 2H), 4.28(s, 2H), 4.21(q, 2H, J=7.14Hz), 3.66(t, 4H, J=4.49Hz), 3.45(s, 2H), 2.56(t, 2H, J=7.33Hz), 2.42(m, 4H), 1.56(m, 2H), 1.24(t, 3H, J=7.14Hz), 0.87(t, 3H, J=7.33Hz), Ethyl {4-[({4-{[4-(4-acetylphenyl)-1-piperazinyl]methyl}-2-[4-(trifluoromethyl)phenyl]-1,3-thiazol-5-yl}methyl)sulfanyl]-2-ethylphenoxy}acetate $^1$H NMR (CDCl$_3$) 400MHz δ 7.97(d, 2H, J=8.24Hz), 7.83 (d, 2H, J=9.16Hz), 7.63(d, 2H, J=8.24Hz), 7.21(d, 1H, J=2.20Hz), 7.16(dd, 1H, J=8.42, 2.20Hz), 6.82(d, 2H, J=9.16Hz), 6.59(d, 1H, J=8.42Hz), 4.59(s, 2H), 4.29(s, 2H), 4.21(q, 2H, J=7.14Hz), 3.52(s, 2H), 3.31(t, 4H, J=4.80Hz), 2.64(q, 2H, J=7.51Hz), 2.55(t, 4H, J=4.80Hz), 2.47(s, 3H), 1.24(t, 3H, J=7.14Hz), 1.14(t, 3H, J=7.51Hz), Ethyl {2-ethyl-4-[({4-{[4-(3-methoxyphenyl)-1-piperazinyl]methyl}-2-[4-(trifluoromethyl)phenyl]-1,3-thiazol-5-yl}methyl)sulfanyl]phenoxy}acetate $^1$H NMR (CDCl$_3$) 400MHz δ 7.98(d, 2H, J=8.24Hz), 7.65 (d, 2H, J=8.24Hz), 7.22(s, 1H), 7.16(m, 2H), 6.60(d, 1H, J=8.42Hz), 6.51(d, 1H, J=8.42Hz), 6.44(s, 1H), 6.39(dd, 1H, J=8.24, 1.28Hz), 4.60(s, 2H), 4.32(s, 2H), 4.22(q, 2H, J=7.14Hz), 3.76(s, 3H), 3.52(s, 2H), 3.16(t, 4H, J=4.67Hz), 2.65(q, 2H, J=7.51Hz), 2.57(t, 4H, J=467Hz), 1.26(t, 3H, J=7.14Hz), 1.16(t, 3H, J=7.51Hz), Ethyl {4-[({4-[(4-acetyl-1-piperazinyl)methyl]-2-[4-(trifluoromethyl)phenyl]-1,3-thiazol-5-yl}methyl)sulfanyl]-2-ethylphenoxy}acetate $^1$H NMR (CDCl$_3$) 400MHz δ 7.93(d, 2H, J=8.28Hz), 7.61 (d, 2H, J=8.28Hz), 7.16(d, 1H, J=2.24Hz), 7.12(dd, 1H, J=8.28, 2.24Hz), 6.56(d, 1H, J=8.28Hz), 4.58(s, 2H), 4 20(m, 4H), 3.55(t, 4H, J=4.91Hz), 3.43(s, 2H), 3.37(t, 4H, J=4.91Hz), 2.60(q, 2H, J=7.50Hz), 2.02(s, 3H), 1.22(t, 3H, J=7.14Hz), 1.11(t, 3H, J=7.50Hz), Ethyl {2-ethyl-4-[({4-{[4-(4-fluorophenyl)-1-piperazinyl]methyl}-2-[4-(trifluoromethyl)phenyl]-1,3-thiazol-5-yl}methyl)sulfanyl]phenoxy}acetate $^1$H NMR (CDCl$_3$) 400MHz δ 8.03(d, 2H, J=8.28Hz), 7.69 (d, 2H, J=8.28Hz), 7.25(m, 2H), 6.93(m, 4H), 6.64(d, 1H, J=8.28Hz), 4.64(s, 2H), 4.36(s, 2H), 4.26(q, 2H, J=7.08Hz), 3.58(s, 2H), 3.11(t, 4H, J=4.97Hz), 2.66(m, 6H), 1.29(t, 3H, J=7.08Hz), 1.19(t, 3H, J=7.54Hz), Ethyl {2-ethyl-4-[({4-(4-morpholinylmethyl)-2-[4-(trifluoromethyl)phenyl]-1,3-thiazol-5-yl}methyl)sulfanyl]phenoxy}acetate $^1$H NMR (CDCl$_3$) 400MHz δ 8.01(d, 2H, J=8.28Hz), 7.68 (d, 2H, J=8.28Hz), 7.24(m, 2H), 6.63(d, 1H, J=8.28Hz), 4.64 (s, 2H), 4.34(s, 2H), 4.26(q, 2H, J=7.17Hz), 3.70(t, 4H, J=4.42Hz), 3.49(s, 2H), 2.67(q, 2H, J=7.54Hz), 2.46(t, 4H, J=4.42Hz), 1.30(t, 3H, J=7.17Hz), 1.19(t, 3H, J=7.54Hz), Ethyl 2-{2-ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 400MHz δ 8.03(d, 2H, J=8.28Hz), 7.70 (d, 2H, J=8.28Hz), 7.26(d, 1H, J=2.21Hz), 7.19(dd, 1H, J=8.28, 2.21Hz), 6.93(d, 2H, J=9.11Hz), 6.86(d, 2H, J=9.11Hz), 6.62(d, 1H, J=8.28Hz), 4.76(q, 1H, J=6.90Hz), 4.36(s, 2H), 4.19(q, 2H, J=7.17Hz), 3.80(s, 3H), 3.58(s, 2H), 3.11(t, 4H, J=4.69Hz), 2.67(m, 6H), 1.65(d, 3H, J=6.90Hz), 1.24(m, 6H), Ethyl 2-{4-[({4-{[4-(4-acetylphenyl)-1-piperazinyl]methyl}-2-[4-(trifluoromethyl)phenyl]-1,3-thiazol-5-yl}methyl)sulfanyl]-2-ethylphenoxy}propanoate $^1$H NMR (CDCl$_3$) 400MHz δ 8.02(d, 2H, J=8.28Hz), 7.89 (d, 2H, J=8.83Hz), 7.69(d, 2H, J=8.28Hz), 7.25(d, 1H, Ethyl 2-{2-ethyl-4-[({4-{[4-(3-methoxyphenyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 400MHz δ 8.03(d, 2H, J=8.28Hz), 7.70 (d, 2H, J=8.28Hz), 7.26(d, 1H, J=2.21Hz), 7.18(m, 2H), 6.62 (d, 1H, J=8.28Hz), 6.56(dd, 1H, J=8.00, 1.66Hz), 6.49(m, 1H), 6.44(dd, 1H, J=8.00, 1.66Hz), 4.76(q, 1H, J=6.62Hz), 4.35(s, 2H), 4.19(q, 2H, J=7.17Hz), 3.81(s, 3H), 3.57(s, 2H), 3.21(t, 4H, J=4.83Hz), 2.66(m, 6H), 1.65(d, 3H, J=6.62Hz), 1.24(m, 6H), Ethyl 2-{4-[({4-[{4-(4-methoxyphenyl)-1-piperazinyl]methyl}-2-[4-(trifluoromethyl)phenyl]-1,3-thiazol-5-yl}methyl)sulfanyl]-2-propylphenoxy}propanoate $^1$H NMR (CDCl$_3$) 400MHz δ 7.97(d, 2H, J=8.24Hz), 7.64 (d, 2H, J=8.24Hz), 7.19(d, 1H, J=2.38Hz), 7.14(dd, 1H, J=8.42, 2.38Hz), 6.88(d, 2H, J=9.16Hz), 6.81(d, 2H, J=9.16Hz), 6.56(d, 1H, J=8.42Hz), 4.70(q, 1H, J=6.78Hz), 4.31(s, 2H), 4.15(q, 2H, J=7.14Hz), 3.74(s, 3H), 3.54(s, 2H), 3.05(t, 4H, J=4.85Hz), 2.57(m, 6H), 1.56(m, 5H), 1.20(t, 3H, J=7.14Hz), 0.86(t, 3H, J=7.33Hz), Ethyl 2-{4-[({4-{[4-(4-acetylphenyl)-1-piperazinyl]methyl}-2-[4-(trifluoromethyl)phenyl]-1,3-thiazol-5-yl}methyl)sulfanyl]-2-propylphenoxy}propanoate $^1$H NMR (CDCl$_3$) 400MHz δ 7.95(d, 2H, J=8.24Hz), 7.84 (d, 2H, J=9.14Hz), 7.63(d, 2H, J=8.24Hz), 7.17(d, 1H, J=2.24Hz), 7.12(dd, 1H, J=8.45, 2.24Hz), 6.82(d, 2H, J=9.14Hz), 6.54(d, 1H, J=8.45Hz), 4.68(q, 1H, J=6.78Hz), 4.27(s, 2H), 4.13(q, 2H, J=7.07Hz), 3.51(m, 2H), 3.31(t, 4H, J=4.91Hz), 2.55(m, 6H), 2.47(s, 3H), 1.55(m, 5H), 1.17(t, 3H, J=7.07Hz), 0.85(t, 3H, J=7.41Hz), Ethyl 2-{4-[({4-{[4-(3-methoxyphenyl)-1-piperazinyl]methyl}-2-[4-(trifluoromethyl)phenyl]-1,3-thiazol-5-yl}methyl)sulfanyl]-2-propylphenoxy}propanoate $^1$H NMR (CDCl$_3$) 400MHz δ 7.97(d, 2H, J=8.28Hz), 7.64 (d, 2H, J=8.28Hz), 7.15(m, 3H), 6.56(d, 1H, J=8.45Hz), 6.50 (dd, 1H, J=8.10, 2.07Hz), 6.43(t, 1H, J=2.07Hz), 6.39(dd, 1H, J=8.10, 2.07Hz), 4.70(q, 1H, J=6.72Hz), 4.29(s, 2H), 4.14(q, 2H, J=7.07Hz), 3.76(s, 3H), 3.52(s, 2H), 3.16(t, 4H, J=4.83Hz), 2.58(m, 6H), 1.57(m, 5H), 1.19(t, 3H, J=7.07Hz), 0.87(t, 3H, J=7.33Hz), Ethyl 2-(4-{[(2-(4-fluorophenyl)-4-{[4-(4-methoxyphenyl)-1-piperazinyl]methyl}-1,3-thiazol-5-yl)methyl]sulfanyl}-2-methylphenoxy)propanoate $^1$H NMR (CDCl$_3$) 400MHz δ 7.85(m, 2H), 7.22(d, 1H, J=2.38Hz), 7.09(m, 3H), 6.87(d, 2H, J=9.16Hz), 6.81(d, 2H, J=9.16Hz), 6.56(d, 1H, J=8.42Hz), 4.68(q, 1H, J=6.78Hz), 4.30(s, 2H), 4.16(q, 2H, J=7.20Hz), 3.74(s, 3H), 3.53(s, 2H), 3.07(t, 4H, J=4.58Hz), 2.62(br s, 4H), 2.21(s, 3H), 1.60(d, 3H, J=6.78Hz), 1.20(t, 3H, J=7.20Hz), Ethyl 2-[4-({[4-{[4-(4-acetylphenyl)-1-piperazinyl]methyl}-2-(4-fluorophenyl)-1,3-thiazol-5-yl]methyl}sulfanyl)-2-methylphenoxy]propanoate $^1$H NMR (CDCl$_3$) 400MHz δ 7.85(m, 4H), 7.23(d, 1H, J=2.38Hz), 7.09(m, 3H), 6.83(d, 2H, J=9.16Hz), 6.55(d, 1H, J=8.42Hz), 4.68(q, 1H, J=6.78Hz), 4.27(s, 2H), 4.16(q, 2H, J=7.14Hz), 3.52(s, 2H), 3.32(t, 4H, J=4.94Hz), 2.59(br s, 4H), 2.49(s, 3H), 2.21(s, 3H), 1.60(d, 3H, J=6.78Hz), 1.21(t, 3H, J=7.14Hz), Ethyl 2-(4-{[2-(4-fluorophenyl)-4-{[4-(3-methoxyphenyl)-1-piperazinyl]methyl}-1,3-thiazol-5-yl)methyl]sulfanyl}-2-methylphenoxy)propanoate $^1$H NMR (CDCl$_3$) 400MHz δ 7.85(m, 2H), 7.23(d, 1H, J=2.20Hz), 7.11(m, 4H), 6.56(d, 1H, J=8.24Hz), 6.51(dd, 1H, J=8.24, 2.20Hz), 6.44(t, 1H, J=2.20Hz), 6.39(dd, 1H, J=8.24, 2.20Hz), 4.69(q, 1H, J=6.78Hz), 4.29(s, 2H), 4.16(q, 2H, J=7.14Hz), 3.76(s, 3H), 3.52(s, 2H), 3.16(t, 4H, J=4.76Hz), 2.60(br s, 4H), 2.21(s, 3H), 1.59(d, 3H, J=6.78Hz), 1.22(t, 3H, J=7.14Hz), Ethyl 4-{[5-({[4-(2-ethoxy-1-methyl-2-oxoethoxy)-3-methylphenyl]sulfanyl}methyl)-2-(4-fluorophenyl)-1,3-thiazol-4-yl]methyl}-1-piperazinecarboxylate $^1$H NMR (CDCl$_3$) 400MHz δ 7.83(m, 2H), 7.20(d, 1H, J=2.20Hz), 7.08(m, 3H), 6.55(d, 1H, J=8.42Hz), 4.68(q, 1H, J=6.78Hz), 4.23(s, 2H), 4.16(q, 2H, J=7.14Hz), 4.09(q, 2H, J=7.14Hz), 3.42(m, 6H), 2.38(br s, 4H), 2.18(s, 3H), 1.57(d, 3H, J=6.78Hz), 1.13(m, 6H), Ethyl {2-ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetate $^1$H NMR (CDCl$_3$) 400MHz δ 7.98(d, 2H, J=8.24Hz), 7.65 (d, 2H, J=8.24Hz), 7.22(s, 1H), 7.17(d, 1H, J=8.42Hz), 6.87 (d, 2H, J=9.16Hz), 6.81(d, 2H, J=9.16Hz), 6.59(d, 1H, J=8.42Hz), 4.60(s, 2H), 4.32(s, 2H), 4.22(q, 2H, J=7.14Hz), 3.74(s, 3H), 3.53(s, 2H), 3.05(t, 4H, J=4.76Hz), 2.62(m, 6H), 1.26(t, 3H, J=7.14Hz), 1.16(t, 3H, J=7.33Hz), Ethyl 2-{4-[({4-[(4-acetyl-1-piperazinyl)methyl]-2-[4-(trifluoromethyl)phenyl]-1,3-thiazol-5-yl}methyl)sulfanyl]-2-ethylphenoxy}propanoate $^1$H NMR (CDCl$_3$) 400MHz δ 7.99(d, 2H, J=8.28Hz), 7.68 (d, 2H, J=8.28Hz), 7.22(d, 1H, J=2.21Hz), 7.15(dd, 1H, J=8.28, 2.21Hz), 6.60(d, 1H, J=8.28Hz), 4.75(q, 1H, J=6.81Hz), 4.29(s, 2H), 4.19(q, 2H, J=7.17Hz), 3.62(t, 2H, J=4.69Hz), 3.50(s, 2H), 3.43(t, 2H, J=4.69Hz), 2.66(q, 2H, J=7.45Hz), 2.43(br s, 4H), 2.09(s, 3H), 1.64(d, 3H, J=6.81Hz), 1.22(m, 6H), Ethyl 2-{2-ethyl-4-[({4-{[4-(4-fluorophenyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 400MHz δ 8.03(d, 2H, J=8.28Hz), 7.69 (d, 2H, J=8.28Hz), 7.26(d, 1H, J=2.21Hz), 7.19(dd, 1H, J=8.55, 2.21Hz), 6.94(m, 4H), 6.62(d, 1H, J=8.55Hz), 4.75 (q, 1H, J=6.90Hz), 4.35(s, 2H), 4.19(q, 2H, J=7.17Hz), 3.58 (s, 2H), 3.12(t, 4H, J=4.97Hz), 2.66(m, 6H), 1.64(d, 3H, J=6.90Hz), 1.24(m, 6H),

Ethyl 2-{2-ethyl-4-[({4-(4-morpholinylmethyl)-2-[4-(trifluoromethyl)phenyl]-1,3-thiazol-5-yl}methyl)sulfanyl]phenoxy}propanoate $^1$H NMR (CDCl$_3$) 400MHz δ 8.01(d, 2H, J=8.28Hz), 7.68 (d, 2H, J=8.28Hz), 7.24(d, 1H, J=2.21Hz), 7.16(dd, 1H, J=8.28, 2.21Hz), 6.60(d, 1H, J=8.28Hz), 4.75(q, 1H, J=6.62Hz), 4.32(s, 2H), 4.17(s, 2H), 3.70(t, 4H, J=4.42Hz), 3.49(s, 2H), 2.66(q, 2H, J=7.54Hz), 2.45(t, 4H, J=4.42Hz), 1.63(d, 3H, J=6.62Hz), 1.22(m, 6H),

Ethyl {4-[({4-{[4-(4-methoxyphenyl)-1-piperazinyl]methyl}-2-[4-(trifluoromethyl)phenyl]-1,3-thiazol-5-yl}methyl)sulfanyl]-2-propylphenoxy}acetate $^1$H NMR (CDCl$_3$) 400MHz δ 8.03(d, 2H, J=8.28Hz), 7.69 (d, 2H, J=8.28Hz), 7.23(m, 2H), 6.89(m, 4H), 6.64(d, 1H, J=8.28Hz), 4.62(s, 2H), 4.36(s, 2H), 4.26(q, 2H, J=7.08Hz), 3.79(s, 3H), 3.60(s, 2H), 3.11(m, 4H), 2.64(m, 6H), 1.62(m, 2H), 1.30(t, 3H, J=7.08Hz), 0.93(t, 3H, J=7.45Hz),

Ethyl {4-[({4-{[4-(4-acetylphenyl)-1-piperazinyl]methyl}-2-[4-(trifluoromethyl)phenyl]-1,3-thiazol-5-yl}methyl)sulfanyl]-2-propylphenoxy}acetate $^1$H NMR (CDCl$_3$) 400MHz δ 8.02(d, 2H, J=8.28Hz), 7.89 (d, 2H, J=9.11Hz), 7.69(d, 2H, J=8.28Hz), 7.24(m, 2H), 6.87 (d, 2H, J=9.11Hz), 6.64(d, 1H, J=8.28Hz), 4.62(s, 2H), 4.34 (s, 2H), 4.26(q, 2H, J=7.17Hz), 3.58(s, 2H), 3.35(t, 4H, J=4.97Hz), 2.62(m, 6H), 2.54(s, 3H), 1.61(m, 2H), 1.29(t, 3H, J=7.17Hz), 0.91(t, 3H, J=7.45Hz),

Ethyl {4-[({4-{[4-(3-methoxyphenyl)-1-piperazinyl]methyl}-2-[4-(trifluoromethyl)phenyl]-1,3-thiazol-5-yl}methyl)sulfanyl]-2-propylphenoxy}acetate $^1$H NMR (CDCl$_3$) 400MHz δ 7.97(d, 2H, J=8.28Hz), 7.64 (d, 2H, J=8.28Hz), 7.17(m, 3H), 6.58(d, 1H, J=8.10Hz), 6.51 (dd, 1H, J=8.10, 2.07Hz), 6.43(t, 1H, J=2.07Hz), 6.38(dd, 1H, J=8.10, 2.07Hz), 4.58(s, 2H), 4.30(s, 2H), 4.21(q, 2H, J=7.13Hz), 3.75(s, 3H), 3.53(s, 2H), 3.15(t, 4H, J=4.66Hz), 2.57(m, 6H), 1.57(m, 2H), 1.24(t, 3H, J=7.13Hz), 0.87(t, 3H, J=7.41Hz),

Ethyl {4-[({(4-[(4-acetyl-1-piperazinyl)methyl]-2-[4-(trifluoromethyl)phenyl]-1,3-thiazol-5-yl}methyl)sulfanyl]-2-propylphenoxy}acetate $^1$H NMR (CDCl$_3$) 400MHz δ 7.93(d, 2H, J=8.28Hz), 7.62 (d, 2H, J=8.28Hz), 7.14(m, 2H), 6.57(d, 1H, J=8.28Hz), 4.58 (s, 2H), 4.20(m, 4H), 3.56(t, 2H, J=4.91Hz), 3.45(s, 2H), 3.38(t, 2H, J=4.91Hz), 2.55(t, 2H, J=7.33Hz), 2.37(m, 4H), 2.03(s, 3H), 1.53(m, 2H), 1.22(t, 3H, J=7.16Hz), 0.85(t, 3H, J=7.33Hz),

Ethyl {4-[({4-{[4-(4--fluorophenyl)-1-piperazinyl]methyl}-2-[4-(trifluoromethyl)phenyl]-1,3-thiazol-5-yl}methyl)sulfanyl]-2-propylphenoxy}acetate $^1$H NMR (CDCl$_3$) 400MHz δ 7.97(d, 2H, J=8.28Hz), 7.64 (d, 2H, J=8.28Hz), 7.19(m, 2H), 6.92(m, 2H), 6.83(m, 2H), 6.58(d, 1H, J=8.28Hz), 4.56(s, 2H), 4.29(s, 2H), 4.20(q, 2H, J=7.13Hz), 3.53(s, 2H), 3.06(t, 4H, J=4.91Hz), 2.57(m, 6H), 1.55(m, 2H), 1.24(t, 3H, J=7.13Hz), 0.86(t, 3H, J=7.41Hz),

Ethyl 2-{4-[({4-{[4-(2,4-dimethoxyphenyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.02(d, 2H, J=8.28Hz), 7.67 (d, 2H, J=8.28Hz), 7.26(d, 1H, J=2.21Hz), 7.16(dd, 1H, J=8.55, 2.21Hz), 6.87(d, 1H, J=8.55Hz), 6.60(d, 1H, J=8.55Hz), 6.50(d, 1H, J=2.48Hz), 6.42(dd, 1H, J=8.55, 2.48Hz), 4.72(q, 1H, J=6.90Hz), 4.38(s, 2H), 4.21(q, 2H, J=7.08Hz), 3.85(s, 3H), 3.79(s, 3H), 3.61(s, 2H), 3.04(br s, 4H), 2.70(br s, 4H), 2.26(s, 3H), 1.63(d, 3H, J=6.90Hz), 1.24(t, 3H, J=7.04Hz), phenyl 4-({5-({[4-(2-ethoxy-1,1-dimethyl-2-oxoethoxy)phenyl]thio}methyl)-2-[4-(trifluoromethyl)phenyl]-1,3-thiazol-4-yl}methyl)piperazine-1-carboxylate To a 500ml 3-neck round-bottom flask equipped with a magnetic stir-bar, low temperature thermometer with thermometer adapter, addition funnel and N$_2$ inlet was added ethyl 2-{4-[({4-(hydroxymethyl)-2-[4-(trifluoromethyl)phenyl]-1,3-thiazol-5-yl}methyl)sulfanyl]phenoxy}-2-methylpropanoate (300mg, 0.59mmoles, 1eq) and dry CH$_2$Cl$_2$(4ml, 0.15M) and cooled to 0° C. Methanesulfonyl chloride (0.055ml, 0.71mmoles, 1.2eq) was added neat all at once. Triethylamine (0.12ml, 0.89mmoles, 1.5eq) was added dropwise maintaining the internal temperature below 5° C. and was stirred at 0° C. for 30minutes. The reaction mixture was transferred to a separatory funnel and washed with H$_2$O, brine and the organic fraction was dried over Na$_2$SO$_4$. After filtration the solvent was removed under reduced pressure to yield the corresponding mesylate in quantitative yield. Because of the unstable nature of the mesylate, the product was not characterized and was progressed onto the next stage without purification.

To the crude mesylate dissolved in dry THF (3ml, 0.20M) was added piperazine (559mg, 5.9mmoles, 10eq) and the reaction mixture was refluxed for 5hours. After cooling to room temperature the solvent was removed in vacuo. The residue was partitioned between EtOAc and H$_2$O and after the phases were separated the organic fraction was dried over Na$_2$SO$_4$, filtered and concentrated in vacuo to yield a quantitative amount of product. The product was used without characterization and purification.

The crude piperazine was dissolved in dry CH$_2$Cl$_2$(5ml, 0.12M) and to it was added phenylchloroformate (0.08ml, 0.65mmoles, 1.1eq) and triethylamine (0.248ml, 1.8mmoles, 3eq) and was stirred at room temperature overnight. The reaction mixture was diluted with EtOAc and washed with 0.1N HCl twice, H$_2$O, brine, dried over Na$_2$SO$_4$, filtered and concentrated in vacuo to yield after silica gel chromatography 125mg (32% over three steps) of product.

$^1$H NMR (CDCl$_3$) 400MHz δ 7.95(d, 2H, J=8.28Hz), 7.65 (d, 2H, J=8.28Hz), 7.33(m, 2H), 7.26(d, 2H, J=8.79Hz), 7.17 (t, 1H, J=7.59Hz), 7.06(d, 2H, J=7.59Hz), 6.74(d, 2H, J=8.79Hz), 4.32(s, 2H), 4.18(q, 2H, J=7.07Hz), 3.61(m, 6H), 2.51(br s, 4H), 1.57(s, 6H), 1.20(t, 3H, J=7.07Hz),

The following compounds were made the same procedure used for phenyl 4-({5-({[4-(2-ethoxy-1,1-dimethyl-2-oxoethoxy)phenyl]thio}methyl)-2-[4-(trifluoromethyl)phenyl]-1,3-thiazol-4-yl}methyl)piperazine-1-carboxylate except no extra base was used when the other reactant was an isocyanate.

Phenyl 4-({5-({[4-(2-ethoxy-1-methyl-2-oxoethoxy)-3-methylphenyl]sulfanyl}methyl)-2-[4-(trifluoromethyl)phenyl]-1,3-thiazol-4-yl}methyl)-1-piperazinecarboxylate $^1$H NMR (CDCl$_3$) 300MHz δ 7.97(d, 2H, J=8.28Hz), 7.77 (d, 2H, J=8.28Hz), 7.60(m, 5H), 7.20(d, 1H, J=2.21Hz), 7.10 (dd, 1H, J=8.55, 2.21Hz), 6.57(d, 1H, J=8.55Hz), 4.74(q, 1H, J=6.71Hz), 4.20(m, 4H), 3.48(s, 2H), 3.06(br s, 4H), 2.56(br s, 4H), 2.24(s, 3H), 1.65(d, 3H, J=6.71Hz), 1.25(t, 3H, J=7.04Hz), benzyl 4-({5-({[4-(2-ethoxy-1-methyl-2-oxoethoxy)-3-methylphenyl]thio}methyl)-2-[4-(trifluoromethyl)phenyl]-1,3-thiazol-4-yl}methyl)piperazine-1-carboxylate $^1$H NMR (CDCl$_3$) 300MHz δ 8.01(d, 2H, J=8.00Hz), 7.69 (d, 2H, J=8.00Hz), 7.36(m, 5H), 7.26(d, 1H, J=2.21Hz), 7.15 (dd, 1H, J=8.55, 2.21Hz), 6.60(d, 1H, J=8.S5Hz), 5.16(s, 2H), 4.74(q, 1H, J=6.62Hz), 4.31(s, 2H), 4.21(q, 2H, J=7.08Hz), 3.55(m, 6H), 2.47(br s, 4H), 2.26(s, 3H), 1.65(d, 3H, J=6.62Hz), 1.25(t, 3H, J=7.08Hz), Isopropyl 4-{[5-({[4-(2-ethoxy-1-methyl-2-oxoethoxy)-3-methylphenyl]sulfanyl}methyl)-2-(4-fluorophenyl)-1,3-thiazol-4-yl]methyl}-1-piperazinecarboxylate $^1$H NMR (CDCl$_3$) 400MHz δ 7.84(m, 2H), 7.22(d, 1H, J=2.20Hz), 7.09(m, 3H), 6.55(d, 1H, J=8.42Hz), 4.89(m, 1H), 4.68(q, 1H, J=6.78Hz), 4.26(s, 2H), 4.16(q, 2H, J=7.20Hz), 3.47(m, 6H), 2.40(br s, 4H), 2.22(s, 3H), 1.61(d, 3H, J=6.78Hz), 1.27(m, 9H), Ethyl 2-{4-[({4-{[4-cyclopentylcarbonyl-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.00(d, 2H, J=8.28Hz), 7.67 (d, 2H, J=8.28Hz), 7.24(d, 1H, J=2.21Hz), 7.14(dd, 1H, J=8.28, 2.21Hz), 6.59(d, 1H, J=8.28Hz), 4.73(q, 1H, J=6.71Hz), 4.31(s, 2H), 4.19(q, 2H, J=7.17Hz), 3.65(br s, 2H), 3.50(br s, 4H), 2.87(m, 1H), 2.45(t, 4H, J=4.69Hz), 2.23(s, 3H), 1.73(m, 11H), 1.24(t, 3H, J=7.17Hz), Ethyl 2-{4-[({4-{[4-cyclopropylcarbonyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.00(d, 2H, J=8.28Hz), 7.68 (d, 2H, J=8.28Hz), 7.27(d, 1H, J=2.21Hz), 7.15(dd, 1H, J=8.28, 2.21Hz), 6.59(d, 1H, J=8.28Hz), 4.73(q, 1H, J=6.71Hz), 4.31(s, 2H), 4.20(q, 2H, J=7.08Hz), 3.67(br s, 4H), 3.55(s, 2H), 2.49(br s, 4H), 2.26(s, 3H), 1.74(m, 1H), 1.64(d, 3H, J=6.71Hz), 1.25(t, 3H, J=7.08Hz), 1.00(m, 2H), 0.76(m, 2H), Ethyl 2-{4-[({4-{[4-(cyclobutylcarbonyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300MHz δ 7.99(d, 2H, J=8.28Hz), 7.67 (d, 2H, J=8.28Hz), 7.24(d, 1H, J=2.21Hz), 7.13(dd, 1H, J=8.28, 2.21Hz), 6.58(d, 1H, J=8.28Hz), 4.73(q, 1H, J=6.71Hz), 4.28(s, 2H), 4.19(q, 2H, J=7.17Hz), 3.64(t, 2H, J=4.83Hz), 3.52(s, 2H), 3.36(t, 2H, J=4.83Hz), 3.24(m, 1H), 2.47(m, 4H), 2.08(m, 9H), 1.63(d, 3H, J=6.71Hz), 1.24(t, 3H, J=7.17Hz), Methyl 4--({5-({[4-(2-ethoxy-1-methyl-2-oxoethoxy)-3-methylphenyl]sulfanyl}methyl)-2-[4-(trifluoromethyl)phenyl]-1,3-thiazol-4-yl}methyl)-1-piperazinecarboxylate $^1$H NMR (CDCl$_3$) 300MHz δ 8.00(d, 2H, J=8.28Hz), 7.68 (d, 2H, J=8.28Hz), 7.26(d, 1H, J=2.21Hz), 7.14(dd, 1H, J=8.28, 2.21Hz), 6.59(d, 1H, J=8.28Hz), 4.73(q, 1H, J=6.71Hz), 4.31(s, 2H), 4.20(q, 2H, J=7.17Hz), 3.71(s, 3H), 3.50(m, 6H), 2.44(br s, 4H), 2.26(s, 3H), 1.65(d, 3H, J=6.71Hz), 1.25(t, 3H, J=7.17Hz), Ethyl 2-{2-methyl-4-[({4-{[4-(3-methylbutanoyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 300MHz δ 8.00(d, 2H, J=8.28Hz), 7.67 (d, 2H, J=8.28Hz), 7.24(d, 1H, J=2.21Hz), 7.14(dd, 1H, J=8.55, 2.48Hz), 6.59(d, 1H, J=8.55Hz), 4.73(q, 1H, J=6.71Hz), 4.30(s, 2H), 4.20(q, 2H, J=7.08Hz), 3.65(br s, 2H), 3.54(s, 2H), 3.47(t, 2H, J=4.69Hz), 2.45(t, 4H, J=4.83Hz), 2.26(s, 3H), 2.12(m, 3H), 1.64(d, 3H, J=6.71Hz), 1.24(t, 3H, J=7.08Hz), 0.96(d, 6H, J=6.35Hz), Ethyl 2-{4-[({4-{[4-(4-fluorobenzoyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.00(d, 2H, J=8.28Hz), 7.69 (d, 2H, J=8.28Hz), 7.43(m, 2H), 7.24(d, 1H, J=2.39Hz), 7.11 (m, 3H), 6.59(d, 1H, J=8.55Hz), 4.73(q, 1H,. J=6.71Hz), 4.30(s, 2H), 4.19(q, 2H, J=7.17Hz), 3.65(m, 6H), 2.53(m, 4H), 2.25(s, 3H), 1.64(d, 3H, J=6.71Hz), 1.25(t, 3H, J=7.17Hz), Ethyl 2-{2-methyl-4-[({4-{[4-(propylsulfonyl)-1-piperazinyl]methyl}-2-[4-(trifluoromethyl)phenyl]-1,3-thiazol-5-yl}methyl)sulfanyl]phenoxy}propanoate $^1$H NMR (CDCl$_3$) 300MHz 6, 8.00(d, 2H, J=8.28Hz), 7.68 (d, 2H, J=8.28Hz), 7.26(d, 1H, J=2.21Hz), 7.15(dd, 1H, J=8.28, 2.21Hz), 6.59(d, 1H, J=8.28Hz), 4.74(q, 1H, J=6.71Hz), 4.28(s, 2H), 4.20(q, 2H, J=7.08Hz), 3.55(s, 2H), 3.30(t, 4H, J=4.55Hz), 2.89(m, 2H), 2.56(t, 4H, J=4.28Hz), 2.26(s, 3H), 1.87(m, 2H), 1.65(d, 3H, J=6.62Hz), 1.25(t, 3H, J=7.04Hz), 1.07(t, 3H, J=7.17Hz).

Ethyl 2-{4-[({4-[(4-butyryl-1-piperazinyl)methyl]-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.00(d, 2H, J=8.28Hz), 7.67 (d, 2H, J=8.28Hz), 7.26(d, 1H, J=2.21Hz), 7.14(dd, 1H, J=8.55, 2.21Hz), 6.59(d, 1H, J=8.55Hz), 4.73(q, 1H, J=6.71Hz), 4.30(s, 2H), 4.20(q, 2H, J=7.08Hz), 3.64(m, 2H), 3.54(s, 2H), 3.45(t, 2H, J=4.83Hz), 2.45(t, 4H, J=4.83Hz), 2.31(t, 2H, J=7.31Hz), 2.25(s, 3H), 1.66(m, 5H), 1.24(t, 3H, J=7.08Hz), 0.98(t, 3H, J=7.31Hz), Ethyl 2-{2-methyl-4-[({4-[(4-pentanoyl-1-piperazinyl)methyl]-2-[4-(trifluoromethyl)phenyl]-1,3-thiazol-5-yl}methyl)sulfanyl]phenoxy}propanoate ¹H NMR (CDCl₃) 300MHz δ 8.00(d, 2H, J=8.28Hz), 7.67 (d, 2H, J=8.28Hz), 7.26(d, 1H, J=2.21Hz), 7.14(dd, 1H, J=8.28, 2.21Hz), 6.58(d, 1H, J=8.28Hz), 4.73(q, 1H, J=6.71Hz), 4.30(s, 2H), 4.19(q, 2H, J=7.27Hz), 3.64(m, 2H), 3.54(s, 2H), 3.46(t, 2H, J=4.83Hz), 2.45(t, 4H, J=4.83Hz), 2.32(t, 2H, J=7.45Hz), 2.24(s, 3H), 1.61(m, 5H), 1.37(m, 2H), 1.24(t, 3H, J=7.27Hz), 0.93(t, 3H, J=7.45Hz), Ethyl 2-{4-[({4-{[4-(4-methoxybenzoyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 300MHz δ 8.00(d, 2H, J=8.28Hz), 7.67 (d, 2H, J=8.28Hz), 7.40(d, 2H, J=8.83Hz), 7.24(d, 1H, J=2.21Hz), 7.14(dd, 1H, J=8.28, 2.21Hz), 6.92(d, 2H, J=8.83Hz), 6.59(d, 1H, J=8.28Hz), 4.73(q, 1H, J=6.71Hz), 4.30(s, 2H), 4.19(q, 2H, J=7.08Hz), 3.84(s, 3H), 3.63(m, 6H), 2.49(br s, 4H), 2.25(s, 3H), 1.64(d, 3H, J=6.71Hz), 1.24(t, 3H, J=7.08Hz), Ethyl 2-{4-[({4-[(4-benzoyl-1-piperazinyl)methyl]-2-[4-(trifluoromethyl)phenyl]-1,3-thiazol-5-yl}methyl)sulfanyl]-2-methylphenoxy}propanoate ¹H NMR (CDCl₃) 300MHz δ 7.99(d, 2H, J=8.55Hz), 7.67 (d, 2H, J=8.55Hz), 7.41(m, 5H), 7.24(d, 1H, J=2.21Hz), 7.15 (dd, 1H, J=8.55, 2.21Hz), 6.59(d, 1H, J=8.55Hz), 4.73(q, 1H, J=6.71Hz), 4.30(s, 2H), 4.19(q, 2H, J=7.04Hz), 3.83(br s, 2H), 3.56(s, 2H), 3.39(br s, 2H), 2.50(br s, 4H), 2.25(s, 3H), 1.64(d, 3H, J=6.71Hz), 1.24(t, 3H, J=7.04Hz), isobutyl 4-({5-({[4-(2-ethoxy-1-methyl-2-oxoethoxy)-3-methylphenyl]sulfanyl}methyl)-2-[4-(trifluoromethyl)phenyl]-1,3-thiazol-4-yl}methyl)-1-piperazinecarboxylate ¹H NMR (CDCl₃) 300MHz δ 8.00(d, 2H, J=8.28Hz), 7.68 (d, 2H, J=8.28Hz), 7.26(d, 1H, J=2.21Hz), 7.14(dd, 1H, J=8.28, 2.21Hz), 6.59(d, 1H, J=8.55Hz), 4.73(q, 1H, J=6.71Hz), 4.32(s, 2H), 4.20(q, 2H, J=7.08Hz), 3.88(d, 2H, J=6.62Hz), 3.53(m, 6H), 2.46(br s, 4H), 2.25(s, 3H), 1.94(m, 1H), 1.65(d, 3H, J=6.62Hz), 1.25(t, 3H, J=7.17Hz), 0.95(d, 6H, J=6.62Hz).

Ethyl 2-{2-methyl-4-[({4-{[4-(2-thienylcarbonyl)-1-piperazinyl]methyl}-2-[4-(trifluoromethyl)phenyl]-1,3-thiazol-5-yl}methyl)sulfanyl]phenoxy}propanoate ¹H NMR (CDCl₃) 300MHz δ 8.01(d, 2H, J=8.28Hz), 7.68 (d, 2H, J=8.28Hz), 7.45(d, 1H, J=4.97Hz), 7.30(d, 1H, J=3.59Hz), 7.25(d, 1H, J=2.21Hz), 7.15(dd, 1H, J=8.28, 2.21Hz), 7.05(m, 1H), 6.60(d, 1H, J=8.28Hz), 4.74(q, 1H, J=6.71Hz), 4.31(s, 2H), 4.19(q, 2H, J=7.08Hz), 3.78(t, 4H, J=4.69Hz), 3.56(s, 2H), 2.55(t, 4H, J=4.69Hz), 2.25(s, 3H), 1.65(d, 3H, J=6.71Hz), 1.25(t, 3H, J=7.08Hz), Phenyl 4-{[5-({[4-(2-ethoxy-1-methyl-2-oxoethoxy)-3-methylphenyl]sulfanyl}methyl)-2-(4-fluorophenyl)-1,3-thiazol-4-yl]methyl}-1-piperazinecarboxylate ¹H NMR (CDCl₃) 400MHz δ 7.85(m, 2H), 7.33(m, 2H), 7.15(m, 7H), 6.57(d, 1H, J=8.61Hz), 4.69(q, 1H, J=6.78Hz), 4.27(s, 2H), 4.14(q, 2H, J=7.14Hz), 3.63(br s, 4H), 3.50(s, 2H), 2.49(br s, 4H), 2.23(s, 3H), 1.60(d, 3H, J=6.78Hz), 1.22(t, 3H, J=7.14Hz), Ethyl 2-{4-[({4-({4-[4-(dimethylamino)benzoyl]-piperazinyl}methyl)-2-[4-(trifluoromethyl)phenyl]-1,3-thiazol-5-yl}methyl)sulfanyl]-2-methylphenoxy}propanoate ¹H NMR (CDCl₃) 300MHz δ 8.01(d, 2H, J=8.28Hz), 7.68 (d, 2H, J=8.28Hz), 7.37(d, 2H, J=8.83Hz), 7.25(d, 1H, J=2.21Hz), 7.15(dd, 1H, J=8.28, 2.21Hz), 6.68(d, 2H, J=8.83Hz), 6.60(d, 1H, J=8.28Hz), 4.73(q, 1H, J=6.71Hz), 4.32(s, 2H), 4.20(q, 2H, J=7.17Hz), 3.67(br s, 4H), 3.55(s, 2H), 3.02(s, 6H), 2.51(br s, 4H), 2.26(s, 3H), 1.65(d, 3H, J=6.71Hz), 1.25(t, 3H, J=7.17Hz), Ethyl 2-{4-[({4-{[4-(cyclohexylcarbonyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 300MHz δ 8.00(d, 2H, J=8.28Hz), 7.68 (d, 2H, J=8.28Hz), 7.26(d, 1H, J=2.21Hz), 7.14(dd, 1H, J=8.28, 2.21Hz), 6.59(d, 1H, J=8.28Hz), 4.73(q, 1H, J=6.71Hz), 4.30(s, 2H), 4.20(q, 2H, J=7.08Hz), 3.58(m, 6H), 2.47(m, 5H), 2.26(s, 3H), 1.63(m, 11H), 1.27(m, 5H), Ethyl 2-{2-methyl-4-[({4-({4-[(methylamino)carbonyl]-1-piperazinyl}methyl)-2-[4-(trifluoromethyl)phenyl]-1,3-thiazol-5-yl}methyl)sulfanyl]phenoxy}propanoate ¹H NMR (CDCl₃) 300MHz δ 8.01(d, 2H, J=8.28Hz), 7.67 (d, 2H, J=8.28Hz), 7.27(d, 1H, J=2.21Hz), 7.14(dd, 1H, J=8.55, 2.21Hz), 6.53(d, 1H, J=8.55Hz), 4.84(m, 1H), 4.70 (q, 1H, J=6.90Hz), 4.25(m, 4H), 3.52(m, 2H), 3.29(m, 4H), 2.80(d, 3H, J=4.42Hz), 2.35(t, 4H, J=4.83Hz), 2.22(s, 3H), 1.64(d, 3H, J=6.90Hz), 1.25(t, 3H, J=7.17Hz), Ethyl 2-{4-[({4-({4-[(tert-butylamino)carbonyl]-1-piperazinyl}methyl)-2-[4-(trifluoromethyl)phenyl]-1,3-thiazol-5-yl}methyl)sulfanyl]-2-methylphenoxy}propanoate ¹H NMR (CDCl₃) 300MHz δ 8.00(d, 2H, J=8.28Hz), 7.67 (d, 2H, J=8.28Hz), 7.27(d, 1H, J=2.21Hz), 7.14(dd, 1H, J=8.28, 2.21Hz), 6.56(d, 1H, J=8.28Hz), 4.72(q, 1H, J=6.81Hz), 4.42(s, 1H), 4.33(d, 1H, J=63Hz), 4.26(d, 1H, J=63Hz), 4.20(q, 2H, J=7.08Hz), 3.53(s, 2H), 3.29(m, 4H), 2.40(t, 4H, J=4.69Hz), 2.25(s, 3H), 1.63(d, 3H, J=6.81Hz), 1.35(s, 5H), 1.25(t, 3H, J=7.09Hz), Ethyl 2-{4-({4-[(4-[(4-methoxyanilino)carbonyl]-piperazinyl}methyl)-2-[4-(trifluoromethyl)phenyl]-1,3-thiazol-5-yl}methyl)sulfanyl]-2-methylphenoxy}propanoate ¹H NMR (CDCl₃) 300MHz δ 8.05(d, 2H, J=8.28Hz), 7.73 (d, 2H, J=8.28Hz), 7.23(m, 4H), 6.84(d, 2H, J=6.90Hz), 6.66 (d, 1H, J=8.55Hz), 4.83(q, 1H, J=6.76Hz), 4.36(d, 1H, J=63Hz), 4.30(d, 1H, J=0.63Hz), 4.16(q, 2H, J=7.08Hz), 3.75(s, 3H), 3.46(m, 6H), 2.43(t, 4H, J=4.83Hz), 2.21(s, 3H), 1.58(d, 3H, J=6.76Hz), 1.20(t, 3H, J=7.08Hz), Ethyl 2-{2-methyl-4-[({4-[{(2-phenylethyl)amino]carbonyl}-1-Piperazinyl)methyl]-2-[4-(trifluoromethyl)phenyl]-1,3-thiazol-5-yl}methyl)sulfanyl]phenoxy}propanoate ¹H NMR (CDCl₃) 300MHz δ 8.01(d, 2H, J=8.28Hz), 7.68 (d, 2H, J=8.28Hz), 7.24(m, 7H), 6.57(d, 1H, J=8.55Hz), 4.74 (m, 2H), 4.33(d, 1H, J=35Hz), 4.26(d, 1H, J=35Hz), 4.20(q, 2H, J=7.04Hz), 3.50(m, 4H), 3.28(m, 4H), 2.84(t, 2H, J=7.04Hz), 2.38(t, 4H, J=4.83Hz), 2.25(s, 3H), 1.65(d, 3H, J=6.62Hz), 1.26(t, 3H, J=7.04Hz), Ethyl 2-{2-methyl-4-[({4-{[4-(phenylsulfonyl)-1-piperazinyl]methyl}-2-[4-(trifluoromethyl)phenyl]-1,3-thiazol-5-yl}methyl)sulfanyl]phenoxy}propanoate ¹H NMR (CDCl₃) 300MHz δ 7.97(d, 2H, J=8.28Hz), 7.77 (d, 2H, J=8.28Hz), 7.59(m, 5H), 7.20(d, 1H, J=2.21Hz), 7.10 (dd, 1H, J=8.55, 2.21Hz), 6.58(d, 1H, J=8.55Hz), 4.73(q, 1H, J=6.71Hz), 4.19(m, 4H), 3.48(s, 2H), 3.07(br s, 4H), 2.56(br s, 4H), 2.25(s, 3H), 1.65(d, 3H, J=6.71Hz), 1.25(t, 3H, J=7.04Hz), Ethyl 2-{2-methyl-4-[({2-[4-(trifluoromethyl)phenyl]-4-[(4-{[4-(trifluoromethyl)phenyl]sulfonyl}-1-piperazinyl)methyl]-1,3-thiazol-5-yl}methyl)sulfanyl]phenoxy}propanoate ¹H NMR (CDCl₃) 300MHz δ 7.98(d, 2H, J=8.28Hz), 7.90 (d, 2H, J=8.55Hz), 7.81(d, 2H, J=8.55Hz), 7.67(d, 2H, J=8.28Hz), 7.21(d, 1H, J=2.21Hz), 7.10(dd, 1H, J=8.28, 2.21Hz), 6.58(d, 1H, J=8.28Hz), 4.74(q, 1H, J=6.71Hz), 4.21 (m, 4H), 3.49(s, 2H), 3.09(br s, 4H), 2.58(br s, 4H), 2.24(s, 3H), 1.66(d, 3H, J=6.71Hz), 1.26(t, 3H, J=7.17Hz), Ethyl 2-{4-[({4-({4-[(4-methoxyphenyl)sulfonyl]-1-piperazinyl}methyl)-2-[4-(trifluoromethyl)phenyl]-1,3-thiazol-5-yl}methyl)sulfanyl]-2-methylphenoxy}propanoate ¹H NMR (CDCl₃) 300MHz δ 7.97(d, 2H, J=8.28Hz), 7.67 (m, 4H), 7.20(d, 1H, J=2.21Hz), 7.09(dd, 1H, J=8.55, 2.21Hz), 6.99(d, 2H, J=8.83Hz), 6.58(d, 1H, J=8.55Hz), 4.74 (q, 1H, J=6.71Hz), 4.20(m, 4H), 3.87(s, 3H), 3.49(s, 2H), 3.05(br s, 4H), 2.54(br s, 4H), 2.24(s, 3H), 1.66(d, 3H, J=6.71Hz), 1.25(t, 3H, J=7.04Hz), Ethyl 2-{4-[({4-{[4-(ethylsulfonyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 300MHz δ 8.00(d, 2H, J=8.28Hz), 7.68 (d, 2H, J=8.28Hz), 7.26(d, 1H, J=2.48Hz), 7.15(d, 1H, J=2.48Hz), 6.59(d, 1H, J=8.28Hz), 4.74(q, 1H, J=6.81Hz), 4.28(s, 2H), 4.20(q, 2H, J=7.17Hz), 3.55(s, 2H), 3.32(t, 4H, J=4.69Hz), 2.96(q, 2H, J=7.45Hz), 2.55(br s, 4H), 2.25(s, 3H), 1.65(d, 3H, J=6.81Hz), 1.38(t, 3H, J=7.45Hz), 1.25(t, 3H, J=7.17Hz), Ethyl 2-{2-methyl-4-[({4-{[4-(methylsulfonyl)-1-piperazinyl]methyl}-2-[4-(trifluoromethyl)phenyl]-1,3-thiazol-5-yl}methyl)sulfanyl]phenoxy}propanoate ¹H NMR (CDCl₃) 300MHz δ 8.00(d, 2H, J=8.55Hz), 7.68 (d, 2H, J=8.55Hz), 7.26(d, 1H, J=2.21Hz), 7.15(dd, 1H, J=8.55, 2.21Hz), 6.59(d, 1H, J=8.55Hz), 4.73(q, 1H, J=6.71Hz), 4.27(s, 2H), 4.20(q, 2H, J=7.17Hz), 3.56(s, 2H), 3.24(t, 4H, J=4.55Hz), 2.78(s, 3H), 2.58(t, 4H, J=4.55Hz), 2.24(s, 3H), 1.64(d, 3H, J=6.71Hz), 1.25(t, 3H, J=7.17Hz), Ethyl 2-{4-[({4-[(4-{[4-(acetylamino)phenyl]sulfonyl}-1-piperazinyl)methyl]-2-[4-(trifluoromethyl)phenyl]-1,3-thiazol-5-yl}methyl)sulfanyl]-2-methylphenoxy}propanoate ¹H NMR (CDCl₃) 300MHz δ 8.40(s, 1H), 7.96(d, 2H, J=8.28Hz), 7.66(m, 6H), 7.16(d, 1H, J=2.21Hz), 7.07(dd, 1H, J=8.28, 2.21Hz), 6.56(d, 1H, J=8.28Hz), 4.73(q, 1H, J=6.71Hz), 4.22(m, 4H), 3.51(s, 2H), 3.03(br s, 4H), 2.55(br s, 4H), 2.19(m, 6H), 1.65(d, 3H, J=6.71Hz), 1.27(t, 3H, J=7.04Hz), Ethyl 2-{4-[({4-({4-[(4-fluorophenyl)sulfonyl]-1-piperazinyl}methyl)-2-[4-(trifluoromethyl)phenyl]-1,3-thiazol-5-yl}methyl)sulfanyl]-2-methylphenoxy}propanoate ¹H NMR (CDCl₃) 300MHz δ 7.97(d, 2H, J=8.28Hz), 7.77 (m, 2H), 7.66(d, 2H, J=8.28Hz), 7.22(m, 3H), 7.10(dd, 1H, J=8.55, 2.21Hz), 6.58(d, 1H, J=8.55Hz), 4.74(q, 1H, J=6.81Hz), 4.20(m, 4H), 3.49(s, 2H), 3.07(br s, 4H), 2.57(t, 4H, J=4.42Hz), 2.24(s, 3H), 1.65(d, 3H, J=6.81Hz), 1.27(t, 3H, J=7.17Hz), Ethyl 2-{4-[({4-{[4-(2-furoyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 300MHz δ 8.00(d, 2H, J=8.28Hz), 7.67 (d, 2H, J=8.28Hz), 7.48(s, 1H), 7.24(d, 1H, J=2.21Hz), 7.15 (dd, 1H, J=8.28, 2.21Hz), 6.99(d, 1H, J=3.59Hz), 6.60(d, 1H, J=8.28Hz), 6.48(m, 1H), 4.73(q, 1H, J=6.71Hz), 4.31(s, 2H), 4.20(q, 2H, J=7.08Hz), 3.83(br s, 4H), 3.55(s, 2H), 2.54(t, 4H, J=4.83Hz), 2.25(s, 3H), 1.64(d, 3H, J=6.71Hz), 1.24(t, 3H, J=7.08Hz), Ethyl 2-{4-[({4-({4-[(isopropylamino)carbonyl]-1-piperazinyl}methyl)-2-[4-(trifluoromethyl)phenyl]-1,3-thiazol-5-yl}methyl)sulfanyl]-2-methylphenoxy}propanoate ¹H NMR (CDCl₃) 300MHz δ 8.01(d, 2H, J=8.28Hz), 7.67 (d, 2H, J=8.28Hz), 7.27(d, 1H, J=−1.93Hz), 7.14(ddd, 1H, J=8.55, 2.21, 0.55Hz), 6.55(d, 1H, J=8.28Hz), 4.72(q, 1H, J=6.81Hz), 4.47(d, 1H, J=7.17Hz), 4.26(m, 4H), 3.99(m, 1H), 3.52(m, 2H), 3.29(m, 4H), 2.37(t, 4H, J=4.69Hz), 2.24 (s, 3H), 1.64(d, 3H, J=6.62Hz), 1.25(t, 3H, J=7.17Hz), 1.15 (m, 6H), Ethyl 2-{4-[({4-{[4-(methoxyacetyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 300MHz δ 8.00(d, 2H, J=8.28Hz), 7.67 (d, 2H, J=8.28Hz), 7.24(d, 1H, J=2.21Hz), 7.14(dd, 1H, J=8.28, 2.21Hz), 6.58(d, 1H, J=8.28Hz), 4.73(q, 1H, J=6.71Hz), 4.29(s, 2H), 4.20(q, 2H, J=7.17Hz), 4.10(s, 2H), 3.64(m, 2H), 3.54(s, 2H), 3.48(m, 2H), 3.42(s, 3H), 2.47(m, 4H), 2.25(s, 3H), 1.64(d, 3H, J=6.71Hz), 1.24(t, 3H, J=7.17Hz),

Ethyl 2-{4-[({4-[(4-isobutyryl-1-piperazinyl)methyl]-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.00(d, 2H, J=8.28Hz), 7.68 (d, 2H, J=8.28Hz), 7.24(d, 1H, J=2.48Hz), 7.14(dd, 1H, J=8.55, 2.48Hz), 6.59(d, 1H, J=8.55Hz), 4.74(q, 1H, J=6.71Hz), 4.30(s, 2H), 4.20(q, 2H, J=7.17Hz), 3.58(m, 6H), 2.79(m, 1H), 2.46(t, 4H, J=4.55Hz), 2.24(s, 3H), 1.64(d, 3H, J=6.71Hz), 1.24(t, 3H, J=7.17Hz), 1.13(d, 6H, J=6.71Hz),

Ethyl 2-{4-[({4-{[4-(2,2-dimethylpropanoyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.00(d, 2H, J=8.28Hz), 7.68 (d, 2H, J=8.28Hz), 7.24(d, 1H, J=2.21Hz), 7.15(dd, 1H, J=8.28, 2.21Hz), 6.60(d, 1H, J=8.28Hz), 4.73(q, 1H, J=6.71Hz), 4.31(s, 2H), 4.20(q, 2H, J=7.08Hz), 3.66(t, 4H, J=4.69Hz), 3.52(s, 2H), 2.48(t, 4H, J=4.69Hz), 2.26(s, 3H), 1.65(d, 3H, J=6.71Hz), 1.27(m, 12H),

Ethyl 2-{4-[({4-({4-[(4-fluoroanilino)carbonyl]-1-piperazinyl}methyl)-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.04(d, 2H, J=8.28Hz), 7.69 (d, 2H, J=8.28Hz), 7.33(m, 2H), 7.17(dd, 1H, J=8.55, 2.21Hz), 6.96(m, 2H), 6.52(d, 1H, J=8.55Hz), 4.72(q, 1H, J=6.90Hz), 4.27(m, 4H), 3.59(d, 1H, J=52Hz), 3.51(d, 1H, J=52Hz), 3.34(m, 4H), 2.33(t, 4H, J=4.97Hz), 2.22(s, 3H), 1.62(d, 3H, J=6.90Hz), 1.26(t, 3H, J=7.17Hz),

Ethyl 2-{4-[({4-({4-[(3-methoxyanilino)carbonyl]-1-piperazinyl}methyl)-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.04(d, 2H, J=8.28Hz), 7.69 (d, 2H, J=8.28Hz), 7.31(d, 1H, J=2.21Hz), 7.16(m, 2H), 6.89 (m, 2H), 6.59(dd, 1H, J=8.28, 2.21Hz), 6.53(m, 1H), 4.73(q, 1H, J=6.90Hz), 4.27(m, 4H), 3.79(s, 3H), 3.56(m, 2H), 3.37 (m, 4H), 2.36(t, 4H, J=4.69Hz), 2.23(s, 3H), 1.63(d, 3H, J=6.90Hz), 1.26(t, 3H, J=7.17Hz),

Ethyl 2-{4-[({4-{[4-(aminocarbonyl)-1-piperazinyl]methyl}-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.01(d, 2H, J=8.28Hz), 7.68 (d, 2H, J=8.28Hz), 7.26(d, 1H, J=2.21Hz), 7.15(dd, 1H, J=8.55, 2.21Hz), 6.56(d, 1H, J=8.55Hz), 4.83(s, 2H), 4.71(q, 1H, J=6.81Hz), 4.26(m, 4H), 3.55(m, 2H), 3.34(m, 4H), 2.41 (t, 4H, J=4.55Hz), 2.24(s, 3H), 1.63(d, 3H, J=6.81Hz), 1.25(t, 3H, J=7.04Hz),

Ethyl 2-{4-[({4-({4-[(cyclohexylamino)carbonyl]-1-piperazinyl}methyl)-2-4-(trifluoromethyl)phenyl]-1,3-thiazol-5-yl}methyl)sulfanyl]-2-methylphenoxy}propanoate $^1$H NMR (CDCl$_3$) 300MHz δ 8.00(d, 2H, J=8.28Hz), 7.67 (d, 2H, J=8.28Hz), 7.26(d, 1H, J=2.21Hz), 7.14(dd, 1H, J=8.55, 2.21Hz), 6.54(d, 1H, J=8.55Hz), 4.72(q, 1H, J=6.81Hz), 4.49(d, 1H, J=7.45Hz), 4.25(m, 4H), 3.64(m, 1H), 3.52(m, 2H), 3.28(m, 4H), 2.38(t, 4H, J=4.83Hz), 2.24 (s, 3H), 1.95(m, 2H), 1.65(m, 7H), 1.38(m, 2H), 1.24(t, 3H, J=7.04Hz), 1.10(m, 2H),

Ethyl 2-{2-methyl-4-[({4-({4-[(propylamino)carbonyl]-1-piperazinyl}methyl)-2-[4-(trifluoromethyl)phenyl]-1,3-thiazol-5-yl}methyl)sulfanyl]phenoxy}propanoate $^1$H NMR (CDCl$_3$) 300MHz δ 8.01(d, 2H, J=8.00Hz), 7.68 (d, 2H, J=8.00Hz), 7.27(d, 1H, J=2.21Hz), 7.14(dd, 1H, J=8.28, 2.21Hz), 6.54(d, 1H, J=8.28Hz), 4.75(m, 2H), 4.26 (m, 4H), 3.53(m, 2H), 3.33(m, 4H), 3.19(m, 2H), 2.36(t, 4H, J=4.69Hz), 2.23(s, 3H), 1.64(d, 3H, J=6.90Hz), 1.52(m, 2H), 1.25(t, 3H, J=7.17Hz), 0.92(t, 3H, J=7.45Hz),

Ethyl 2-{4-[({4-({4-[(ethylamino)carbonyl]-1-piperazinyl}methyl)-2-[4-(trifluoromethyl)phenyl]-1,3-thiazol-5-yl}methyl)sulfanyl]-2-methylphenoxy}propanoate $^1$H NMR (CDCl$_3$) 300MHz δ 8.02(d, 2H, J=8.28Hz), 7.69 (d, 2H, J=8.28Hz), 7.27(d, 1H, J=2.21Hz), 7.15(dd, 1H, J=8.55, 2.21Hz), 6.54(d, 1H, J=8.55Hz), 4.72(m, 2H), 4.26 (m, 4H), 3.54(m, 2H), 3.29(m, 6H), 2.38(t, 4H, J=4.28Hz), 2.25(s, 3H), 1.65(d, 3H, J=6.90Hz), 1.26(t, 3H, J=7.04Hz), 1.15(t, 3H, J=7.31Hz),

Ethyl [2-methyl-4-({[4-{[3-(5-methyl-1,2,4-oxadiazol-3-yl)phenoxy]methyl}-2-(4-{trifluoromethyl}phenyl)-1,3-thiazol-5-yl]methyl}sulfanyl)phenoxy]acetate To a stirred solution of ethyl [4-({[4-(hydroxymethyl)-2-(4-{trifluoromethyl}phenyl)-1,3-thiazol-5-yl]methyl}sulfanyl)-2-methylphenoxy]acetate (40mg, 0.08mmoles, 1eq) in dry toluene (2ml) was added 3-(5-methyl-1,2,4-oxadiazol-3-yl)phenol (15mg, 0.088mmoles, 1.1eq) followed by triphenylphosphine (25mg, 0.096mmoles, 1.2eq) as a solid. Diisopropylazodicarboxylate (0.017ml, 0.088mmoles, 1.1eq) was then added dropwise and the reaction was stirred for 2hours at room temperature. The reaction was then partitioned between EtOAc and H$_2$O. After the separation of the phases the organic phase washed with 0.1N NaOH, brine, dried over Na$_2$SO$_4$, filtered, concentrated in vacuo and purified via flash chromatography (10% EtOAc/Hexanes to 35% EtOAc/Hexanes) to yield 40mg (76%) of product.

$^1$H (CDCl$_3$) 400MHz δ 8.02(d, 2H, J=8.20Hz), 7.68(m, 4H), 7.38(t, 1H, J=7.95Hz), 7.19(d, 1H, J=1.54), 7.12(dd, 1H, J=8.37, 2.39Hz), 7.06(dd, 1H, J=8.20, 2.39Hz), 6.57(d, 1H, J=8.20Hz), 4.95(s, 2H), 4.59(s, 2H), 4.27(s, 2H), 4.22(q, 2H, J=7.12Hz), 2.65(s, 3H), 2.18(s, 3H), 1.25(t, 3H, J=7.12Hz). TLC(50% EtOAc/Hexanes) R$_f$=0.76

The following compounds were made using the general Mitsunobu reaction conditions detailed above:

Ethyl 2-{2-methyl-4-[({4-{[3-(5-methyl-1,2,4-oxadiazol-3-yl)phenoxy]methyl}-2-[4-(trifluoromethyl)phenyl]-1,3-thiazol-5-yl}methyl)sulfanyl]phenoxy}propanoate $^1$H NMR (CDCl$_3$) 400MHz δ 8.03(d, 2H, J=8.20Hz), 7.69 (m, 4H), 7.39(m, 1H), 7.20(m, 1H), 7.09(m, 2H), 6.55(d, 1H, J=8.37Hz), 4.99(d, 1H, J=62Hz), 4.95(d, 1H, J=62Hz), 4.70 (q, 1H, J=6.78Hz), 4.16(q, 2H, J=7.18Hz), 2.65(m, 3H), 2.18 (s, 3H), 1.61(d, 3H, J=6.78Hz), 1.20(t, 3H, J=7.18Hz),

Ethyl (2-methyl-4-{[(4-{[3-(5-methyl-1,2,4-oxadiazol-3-yl)phenoxy]methyl}-2-phenyl-1,3-thiazol-5-yl)methyl]sulfanyl}phenoxy)acetate ¹H NMR (CDCl₃) 400MHz δ 7.91(m, 2H), 7.69(m, 2H), 7.40(m, 4H), 7.20(d, 1H, J=2.39Hz), 7.13(dd, 1H, J=8.37, 2.39Hz), 7.07(dd, 1H, J=8.37, 2.39Hz), 6.57(d, 1H, J=8.37Hz), 5.29(s, 2H), 4.59(s, 2H), 4.27(s, 2H), 4.23(q, 2H, J=7.18Hz), 2.65(s, 3H), 2.19(s, 3H), 1.27(t, 3H, J=7.18Hz).

Ethyl [2-methyl-4-({[2-(4-{trifluoromethyl}phenyl)-4-(phenoxymethyl)-1,3-thiazol-5-yl]methyl}sulfanyl phenoxy]acetate ¹H NMR (CDCl₃) 300MHz δ 8.04(d, 2H, J=8.23Hz), 7.71 (d, 2H, J=8.23Hz), 7.34(m, 2H), 7.23(d, 1H, J=2.39Hz), 7.15 (dd, 1H, J=8.49, 2.39Hz), 7.00(m, 3H), 6.59(d, 1H, J=8.49Hz), 4.94(s, 2H), 4.64(s, 2H), 4.27(m, 4H), 2.26(s, 3H), 1.32(t, 3H, J=7.17Hz). TLC(30% EtOAc/Hexanes) R_f=0.71

Ethyl [2-methyl-4-({[4-[(2-methylphenoxy)methyl]-2-(4-{trifluoromethyl}phenyl)-1,3-thiazol-5-yl]methyl}sulfanyl)phenoxy]acetate ¹H (CDCl₃) 300MHz δ 8.05(d, 2H, J=8.23Hz), 7.72(d, 2H, J=8.23Hz), 7.21(m, 4H), 6.93(m, 2H), 6.59(d, 1H, J=8.49Hz), 5.00(s, 2H), 4.64(s, 2H), 4.29(m, 4H), 2.26(m, 6H), 1.32(t, 3H, J=7.17Hz). TLC(20% EtOAc/Hexanes) R_f=0.70

Ethyl [2-methyl-4-({[4-[(3-methylphenoxy)methyl]-2-(4-{trifluoromethyl}phenyl)-1,3-thiazol-5-yl]methyl}sulfanyl)phenoxy]acetate ¹H (CDCl₃) 300MHz δ 8.05(d, 2H, J=8.49Hz), 7.71(d, 2H, J=8.49Hz), 7.35(m, 1H), 7.26(dd, 1H, J=2.39, 0.53Hz), 7.21 (t, 1H, J=7.43Hz), 7.15(ddd, 1H, J=8.49, 2.39, 0.53Hz), 6.81 (m, 2H), 6.60(d, 1H, J=8.49Hz), 4.92(s, 2H), 4.65(s, 2H), 4.29(m, 4H), 2.38(s, 3H), 2.25(s, 3H), 1.32(t, 3H, J=7.17Hz). TLC(20% EtOAc/Hexanes) R_f=0.70

Ethyl [2-methyl-4-({[4-[(4-methylphenoxy)methyl]-2-(4-{trifluoromethyl}phenyl)-1,3-thiazol-5-yl]methyl}sulfanyl)phenoxy]acetate ¹H (CDCl₃) 300MHz δ 8.04(d, 2H, J=8.23Hz), 7.71(d, 2H, J=8.23Hz), 7.27(dd, 1H, J=2.39, 0.80Hz), 7.14(m, 3H), 6.88 (d, 2H, J=8.49Hz), 6.60(d, 1H, J=8.23Hz), 4.92(s, 2H), 4.64 (s, 2H), 4.29(m, 4H), 2.33(s, 3H), 2.26(s, 3H), 1.32(t, 3H, J=7.17Hz). TLC(20% EtOAc/Hexanes) R_f=0.70

Ethyl [4-({[4-[(3-cyanophenoxy)methyl]-2-(4-{trifluoromethyl}phenyl)-1,3-thiazol-5-yl]methyl}sulfanyl)-2-methylphenoxy]acetate ¹H (CDCl₃) 300MHz δ 8.03(d, 2H, J=8.23Hz), 7.71(d, 2H, J=8.23Hz), 7.24(m, 6H), 6.61(d, 1H, J=8.23Hz), 4.88(s, 2H), 4.67(s, 2H), 4.28(m, 4H), 2.24(s, 3H), 1.31(t, 3H, J=7.17Hz) TLC(20% EtOAc/Hexanes) R_f=0.52

Ethyl [4-({[4-[(4-cyanophenoxy)methyl]-2-(4-{trifluoromethyl}phenyl)-1,3-thiazol-5-yl]methyl}sulfanyl)-2-methylphenoxy]acetate ¹H (CDCl₃) 300MHz δ 8.03(d, 2H, J=8.23Hz), 7.73(d, 2H, J=8.23Hz), 7.61(d, 2H, J=9.03Hz), 7.23(dd, 1H, J=2.39, 0.53Hz), 7.14(ddd, 1H, J=8.49, 2.39, 0.53Hz), 7.01(d, 2H, J=9.03Hz), 6.59(d, 1H, J=8.49Hz), 4.91(s, 2H), 4.66(s, 2H), 4.28(m, 4H), 2.25(s, 3H), 1.32(t, 3H, J=7.17Hz). TLC(20% EtOAc/Hexanes) R_f=0.52

Ethyl [2-methyl-4-({[4-{[4-(5-methyl-1,2,4-oxadiazol-3-yl)phenoxy]methyl}-2-(4-{trifluoro}methylphenyl)-1,3-thiazol-5-yl]methyl}sulfanyl phenoxy]acetate ¹H (CDCl₃) 400MHz δ 7.99(m, 4H), 7.67(d, 2H, J=8.20Hz), 7.21(dd, 1H, J=2.39, 0.68Hz), 7.10(m, 1H), 7.02 (m, 2H), 6.54(d, 1H, J=8.37Hz), 4.90(s, 2H), 4.59(s, 2H), 4.23(m, 4H), 2.62(s, 3H), 2.20(s, 3H), 1.26(t, 3H, J=7.18Hz). TLC(50% EtOAc/Hexanes) R_f=0.68

Ethyl (2-methyl-4-{[(4-{[4-(5-methyl-1,2,4-oxadiazol-3-yl)phenoxy]methyl}-2-phenyl-1,3-thiazol-5-yl)methyl]sulfanyl}phenoxy)acetate ¹H NMR (CDCl₃) 400MHz δ 7.98(d, 2H, J=8.89Hz), 7.89 (m, 2H), 7.42(m, 3H), 7.21(d, 1H, J=2.39Hz), 7.10(dd, 1H, J=8.37, 2.39Hz), 7.02(d, 2H, J=8.89Hz), 6.54(d, 1H, J=8.37Hz), 4.89(s, 2H), 4.59(s, 2H), 4.23(q, 2H, J=7.18Hz), 3.47(s, 2H), 2.62(s, 3H), 2.20(s, 3H), 1.27(t, 3H, J=7.18Hz),

Ethyl 2-[2-methyl-4-[({4-{[4-(5-methyl-1,2,4-oxadiazol-3-yl)phenoxy]methyl}-2-4-(trifluoromethyl)phenyl]-1,3-thiazol-5-yl}methyl)sulfanyl]phenoxy}propanoate ¹H NMR (CDCl₃) 300MHz δ 8.04(m, 4H), 7.71(d, 2H, J=8.23Hz), 7.25(d, 1H, J=2.39Hz), 7.11(dd, 1H, J=8.49, 2.39Hz), 7.06(d, 2H, J=9.03Hz), 6.57(d, 1H, J=8.49Hz), 4.97 (d, 1H, J□.68Hz), 4.91(d, 1H, J=68Hz), 4.73(q, 1H, J=6.81Hz), 4.29(s, 2H), 4.20(q, 2H, J=7.17Hz), 2.67(s, 3H), 2.23(s, 3H), 1.65(d, 3H, J=6.81Hz), 1.25(t, 3H, J=7.17Hz),

Ethyl 2-(2-methyl-4-{[(4-{[4-(5-methyl-1,2,4-oxadiazol-3-yl)phenoxy]methyl}-2-phenyl-1,3-thiazol-5-yl)methyl]sulfanyl}phenoxy)propanoate ¹H NMR (CDCl₃) 400MHz δ 7.99(d, 2H, J=9.06Hz), 7.89 (m, 2H), 7.42(m, 3H), 7.20(d, 1H, J=2.22Hz), 7.06(dd, 1H, J=8.37, 2.22Hz), 7.02(d, 2H, J=9.06Hz), 6.52(d, 1H, J=8.37Hz), 4.89(d, 1H, J=62Hz), 4.85(d, 1H, J=62Hz), 4.68 (q, 1H, J=6.78Hz), 4.23(s, 2H), 4.17(q, 2H, J=7.12Hz), 2.62 (s, 2H), 2.19(s, 3H), 1.61(d, 3H, J=6.78Hz), 1.21(t, 3H, J=7.12Hz),

4-(Chloromethyl)-2-methylphenyl methyl ether

To a stirred solution of (4-methoxy-3-methylphenyl)methanol (2.31g, 15.18mmoles, 1eq) in anhydrous CH₂Cl₂ (50ml, 0.3M) was added hexachloroethane (3.59g, 15.18mmoles, 1eq) and triphenylphosphine (3.98g, 15.18mmoles, 1eq). This mixture was stirred at room temperature overnight at which point the reaction was transferred to a separatory funnel and washed with H₂O, brine, dried over Na₂SO₄, filtered, concentrated in vacuo and filtered through a plug of silica gel (30% EtOAc/Hexanes) to yield 2.59g (100%) of product.

¹H NMR (CDCl₃) 400MHz δ 7.16(m, 2H), 6.76(d, 1H, J=8.10Hz), 4.52(s, 2H), 3.81(s, 3H), 2.19(s, 3H),

(4-Methoxy-3-methylbenzyl)(triphenyl)phosphonium chloride

To a 250ml round-bottom flask equipped with a magnetic stir-bar and $N_2$ inlet was added 4-(Chloromethyl)-2-methylphenyl methyl ether (2.59g, 15.18mmoles, 1eq), dry toluene (50ml, 0.3M) and triphenylphosphine (3.98g, 15.18mmoles, 1eq). The reaction mixture was refluxed overnight. After cooling to room temperature the solvent was removed in vacuo, the residue washed with hexanes and the solid/liquid mixture was filtered to yield 4.48g (71%) of solid product.

$^1$H NMR (CDCl$_3$) 400MHz δ 7.66(m, 15H), 6.93(m, 1H), 6.54(m, 2H), 5.24(d, 2H, J□.79Hz), 3.68(s, 3H), 1.90(s, 3H),

4-[(Tetrahydro-2H-pyran-2-yloxy)methyl]-2-[4-trifluoromethyl)phenyl]-1,3-thiazole-5-carbaldehyde To a stirred mixture of pyridinium chlorochromate (6.9g, 32.12mmoles, 4eq) in dry CH$_2$Cl$_2$(40ml, 0.2M) was added {4-[(tetrahydro-2H-pyran-2-yloxy)methyl]-2-[4-(trifluoromethyl)phenyl]-1,3-thiazol-5-yl}methanol (3.0g, 8.03mmoles, 1eq) in CH$_2$Cl$_2$(10ml). The mixture was stirred at room temperature for 4hours at which time the reaction mixture was quenched by allowing it to stir with sat. NaHCO$_3$. Once the quenching had ceased the reaction was filtered through Celite and the filtrate was transferred to a separatory funnel where the phases were separated. The organic phase was dried over Na$_2$SO$_4$ and concentrated in vacuo to yield 2.18g (73%) of clean aldehyde. The crude product was used without purification.

$^1$H NMR (CDCl$_3$) 400MHz δ 10.39(s, 1H), 8.09(d, 2H, J=8.28Hz), 7.70(d, 2H, J=8.28Hz), 5.22(d, 1H, J=97Hz), 4.96(d, 1H, J=97Hz), 4.83(m, 1H), 3.87(m, 1H), 3.58(m, 1H), 1.81(m, 2H), 1.61(m, 4H),

5-[(E)-2-(4-Methoxy-3-methylphenyl)ethenyl]-4-[(tetrahydro-2H-pyran-2-yloxy)methyl]-2-[4-(trifluoromethyl)phenyl]-1,3-thiazole To a suspension of NaH (60% dispersion in mineral oil, 242mg, 6.32mmoles, 1.4eq) in dry CH$_2$Cl$_2$(15ml) was added (4-Methoxy-3-methylbenzyl)(triphenyl)phosphonium chloride (2.62g, 6.32mmoles, 1.4eq). This was allowed to stir at room temperature for 1.5hours followed by the dropwise addition of 4-[(tetrahydro-2H-pyran-2-yloxy)methyl]-2-[4-(trifluoromethyl)phenyl]-1,3-thiazole-5-carbaldehyde (1.68g, 4.51mmoles, 1eq) in anhydrous carbon tetrachloride (25ml). The resulting reaction mixture was refluxed overnight at which point (after cooling to room temperature) the reaction washed with 1N NaOH, H$_2$O, brine, dried over Na$_2$SO$_4$ and concentrated in vacuo to yield a >100% yield of a light green oil. The crude material was used without purification.

$^1$H NMR (CDCl$_3$) 400MHz δ 8.05(d, 2H, J=8.24Hz), 7.68 (d, 2H, J=8.24Hz), 7.29(m, 3H), 6.85(m, 2H), 4.98(d, 1H, J=12.09Hz), 4.81(m, 2H), 4.01(m, 1H), 3.86(m, 3H), 3.62(m, 1H), 2.26(s, 3H), 1.72(m, 6H),

{5-[2-(4-Methoxy-3-methylphenyl)ethyl]-2-[4-(trifluoromethyl)phenyl]-1,3-thiazol-4-yl}methanol To a stirred solution of 5-[(E)-2-(4-Methoxy-3-methylphenyl)ethenyl]-4-[(tetrahydro-2H-pyran-2-yloxy)methyl]-2-[4-(trifluoromethyl)phenyl]-1,3-thiazole (2.20g, 4.51mmoles, 1eq) in EtOH (50ml 0.1M) was added 10% Pd/C (500mg). The system was degassed using an aspirator and H$_2$ was introduced via a balloon. The reaction was heated to 60° C. overnight which, after cooling to room temperature, was filtered through Celite, washed with EtOAc and concentrated in vacuo. This reaction yielded after chromatography 760mg (41%) of clean alcohol.

$^1$H NMR (CDCl$_3$) 400MHz δ 7.98(d, 2H, J=8.24Hz), 7.66 (d, 2H, J=8.24Hz), 6.91(m, 2H), 6.72(d, 1H, J=8.10Hz), 4.54 (s, 2H), 3.80(s, 3H), 3.11(t, 2H, J=7.42Hz), 2.87(t, 2H, J=7.42Hz), 2.18(s, 3H), 2.05(br s, 1H),

4-(Bromomethyl)-5-[2-4-methoxy-3-methylphenyl) ethyl]-2-[4-(trifluoromethyl)phenyl]-1,3-thiazole To a 100ml round-bottom flask equipped with a magnetic stir-bar and N$_2$ inlet was added {5-[2-(4-Methoxy-3-methylphenyl)ethyl]-2-[4-(trifluoromethyl)phenyl]-1,3-thiazol-4-yl}methanol (0.708g, 1.74mmoles, 1eq), CH$_2$Cl$_2$(20ml), carbon tetrabromide (0.634g, 1.91mmoles, 1.1eq) and triphenylphosphine (0.501g, 1.91mmoles, 1.1eq) in that order. The reaction was stirred overnight at which time it was diluted with CH$_2$Cl$_2$ and washed with H$_2$O, brine, dried over Na$_2$SO$_4$, concentrated in vacuo and purified via silica gel chromatography to yield 573mg (70%) of product.

$^1$H NMR (CDCl$_3$) 400MHz δ 7.97(d, 2H, J=8.10Hz), 7.64 (d, 2H, J=8.10Hz), 6.94(m, 2H), 6.73(d, 1H, J=8.10Hz), 4.46 (m, 2H), 3.79(m, 3H), 3.12(t, 2H, J=7.24Hz), 2.91(t, 2H, J=7.24Hz), 2.19(s, 3H),

4-(2-{4-(Bromomethyl)-2-[4-(trifluoromethyl)phenyl]-1,3-thiazol-5-yl}ethyl)-2-methylphenol To a 50ml round-bottom flask equipped with a magnetic stir-bar, an addition funnel and N$_2$ inlet was added 4-(Bromomethyl)-5-[2-(4-methoxy-3-methylphenyl)ethyl]-2-[4-(trifluoromethyl)phenyl]-1,3-thiazole (468mg, 1.0mmoles, 1eq) and dry CH$_2$Cl$_2$(15ml, 0.1M). The mixture was cooled to −78° C. (dry ice/acetone) after which boron tribromide (1M in CH$_2$Cl$_2$, 3ml, 3.0mmoles, 3eq) was added dropwise over the course of 15minutes. After the addition was complete, the cold bath was removed and the reaction was allowed to warm to room temperature and stirred for 1hour. After this time, the reaction was cooled to 0° C. and quenched very carefully with water. Once the reaction was quenched, it was transferred to a separatory funnel where the phases were separated. The aqueous fraction washed three times with CH$_2$Cl$_2$ and the combined organic fractions were dried over Na$_2$SO$_4$, filtered, concentrated in vacuo to yield a quantitative yield of the titled phenol. The product was used without purification.

$^1$H NMR (CDCl$_3$) 400MHz δ 7.96(d, 2H, J=8.28Hz), 7.65 (d, 2H, J=8.28Hz), 6.93(m, 1H), 6.85(d, 1H, J=8.10Hz), 6.68 (d, 1H, J=8.10Hz), 5.42(br s, 1H), 4.45(s, 2H), 3.10(t, 2H, J=7.41Hz), 2.89(t, 2H, J=7.41Hz), 2.20(s, 3H),

The following compounds were made by amine displacement as described above for General Alkylation with an Amine:

4-(2-{4-{[4-(4-Methoxyphenyl)-1-piperazinyl]methyl}-2-[4-(trifluoromethyl)phenyl]-1,3-thiazol-5-yl}ethyl)-2-methylphenol $^1$H NMR (CDCl$_3$) 400MHz δ 7.94(d, 2H, J=8.28Hz), 7.59 (d, 2H, J=8.28Hz), 6.91(d, 1H, J=2.24Hz), 6.86(d, 2H, J=9.31Hz), 6.80(d, 2H, J=9.31Hz), 6.74(dd, 1H, J=8.10, 2.24Hz), 6.58(s, 1H), 6.51(d, 1H, J=8.10Hz), 3.73(s, 3H), 3.58(s, 2H), 3.12(t, 2H, J=7.50Hz), 3.05(t, 4H, J=4.48Hz), 2.84(t, 2H, J=7.50Hz), 2.64(t, 4H, J=4.48Hz), 2.20(s, 3H),

1-{4-[4-[{5-[2-(4-Hydroxy-3-methylphenyl)ethyl]-2-[4-(trifluoromethyl)phenyl]-1,3-thiazol-4-yl}methyl]-1-piperazinyl]phenyl}ethanone $^1$H NMR (CD$_3$OD) 400MHz δ 8.07(d, 2H, J=8.28Hz), 7.85(d, 2H, J=9.14Hz), 7.73(d, 2H, J=8.28Hz), 6.92(d, 2H, J=9.14Hz), 6.88(d, 1H, J=2.24Hz), 6.77(dd, 1H, J=8.28, 2.24Hz), 6.60(d, 1H, J=8.28Hz), 3.49(s, 2H), 3.32(t, 4H, J=4.83Hz), 3.18(t, 2H, J=7.07Hz), 2.88(t, 2H, J=7.07Hz), 2.51(t, 4H, J=4.83Hz), 2.47(s, 3H), 2.10(s, 3H),

4-(2-{4-{[4-(3-Methoxyphenyl)-1-piperazinyl]methyl}-2-[4-(trifluoromethyl)phenyl]-1,3-thiazol-5-yl}ethyl)-2-methylphenol $^1$H NMR (CD$_3$OD) 400MHz δ 8.07(d, 2H, J=8.10Hz), 7.72(d, 2H, J=8.10Hz), 7.09(t, 1H, J=8.28Hz), 6.88(s, 1H), 6.77(dd, 1H, J=8.45, 2.24Hz), 6.59(d, 1H, J=8.45Hz), 6.51(dd, 1H, J=8.28, 2.24Hz), 6.46(t, 1H, J=2.24Hz), 6.38(dd, 1H, J=8.28, 2.24Hz), 3.72(s, 3H), 3.49(s, 2H), 3.18(t, 2H, J=6.47Hz), 3.09(br s, 4H), 2.87(t, 2H, J=6.47Hz), 2.52(br s, 4H), 2.10(s, 3H),

4-(2-{4-{[4-(4-Chlorophenyl)-1-piperazinyl]methyl}-2-[4-(trifluoromethyl)phenyl]1,3-thiazol-5-yl}ethyl)-2-methylphenol $^1$H NMR (CD$_3$OD) 400MHz δ 8.07(d, 2H, J=8.10Hz), 7.73(d, 2H, J=8.10Hz), 7.15(d, 2H, J=9.14Hz), 6.89(m, 3H), 6.77(dd, 1H, J=8.45, 2.41Hz), 6.59(d, 1H, J=8.45Hz), 3.49(s, 2H), 3.18(t, 2H, J=7.16Hz), 3.09(t, 4H, J=5.09Hz), 2.87(t, 2H, J=7.16Hz), 2.53(t, 4H, J=5.09Hz), 2.10(s, 3H),

2-[4-(2-{4-{[4-(4-Methoxyphenyl)-1-piperazinyl]methyl}-2-[4-(trifluoromethyl)phenyl]-1,3-thiazol-5-yl}ethyl)-2-methylphenoxy]-2-methylpropanoic acid To a 25ml round-bottom flask equipped with a magnetic stir-bar and N$_2$ inlet was added 4-(2-{4-{[4-(4-Methoxyphenyl)-1-piperazinyl]methyl}-2-[4-(trifluoromethyl)phenyl]-1,3-thiazol-5-yl}ethyl)-2-methylphenol (53mg, 0.094mmoles, 1eq) in acetone (2ml, 0.05M) followed by the addition of 2-trichloromethyl-2-propanol (33mg, 0.188mmoles, 2eq) and NaOH (pellets, 30mg, 0.752mmoles, 8eq). This was stirred at room temperature overnight after which the acetone was removed in vacuo and the resulting residue was partitioned between EtOAc and 1N HCl. The phases were then separated and the organic fraction washed with brine, dried over Na$_2$SO$_4$ and concentrated in vacuo to yield after chromatography 23mg (40%) of product.

$^1$H NMR (CDCl$_3$) 400MHz δ 7.95(d, 2H, J=8.28Hz), 7.62 (d, 2H, J=8.28Hz), 6.88(m, 5H), 6.67(br s, 1H), 6.54(br s, 1H), 3.72(s, 3H), 3.61(s, 2H), 3.23(m, 8H), 2.80(m, 4H), 2.15(s, 3H), 1.54(s, 6H),
MS(ES$^-$) M–H=652.2

The following compounds were also made by alkylation of a phenol with trichloromethyl-2-propanol as above:

2-[4-(2-{4-{[4-(4-Chlorophenyl)-1-piperazinyl]methyl}-2-[4-(trifluoromethyl)phenyl]-1,3-thiazol-5-yl}ethyl)-2-methylphenoxy]-2-methylpropanoic acid $^1$H NMR (CD$_3$OD) 400MHz δ 7.99(d, 2H, J=8.28Hz), 7.66(d, 2H, J=8.28Hz), 7.55(s, 1H), 7.14(d, 2H, J=8.10Hz), 6.91(s, 1H), 6.82(d, 2H, J=8.10Hz), 6.66(br s, 1H), 3.55(s, 2H), 3.28(m, 2H) buried under MeOH signal, 3.12(br s, 4H), 2.85(s, 2H), 2.65(br s, 4H), 2.13(s, 3H), 1.52(s, 6H),
MS(ES$^+$) M+H=659.0

2-[4-(2-{4-{[4-(3-Methoxyphenyl)-1-piperazinyl]methyl}-2-[4-(trifluoromethyl)phenyl]-1,3-thiazol-5-yl}ethyl)-2-methylphenoxy]-2-methylpropanoic acid $^1$H NMR (CD$_3$OD) 400MHz δ 8.02(d, 2H, J=8.10Hz), 7.68(d, 2H, J=8.10Hz), 7.09(t, 1H, J=8.10Hz), 6.92(s, 1H), 6.76(m, 2H), 6.50(dd, 1H, J=8.10, 2.07Hz), 6.42(t, 1H, J=2.07Hz), 6.37(dd, 1H, J=8.10, 2.07Hz), 3.72(s, 3H), 3.51 (s, 2H), 3.28(m, 2H) buried under MeOH signal, 3.12(m, 4H), 2.83(t, 2H, J=7.16Hz), 2.61(m, 4H), 2.15(s, 3H), 1.48(s, 6H),
MS(ES$^-$) M–H=652.1

2-[4-(2-{4-{[4-(4-Acetylphenyl)-1-piperazinyl]methyl}-2-[4-(trifluoromethyl)phenyl]-1,3-thiazol-5-yl}ethyl)-2-methylphenoxy]-2-methylpropanoic acid $^1$H NMR (CD$_3$OD) 400MHz δ 8.01(d, 2H, J=8.10Hz), 7.82(d, 2H, J=9.14Hz), 7.67(d, 2H, J=8.10Hz), 6.90(m, 3H), 6.66(m, 2H), 3.61(s, 2H), 3.37(br s, 4H), 3.13(t, 2H, J=6.81Hz), 2.82(t, 2H, J=6.81Hz), 2.68(br s, 4H), 2.44(s, 3H), 2.11(s, 3H), 1.50(s, 6H),

2-Methyl-2-{2-methyl-4-[({4-[4-(trifluoromethyl)benzyl]-2-[4-(trifluoromethyl)phenyl]-1,3-thiazol-5-yl}methyl)sulfanyl]phenoxy}propanoic acid From 2-methyl-4-[({4-(4-trifluoromethyl)benzyl]-2-[4-(trifluoromethyl)phenyl]-1,3-thiazol-5-yl}methyl)sulfanyl] phenol (0.021g, 0.04mmol), 2-methyl-2-{2-methyl-4-[({4-[4-(trifluoromethyl)benzyl]-2-[4-(trifluoromethyl)phenyl]-1,3-thiazol-5-yl}methyl)sulfanyl]phenoxy}propanoic acid (0.006g, 25%) was obtained as a white solid.

$^1$H NMR (CD$_3$OD): δ 8.02(d, 2H), 7.78(d, 2H), 7.60(d, 2H), 7.30(d, 2H), 7.23(s, 1H), 7.16(d, 1H), 6.73(d, 1H), 4.29 (s, 2H), 4.00(s, 2H), 2.17(s, 3H), 1.61(s, 6H); $^{19}$F NMR (CD$_3$OD): δ –64.18(s), –64.73(s); MS m/z 626(M+1); HPLC RT 4.273(C18 4.2×100mm, 0-100% ACN/H$_2$O (0.1% TFA), 6min @ 2ml/min @254/220nm).

2-Methyll-2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoic acid From 2-methyl-4-[({4-(4-trifluoromethoxy)benzyl]-2-[4-(trifluoromethyl)phenyl]-1,3-thiazol-5-yl}methyl)sulfanyl] phenol (0.048g, 0.086mmol), 2-methyl-2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoic acid (0.013g, 23%) was obtained as a white solid.

$^1$H NMR (CD$_3$OD): δ 8.04(d, 2H), 7.74(d, 2H), 7.20(m, 6H), 6.72(d, 1H), 4.26(s, 2H), 3.95(s, 2H), 2.15(s, 3H), 1.61 (s, 6H); $^{19}$F NMR (CD$_3$OD): 6-59.86(s), –64.72(s); MS m/z 642(M+1); HPLC RT 4.307(C18 4.2×100mm, 0-100% ACN/H$_2$O (0.1% TFA), 6min @ 2ml/min @254/220nm).

2-{4-[({4-(4-methoxybenzyl)-2-[4-(trifluoromethyl)phenyl]-1,3-thiazol-5-yl}methyl)sulfanyl]-2-methylphenoxy}-2-methylpropanoic acid From 4-[({4-(4-methoxybenzyl)-2-[4-(trifluoromethyl)phenyl]-1,3-thiazol-5-yl}methyl)sulfanyl]-2-methylphenol (0.022g, 0.04mmol), 2-{4-[({4-(4-methoxybenzyl)-2-[4-(trifluoromethyl)phenyl]-1,3-thiazol-5-yl}methyl)sulfanyl]-2-methylphenoxy}-2-methylpropanoic acid (0.003g, 12%) was obtained as a white solid.

¹H NMR (CD₃OD): δ8.04(d, 2H), 7.76(d, 2H), 7.19(s, 1H), 7.14(d, 1H), 7.02(d, 2H), 6.81(d, 2H), 6.69(d, 1H), 4.21 (s, 2H), 3.83(s, 2H), 3.78(s, 3H), 2.17(s, 3H), 1.60(s, 6H); MS m/z 588(M+1); HPLC RT 4.136(C18 4.2×100mm, 0-100% ACN/H₂O (0.1% TFA), 6min @ 2ml/min @254/220nm).

2-Methyl1-2-{2-methyl-4-[({4-[4-(methylsulfanyl) benzyl-2-[4-(trifluoromethyl)phenyl]-1,3-thiazol-5-yl}methyl]sulfanyl]phenoxy}propanoic acid From 2-methyl-4-[({4-(4-methylsulfanyl)benzyl]-2-[4-(trifluoromethyl)phenyl]-1,3-thiazol-5-yl}methyl)sulfanyl] phenol (0.296g, 0.57mmol), 2-methyl-2-{2-methyl-4-[({4-[4-(methylsulfanyl)benzyl]-2-[4-(trifluoromethyl)phenyl]-1,3-thiazol-5-yl}methyl)sulfanyl]phenoxy}propanoic acid (0.087g, 25%) was obtained as a white solid.

¹H NMR (CD₃OD): δ 8.04(d, 2H), 7.78(d, 2H), 7.13(m, 6H), 6.70(d, 1H), 4.22(s, 2H), 3.87(s, 2H) 2.47(s, 3H), 2.15(s, 3H), 1.60(s, 6H); MS m/z 604(M+1); HPLC RT 4.220(C18 4.2×100mm, 0-100% ACN/H₂O (0.1% TFA), 6min @ 2ml/min @254/220nm).

2-{4-[({4-(4-tert-butylbenzyl)-2-[4-(trifluoromethyl) phenyl]-1,3-thiazol-5-yl}methyl)sulfanyl]-2-methylphenoxy}-2-methylpropanoic acid From 4-[({4-(4-tert-butylbenzyl)-2-[4-(trifluoromethyl) phenyl]-1,3-thiazol-5-yl}methyl)sulfanyl]-2-methylphenol (0.113g, 0.21mmol), 2-{4-[({4-(4-tert-butylbenzyl)-2-[4-(trifluoromethyl)phenyl]-1,3-thiazol-5-yl}methyl)sulfanyl]-2-methylphenoxy}-2-methylpropanoic acid (0.012g, 9%) was obtained as a white solid.

¹H NMR (CD₃OD): δ 8.04(d, 2H), 7.76(d, 2H), 7.29(d, 2H), 7.22(s, 1H), 7.16(d, 1H), 7.03(d, 2H), 6.74(d, 1H); MS m/z 614(M+1); HPLC RT 4.464(C18 4.2×100mm, 0-100% ACN/H₂O (0.1% TFA), 6min @ 2ml/min @254/220nm).

2-Methyl1-2-{2-methyl-4-[({4-(3-thienylmethyl)-2-[4-(trifluoromethyl)phenyl]-1,3-thiazol-5-yl}methyl) sulfanyl]phenoxy}propanoic acid From 2-methyl-4-[({4-(3-thienylmethyl)-2-[4-(trifluoromethyl)phenyl]-1,3-thiazol-5-yl}methyl)sulfanyl]phenol (0.072g, 0.15mmol), 2-methyl-2-{2-methyl-4-[({4-(3-thienylmethyl)-2-[4-(trifluoromethyl)phenyl]-1,3-thiazol-5-yl}methyl)sulfanyl]phenoxy}propanoic acid (0.039g, 46%) was obtained as a cream solid.

¹H NMR (CD₃OD): δ 8.05(d, 2H), 7.76(d, 2H), 7.37(t, 1H), 7.20(s, 1H), 7.15(d, 1H), 7.02(s, 1H), 6.96(d, 1H), 6.70 (d, 1H), 4.23(s, 2H), 3.96(s, 2H), 2.20(s, 3H), 1.60(s, 6H); MS m/z 564(M+1); HPLC RT 4.112(C18 4.2×100mm, 0-100% ACN/H₂O (0.1% TFA), 6min @ 2ml/min @254/220nm).

Ethyl 2-{2-methyl-4-[({4-[4-trifluoromethoxy)benzyl]-2-[4-(trifluoromethyl)phenyl]-1,3-thiazol-5-yl}methyl)sulfanyl]phenoxy}propanoate From 2-methyl-4-[({4-(4-trifluoromethoxy)benzyl]-2-[4-(trifluoromethyl)phenyl]-1,3-thiazol-5-yl}methyl)sulfanyl] phenol (0.17g, 0.31mmol), ethyl 2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoate (0.17g, 83%) was obtained as a white solid. MS m/z 656(M+1); HPLC RT 4.553(C18 4.2×100mm, 0-100% ACN/H₂O (0.1% TFA), 6min @ 2ml/min @254/220nm).

Methyl {2-methyl-4-[({4-[4-(trifluoromethoxy)benzyl]-2-[4-(trifluoromethyl)phenyl]-1,3-thiazol-5-yl}methyl)sulfanyl]phenoxy}acetate From 2-methyl-4-[({4-(4-trifluoromethoxy)benzyl]-2-[4-(trifluoromethyl)phenyl]-1,3-thiazol-5-yl}methyl)sulfanyl] phenol (0.17g, 0.31mmol), methyl {2-methyl-4-[({4-[4-(trifluoromethoxy)benzyl]-2-[4-(trifluoromethyl)phenyl]-1,3-thiazol-5-yl}methyl)sulfanyl]phenoxy}acetate (0.15g, 80%) was obtained as a white solid. MS m/z 628(M+1); HPLC RT 4.398(C18 4.2×100mm, 0-100% ACN/H₂O (0.1% TFA), 6min @ 2ml/min @254/220nm).

Ethyl 2-{2-methyl-4-[({4-(3-thienylmethyl)-2-[4 (trifluoromethyl)phenyl]-1,3-thiazol-5-yl}methyl) sulfanyl]phenoxy}propanoate From 2-methyl-4-[({4-(3-thienylmethyl)-2-[4-(trifluoromethyl)phenyl]-1,3-thiazol-5-yl}methyl)sulfanyl]phenol, ethyl 2-{2-methyl-4-[({4-(3-thienylmethyl)-2-[4-(trifluoromethyl)phenyl]-1,3-thiazol-5-yl}methyl)sulfanyl] phenoxy}propanoate (0.225g, 0.47mmol), (0.255g, 91%) was obtained as a yellow oil.

MS m/z 578(M+1); HPLC RT 4.412(C18 4.2×100mm, 0-100% ACN/H₂O (0.1% TFA), 6min @ 2ml/min @254/220nm).

Methyl {2-methyl-4-[({4-(3-thienylmethyl)-2-[4-(trifluoromethyl)phenyl]-1,3-thiazol-5-yl}methyl) sulfanyl]phenoxy}acetate From 2-methyl-4-[({4-(3-thienylmethyl)-2-[4-(trifluoromethyl)phenyl]-1,3-thiazol-5-yl}methyl)sulfanyl]phenol, methyl {2-methyl-4-[({4-(3-thienylmethyl)-2-[4-(trifluoromethyl)phenyl]-1,3-thiazol-5-yl}methyl)sulfanyl] phenoxy}acetate (0.225g, 0.47mmol), (0.259g, 94%) was obtained as a yellow oil.

MS m/z 550(M+1); HPLC RT 4.243(C18 4.2×100mm, 0-100% ACN/H₂O (0.1% TFA), 6min @ 2ml/min @254/220nm).

The following 2compounds were made by the Mitsunobu reaction of 4-[({4-{[4-(4-Methoxyphenyl)-1-piperazinyl] methyl}-2-[4-(trifluoromethyl)phenyl]-1,3-thiazol-5-yl}methyl)sulfanyl]-2-methylphenol with R and S Methyl lactate:

Methyl (2S)-2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 400MHz δ 7.97(d, 2H, J=8.24Hz), 7.64 (d, 2H, J=8.24Hz), 7.21(d, 1H, J=2.20Hz), 7.11(dd, 1H, J=8.42, 2.20Hz), 6.86(d, 2H, J=9.16Hz), 6.80(d, 2H, J=916Hz), 6.54(d, 1H, J=8.42Hz), 4.70(q, 1H, J=6.78Hz), 4.30(s, 2H), 3.74(s, 3H), 3.69(s, 3H), 3.55(s, 2H), 3.06(br s, 4H), 2.62(br s, 4H), 2.21(s, 3H), 1.60(d, 3H, J=6.78Hz),

Methyl (2R)-2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}propanoate ¹H NMR (CDCl₃) 400MHz δ 7.97(d, 2H, J=8.24Hz), 7.64 (d, 2H, J=8.24Hz), 7.22(d, 1H, J=2.01Hz), 7.12(dd, 1H, J=8.42, 2.01Hz), 6.88(d, 2H, J=9.16Hz), 6.80(d, 2H, J=9.16Hz), 6.55(d, 1H, J=8.42Hz), 4.70(q, 1H, J=6.78Hz), 4.32(s, 2H), 3.73(s, 3H), 3.69(s, 3H), 3.55(s, 2H), 3.06(t, 4H, J=4.76Hz), 2.61(br s, 4H), 2.22(s, 3H), 1.60(d, 3H, J=6.78Hz),

2-{4-[({4-{[4-(4-Methoxyphenyl)-1-piperazinyl]methyl}-2-[4-(trifluoromethyl)phenyl]-1,3-thiazol-5-yl}methyl)sulfanyl]phenoxy}-2-methylpropanoic acid To a stirred solution of ethyl 2-{4-[({4-{[4-(4-methoxyphenyl)-1-piperazinyl]methyl}-2-[4-(trifluoromethyl)phenyl]-1,3-thiazol-5-yl}methyl)sulfanyl]phenoxy}-2-methylpropanoate (77.0g, 0.112moles, 1eq) in THF (600ml, 0.19M) was added MeOH (50ml) and a 1N LiOH solution (6.18g in 250ml $H_2O$, 2.3eq). The mixture was refluxed for 5hrs after which the THF was removed in vacuo. The residue was diluted with EtOAc and to it was added 1N HCl until a pH of about 5 was reached. The phases were separated and the organic fraction was concentrated in vacuo, then titrated with isopropyl acetate twice which was subsequently removed in vacuo each time. The crude product was then recrystallized from EtOH to yield 52g (71%) of a white solid.

$^1$H NMR ($CD_3OD$) 400MHz δ 8.08(d, 2H, J=8.24Hz), 7.75(d, 2H, J=8.24Hz), 7.25(d, 2H, J=8.61Hz), 6.94(d, 2H, J=9.16Hz), 6.82(m, 4H), 4.28(s, 2H), 3.72(s, 3H), 3.59(s, 2H), 3.16(t, 4H, J=4.94Hz), 2.96(t, 4H, J=4.94Hz), 1.54(s, 6H),

CHN Analysis. Theory (C, 60.26%; H, 5.21%; N, 6.39%) Found (C, 60.11%; H, 5.31%; N, 6.23%)

HPLC(C-18, 3μm) 0%-95% Acetonitrile/Water over 8minutes $R_t$=5.48minutes

{4-[({4-benzyl-2-[4-(trifluoromethyl)phenyl]-1,3-thiazol-5-yl}methyl)sulfanyl]-2,5-dimethylphenoxy}acetic acid Mass spec: calculated for $C_{28}H_{24}F_3NO_3S_2$: 543. Found: 544(MH$^+$). HPLC trace: retention time=13.5min (Alitima $C_{18}$, 5micron, 250mm column, Gradient elution with 70-100% $CH_3CN/H_2O$).

2-{4-[({4-benzyl-2-[4-(trifluoromethyl)phenyl]-1,3-thiazol-5-yl}methyl)sulfanyl]-2-methylphenoxy}propanoic acid Elemental analysis calculated for $C_{28}H_{24}F_3NO_3S_2$: C, 61.8%; H, 4.5%; N, 2.6%. Found: C, 61.77%; H, 4.64%; N, 2.51%. HPLC trace: retention Time=7min (Alltima $C_{18}$, 5micron, 250mm column, gradient elution with 70-100% $CH_3CN/H_2O$).

2-{4-[({4-benzyl-2-[4-(trifluoromethyl)phenyl]-1,3-thiazol-5-yl}methyl)sulfanyl]-2,3-dimethylphenoxy}propanoic acid Elemental analysis calculated for $C_{29}H_{26}F_3NO_3S_2$; C, 62.4%; H, 4.7%; N, 2.5%. Found; C, 62.58%; H, 4.93%; N, 2.44%. HPLC trace: retention time=14.7min (Alltima $C_{18}$, 5micron, 250mm column using gradient elution with 70-100% $CH_3CN/H_2O$).

2-{4-[({4-benzyl-2-[4-(trifluoromethyl)phenyl]-1,3-thiazol-5-yl}methyl)sulfanyl]-2-fluorophenoxy}propanoic acid Mass spec calculated for $C_{27}H_{21}F_4NO_3S_2$: 547. Found: 548(MH$^+$). HPLC, Trace: retention time=12.1min (Alltima $C_{18}$, 5micron, 250mm column using gradient elution with 70-100% $CH_3CN/H_2O$).

(2S)-2-{4-[({4-{[4-(4-Methoxyphenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR ($CD_3OD$) 400MHz δ 8.07(d, 2H, J=8.24Hz), 7.74(d, 2H, J=8.24Hz), 7.19(d, 1H, J=2.20Hz), 7.09(dd, 1H, J=8.42, 2.20Hz), 6.91(d, 2H, J=9.16Hz), 6.80(d, 2H, J=9.16Hz), 6.62(d, 1H, J=8.42Hz), 4.68(q, 1H, J=6.78Hz), 4.28(s, 2H), 3.71(s, 3H), 3.48(s, 2H), 3.05(t, 4H, J=4.76Hz), 2.69(t, 4H, J=4.76Hz), 2.18(s, 3H), 1.57(d, 3H, J=6.78Hz), Chiral HPLC(Chiralpak, 2cm) 75% Carbon Dioxide/25% Methanol over 65minutes $R_1$@0.88minutes

(2R)-2-{4-[({4-{[4-(4-Methoxyphenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR ($CD_3OD$) 400MHz δ 8.11(d, 2H, J=8.24Hz), 7.76(d, 2H, J=8.24Hz), 7.15(d, 1H, J=2.20Hz), 7.08(dd, 1H, J=8.42, 2.20Hz), 6.93(d, 2H, J=9.16Hz), 6.82(d, 2H, J=9.16Hz), 6.67(d, 1H, J=8.42Hz), 4.57(q, 1H, J=6.78Hz), 4.24(s, 2H), 3.71(s, 3H), 3.54(s, 2H), 3.17(t, 4H, J=4.76Hz), 3.02(t, 4H, J=4.76Hz), 2.18(s, 3H), 1.55(d, 3H, J=6.78Hz), Chiral HPLC(Chiralpak, 2cm) 75% Carbon Dioxide/25% Methanol over 65minutes $R_t$T.58minutes

2-(4-{[(2-(4-Fluorophenyl)-4-{[4-(4-methoxyphenyl)-1-piperazinyl]methyl}-1,3-thiazol-5-yl)methyl]sulfanyl}-2-methylphenoxy)-2-methylpropanoic acid $^1$H NMR ($CD_3OD$) 400MHz δ 7.95(m, 2H), 7.18(m, 3H), 7.05(br s, 1H), 6.93(d, 2H, J=8.61Hz), 6.81(d, 2H, J=8.61Hz), 6.69(br s, 1H), 4.22(s, 2H), 3.72(s, 3HK, 3.55(s, 2H), 3.17(br s, 4H), 2.93(br s, 4H), 2.14(s, 3H), 1.59(s, 6H),

[4-({[4-[(4-Benzyl-1-piperazinyl)methyl]-2-(4-{trifluoromethyl}phenyl)-1,3-thiazol-5-yl]methyl}sulfanyl)-2-methylphenoxy]acetic acid $^1$H ($CD_3OD$) 300MHz δ 8.15(d, 2H, J=8.23Hz), 7.81(d, 2H, J=8.23Hz), 7.48(m, 5H), 7.24(s, 2H), 6.74(s, 1H), 4.55(s, 2H), 4.28(s, 2H), 4.15(s, 2H), 3.46(s, 2H), 3.06(s, 4H), 2.49(s, 4H), 2.09(s, 3H). MS(ES$^-$) M−H=625.98. TLC(10% MeOH/$CH_2Cl_2$) $R_f$=0.35

{2-Methyl-4-[({2-(4-{trifluoromethyl}phenyl)-4-[(4-methyl-1-piperidinyl)methyl]-1,3-thiazol-5-yl}methyl)sulfanyl]phenoxy}acetic acid $^1$H ($CD_3OD$) 300MHz δ 8.20(d, 2H, J=7.97Hz), 7.85(d, 2H, J=7.97Hz), 7.27(s, 1H), 7.08(s, 1H), 6.68(s, 1H), 4.62(s, 2H), 4.29(s, 2H), 3.70(s, 2H), 2.86(s, 2H), 2.26(s, 3H), 1.90(s, 2H), 1.48(m, 5H), 1.06(s, 3H). MS(ES$^-$) M−H=548.91. TLC (10% MeOH/$CH_2Cl_2$) $R_f$=0.24

[2-Methyl-4-({[4-{[4-(5-methyl-1,2,4-oxadiazol-3-yl)phenoxy]methyl}-2-(4-{trifluoromethyl}phenyl)-1,3-thiazol-5-yl]methyl}sulfanyl)phenoxy]acetic acid $^1$H ($CDCl_3$) 400MHz δ 8.03(d, 2H, J=8.03Hz), 7.93(d, 2H, J=8.89Hz), 7.70(d, 2H, J=8.03Hz), 7.19(d, 1H, J=2.22Hz), 7.07(dd, 1H, J=8.37, 2.22Hz), 6.96(d, 2H, J=8.89Hz), 6.53(d,

[2-Methyl-4-({[4-{[3-(5-methyl-1,24-oxadiazol-3-yl)phenoxy]methyl}-2-(4-{trifluoromethyl}phenyl)-1,3-thiazol-5-yl]methyl}sulfanyl)phenoxy]acetic acid $^1$H (CDCl$_3$) 400MHz δ 8.04(d, 2H, J=8.20Hz), 7.69(m, 3H), 7.37(s, 2H), 7.16(dd, 1H, J=8.20, 2.22Hz), 7.05(dd, 1H, J=8.20, 2.22Hz), 6.91(d, 1H, J=2.22Hz), 6.62(d, 1H, J=8.20Hz), 4.72(s, 2H), 4.43(s, 2H), 4.19(s, 2H), 2.73(s, 3H), 2.09(s, 3H). TLC(5% MeOH/CH$_2$Cl$_2$) R$_f$=0.13. MS(ES$^-$) M−H=625.86

(2-Methyl-4-{[(2-(4-{trifluoromethyl}phenyl)-4-[[4-(2-methylphenyl)-1-piperazinyl]methyl]-1,3-thiazol-5-yl)methyl]sulfanyl}phenoxy)acetic acid $^1$H (CDCl$_3$) 400MHz δ 8.10(d, 2H, J=8.03Hz), 7.73(d, 2H, J=8.03Hz), 7.16(m, 4H), 7.01(br s, 2H), 6.73(d, 1H, J=8.37Hz), 4.79(s, 2H), 4.08(s, 2H), 3.80(m, 4H), 3.53(m, 2H), 3.24(m, 4H), 2.40(s, 3H), 2.18(s, 3H). TLC(5% MeOH/CH$_2$Cl$_2$) R$_f$=0.10. MS(ES$^-$) M−H=625.94

[4-({[4-{[4-(4-Methoxyphenyl)-1-piperazinyl]methyl}-2-(4-{trifluoromethyl}phenyl)-1,3-thiazol-5-yl]methyl}sulfanyl)-2-methylphenoxy]acetic acid $^1$H (CDCl$_3$) 400MHz δ 8.04(d, 2H, J=8.20Hz), 7.72(d, 2H, J=8.20Hz), 7.12(s, 1H), 6.96(m, 3H), 6.81(d, 2H, J=8.89Hz), 6.74(d, 1H, J=8.37Hz), 4.76(s, 2H), 4.05(s, 2H), 3.74(s, 3H), 3.38(m, 10H), 2.16(s, 3H). TLC(5% MeOH/CH$_2$Cl$_2$) R$_f$=0.13. MS(ES$^-$) M−H=641.90

(2-Methyl-4-{[(2-(4-{trifluoromethyl}phenyl)-4-{[4-(3-methylphenyl)-1-piperazinyl]methyl}-1,3-thiazol-5-yl)methyl]sulfanyl}phenoxy)acetic acid $^1$H (CDCl$_3$) 400MHz δ 8.05(d, 2H, J=8.20Hz), 7.72(d, 2H, J=8.20Hz), 7.20(s, 1H), 7.06(d, 2H, J=9.06Hz), 6.91(m, 3H), 6.72(d, 1H, J=8.37Hz), 4.77(s, 2H), 4.06(s, 2H), 3.54(br s, 8H), 3.27(s, 2H), 2.30(s, 3H), 2.16(s, 3H). TLC(5% MeOH/CH$_2$Cl$_2$) R$_f$=0.10. MS(ES$^-$) M−H=625.99

(2-Methyl-4-{[(2-(4-{trifluoromethyl}phenyl)-4-{[4-(4-methylphenyl)-1-piperazinyl]methyl}-1,3-thiazol-5-yl)methyl]sulfanyl}phenoxy)acetic acid $^1$H (CDCl$_3$) 400MHz δ 8.03(d, 2H, J=8.20Hz), 7.71(d, 2H, J=8.20Hz), 7.02(m, 6H), 6.71(d, 1H, J=8.55Hz), 4.76(s, 2H), 4.08(s, 2H), 3.52(br s, 8H), 3.31(s, 2H), 2.27(s, 3H), 2.16(s, 3H). TLC(5% MeOH/CH$_2$Cl$_2$) R$_f$=0.10. MS(ES$^-$) M−H=625.94

[4-({[4-{[4-(2-Furoyl)-1-piperazinyl]methyl}-2-(4-{trifluoromethyl}phenyl)-1,3-thiazol-5-yl]methyl}sulfanyl)-2-methylphenoxy]acetic acid $^1$H (CDCl$_3$) 400MHz δ 8.02(d, 2H, J=8.20Hz), 7.71(d, 2H, J=8.20Hz), 7.48(d, 1H, J=2.05Hz), 7.16(dd, 1H, J=8.20, 2.05Hz), 7.07(m, 1H), 6.90(d, 1H, J=2.39Hz), 6.74(d, 1H, J=8.20Hz), 6.49(m, 1H), 4.77(s, 2H), 4.62(s, 2H), 4.05(s, 2H), 3.46(s, 2H), 3.27(s, 2H), 3.05(br s, 4H), 2.15(s, 3H). TLC(5% MeOH/CH$_2$Cl$_2$) R$_f$=0.10. MS(ES$^-$) M−H=629.83

(2-Methyl-4-{[(2-(4-{trifluoromethyl}phenyl)-4-{[4-(2-pyridinyl)-1-piperazinyl]methyl}-1,3-thiazol-5-yl)methyl]sulfanyl}phenoxy)acetic acid $^1$H (CDCl$_3$) 400MHz δ 8.22(m, 1H), 7.99(d, 2H, J=8.20Hz), 7.68(d, 2H, J=8.20Hz), 7.60(s, 1H), 7.20(dd, 1H, J=8.37, 2.39Hz), 7.14(s, 1H), 6.76(m, 1H), 6.68(m, 1H), 4.68(s, 2H), 4.14(s, 2H), 3.72(br s, 4H), 3.59(s, 2H), 2.87(br s, 4H), 2.17(s, 3H). TLC(5% MeOH/CH$_2$Cl$_2$) R$_f$=0.10. MS(ES$^-$) M−H=612.99

[4-({[4-{[4-(4-Chlorobenzyl)-1-piperazinyl]methyl}-2-{4-trifluoromethyl}phenyl)-1,3-thiazol-5-yl]methyl}sulfanyl)-2-methylphenoxy]acetic acid $^1$H(CDCl$_3$) 400MHz δ 8.04(d, 2H, J=8.20Hz), 7.70(d, 2H, J=8.20Hz), 7.41(m, 4H), 7.14(m, 1H), 7.03(m, 1H), 6.69(d, 1H, J=8.37Hz), 4.72(s, 2H), 4.02(s, 2H), 3.18(m, 12H), 2.10(s, 3H). TLC(5% MeOH/CH$_2$Cl$_2$) R$_f$=0.10. MS(ES$^-$) M−H=659.78

[4-({[4-{[4-(4-acetylphenyl)-1-piperazinyl]methyl}-2-(4-{trifluoromethyl}phenyl)-1,3-thiazol-5-yl]methyl}sulfanyl)-2-methylphenoxy]acetic acid $^1$H (CDCl$_3$) 400MHz δ 7.97(d, 2H, J=8.03Hz), 7.85(d, 2H, J=8.89Hz), 7.70(d, 2H, J=8.03Hz), 7.16(dd, 1H, J=8.37, 2.22Hz), 6.86(m, 3H), 6.75(d, 1H, J=8.37Hz), 4.77(s, 2H), 4.04(s, 2H), 3.80(m, 4H), 3.45(m, 4H), 3.29(s, 2H), 2.51(s, 3H), 2.17(s, 3H). TLC(5% MeOH/CH$_2$Cl$_2$) R$_f$=0.10. MS(ES$^-$) M−H=653.99

(4-{[(4-{[4-(4-Methoxyphenyl)-1-piperazinyl]methyl}-2-phenyl-1,3-thiazol-5-yl)methyl]sulfanyl}-2-methylphenoxy)acetic acid $^1$H NMR (CDCl$_3$) 400MHz 9.94(s, 1H), 7.84(m, 2H), 7.41(m, 3H), 7.11(d, 1H, J=2.22Hz), 7.06(dd, 1H, J=8.37, 2.22Hz), 6.79(m, 4H), 6.60(d, 1H, J=8.37Hz), 4.54(s, 2H), 4.18(s, 2H), 3.76(s, 3H), 3.22(m, 8H), 2.18(s, 3H). HPLC(C-18, 3μm) 1% MeOH/0-90% CH$_3$CN/Water (0.1% TFA)/(50mM Et$_3$/TFA) 4min run R$_t$=2.67min

2-{4-[({4-{[4-(4-Methoxyphenyl)-1-piperazinyl]methyl}-2-[4-(trifluoromethyl)phenyl]-1,3-thiazol-5-yl}methyl-sulfanyl]-2-methylphenoxy}propanoic acid $^1$H NMR (CDCl$_3$) 400MHz δ 9.69(s, 1H), 7.96(d, 2H, J=8.20Hz), 7.65(d, 2H, J=8.20Hz), 7.07(d, 1H, J=2.05Hz), 7.02(dd, 1H, J=8.55, 2.05Hz), 6.87(d, 2H, J=9.23Hz), 6.80(d, 2H, J=9.23Hz), 6.66(d, 1H, J=8.55Hz), 4.66(q, 1H, J=6.95Hz), 4.10(d, 1H, J=70Hz), 4.05(d, 1H, J=70Hz), 3.74(s, 3H), 3.57(d, 1H, J=18Hz), 3.51(d, 1H, J=18Hz), 3.15(br s, 4H), 2.96(br s, 4H), 2.17(s, 3H), 1.59(d, 3H, J=6.95Hz). HPLC(C-18, 3μm) 1% MeOH/0-90% CH$_3$CN/Water(0.1% TFA)/(50mM Et$_3$N/TFA) 4min run R$_t$=2.91min

2-(4-{[(4-{[4-(4-Methoxyphenyl-1-piperazinyl]methyl}-2-phenyl-1,3-thiazol-5-yl)methyl]sulfanyl}-2-methylphenoxy)propanoic acid $^1$H NMR (CDCl$_3$) 400MHz δ, 7.81(m, 2H), 7.34(m, 3H), 7.09(m, 1H), 6.90(m, 1H), 6.79(m, 4H), 6.48(d, 1H, J=8.37Hz), 4.35(m, 1H), 4.16(s, 2H), 3.70(s, 3H), 3.32(s, 2H), 3.00(m, 4H), 2.60(m, 4H), 2.09(s, 3H), 1.34(m, 3H).

{2-Methyl-4-[({2-(4-{trifluoromethyl}phenyl)-4-[(4-phenyl-1-piperazinyl)methyl]-1,3-thiazol-5-yl}methyl)sulfanyl]phenoxy}acetic acid $^1$H (CD$_3$OD) 300MHz δ 8.16(d, 2H, J=8.49Hz), 7.81(d, 2H, J=8.49Hz), 7.26(br s, 3H), 7.09(br s, 1H), 6.98(d, 2H, J=7.96Hz), 6.88(m, 1H), 6.66(br s, 1H), 4.57(s, 2H), 4.29(s, 2H), 3.55(s, 2H), 3.26(br s, 4H), 2.91(br s, 4H), 2.23(s, 3H). MS(ES$^-$) M–H=611.85. TLC(10% MeOH/CH$_2$Cl$_2$) R$_f$=0.30

[4-({[4-{[4-(Ethoxycarbonyl)-1-piperazinyl]methyl}-2-(4-{trifluoromethyl}phenyl)-1,3-thiazol-5-yl]methyl}sulfanyl)-2-methylphenoxy]acetic acid $^1$H (CD$_3$OD) 300MHz δ 8.14(d, 2H, J=8.23Hz), 7.81(d, 2H, J=8.23Hz), 7.26(s, 1H), 7.12(s, 1H), 6.71(s, 1H), 4.63(s, 2H), 4.32(s, 2H), 4.16(q, 2H, J=7.08Hz), 3.55(br s, 4H), 3.44(s, 2H), 2.60(br s, 4H), 2.25(s, 3H), 1.30(t, 3H, J=7.08Hz). MS(ES$^-$) M–H=607.86. TLC(10% MeOH/CH$_2$Cl$_2$) R$_f$=0.28

{2-Methyl-4-[({2-(4-{trifluoromethyl}phenyl)-4-[(4-phenyl-1-piperidinyl)methyl]-1,3-thiazol-5-yl}methyl)sulfanyl]phenoxy}acetic acid $^1$H (CD$_3$OD) 300MHz δ 8.14(d, 2H, J=8.23Hz), 7.77(d, 2H, J=8.23Hz), 7.28(s, 7H), 6.75(d, 1H, J=8.23Hz), 4.45(s, 2H), 4.34(s, 2H), 3.53(s, 2H), 3.08(m, 2H), 2.57(m, 1H), 2.35(m, 2H), 2.22(s, 3H), 1.80(m, 4H). MS(ES$^-$) M–H=610.91. TLC(10% MeOH/CH$_2$Cl$_2$) R$_f$=0.30

[4-({[4-{[(Cyclopropylmethyl)amino]methyl}-2-(4-trifluoromethyl}phenyl)-1,3-thiazol-5-yl]methyl)sulfanyl)-2-methylphenoxy]acetic acid $^1$H NMR 300MHz δ 8.08(d, 2H, J=8.20Hz), 7.74(d, 2H, J=8.20Hz), 7.14(dd, 1H, J=8.49, 2.39Hz), 7.01(s, 1H), 6.72(d, 1H, J=8.49Hz), 4.77(s, 2H), 4.03(s, 2H), 3.29(s, 2H), 2.77(d, 2H, J=7.43Hz), 2.17(s, 3H), 1.17(m, 1H), 0.62(m, 2H), 0.28(m, 2H). MS(ES$^-$) M–H=520.90. HPLC(C-18, 3μm) 1% MeOH/0-90% CH$_3$CN/Water (0.1% TFA)/(50mM Et$_3$N/TFA) 4min run R$_t$=2.67min {2-Methyl-4-[({2-(4-{trifluoromethyl}phenyl)-4-[(pentylamino)methyl]-1,3-thiazol-5-yl}methyl)sulfanyl]phenoxy}acetic acid $^1$H NMR 300MHz δ 8.06(d, 2H, J=8.23Hz), 7.69(d, 2H, J=8.23Hz), 7.05(m, 2H), 6.66(d, 1H, J=8.23Hz), 4.67(s, 2H), 4.06(s, 2H), 3.35(s, 2H), 2.78(t, 2H, J=6.64Hz), 2.17(s, 3H), 1.71(m, 2H), 1.22(m, 4H), 0.83(t, 3H, J=6.64Hz). MS(ES$^-$) M–H=536.90. HPLC(C-18, 3μm) 1% MeOH/0-90% CH$_3$CN/Water (0.1% TFA)/(50mM Et$_3$N/TFA) 4min run R$_t$=2.80min 4-({[4-{[4-(2-Hydroxyethyl)-1-piperazinyl]methyl}-2-(4-{trifluoromethyl}phenyl)-1,3-thiazol-5-yl]methyl)sulfanyl}-2-methylphenoxy]acetic acid $^1$H NMR (CD$_3$OD) 300MHz δ 8.16(d, 2H, J=8.23Hz), 7.80(d, 2H, J=8.23Hz), 7.26(m, 2H), 6.80(d, 2H, J=8.49Hz), 4.76(s, 2H), 4.40(s, 2H), 3.95(m, 2H), 3.84(s, 2H), 3.54(br s, 4H), 3.33(m, 2H), 3.20(br s, 4H), 2.22(s, 3H). HPLC(C-18, 3μm) 1% MeOH/0-90% CH$_3$CN/Water (0.1% TFA)/(50mM Et$_3$N/TFA) 4min run R$_t$=2.48min (2-Methyl-4-{[(2-(4-{trifluoromethyl}phenyl)-4-{[(3-pyridinylmethyl)amino]methyl}-1,3-thiazol-5-yl)methyl]sulfanyl}phenoxy)acetic acid $^1$H NMR (CDCl$_3$) 300MHz δ 8.58(d, 1H, J=1.59Hz), 8.48 (dd, 1H, J=4.78, 1.59Hz), 8.03(m, 3H), 7.66(d, 2H, J=8.23Hz), 7.24(m, 1H), 7.06(d, 1H, J=2.39Hz), 6.99(d, 1H, J=2.39Hz), 6.59(d, 1H, J=8.49Hz), 4.61(s, 2H), 4.04(s, 2H), 3.93(s, 2H), 3.28(s, 2H), 2.13(s, 3H). MS(ES$^-$) M–H=557.80. HPLC(C-18, 3μm) 1% MeOH/0-90% CH$_3$CN/Water (0.1% TFA)/(50mM Et$_3$N/TFA) 4min run R$_t$=2.44min

[4-({[4-[(3-Hydroxy-1-piperidinyl)methyl]-2-(4-{trifluoromethyl}phenyl)-1,3-thiazol-5-yl]methyl}sulfanyl)-2-methylphenoxy]acetic acid $^1$H NMR (CDCl$_3$) 300MHz δ 8.00(d, 2H, J=8.37Hz), 7.69 (d, 2H, J=8.37Hz), 7.23(dd, 1H, J=8.55, 2.20Hz), 6.94(d, 1H, J=2.20Hz), 6.69(d, 1H, J=8.55Hz), 4.68(s, 2H), 4.21(s, 2H), 3.16(m, 7H), 2.12(s, 3H), 1.63(m, 4H). MS(ES$^-$) M–H=550.8. HPLC(C-18, 3μm) 1% MeOH/0-90% CH$_3$CN/Water (0.1% TFA)/(50mM Et$_3$N/TFA) 4min run R$_t$=2.58min

[4-({[4-[(4-Hydroxy-1-piperidinyl)methyl]-2-(4-{trifluoromethyl}phenyl)-1,3-thiazol-5-yl]methyl}sulfanyl)-2-methylphenoxy]acetic acid $^1$H NMR (CDCl$_3$) 300MHz δ 7.97(d, 2H, J=8.23Hz), 7.65 (d, 2H, J=8.23Hz), 7.11(m, 2H), 6.58(d, 1H, J=8.23Hz), 4.53 (s, 2H), 4.18(s, 2H), 3.86(br s, 1H), 3.62(m, 2H), 3.12(m, 2H), 2.95(m, 2H), 2.15(s, 3H), 2.04(m, 2H), 1.77(m, 2H). HPLC (C-18, 3μm) 1% MeOH/0-90% CH$_3$CN/Water (0.1% TFA)/(50mM Et$_3$N/TFA) 4min run R$_t$=2.54min

[4-({[4-{[2-(hydroxymethyl)-1-piperidinyl]methyl}-2-(4-{trifluoromethyl}phenyl)-1,3-thiazol-5-yl]methyl}sulfanyl]-2-methylphenoxy}acetic acid MS(ES$^-$) M–H=564.94. HPLC(C-18, 3μm) 1% MeOH/0-90% CH$_3$CN/Water (0.1% TFA)/(50mM Et$_3$N/TFA) 4min run R$_t$=2.66min

[4-({[4-{[4-(Hydroxymethyl)-1-piperidinyl]methyl}-2-4-{trifluoromethyl}phenyl)-1,3-thiazol-5-yl]methyl}sulfanyl)-2-methylphenoxy]acetic acid $^1$H NMR (CDCl$_3$) 400MHz δ 7.94(d, 2H, J=8.20Hz), 7.64 (d, 2H, J=8.20Hz), 7.13(dd, 1H, J=8.55, 2.39Hz), 7.06(d, 1H, J=2.39Hz), 6.58(d, 1H, J=8.55Hz), 4.60(s, 2H), 4.45(s, 2H), 4.18(s, 2H), 3.56(m, 6H), 2.75(br s, 1H), 2.11(s, 3H), 1.68(m, 4H). MS(ES$^-$) M–H=564.93. HPLC(C-18, 3μm) 1% MeOH/0-90% CH$_3$CN/Water (0.1% TFA)/(50mM Et$_3$N/TFA) 4min run R$_t$=2.56min

[2-Methyl-4-({[2-(4-{trifluoromethyl}phenyl)-4-(4-morpholinylmethyl)-1,3-thiazol-5-yl]methyl}sulfanyl)phenoxy]acetic acid $^1$H NMR (CD$_3$OD) 300MHz δ 8.11(d, 2H, J=8.23Hz), 7.79(d, 2H, J=8.23Hz), 7.25(br s, 1H), 7.17(dd, 1H, J=8.23, 2.39Hz), 6.74(d, 2H, J=8.23Hz), 4.46(s, 2H), 4.32(s, 2H), 3.69(br s, 4H), 3.47(s, 2H), 2.50(br s, 4H), 2.23(s, 3H). MS(ES$^-$) M–H=536.43. TLC(20% MeOH/CH$_2$Cl$_2$) R$_f$=0.39

[4-({[4-[(Cyclohexylamino)methyl]-2-(4-{trifluoromethyl}phenyl)-1,3-thiazol-5-yl]methyl}sulfanyl)-2-methylphenoxy]acetic acid $^1$H NMR (CDCl$_3$) 400MHz δ 8.01(d, 2H, J=8.20Hz), 7.66 (d, 2H, J=8.20Hz), 7.04(m, 2H), 6.61(d, 1H, J=8.20Hz), 4.64 (s, 2H), 4.14(s, 2H), 3.39(s, 2H), 2.86(m, 1H), 2.14(s, 3H), 2.01(m, 2H), 1.73(m, 2H), 1.48(m, 4H), 1.08(m, 2H). MS(ES$^-$) M−H=548.7-. HPLC(C-18, 3μm) 1% MeOH/0-90% CH$_3$CN/Water (0.1% TFA)/(50mM Et$_2$N/TFA) 4min run R$_t$=2.75min

[2-Methyl-4-({[4-{[(2-methylcyclohexyl)amino]methyl}-2-(4-{trifluoromethyl}phenyl)-1,3-thiazol-5-yl]methyl}sulfanyl)phenoxy]acetic acid $^1$H NMR 400MHz δ 7.98(d, 2H, J=8.20Hz), 7.68(d, 2H, J=8.20Hz), 7.09(dd, 1H, J=8.37, 2.39Hz), 6.98(d, 1H, J=2.39Hz), 6.65(d, 1H, J=8.37Hz), 4.66(s, 2H), 4.15(d, 1H, J=70Hz), 4.00(d, 1H, J=70Hz), 3.53(d, 1H, J=04Hz), 3.33(d, 1H, J=04Hz), 2.53(m, 1H), 2.10(s, 3H), 1.74(m, 7H), 1.37(m, 2H), 1.03(d, 3H, J=6.32Hz). MS(ES$^-$) M−H=562.80. HPLC (C-18, 3μm) 1% MeOH/0-90% CH$_3$CN/Water (0.1% TFA)/(50mM Et$_3$N/TFA) 4min run R$_t$=2.87min

[2-Methyl-4-({[4-{[(3-methylcyclohexyl)amino]methyl}-2-(4-{trifluoromethyl}phenyl)-1,3-thiazol-5-yl]methyl}sulfanyl)phenoxy]acetic acid $^1$H NMR 400MHz δ 8.01(d, 2H, J=8.20Hz), 7.68(d, 2H, J=8.20Hz), 7.05(m, 2H), 6.62(d, 1H, J=8.37Hz), 4.68(s, 2H), 4.29(s, 2H), 3.32(s, 2H), 2.90(m, 1H), 2.15(s, 3H), 2.00(m, 5H), 1.56(m, 4H), 0.89(d, 3H, J=6.32Hz). MS(ES$^-$) M−H=562.9. HPLC(C-18, 3μm) 1% MeOH/0-90% CH$_3$CN/Water (0.1% TFA)/(50mM Et$_3$N/TFA) 4min run R$_t$=2.85min

[2-Methyl-4-({[4-{[(4-methylcyclohexyl)amino]methyl}-2-(4-{trifluoromethyl}phenyl)-1,3-thiazol-5-yl]methyl}sulfanyl)phenoxy]acetic acid $^1$H NMR 400MHz δ 7.99(d, 2H, J=8.20Hz), 7.64(d, 2H, J=8.20Hz), 7.02(m, 2H), 6.59(d, 1H, J=8.03Hz), 4.58(s, 2H), 4.16(s, 2H), 3.44(s, 2H), 2.90(br s, 1H), 2.12(s, 3H), 2.01(m, 3H), 1.62(m, 6H), 0.90(d, 3H, J=6.84Hz). MS(ES$^-$) M−H=562.90. HPLC(C-18, 3μm) 1% MeOH/0-90% CH$_3$CN/Water (0.1% TFA)/(50mM Et$_3$N/TFA) 4min run R$_t$=2.85min

[2-Methyl-4-({[4-[(2-methylphenoxy)methyl]-2-(4-{trifluoromethyl}phenyl)-1,3-thiazol-5-yl]methyl}sulfanyl)phenoxy]acetic acid $^1$H (CDCl$_3$) 300MHz δ 8.03(d, 2H, J=8.23Hz), 7.72(d, 2H, J=8.23Hz), 7.17(m, 4H), 6.91(m, 2H), 6.59(d, 1H, J=8.49Hz), 4.96(s, 2H), 4.67(s, 2H), 2.25(s, 3H), 2.21(s, 3H). MS(ES$^-$) M−H=557.8

[2-Methyl-4-({[4-[(3-methylphenoxy)methyl]-2-(4-{trifluoromethyl}phenyl)-1,3-thiazol-5-yl]methyl}sulfanyl)phenoxy]acetic acid $^1$H (CDCl$_3$) 300MHz δ 8.06(d, 2H, J=8.23Hz), 7.73(d, 2H, J=8.23Hz), 7.26(dd, 1H, J=2.39, 0.53Hz), 7.20(t, 111, J=7.83Hz), 7.12(ddd, 1H, J=8.49, 2.39, 0.53Hz), 6.80(m, 3H), 6.61(d, 1H, J=8.49Hz), 4.86(s, 2H), 4.67(s, 2H), 4.32(s, 2H), 2.36(s, 3H), 2.23(s, 3H). MS(ES$^-$) M−H=557.83

[2-Methyl-4-({[4-[(4-Methylphenoxy)methyl]-2-(4-{trifluoromethyl}phenyl)-1,3-thiazol-5-yl]methyl}sulfanyl)phenoxy]acetic acid MS(ES$^-$) M−H=557.8
CHN Analysis: Theory 1.5H$_2$0(C, 57.33%; H, 4.64%; N, 2.39%) Found (C, 57.34%; H, 4.24%; N, 2.37%)

[4-({[4-[(3-Cyanophenoxy)methyl]-2-(4-{trifluoromethyl}phenyl)-1,3-thiazol-5-yl]methyl}sulfanyl)-2-Methylphenoxy]acetic acid $^1$H (CDCl$_3$) 300MHz δ 8.05(d, 2H, J=8.23Hz), 7.74(d, 2H, J=8.23Hz), 7.35(m, 2H), 7.17(m, 4H), 6.67(d, 1H, J=8.23Hz), 4.76(s, 2H), 4.72(s, 2H), 4.25(s, 2H), 2.23(s, 3H). MS(ES$^-$) M−H=569.2

[4-({[4-[(4-Cyanophenoxy)methyl]-2-(4-{trifluoromethyl}phenyl)-1,3-thiazol-5-yl]methyl}sulfanyl)-2-methylphenoxy]acetic acid $^1$H (CDCl$_3$) 300MHz δ 9.94(s, 1H), 8.03(d, 2H, J=8.23Hz), 7.73(d, 2H, J=8.23Hz), 7.60(d, 2H, J=9.03Hz), 7.27(d, 1H, J=2.12Hz), 7.10(dd, 1H, J=8.49, 2.12Hz), 7.00(d, 2H, J=9.03Hz), 6.61(d, 1H, J=8.49Hz), 4.85(s, 2H), 4.69(s, 2H), 4.25(s, 2H), 2.21(s, 3H). MS(ES$^-$) M−H=569.2

(2-Methyl-4-{[(4-{[4-(5-methyl-1,2,4-oxadiazol-3-yl)phenoxy]methyl}-2-phenyl-1,3-thiazol-5-yl)methyl]sulfanyl}phenoxyacetic acid $^1$H (CDCl$_3$) 400MHz 7.95(d, 2H, J=9.06Hz), 7.87(m, 2H), 7.43(m, 3H), 7.20(d, 1H, J=2.39Hz), 7.05(dd, 1H, J=8.55, 2.39Hz), 6.95(d, 2H, J=9.06Hz), 6.52(d, 1H, J=8.55Hz), 4.80 (s, 2H), 4.61(s, 2H), 4.24(s, 2H), 2.63(s, 3H), 2.17(s, 3H). MS(ES$^-$) M−H=558.40

2-(2-Methyl-4-{[(4-{[4-(5-methyl-1,2,4-oxadiazol-3-yl)phenoxy]methyl}-2-phenyl-1,3-thiazol-5-yl)methyl]sulfanyl}phenoxy)propanoic acid $^1$H (CDCl$_3$) 400MHz δ 7.93(d, 2H, J=9.06Hz), 7.85(m, 2H), 7.40(m, 3H), 7.19(d, 1H, J=2.22Hz), 7.02(dd, 1H, J=8.37, 2.22Hz), 6.94(d, 2H, J=9.06Hz), 6.52(d, 1H, J=8.37Hz), 4.81(d, 1H, J=79Hz), 4.74(d, 1H, J=79Hz), 4.68 (q, 1H, J=6.78Hz), 4.21(s, 2H), 2.62(m, 3H), 2.16(s, 3H), 1.61(d, 3H, J=6.78Hz). MS(ES$^-$) M−H=571.50

2-{2-Methyl-4-[({4-{[3-(5-methyl-1,2,4-oxadiazol-3-yl)phenoxy]methyl}-2-[4-(trifluoromethyl)phenyl]-1,3-thiazol-5-yl}methyl)sulfanyl]phenoxy}propanoic acid $^1$H NMR (CDCl$_3$) 400MHz δ 7.99(d, 2H, J=8.20Hz), 7.67 (m, 3H), 7.47(m, 1H), 7.36(t, 1H, J=8.03Hz), 7.10(dd, 1H, J=8.37, 2.39Hz), 7.04(dd, 1H, J=8.37, 2.39Hz), 6.99(m, 1H), 6.61(d, 1H, J=8.37Hz), 4.75(q, 1H, J=6.84Hz), 4.62(d, 1H, J=45Hz), 4.43(d, 1H, J=45Hz), 4.23(d, 1H, J=70Hz), 4.16(d, 1H, J=70Hz), 2.70(s, 3H), 2.12(s, 3H), 1.68(d, 3H, J=6.84Hz). MS(ES$^+$) M+H=642.00

2-(2-Methyl-4-{[(4-{[3-(5-methyl-1,2,4-oxadiazol-3-yl)phenoxy]methyl}-2-phenyl-1,3-thiazol-5-yl)methyl]sulfanyl}phenoxy)propanoic acid $^1$H NMR (CDCl$_3$) 400MHz 0 7.90(m, 2H), 7.67(t, 1H, J=7.52Hz), 7.46(m, 1H), 7.42(m, 3H), 7.35(t, 1H, J=7.52Hz), 7.08(dd, 1H, J=8.37, 2.39Hz), 7.04(d, 1H, J=8.37Hz), 7.00(d, 1H, J=2.39Hz), 6.61(d, 1H, J=8.37Hz), 4.73(q, 1H, J=6.84Hz), 4.58(d, 1H, J=45Hz), 4.43(d, 1H, J=45Hz), 4.20 (d, 1H, J=70Hz), 4.15(d, 1H, J=70Hz), 2.69(s, 3H), 2.12(s, 3H), 1.66(d, 3H, J=6.84Hz). MS(ES⁺) M+H=573.80

[2-Methyl-4-({[2-(4-{trifluoromethyl}phenyl)-4-(phenoxymethyl)-1,3-thiazol-5-yl]methyl}sulfanyl)phenoxy]acetic acid ¹H (CDCl₃) 300MHz δ 8.02(d, 2H, J=8.23Hz), 7.70(d, 2H, J=8.23Hz), 7.33(m, 2H), 7.22(s, 1H), 7.12(d, 1H, J=9.03Hz), 6.98(m, 3H), 6.58(d, 1H, J=8.49Hz), 4.87(s, 2H), 4.63(s, 2H), 4.30(s, 2H), 2.22(s, 3H). TLC(5% MeOH/CH₂Cl₂) R$_f$=0.17

(2-Methyl-4-{[4-{[3-(5-methyl-1,2,4-oxadiazol-3-yl)phenoxy]methyl}-2-phenyl-1,3-thiazol-5-yl)methyl]sulfanyl}phenoxy)acetic acid ¹H NMR (CDCl₃) 400MHz δ 7.91(m, 2H), 7.95(d, 1H, J=7.69Hz), 7.47(m, 1H), 7.42(m, 3H), 7.35(t, 1H, J=7.95Hz), 7.13(dd, 1H, J=8.37, 2.39Hz), 7.04(s, 2H), 6.60(d, 1H, J=8.37Hz), 4.67(s, 2H), 4.57(s, 2H), 4.20(s, 2H), 2.69(s, 3H), 2.12(s, 3H),
MS(ES⁺) M+H=560.30

2-{2-Methyl-4-[({4-{[4-(5-methyl-1,2,4-oxadiazol-3-yl)phenoxy]methyl}-2-[4-(trifluoromethyl)phenyl]-1,3-thiazol-5-yl}methyl)sulfanyl]phenoxy}propanoic acid ¹H (CDCl₃) 400MHz δ 7.94(m, 4H), 7.66(d, 2H, J=8.20Hz), 7.18(d, 1H, J=2.22Hz), 7.03(dd, 1H, J=8.20, 2.22Hz), 6.94(d, 2H, J=8.89Hz), 6.53(d, 1H, J=8.20Hz), 4.85 (d, 1H, J=79Hz), 4.80(d, 1H, J=79Hz), 4.69(q, 1H, J=6.84Hz), 4.26(d, 1H, J=70Hz), 4.21(d, 1H, J=70Hz), 2.63 (m, 3H), 2.18(s, 3H), 1.62(d, 3H, J=6.84Hz),
MS(ES⁻) M−H=640.00

{2-Ethyl-4-[({4-{[4-(4-fluorophenyl)-1-piperazinyl]methyl}-2-[4-(trifluoromethyl)phenyl]-1,3-thiazol-5-yl}methyl)sulfanyl]phenoxy}acetic acid ¹H NMR (CDCl₃) 400MHz δ 7.98(d, 2H, J=8.06Hz), 7.67 (d, 2H, J=8.06Hz), 7.11(dd, 1H, J=8.61, 2.20Hz), 7.02(d, 1H, J=2.20Hz), 6.93(m, 2H), 6.82(m, 2H), 6.68(d, 1H, J=8.61Hz), 4.62(s, 2H), 4.12(s, 2H), 3.44(s, 2H), 3.25(m, 4H), 3.02(br s, 4H), 2.58(q, 2H, J=7.51Hz), 1.10(t, 3H, J=7.51Hz),
MS(ES⁻) M−H=644.5

{4-[({4-[(4-Acetyl-1-piperazinyl)methyl]-2-[4-(trifluoromethyl)phenyl]-1,3-thiazol-5-yl}methyl)sulfanyl]-2-ethylphenoxy}acetic acid ¹H NMR (CDCl₃) 300MHz δ 8.04(d, 2H, J=8.28Hz), 7.75 (d, 2H, J=8.28Hz), 7.22(dd, 1H, J=8.55, 2.21Hz), 7.03(s, 1H), 6.74(d, 1H, J=8.55Hz), 4.74(s, 2H), 4.13(s, 2H), 3.76(br s, 4H), 3.36(s, 2H), 2.99(br s, 2H), 2.72(br s, 2H), 2.61(q, 2H, J=7.45Hz), 2.09(s, 3H), 1.12(t, 3H, J=7.45Hz),
MS(ES⁺) M+H=594.1

{4-[({4-{[4-(4-Acetylphenyl)-1-piperazinyl]methyl}-2-[4-(trifluoromethyl)phenyl]-1,3-thiazol-5-yl}methyl)sulfanyl]-2-ethylphenoxy}acetic acid ¹H NMR (CDCl₃) 400MHz δ 7.95(d, 2H, J=8.42Hz), 7.84 (d, 2H, J=8.97Hz), 7.67(d, 2H, J=8.42Hz), 7.14(dd, 1H, J=8.42, 2.20Hz), 6.95(s, 1H), 6.80(d, 2H, J=8.97Hz), 6.70(d, 1H, J=8.42Hz), 4.66(s, 2H), 4.08(s, 2H), 3.54(br s, 4H), 3.38 (s, 2H), 3.06(br s, 4H), 2.56(q, 2H, J=7.60Hz), 2.49(s, 3H), 1.08(t, 3H, J=7.60Hz),

{2-Ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetic acid ¹H NMR (CDCl₃) 400MHz δ 7.97(d, 2H, J=8.28Hz), 7.68 (d, 2H, J=8.28Hz), 7.15(dd, 1H, J=8.45, 2.24Hz), 6.94(d, 1H, J=2.24Hz), 6.88(d, 2H, J=9.14Hz), 6.79(d, 2H, J=9.14Hz), 6.72(d, 1H, J=8.45Hz), 4.66(s, 2H), 4.08(s, 2H), 3.72(s, 3H), 3.32(m, 6H), 3.09(br s, 4H), 2.56(q, 2H, J=7.50Hz), 1.08(t, 3H, J=7.50Hz),
MS(ES⁻) M−H=656.2

2-(4-{[(2-(4-Fluorophenyl)-4-{[4-(phenoxycarbonyl)-1-piperazinyl]methyl}-1,3-thiazol-5-yl)methyl]sulfanyl}-2-methylphenoxy)propanoic acid ¹H NMR (CDCl₃) 400MHz δ 7.91(m, 2H), 7.35(m, 3H), 7.19(m, 3H), 7.12(br s, 1H), 7.07(d, 2H, J=8.79Hz), 6.67(br s, 1H), 4.58(br s, 1H), 4.27(s, 2H), 3.59(m, 4H), 3.41(s, 2H), 2.51(br s, 4H), 2.19(s, 3H), 1.54(d, 1H, J=6.59Hz),
MS(ES⁻) M−H=620.4

2-(4-{[(2-(4-Fluorophenyl)-4-{[4-(isopropoxycarbonyl)-1-piperazinyl]methyl}-1,3-thiazol-5-yl)methyl]sulfanyl}-2-methylphenoxy)propanoic acid ¹H NMR (CDCl₃) 400MHz δ 7.94(m, 2H), 7.19(m, 3H), 7.05(br s, 1H), 6.64(d, 1H, J=8.42Hz), 4.69(br s, 1H), 4.47(br s, 1H), 4.21(s, 2H), 3.50(br s, 4H), 3.36(s, 2H), 2.64(br s, 4H), 2.18(s, 3H), 1.57(d, 3H, J=5.68Hz), 1.22(d, 6H, J=6.23Hz),
MS(ES⁻) M−H=586.2

2-[4-({[4-{[4-(Ethoxycarbonyl-1-piperazinyl]methyl}-2-(4-fluorophenyl)-1,3-thiazol-5-yl]methyl}sulfanyl)-2-methylphenoxy]propanoic acid ¹H NMR (CD₃OD) 400MHz δ 7.93(m, 2H), 7.19(m, 3H), 7.09(br s, 1H), 6.67(br s, 1H), 4.70(br s, 1H), 4.21(s, 2H), 4.10(q, 2H, J=7.14Hz), 3.49(m, 4H), 3.37(s, 2H), 2.60(br s, 4H), 2.18(s, 3H), 1.58(br s, 3H), 1.23(t, 3H, J=7.14Hz),
MS(ES⁻) M−H=572.2

2-(4-{[(2-(4-Fluorophenyl)-4-{[4-(3-methoxyphenyl)-1-piperazinyl]methyl}-1,3-thiazol-5-yl)methyl]sulfanyl}-2-methylphenoxy)propanoic acid ¹H NMR (CDCl₃) 400MHz δ 7.84(m, 2H), 7.13(m, 4H), 6.92(br s, 1H), 6.72(br s, 1H), 6.44(m, 3H), 4.38(br s, 1H), 4.00(s, 2H), 3.74(s, 3H), 3.40(m, 6H), 3.03(m, 4H), 2.17(s, 3H), 1.61(m, 3H),
MS(ES⁻) M−H=606.2

2-[4-({[4-{[4-(4-Acetylphenyl)-1-piperazinyl]methyl}-2-(4-fluorophenyl)-1,3-thiazol-5-yl]methyl}sulfanyl)-2-methylphenoxy]propanoic acid ¹H NMR (CD₃OD) 400MHz δ 7.94(m, 2H), 7.85(d, 2H, J=8.97Hz), 7.18(m, 3H), 7.03(br s, 1H), 6.92(d, 2H, J=8.97Hz), 6.67(br s, 1H), 4.61(br s, 1H), 4.19(s, 2H), 3.41 (m, 6H), 2.73(br s, 4H), 2.48(s, 3H), 2.17(s, 3H), 1.61(br s, 3H),
MS(ES⁻) M−H=618.2

2-(4-{[(2-(4-Fluorophenyl)-4-{[4-(4-methoxyphenyl)-1-piperazinyl]methyl}-1,3-thiazol-5-yl)methyl]sulfanyl}-2-methylphenoxy)propanoic acid $^1$H NMR (CD$_3$OD) 400MHz δ 7.97(m, 2H), 7.18(m, 3H), 7.02(br s, 1H), 6.91(d, 2H, J=8.79Hz), 6.81(d, 2H, J=8.79Hz), 6.62(br s, 1H), 4.66(br s, 1H), 4.17(s, 2H), 3.72(s, 3H), 3.41(s, 2H), 3.15(br s, 4H), 2.92(br s, 4H), 2.18(s, 3H), 1.59(br s, 3H),
MS(ES$^-$) M−H=606.2

{4-[({4-[(4-Acetyl-1-piperazinyl)methyl]-2-[4-(trifluoromethyl)phenyl]-1,3-thiazol-5-yl}methyl)sulfanyl]-2-propylphenoxy}acetic acid $^1$H NMR (CD$_3$OD) 400MHz δ 8.07(d, 2H, J=8.28Hz), 7.75(d, 2H, J=8.28Hz), 7.21(dd, 1H, J=8.45, 2.41Hz), 7.09(d, 1H, J=2.41Hz), 6.74(d, 1H, J=8.45Hz), 4.65(s, 2H), 4.26(s, 2H), 3.60(br s, 4H), 3.53(s, 2H), 2.75(t, 2H, J=4.74Hz), 2.69(t, 2H, J=4.74Hz), 2.52(t, 2H, J=7.41Hz), 2.07(s, 3H), 1.50(m, 2H), 0.80(t, 3H, J=7.41Hz),
MS(ES$^-$) M−H=606.3

{4-[({4-{[4-(3-Methoxyphenyl)-1-piperazinyl]methyl}-2-[4-(trifluoromethyl)phenyl]-1,3-thiazol-5-yl}methyl)sulfanyl]-2-propylphenoxy}acetic acid $^1$H NMR (CD$_3$OD) 400MHz δ 8.11(d, 2H, J=8.28Hz), 7.77(d, 2H, J=8.28Hz), 7.19(dd, 1H, J=8.28, 2.41Hz), 7.13(t, 1H, J=8.45Hz), 7.08(d, 1H, J=2.41Hz), 6.73(t, 1H, J=8.45Hz), 6.54(dd, 1H, J=8.28, 2.41Hz), 6.49(t, 1H, J=2.33Hz), 6.45(dd, 1H, J=8.28, 2.41Hz), 4.58(s, 2H), 4.26(s, 2H), 3.73(s, 3H), 3.69(s, 2H), 3.31(m, 4H), 3.11(t, 4H, J=4.66Hz), 2.52(t, 2H, J=7.33Hz), 1.49(s, 2H), 0.80(t, 3H, J=7.33Hz),
MS(ES$^-$) M−H=670.3

{4-[({4-{[4-(4-Acetylphenyl)-1-piperazinyl]methyl}-2-[4-(trifluoromethyl)phenyl]-1,3-thiazol-5-yl}methyl)sulfanyl]-2-propylphenoxy}acetic acid $^1$H NMR (CDCl$_3$) 400MHz δ 7.93(d, 2H, J=8.45Hz), 7.82(d, 2H, J=8.97Hz), 7.68(d, 2H, J=8.45Hz), 7.19(dd, 1H, J=8.45, 2.41Hz), 6.78(m, 4H), 4.73(s, 2H), 4.03(s, 2H), 3.71(t, 4H, J=5.09Hz), 3.28(m, 6H), 2.47(m, 5H), 1.46(m, 2H), 0.86(t, 3H, J=7.24Hz),
MS(ES$^-$) M−H=682.1

{4-[({4-{[4-Methoxyphenyl)-1-piperazinyl]methyl}-2-[4-(trifluoromethyl)phenyl]-1,3-thiazol-5-yl}methyl)sulfanyl]-2-propylphenoxy}acetic acid $^1$H NMR (CD$_3$OD) 400MHz δ 8.11(d, 2H, J=8.10Hz), 7.77(d, 2H, J=8.10Hz), 7.19(dd, 1H, J=8.62, 2.24Hz), 7.08(d, 1H, J=2.24Hz), 6.93(d, 2H, J=9.14Hz), 6.82(d, 2H, J=9.14Hz), 6.74(d, 1H, J=8.62Hz), 4.59(s, 2H), 4.26(s, 2H), 3.73(s, 2H), 3.71(s, 3H), 3.18(m, 8H), 2.52(t, 2H, J=7.33Hz), 1.48(m, 2H), 0.80(t, 3H, J=7.33Hz),
MS(ES$^+$) M+H=672.2

2-{2-Ethyl-4-[({4-{[4-(3-methoxyphenyl)-1-piperazinyl]methyl}-2-[4-(trifluoromethyl)phenyl]-1,3-thiazol-5-yl}methyl)sulfanyl]phenoxy}propanoic acid $^1$H NMR (CDCl$_3$) 400MHz δ 7.95(d, 2H, J=8.28Hz), 7.66(d, 2H, J=8.28Hz), 7.12(m, 2H), 6.90(s, 1H), 6.76(d, 1H, J=8.28Hz), 6.45(m, 3H), 4.80(q, 1H, J=6.90Hz), 4.02(s, 2H), 3.73(s, 3H), 3.35(m, 4H), 3.21(d, 1H, J=66Hz), 3.15(d, 1H, J=66Hz), 2.95(br s, 4H), 2.55(s, 2H), 1.62(d, 3H, J=6.90Hz), 1.07(t, 3H, J=7.50Hz),
MS(ES$^-$) M−H=670.0

2-{4-[({4-{[4-(4-Acetylphenyl)-1-piperazinyl]methyl}-2-[4-(trifluoromethyl)phenyl]-1,3-thiazol-5-yl}methyl)sulfanyl]-2-ethylphenoxy}propanoic acid $^1$H NMR (CDCl$_3$) 400MHz δ 7.93(d, 2H, J=8.28Hz), 7.82(d, 2H, J=8.97Hz), 7.65(d, 2H, J=8.28Hz), 7.08(dd, 1H, J=8.62, 2.41Hz), 6.87(d, 1H, J=2.41Hz), 6.79(d, 2H, J=8.97Hz), 6.72(d, 1H, J=8.62Hz), 4.80(q, 1H, J=6.72Hz), 4.04(d, 1H, J=66Hz), 3.98(d, 1H, J=66Hz), 3.49(br s, 4H), 3.28(d, 1H, J=83Hz), 3.14(d, 1H, J=83Hz), 3.00(br s, 4H), 2.54(m, 5H), 1.63(d, 3H, J=6.72Hz), 1.06(t, 3H, J=7.50Hz),
MS(ES$^-$) M−H=682.2

2-{2-Ethyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}propanoic acid $^1$H NMR (CDCl$_3$) 400MHz δ 7.97(d, 2H, J=8.45Hz), 7.66(d, 2H, J=8.45Hz), 7.10(dd, 1H, J=8.45, 2.24Hz), 6.94(d, 1H, J=2.24Hz), 6.89(d, 2H, J=9.14Hz), 6.80(d, 2H, J=9.14Hz), 6.75(d, 1H, J=8.45Hz), 4.77(q, 1H, J=6.72Hz), 4.04(s, 2H), 3.73(s, 3H), 3.25(m, 6H), 2.96(br s, 4H), 2.57(s, 2H), 1.61(d, 3H, J=6.72Hz), 1.09(t, 3H, J=7.50Hz),
MS(ES$^-$) M−H=670.3

2-{2-Ethyl-4-[({4-(4-morpholinylmethyl)-2-[4-(trifluoromethyl)phenyl]-1,3-thiazol-5-yl}methyl)sulfanyl]phenoxy}propanoic acid $^1$H NMR (CDCl$_3$) 400MHz δ 8.01(d, 2H, J=8.42Hz), 7.70(d, 2H, J=8.42Hz), 7.13(dd, 1H, J=8.42, 2.20Hz), 6.86(s, 1H), 6.76(d, 1H, J=8.42Hz), 4.84(q, 1H, J=6.65Hz), 4.04(d, 1H, J=47Hz), 3.98(d, 1H, J=47Hz), 3.87(br s, 4H), 3.21(d, 1H, J=83Hz), 3.08(d, 1H, J=83Hz), 2.95(br s, 4H), 2.55(s, 2H), 1.64(d, 3H, J=6.65Hz), 1.07(t, 3H, J=7.51Hz),
MS(ES$^-$) M−H=565.0

2-{2-Ethyl-4-[({4-{[4-(4-fluorophenyl)-1-piperazinyl]methyl}-2-[4-trifluoromethyl)phenyl]-1,3-thiazol-5-yl}methyl)sulfanyl]phenoxy}propanoic acid $^1$H NMR (CD$_3$OD) 400MHz δ 8.12(d, 2H, J=8.24Hz), 7.78(d, 2H, J=8.24Hz), 7.17(dd, 1H, J=8.61, 2.20Hz), 7.10(d, 1H, J=2.20Hz), 6.98(m, 4H), 6.71(d, 1H, J=8.61Hz), 4.71(q, 1H, J=6.90Hz), 4.27(s, 2H), 3.66(s, 2H), 3.20(m, 8H), 2.59(q, 2H, J=7.51Hz), 1.57(d, 3H, J=6.90Hz), 1.09(t, 3H, J=7.51Hz),
MS(ES$^-$) M−H=658.0

2-{4-[({4-[(4-Acetyl-1-piperazinyl)methyl]-2-[4-(trifluoromethyl)phenyl]-1,3-thiazol-5-yl}methyl)sulfanyl]-2-ethylphenoxy}propanoic acid $^1$H NMR (CD$_3$OD) 400MHz δ 8.10(d, 2H, J=8.24Hz), 7.77(d, 2H, J=8.24Hz), 7.19(t, 1H, J=2.38Hz), 7.09(d, 1H, J=2.38Hz), 6.71(d, 1H, J=8.24Hz), 4.80(q, 1H, J=6.78Hz), 4.26(s, 2H), 3.65(m, 6H), 3.56(d, 1H, J=92Hz), 3.51(d, 1H, J=92Hz), 2.83(m, 4H), 2.58(q, 2H, J=7.60Hz), 2.09(s, 3H), 1.60(d, 3H, J=6.78Hz), 1.09(t, 3H, J=7.60Hz),
MS(ES$^-$) M−H=606.0

{2-Ethyl-4-[({4-(4-morpholinylmethyl)-2-[4-(trifluoromethyl)phenyl]-1,3-thiazol-5-yl}methyl)sulfanyl]phenoxy}acetic acid ¹H NMR (CDCl₃) 300MHz δ 8.05(d, 2H, J=8.28Hz), 7.75 (d, 2H, J=8.28Hz), 7.19(dd, 1H, J=8.55, 2.21Hz), 6.98(s, 1H), 6.76(d, 1H, J=8.55Hz), 4.74(s, 2H), 4.12(s, 2H), 3.95(br s, 4H), 3.32(s, 2H), 3.06(br s, 4H), 2.61(q, 2H, J=7.54Hz), 1.14(t, 3H, J=7.54Hz),
MS(ES⁻) M−H=551.3

2-{2-Isopropyl-4-[({4-(4-morpholinylmethyl)-2-[4-(trifluoromethyl)phenyl]-1,3-thiazol-5-yl}methyl)sulfanyl]phenoxy}propanoic acid ¹H NMR (CD₃OD) 400MHz δ 8.11(d, 2H, J=8.24Hz), 7.78(d, 2H, J=8.24Hz), 7.25(dd, 1H, J=8.42, 2.38Hz), 7.00(d, 1H, J=2.38Hz), 6.74(d, 1H, J=8.42Hz), 4.88(q, 1H, J=6.78Hz), 4.25(s, 2H), 3.84(m, 5H), 3.66(d, 1H, J=28Hz), 3.22(m, 5H), 1.60(d, 3H, J=6.78Hz), 1.05(m, 6H),
MS(ES⁻) M−H=579.0

2-{4-[({4-{[4(4-Fluorophenyl)-1-piperazinyl]methyl}-2-[4-(trifluoromethyl)phenyl]-1,3-thiazol-5-yl}methyl)sulfanyl]-2-isopropylphenoxy}propanoic acid ¹H NMR (CD₃OD) 400MHz δ 8.13(d, 2H, J=8.06Hz), 7.79(d, 2H, J=8.06Hz), 7.26(d, 1H, J=8.42Hz), 7.06(s, 1H), 6.99(m, 4H), 6.75(d, 1H, J=8.42Hz), 4.88(q, 1H, J=6.78Hz), 4.29(s, 2H), 3.91(d, 1H, J=10Hz), 3.80(d, 1H, J=10Hz), 3.33 (m, 9H), 1.60(d, 3H, J=6.78Hz), 1.08(m, 6H),
MS(ES⁻) M−H=672.0

2-{4-[({4-[(4-Acetyl-1-piperazinyl)methyl]-2-[4-(trifluoromethyl)phenyl]-1,3-thiazol-5-yl}methyl)sulfanyl]-2-isopropylphenoxy}propanoic acid

MS(ES⁻) M−H=620.0

2-{2-Isopropyl-4-[({4-{[4-(3-methoxyphenyl)-1-piperazinyl]methyl}-2-[4-(trifluoromethyl)phenyl]-1,3-thiazol-5-yl}methyl)sulfanyl]phenoxy}propanoic acid ¹H NMR (CD₃OD) 400MHz δ 8.13(d, 2H, J=8.06Hz), 7.79(d, 2H, J=8.06Hz), 7.26(d, 1H, J=8.42Hz), 7.16(t, 1H, J=8.42Hz), 7.06(s, 1H), 6.74(d, 1H, J=8.42Hz), 6.56(d, 1H, J=8.42Hz), 6.50(br s, 2H), 4.90(q, 1H, J=6.78Hz), 4.27(s, 2H), 3.89(d, 1H, J=10Hz), 3.79(d, 1H, J=10Hz), 3.74(s, 3H), 3.34(m, 9H), 1.60(d, 3H, J=6.78Hz), 1.07(m, 6H),
MS(ES⁻) M−H=684.1

2-{4-[({4-{[4-(4-Acetylphenyl)-1-piperazinyl]methyl}-2-[4-(trifluoromethyl)phenyl]-1,3-thiazol-5-yl}methyl)sulfanyl]-2-isopropylphenoxy}propanoic acid ¹H NMR (CD₃OD) 400MHz δ 8.13(d, 2H, J=8.24Hz), 7.91(d, 2H, J=8.97Hz), 7.78(d, 2H, J=8.24Hz), 7.25(d, 1H, J=8.97Hz), 7.04(m, 3H), 6.74(d, 1H, J=8.24Hz), 4.89(q, 1H, J=6.78Hz), 4.28(s, 2H), 3.90(d, 1H, J=55Hz), 3.79(d, 1H, J=55Hz), 3.60(br s, 4H), 3.32(m, 5H), 2.50(s, 3H), 1.61(d, 3H, J=6.78Hz), 1.07(d, 6H, J=7.51Hz),
MS(ES⁻) M−H=696.2

2-{2-Isopropyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}propanoic acid ¹H NMR (CD₃OD) 400MHz δ 8.13(d, 2H, J=8.24Hz), 7.79(d, 2H, J=8.24Hz), 7.27(d, 1H, J=8.61Hz), 7.05(s, 1H), 6.95(d, 2H, J=8.79Hz), 6.84(d, 2H, J=8.79Hz), 6.75(d, 1H, J=8.61Hz), 4.88(m, 1H) buried under MeOH signal, 4.28(s, 2H), 3.90(d, 1H, J=28Hz), 3.80(d, 1H, J=28Hz), 3.71(s, 3H), 3.56(br s, 4H), 3.28(m, 1H) buried under MeOH signal, 2.96 (br s, 4H), 1.58(d, 3H, J=6.59Hz), 1.07(m, 6H),
MS(ES⁻) M−H=684.1

{2-Isopropyl-4-[({4-(4-morpholinylmethyl)-2-[4-(trifluoromethyl)phenyl]-1,3-thiazol-5-yl}methyl)sulfanyl]phenoxy}acetic acid ¹H NMR (CD₃OD) 400MHz δ 8.12(d, 2H, J=8.06Hz), 7.79(d, 2H, J=8.06Hz), 7.27(d, 1H, J=8.42Hz), 7.04(s, 1H), 6.80(d, 1H, J=8.42Hz), 4.76(s, 2H), 4.27(s, 2H), 3.87(m, 6H), 3.22(m, 5H), 1.07(d, 6H, J=6.78Hz),
MS(ES⁻) M−H=565.0

{4-[({4-{[4-(4-Fluorophenyl)-1-piperazinyl]methyl}-2-[4-(trifluoromethyl)phenyl]-1,3-thiazol-5-yl}methyl)sulfanyl]-2-isopropylphenoxy}acetic acid ¹H NMR (CD₃OD) 400MHz δ 8.13(d, 2H, J=8.06Hz), 7.79(d, 2H, J=8.06Hz), 7.28(d, 1H, J=8.42Hz), 7.09(s, 1H), 6.98(m, 4H), 6.81(d, 1H, J=8.42Hz), 4.74(s, 2H), 4.28(s, 2H), 3.89(s, 2H), 3.61(br s, 4H), 3.29(m, 1H) buried under MeOH signal, 3.02(br s, 4H), 1.07(d, 6H, J=6.78Hz),
MS(ES⁻) M−H=658.0

{4-[({4-[(4-Acetyl-1-piperazinyl)methyl]-2-[4-(trifluoromethyl)phenyl]-1,3-thiazol-5-yl}methyl)sulfanyl]-2-isopropylphenoxy}acetic acid ¹H NMR (CD₃OD) 400MHz δ 8.13(d, 2H, J=8.06Hz), 7.79(d, 2H, J=8.06Hz), 7.28(d, 1H, J=8.42Hz), 7.03(br s, 1H), 6.80(d, 1H, J=8.42Hz), 4.76(s, 2H), 4.27(s, 2H), 3.80(m, 6H), 3.21(m, 5H), 2.11(s, 3H), 1.06(d, 6H, J=6.78Hz),
MS(ES⁻) M−H=606.2

2-{4-[({4-{[4-(4-Methoxyphenyl)-1-piperazinyl]methyl}-2-[4-(trifluoromethyl)phenyl]-1,3-thiazol-5-yl}methyl)sulfanyl]-2-propylphenoxy}propanoic acid ¹H NMR (CD₃OD) 400MHz δ 8.12(d, 2H, J=8.28Hz), 7.79(d, 2H, J=8.28Hz), 7.23(dd, 1H, J=8.45, 2.24Hz), 7.09(d, 1H, J=2.24Hz), 6.95(d, 2H, J=9.14Hz), 6.84(d, 2H, J=9.14Hz), 6.71(d, 1H, J=8.45Hz), 4.81(q, 1H, J=6.72Hz), 4.29(s, 2H), 3.98(d, 1H, J=14Hz), 3.90(d, 1H, J=14Hz), 3.71 (s, 3H), 3.50(br s, 4H), 3.21(m, 4H), 2.50(t, 2H, J=7.33Hz), 1.58(d, 3H, J=6.72Hz), 1.48(m, 2H), 0.79(t, 3H, J=7.33Hz),
MS(ES⁻) M−H=684.0

{4-[({4-(4-Morpholinylmethyl)-2-[4-(trifluoromethyl)phenyl]-1,3-thiazol-5-yl}methyl)sulfanyl]-2-propylphenoxy}acetic acid ¹H NMR (CD₃OD) 400MHz δ 8.10(d, 2H, J=8.79Hz), 7.78(d, 2H, J=8.79Hz), 7.20(dd, 1H, J=8.42, 2.20Hz), 7.08(d, 1H, J=2.20Hz), 6.75(d, 1H, J=8.42Hz), 4.63(s, 2H), 4.26(s, 2H), 3.79(t, 4H, J=4.21Hz), 3.64(s, 2H), 2.97(t, 4H, J=4.21Hz), 2.53(t, 2H, J=7.42Hz), 1.50(s, 2H), 0.82(t, 3H, J=7.42Hz),

MS(ES⁻) M−H=658.0

{4-[({4-{[4-(4-Fluorophenyl)-1-piperazinyl]methyl}-2-[4-(trifluoromethyl)phenyl]-1,3-thiazol-5-yl}methyl)sulfanyl]-2-propylphenoxy}acetic acid ¹H NMR (CDCl₃) 400MHz δ 7.97(d, 2H, J=8.24Hz), 7.67 (d, 2H, J=8.24Hz), 7.12(dd, 1H, J=8.42, 2.20Hz), 7.01(d, 1H, J=2.20Hz), 6.93(m, 2H), 6.83(m, 2H), 6.69(d, 1H, J=8.42Hz), 4.62(s, 2H), 4.12(s, 2H), 3.45(s, 2H), 3.26(t, 4H, J=4.85Hz), 3.04(t, 4H, J=4.85Hz), 2.52(t, 2H, J=7.33Hz), 1.51(s, 2H), 0.83(t, 3H, J=7.33Hz), 2-{4-[({4-[(3,5-Dimethyl-1-piperazinyl)methyl]-2-[4-(trifluoromethyl)phenyl]-1,3-thiazol-5-yl}methyl)sulfanyl]-2-methylphenoxy}propanoic acid ¹H NMR (CDCl₃) 400MHz δ 8.03(d, 2H, J=8.23Hz), 7.71 (d, 2H, J=8.23Hz), 7.20(m, 2H), 6.66(d, 1H, J=8.55Hz), 4.72 (q, 1H, J=6.64Hz), 4.26(d, 1H, J□.87Hz), 4.18(d, 1H, J□.87Hz), 3.34(m, 2H), 3.05(m, 2H), 2.71(m, 2H), 2.21(s, 3H), 1.97(m, 2H), 1.63(d, 3H, J=6.64Hz), 1.35(m, 6H),

MS(ES⁺) M+H=580.1

HPLC(C-18 3μm) 1% MeOH/0-99% Acetonitrile/Water (0.1% TFA) 5min run R_f=3.98

2-{4-[({4-{[4-(4-Chlorophenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CDCl₃) 400MHz δ 10.42(s, 1H), 7.92(d, 2H, J=8.20Hz), 7.64(d, 2H, J=8.20Hz), 7.15(d, 2H, J=9.06Hz), 7.01(d, 1H, J=2.20Hz), 6.96(d, 1H, J=8.37Hz), 6.72(d, 2H, J=9.06Hz), 6.59(d, 1H, J=8.37Hz), 4.64(q, 1H, J=6.78Hz), 4.09(s, 2H), 3.58(d, 1H, J=18Hz), 3.49(d, 1H, J=18Hz), 3.26 (m, 4H), 3.05(m, 4H), 2.13(s, 3H), 1.56(d, 3H, J=6.78Hz),

MS(ES⁺) M+H=662.0

HPLC(C-18 3μm) 1% MeOH/0-99% Acetonitrile/Water (0.1% TFA) 5min run R_f=4.13

2-{4-[({4-{[4-(tert-Butoxycarbonyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CDCl₃) 400MHz δ 10.07(s, 1H), 7.93(d, 2H, J=8.23Hz), 7.63(d, 2H, J=8.23Hz), 7.04(s, 1H), 6.98(d, 1H, J=8.37Hz), 6.58(d, 1H, J=8.37Hz), 4.65(q, 1H, J=6.78Hz), 4.12(d, 1H, J=70Hz), 4.05(d, 1H, J=70Hz), 3.47(m, 6H), 2.73(m, 4H), 2.14(s, 3H), 1.57(d, 3H, J=6.78Hz), 1.38(s, 9H),

MS(ES⁺) M+H=652.0

HPLC(C-18 3μm) 1% MeOH/0-99% Acetonitrile/Water (0.1% TFA) 5min run R_f=4.16

2-{2-Methyl-4-[({4-(1-piperazinylmethyl)-2-[4-(trifluoromethyl)phenyl]-1,3-thiazol-5-yl}methyl)sulfanyl]phenoxy}propanoic acid ¹H NMR (CDCl₃) 400MHz δ 9.26(br s, 1H), 7.97(br s, 2H), 7.63(br s, 2H), 7.10(br s, 2H), 6.67(br s, 1H), 4.56(br s, 1H), 4.11(br s, 2H), 3.39(br s, 2H), 2.98(br s, 4H), 2.41(br s, 4H), 2.07(br s, 3H), 1.44(br s, 3H),

MS(ES⁺) M+H=552

HPLC(C-18 3μm) 1% MeOH/0-99% Acetonitrile/Water (0.1% TFA) 5min run R_f=3.80

{2-Isopropyl-4-[({4-{[4-(3-methoxyphenyl)-1-piperazinyl]methyl}-2-[4-(trifluoromethyl)phenyl]-1,3-thiazol-5-yl}methyl)sulfanyl]-phenoxy}acetic acid ¹H NMR (CD₃OD) 400MHz δ 8.13(d, 2H, J=8.06Hz), 7.79(d, 2H, J=8.06Hz), 7.28(d, 1H, J=8.24Hz), 7.15(m, 1H), 7.09(s, 1H), 6.80(d, 1H, J=8.24Hz), 6.52(m, 3H), 4.74(s, 2H), 4.28(s, 2H), 3.88(s, 2H), 3.73(m, 3H), 3.48(br s, 4H), 3.29(m, 1H) buried under MeOH signal, 3.05(s, 4H), 1.06(d, 6H, J=6.59Hz),

MS(ES⁻) M−H=670.0

{4-[({4-{[4-(4-Acetylphenyl)-1-piperazinyl]methyl}-2-[4-(trifluoromethyl)phenyl]-1,3-thiazol-5-yl}methyl)sulfanyl]-2-isopropylphenoxy}acetic acid ¹H NMR (CD₃OD) 400MHz δ 8.13(d, 2H, J=7.87Hz), 7.91(d, 2H, J=8.79Hz), 7.78(d, 2H, J=7.87Hz), 7.27(d, 1H, J=8.24Hz), 7.09(br s, 1H), 7.02(d, 2H, J=8.24Hz), 6.80(d, 1H, J=8.79Hz), 4.74(s, 2H), 4.29(s, 2H), 3.89(s, 2H), 3.62(br s, 4H), 3.30(m, 5H), 2.51(s, 3H), 1.07(d, 6H, J=6.78Hz),

MS(ES⁻) M−H=682.0

{2-Isopropyl-4-[({4-{[4-(4-methoxyphenyl)-1-piperazinyl]methyl}-2-[4-(trifluoromethyl)phenyl]-1,3-thiazol-5-yl}methyl)sulfanyl]phenoxy}acetic acid ¹H NMR (CD₃OD) 400MHz δ 8.13(d, 2H, J=8.06Hz), 7.79(d, 2H, J=8.06Hz), 7.29(d, 1H, J=8.45Hz), 7.09(s, 1H), 6.98(d, 2H, J=8.45Hz), 6.83(m, 3H), 4.73(s, 2H), 4.30(s, 2H), 3.90(s, 3H), 3.35(m, 11H), 1.07(d, 6H, J=6.59Hz),

MS(ES⁻) M−H=670.0

2-{4-[({4-(4-Morpholinylmethyl)-2-[4-(trifluoromethyl)phenyl]-1,3-thiazol-5-yl}methyl)sulfanyl]-2-propylphenoxy}propanoic acid ¹H NMR (CD₃OD) 400MHz δ 8.18(d, 2H, J=8.00Hz), 7.84(d, 2H, J=8.00Hz), 7.30(dd, 1H, J=8.55, 2.48Hz), 7.11(d, 1H, J=2.48Hz), 6.78(d, 1H, J=8.55Hz), 4.91(s, 1H) buried under MeOH signal, 4.33(s, 2H), 3.94(m, 6H), 3.24(br s, 4H), 2.56(t, 2H, J=7.45Hz), 1.59(m, 5H), 0.86(t, 3H, J=7.45Hz),

MS(ES⁻) M−H=579.0

2-{4-[({4-{[4-(4-Fluorophenyl)-1-piperazinyl]methyl}-2-[4-(trifluoromethyl)phenyl]-1,3-thiazol-5-yl}methyl)sulfanyl]-2-propylphenoxy}propanoic acid ¹H NMR (CD₃OD) 400MHz δ 8.18(d, 2H, J=8.28Hz), 7.85(d, 2H, J=8.28Hz), 7.30(dd, 1H, J=8.55, 2.21Hz), 7.16(d, 1H, J=2.21Hz), 7.06(m, 4H), 6.78(d, 1H, J=8.55Hz), 4.89(br s, 1H) hidden under MeOH signal, 4.35(s, 2H), 4.06(d, 1H, J=35Hz), 3.98(d, 1H, J=35Hz), 3.68(br s, 4H), 3.08(br s, 4H), 2.56(t, 2H, J=7.45Hz), 1.57(m, 5H), 0.86(t, 3H, J=7.45Hz),

MS(ES⁻) M−H=672.0

2-{4-[({4-[(4-Acetyl-1-piperazinyl)methyl]-2-[4-(trifluoromethyl)phenyl]-1,3-thiazol-5-yl}methyl)sulfanyl]-2-propylphenoxy}propanoic acid ¹H NMR (CD₃OD) 400MHz δ 8.17(d, 2H, J=8.28Hz), 7.84(d, 2H, J=8.28Hz), 7.29(dd, 1H, J=8.55, 2.21Hz), 7.10(d, 1H, J=2.21Hz), 6.77(d, 1H, J=8.55Hz), 4.93(q, 1H, J=6.78Hz), 4.32(s, 2H), 3.86(m, 6H), 3.27(m, 4H), 2.56(m, 2H), 2.18(s, 3H), 1.66(d, 3H, J=6.78Hz), 1.54(m, 2H), 0.85(t, 3H, J=7.31Hz),

MS(ES⁻) M−H=620.0

2-{4-[({4-{[4-(3-Methoxyphenyl)-1-piperazinyl]methyl}-2-[4-(trifluoromethyl)phenyl]-1,3-thiazol-5-yl}methyl)sulfanyl]-2-propylphenoxy}propanoic acid ¹H NMR (CD₃OD) 400MHz δ 8.18(d, 2H, J=8.55Hz), 7.85(d, 2H, J=8.55Hz), 7.30(dd, 1H, J=8.55, 2.21Hz), 7.22(t, 1H, J=8.55Hz), 7.16(d, 1H, J=2.21Hz), 6.77(d, 1H, J=8.55Hz), 6.58(m, 3H), 4.80(m, 1H), 4.34(s, 2H), 4.06(d, 1H, J=07Hz), 3.97(d, 1H, J=07Hz), 3.79(s, 3H), 3.60(br s, 4H), 3.08(br s, 4H), 2.56(t, 2H, J=7.17Hz), 1.58(m, 5H), 0.85(t, 3H, J=7.17Hz),

MS(ES⁻) M−H=684.1

2-{4-[({4-{[4-(4-Acetylphenyl)-1-piperazinyl]methyl}-2-[4-(trifluoromethyl)phenyl]-1,3-thiazol-5-yl}methyl)sulfanyl]-2-propylphenoxy}propanoic acid ¹H NMR (CD₃OD) 400MHz δ 8.12(d, 2H, J=8.28Hz), 7.91(d, 2H, J=9.14Hz), 7.78(d, 2H, J=8.28Hz), 7.22(dd, 1H, J=8.28, 2.24Hz), 7.10(d, 1H, J=2.24Hz), 7.03(d, 2H, J=9.14Hz), 6.71(d, 1H, J=8.28Hz), 4.81(q, 1H, J=6.72Hz), 4.29(s, 2H), 3.99(d, 1H, J=0.14Hz), 3.91(d, 1H, J=0.14Hz), 3.60(br s, 4H), 3.33(m, 4H), 2.48(m, 5H), 1.59(d, 3H, J=6.72Hz), 1.48(m, 2H), 0.78(t, 3H, J=7.41Hz),

MS(ES⁻) M−H=696.1

2-{2-Methyl-4-[({4-{[4-(2-pyrimidinyl)-1-piperazinyl]methyl}-2-[4-(trifluoromethyl)phenyl]-1,3-thiazol-5-yl}methyl)sulfanyl]phenoxy}propanoic acid ¹H NMR (CD₃OD) 300MHz δ 8.35(d, 2H, J=4.69Hz), 8.13(d, 2H, J=8.28Hz), 7.80(d, 2H, J=8.28Hz), 7.21(s, 1H), 7.13(d, 1H, J=8.28Hz), 6.71(d, 1H, J=8.28Hz), 6.63(t, 1H, J=4.69Hz), 4.59(m, 1H), 4.31(s, 2H), 3.86(t, 4H, J=4.69Hz), 3.50(s, 2H), 2.69(t, 4H, J=4.69Hz), 2.22(s, 3H), 1.59(d, 3H, J=6.78Hz),

MS(ES⁻) M−H=628.5

2-{4-[({4-{[4-(2,4-Dimethoxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 300MHz δ 8.17(d, 2H, J=8.00Hz), 7.80(d, 2H, J=8.00Hz), 7.20(br s, 1H), 7.04(br s, 1H), 6.92(d, 1H, J=8.55Hz), 6.67(br s, 1H), 6.56(m, 1H), 6.48(m, 1H), 4.59(br s, 1H), 4.27(s, 2H), 3.84(s, 3H), 3.78(s, 3H), 3.55(s, 2H), 3.07(m 8H), 2.21(s, 3H), 1.56(br s, 3H),

MS(ES⁻) M−H=685.6

2-{2-Methyl-4-[({4-({4-[2-oxo-2-(1-pyrrolidinyl)ethyl]-1-piperazinyl}methyl)-2-[4-(trifluoromethyl)phenyl]-1,3-thiazol-5-yl}methyl)sulfanyl]phenoxy}propanoic acid

MS(ES⁻) M−H=660.7

CHN Analysis 0.3H₂O (Theoretical % C=53.62; % H=6.05; % N=7.82; Found % C=53.33; % H=6.01; % N=7.95)

2-[2-Methyl 4-({[2-[4-(trifluoromethyl)phenyl]-4-({4-[3-(trifluoromethyl)phenyl]-1-piperazinyl}methyl)-1,3-thiazol-5-yl]methyl}sulfanyl)phenoxy]propanoic acid ¹H NMR (CD₃OD) 300MHz δ 8.09(d, 2H, J=8.28Hz), 7.77(d, 2H, J=8.28Hz), 7.40(s, 1H), 7.19(m, 4H), 7.07(d, 1H, J=7.73Hz), 6.71(d, 1H, J=8.28Hz), 4.47(m, 1H), 4.33(s, 2H), 3.53(s, 2H), 3.23(m, 4H), 2.64(m, 4H), 2.22(s, 3H), 1.57(d, 3H, J=6.78Hz),

MS(ES⁻) M−H=694.5

2-{4-[({4-{[4-(2-Methoxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 300MHz δ 8.09(d, 2H, J=8.28Hz), 7.77(d, 2H, J=8.28Hz), 7.25(s, 1H), 7.17(s, 1H), 6.96(m, 4H), 6.70(s, 1H), 4.51(m, 1H), 4.34(s, 2H), 3.86(s, 3H), 3.57(s, 2H), 3.07(br s, 4H), 2.76(br s, 4H), 2.23(br s, 3H), 1.54(br s, 3H),

MS(ES⁻) M−H=656.5

2-{4-[({4-[(4-Acetyl-1-piperazinyl)methyl]-2-[4-(trifluoromethyl)phenyl]-1,3-thiazol-5-yl}methyl)sulfanyl]-2-methylphenoxy}propanoic acid ¹H NMR (CDCl₃) 400MHz δ 7.93(d, 2H, J=8.20Hz), 7.63(d, 2H, J=8.20Hz), 7.02(m, 2H), 6.57(d, 1H, J=8.20Hz), 4.65(q, 1H, J=6.78Hz), 4.16(d, 1H, J=87Hz), 4.09(d, 1H, J=87Hz), 3.55(m, 6H), 2.74(m, 4H), 2.11(s, 3H), 1.98(s, 3H), 1.55(d, 3H, J=6.78Hz),

MS(ES⁺) M+H=594.0

HPLC(C-18 3μm) 1% MeOH/0-99% Acetonitrile/Water (0.1% TFA) 5min run R_f=3.79

2-{2-Methyl-4-[({4-{[4-(4-pyridinyl)-1-piperazinyl]methyl}-2-[4-(trifluoromethyl)phenyl]-1,3-thiazol-5-yl}methyl)sulfanyl]phenoxy}propanoic acid ¹H NMR (CD₃OD) 400MHz δ 8.01(d, 2H, J=8.20Hz), 7.95(d, 2H, J=8.20Hz), 7.64(d, 2H, J=8.20Hz), 7.16(d, 1H, J=2.22Hz), 7.09(dd, 1H, J=8.37, 2.22Hz), 6.97(d, 2H, J=8.20Hz), 6.63(d, 1H, J=8.37Hz), 4.48(q, 1H, J=6.78Hz), 4.19(s, 2H), 3.57(t, 4H, J=5.10Hz), 3.48(s, 2H), 2.46(t, 4H, J=5.10Hz), 2.14(s, 3H), 1.54(d, 3H, J=6.78Hz),

MS(ES⁺) M+H=629.0

HPLC(C-18 3μm) 1% MeOH/0-99% Acetonitrile/Water (0.1% TFA) 5min run R_f=4.22

2-{4-[({4-{[4-(3-Methoxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CDCl₃) 400MHz δ 10.57(s, 1H), 7.91(d, 2H, J=8.20Hz), 7.63(d, 2H, J=8.20Hz), 7.11(t, 1H, J=8.20Hz), 6.98(m, 2H), 6.60(d, 1H, J=8.20Hz), 6.41(dd, 2H, J=8.20, 2.22Hz), 6.35(t, 1H, J=2.22Hz), 4.65(q, 1H, J=6.84Hz), 4.10(s, 2H), 3.72(s, 3H), 3.59(d, 1H, J=18Hz), 3.49(d, 1H, J=18Hz), 3.35(m, 4H), 3.10(m, 4H), 2.12(s, 3H), 1.55(d, 3H, J=6.84Hz),

MS(ES⁺) M+H=658.0

HPLC(C-18 3μm) 1% MeOH/0-99% Acetonitrile/Water (0.1% TFA) 5min run R_f=4.09

2-{2-Methyl-4-[({4-(4-morpholinylmethyl)-2-[4-(trifluoromethyl)phenyl]-1,3-thiazol-5-yl}methyl)sulfanyl]phenoxy}propanoic acid $^1$H NMR (CDCl$_3$) 400MHz δ 11.61(s, 1H), 8.00(d, 2H, J=8.23Hz), 7.69(d, 2H, J=8.23Hz), 7.10(dd, 1H, J=8.37, 2.20Hz), 6.83(d, 1H, J=2.20Hz), 6.71(d, 1H, J=8.37Hz), 4.84 (q, 1H, J=6.72Hz), 4.12(m, 4H), 3.84(m, 2H), 3.43(m, 3H), 3.19(m, 2H), 2.88(m, 1H), 2.10(s, 3H), 1.61(d, 3H, J=6.72Hz),

MS(ES$^+$) M+H=553.0

HPLC(C-18 3μm) 1% MeOH/0-99% Acetonitrile/Water (0.1% TFA) 5min run R$_t$=3.89

2-{4-[({4-{[4-(Ethoxycarbonyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CDCl$_3$) 400MHz δ 10.39(s, 1H), 7.93(d, 2H, J=8.23Hz), 7.64(d, 2H, J=8.23Hz), 7.05(d, 1H, J=2.39Hz), 6.97(d, 1H, J=8.37Hz), 6.57(d, 1H, J=8.37Hz), 4.65(q, 1H, J=6.78Hz), 4.09(q, 4H, J=7.06Hz), 3.58(m, 4H), 3.39(m, 2H), 2.74(m, 4H), 2.14(s, 3H), 1.57(d, 3H, J=6.78Hz), 1.21(t, 3H, J=7.06Hz),

MS(ES$^+$) M+H=624.0

HPLC(C-18 3μm) 1% MeOH/0-99% Acetonitrile/Water (0.1% TFA) 5min run R$_t$=3.93

2-{4-[({4-{[4-(4-Acetylphenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CDCl$_3$) 400MHz δ 9.84(s, 1H), 7.91(d, 2H, J=8.20Hz), 7.81(d, 2H, J=8.89Hz), 7.63(d, 2H, J=8.20Hz), 7.00(d, 1H, J=2.20Hz), 6.93(dd, 1H, J=8.37, 2.20Hz), 6.76(d, 2H, J=8.89Hz), 6.58(d, 1H, J=8.37Hz), 4.66(q, 1H, J=6.78Hz), 4.08(s, 2H), 3.45(m, 6H), 2.96(m, 4H), 2.47(s, 3H), 2.13(s, 3H), 1.59(d, 3H, J=6.78Hz),

MS(ES$^+$) M+H=670.0

HPLC(C-18 3μm) 1% MeOH/0-99% Acetonitrile/Water (0.1% TFA) 5min run R$_t$=4.03

2-{4-[({4-{[4-(4-Fluorophenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CDCl$_3$) 400MHz δ 7.92(d, 2H, J=8.23Hz), 7.62 (d, 2H, J=8.23Hz), 7.05(s, 1H), 6.89(m, 2H), 6.75(m, 2H), 6.55(d, 1H, J=8.23Hz), 4.59(m, 1H), 4.17(m, 2H), 3.53(m, 2H), 3.21(m, 4H), 2.97(m, 4H), 2.12(s, 3H), 1.51(d, 3H, J=6.78Hz),

MS(ES$^+$) M+H=646.0

HPLC(C-18 3μm) 1% MeOH/0-99% Acetonitrile/Water (0.1% TFA) 5min run R$_t$=4.11

2-{4-[({4-({4-[(4-Fluorophenyl)sulfonyl]-1-piperazinyl}methyl)-2-[4-(trifluoromethyl)phenyl]-1,3-thiazol-5-yl}methyl)sulfanyl]-2-methylphenoxy}propanoic acid $^1$H NMR (CD$_3$OD) 400MHz δ 8.03(d, 2H, J=8.20Hz), 7.83(t, 2H, J=7.69Hz), 7.73(d, 2H, J=8.20Hz), 7.33(t, 2H, J=7.69Hz), 7.17(s, 1H), 7.08(d, 1H, J=8.20Hz), 6.64(d, 1H, J=8.20Hz), 4.67(br s, 1H), 4.22(s, 2H), 3.37(s, 2H), 2.99(br s, 4H), 2.50(br s, 4H), 2.16(s, 3H), 1.57(d, 3H, J=6.84Hz),

MS(ES$^-$) M−H=708.0

2-{2-Methyl-4-[({4-{[4-(3-methylbutanoyl)-1-piperazinyl]methyl}-2-[4-(trifluoromethyl)phenyl]-1,3-thiazol-5-yl}methyl)sulfanyl]phenoxy}propanoic acid $^1$H NMR (CD$_3$OD) 400MHz δ 8.12(d, 2H, J=8.28Hz), 7.80(d, 2H, J=8.28Hz), 7.23(d, 1H, J=2.21Hz), 7.17(dd, 1H, J=8.28, 2.21Hz), 6.72(d, 1H, J=8.28Hz), 4.72(q, 1H, J=6.44Hz), 4.32(s, 2H), 3.63(br s, 4H), 3.44(s, 2H), 2.59(br s, 4H), 2.31(d, 2H, J=6.90Hz), 2.21(s, 3H), 2.06(m, 1H), 1.62 (d, 3H, J=6.44Hz), 0.98(d, 6H, J=6.90Hz),

MS(ES$^-$) M−H=634.0

2-{4-[({4-{[4-(Cyclohexylcarbonyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 400MHz δ 8.06(d, 2H, J=8.10Hz), 7.74(d, 2H, J=8.10Hz), 7.16(d, 1H, J=2.24Hz), 7.09(dd, 1H, J=8.45, 2.24Hz), 6.64(d, 1H, J=8.45Hz), 4.68(q, 1H, J=6.78Hz), 4.25(s, 2H), 3.60(br s, 4H), 3.42(s, 2H), 2.62(br s, 4H), 2.16(s, 3H), 1.72(m, 5H), 1.56(d, 3H, J=6.72Hz), 1.31 (m, 6H),

MS(ES$^-$) M−H=661.0

2-{2-Methyl-4-[({-4-{[4-(2-pyrazinyl)-1-piperazinyl]methyl}-2-[4-(trifluoromethyl)phenyl]-1,3-thiazol-5-yl}methyl)sulfanyl]phenoxy}propanoic acid $^1$H NMR (CD$_3$OD) 300MHz δ
8.17(m, 4H), 7.81(m, 3H), 7.26(br s, 1H), 7.13(br s, 1H), 6.75(br s, 1H), 4.68(br s, 1H), 4.32(s, 2H), 3.65(br s, 4H), 3.48(s, 2H), 2.64(br s, 4H), 2.20(s, 3H), 1.60(br s, 3H),

MS(ES$^-$) M−H=628.3

2-{4-[({4-({4-[4-(dimethylamino)benzoyl]-1-piperazinyl}methyl)-2-[4-(trifluoromethyl)phenyl]-1,3-thiazol-5-yl}methyl)sulfanyl]-2-methylphenoxy}propanoic acid $^1$H NMR (CD$_3$OD) 400MHz δ,
8.12(d, 2H, J=8.28Hz), 7.80(d, 2H, J=8.28Hz), 7.35(d, 2H, J=9.11Hz), 7.21(d, 1H, J=2.21Hz), 7.14(d, 1H, J=8.55Hz), 6.78(d, 2H, J=9.11Hz), 6.70(d, 1H, J=8.55Hz), 4.68(q, 1H, J=6.62Hz), 4.31(s, 2H), 3.70(br s, 4H), 3.45(s, 2H), 3.02(s, 6H), 2.63(br s, 4H), 2.19(s, 3H), 1.59(d, 3H, J=6.62Hz),

MS(ES$^-$) M−H=697.0

2-{4-[({4-{[4-(2-Furoyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 400MHz δ 8.06(d, 2H, J=8.28Hz), 7.73(d, 2H, J=8.28Hz), 7.65(m, 1H), 7.16(d, 1H, J=2.20Hz), 7.07(d, 1H, J=8.55Hz), 7.01(d, 1H, J=3.62Hz), 6.63(d, 1H' J=8.45Hz), 6.55(m, 1H), 4.66(q, 1H, J=6.55Hz), 4.25(s, 2H), 3.77(br s, 4H), 3.39(s, 2H), 2.59(br s, 4H), 2.14(s, 3H), 1.54 (d, 3H, J=6.55Hz),

MS(ES$^-$) M−H=644.1

2-{4-[({4-{[4-(Cyclopentylcarbonyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 400MHz δ 8.13(d, 2H, J=8.28Hz), 7.80(d, 2H, J=8.28Hz), 7.23(d, 1H, J=2.39Hz), 7.15(d, 1H, J=8.28Hz), 6.71(br s, 1H), 4.73(q, 1H, J=6.78Hz), 4.31(s, 2H), 3.67(br s, 4H), 3.45(s, 2H), 3.06(m, 1H), 2.62(br s, 4H), 2.22(s, 3H), 1.75(m, 14H),
MS(ES$^-$) M−H=646.2

2-{4-[({4-{[4-(Cyclobutylcarbonyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 400MHz δ 8.09(d, 2H, J=8.20Hz), 7.77(d, 2H, J=8.20Hz), 7.18(d, 1H, J=2.22Hz), 7.13(dd, 1H, J=8.55, 2.22Hz), 6.68(d, 1H, J=8.55Hz), 4.71(q, 1H, J=6.75Hz), 4.28(s, 2H), 3.60(br s, 2H), 3.46(br s, 2H), 3.41(s, 2H), 2.57(t, 4H, J=4.44Hz), 2.22(m, 6H), 2.00(m, 2H), 1.83(m, 2H), 1.60(d, 3H, J=6.75Hz),
MS(ES$^-$) M−H=633.1

2-{4-[({4-{[4-cyclopropylcarbonyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 400MHz δ 8.10(d, 2H, J=8.23Hz), 7.76(d, 2H, J=8.23Hz), 7.21(d, 1H, J=2.20Hz), 7.11(d, 1H, J=8.20Hz), 6.67(s, 1H), 4.68(q, 1H, J=6.84Hz), 4.28(s, 2H), 3.68(br s, 4H), 3.42(s, 2H), 2.59(br s, 4H), 2.19(s, 3H), 1.95(m, 1H), 1.57(d, 3H, J=6.84Hz), 0.84(m, 4H),
MS(ES$^-$) M−H=619.1

2-{2-Methyl-4-[({4-{[4-(2-thienylcarbonyl)-1-piperazinyl]methyl}-2-[4-(trifluoromethyl)phenyl]-1,3-thiazol-5-yl}methyl)sulfanyl]phenoxy}propanoic acid $^1$H NMR (CD$_3$OD) 300MHz δ 8.10(d, 2H, J=8.20Hz), 7.76(d, 2H, J=8.20Hz), 7.63(d, 1H, J=5.13Hz), 7.37(d, 1H, J=5.13Hz), 7.22(br s, 1H), 7.10(br s, 1H), 7.02(br s, 1H), 6.64(br s, 1H), 4.67(br s, 1H), 4.27(s, 2H), 3.74(br s, 4H), 3.40(s, 2H), 2.53(br s, 4H), 2.16(br s, 3H), 1.57(br s, 3H),
MS(ES$^-$) M−H=660.1

2-{4-[({4-{[4-(2,4-Difluorophenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 300MHz δ 8.10(d, 2H, J=8.28Hz), 7.73(d, 2H, J=8.28Hz), 7.20(br s, 1H), 6.92(m, 4H), 6.60(d, 1H, J=8.55Hz), 4.59(br s, 1H), 4.23(s, 2H), 3.44(s, 2H), 3.06(br s, 4H), 2.80(br s, 4H), 2.17(s, 3H), 1.53(d, 3H, J=6.35Hz),
MS(ES$^-$) M−H=661.2

2-[2-Methyl-4-({[2-[4-(trifluoromethyl)phenyl]-4-({4-[4-(trifluoromethyl)phenyl]-1-piperazinyl}methyl-1,3-thiazol-5-yl]methyl}sulfanyl)phenoxy]propanoic acid $^1$H NMR (CD$_3$OD) 300MHz δ 8.11(d, 2H, J=8.28Hz), 7.78(d, 2H, J=8.28Hz), 7.49(d, 2H, J=8.55Hz), 7.24(d, 1H, J=2.39Hz), 7.15(d, 1H, J=8.55Hz), 7.04(d, 2H, J=8.55Hz), 6.71(d, 1H, J=8.55Hz), 4.55(br s, 1H), 4.32(s, 2H), 3.51(s, 2H), 3.31(m, 4H), 2.68(t, 4H, J=4.97Hz), 2.22(s, 3H), 1.59(d, 3H, J=6.07Hz),
MS(ES) M−H=694.5

2-{4-[({4-{[4-(Isobutoxycarbonyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 400MHz δ 8.13(d, 2H, J=8.28Hz), 7.80(d, 2H, J=8.28Hz), 7.22(d, 1H, J=2.21Hz), 7.15(dd, 1H, J=8.28, 2.21Hz), 6.71(d, 1H, J=8.28Hz), 4.75(q, 1H, J=6.90Hz), 4.31(s, 2H), 3.89(d, 2H, J=6.90Hz), 3.57(br s, 4H), 2.68(t, 4H, J=4.69Hz), 2.22(s, 3H), 1.96(m, 1H), 1.62(d, 3H, J=6.90Hz), 0.96(d, 6H, J=6.90Hz),
MS(ES$^-$) M−H=650

2-{4-[({4-{[4-[(Benzyloxy)carbonyl]-1-piperazinyl}methyl)-2-[4-(trifluoromethyl)phenyl]-1,3-thiazol-5-yl}methyl)sulfanyl]-2-methylphenoxy}propanoic acid $^1$H NMR (CD$_3$OD) 400MHz δ 8.06(d, 2H, J=8.03Hz), 7.73(d, 2H, J=8.03Hz), 7.30(m, 5H), 7.15(br s, 1H), 7.08(dd, 1H, J=8.20, 2.22Hz), 6.64(d, 1H, J=8.20Hz), 5.08(s, 2H), 4.65(q, 1H, J=6.72Hz), 4.23(s, 2H), 3.51(br s, 4H), 3.37(s, 2H), 2.57(br s, 4H), 2.15(s, 3H), 1.55(d, 3H, J=6.72Hz),
MS(ES$^-$) M−H=684.0

2-{4-[({4-{[4-(Methoxycarbonyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 400MHz δ 8.06(d, 2H, J=8.37Hz), 7.74(d, 2H, J=8.37Hz), 7.16(d, 1H, J=2.21Hz), 7.10(dd, 1H, J=8.55, 2.39Hz), 6.66(d, 1H, J=8.55Hz), 4.59(br s, 1H), 4.25(s, 2H), 3.65(s, 3H), 3.45(t 4H, J=4.79Hz), 3.38(s, 2H), 2.49(br s, 4H), 2.17(s, 3H), 1.55(d, 3H, J=6.32Hz),
MS(ES$^-$) M−H=608.0

2-{2-Methyl-4-[({4-{[4-phenoxycarbonyl)-1-piperazinyl]methyl}-2-[4-(trifluoromethyl)phenyl]-1,3-thiazol-5-yl}methyl)sulfanyl]phenoxy}propanoic acid $^1$H NMR (CD$_3$OD) 400MHz δ 8.08(d, 2H, J=8.20Hz), 7.75(d, 2H, J=8.20Hz), 7.34(m, 2H), 7.19(m, 2H), 7.13(dd, 1H, J=8.20, 2.22Hz), 7.06(m, 2H), 6.66(d, 1H, J=8.20Hz), 4.69(q, 1H, J=6.78Hz), 4.27(s, 2H), 3.69(br s, 2H), 3.54(br s, 2H), 3.43(s, 2H), 2.62(br s, 4H), 2.17(s, 3H), 1.54(d, 3H, J=6.78Hz),
MS(ES$^-$) M−H=670.0

2-{2-Methyl-4-[({4-{[4-(phenylsulfonyl)-1-piperazinyl]methyl}-2-[4-(trifluoromethyl)phenyl]-1,3-thiazol-5-yl}methyl)sulfanyl]phenoxy}propanoic acid $^1$H NMR (CD$_3$OD) 400MHz δ 8.01(d, 2H, J=8.20Hz), 7.72(m, 4H), 7.63(d, 1H, J=8.20Hz), 7.56(M, 2H), 7.13(d, 1H, J=2.22Hz), 7.05(dd, 1H, J=8.20, 2.22Hz), 6.62(d, 1H, J=8.20Hz), 4.70(q, 1H, J=6.61Hz), 4.19(s, 2H), 3.34(s, 2H), 2.97(br s, 4H), 2.51(br s, 4H), 2.13(s, 3H), 1.57(d, 3H, J=6.61Hz),
MS(ES$^-$) M−H=690.0

2-(2-Methyl-4-[({2-[4-(trifluoromethyl)phenyl]-4-[(4-{[4-(trifluoromethyl)phenyl]sulfonyl}-1-piperazinyl)methyl]-1,3-thiazol-5-yl}methyl)sulfanyl]phenoxy}propanoic acid ¹H NMR (CD₃OD) 400MHz δ 8.01(d, 2H, J=8.20Hz), 7.91(m, 4H), 7.71(d, 2H, J=8.20Hz), 7.15(d, 1H, J=2.22Hz), 7.08(dd, 1H, J=8.20, 2.22Hz), 6.62(d, 1H, J=8.20Hz), 4.71(q, 1H, J=6.58Hz), 4.20(s, 2H), 3.33(s, 2H), 3.01(br s, 4H), 2.49(br s, 4H), 2.14(s, 3H), 1.57(d, 3H, J=6.58Hz),
MS(ES⁻) M−H=758.0

2-{4-[({4-({4-[(4-Methoxyphenyl)sulfonyl]-1-piperazinyl}methyl)-2-[4-(trifluoromethyl)phenyl]-1,3-thiazol-5-yl}methyl)sulfanyl]-2-methylphenoxy}propanoic acid ¹H NMR (CD₃OD) 400MHz δ 8.02(d, 2H, J=8.37Hz), 7.72(d, 2H, J=8.37Hz), 7.66(d, 2H, J=8.72Hz), 7.14(d, 1H, J=2.21Hz), 7.07(m, 3H), 6.63(d, 1H, J=8.37Hz), 4.71(q, 1H, J=6.72Hz), 4.20(s, 2H), 3.84(s, 3H), 3.35(s, 2H), 2.97(br s, 4H), 2.53(t, 4H, J=4.61Hz), 2.14(s, 3H), 1.58(d, 3H, J=6.72Hz),
MS(ES⁻) M−H=720.0

2-{2-Methyl-4-[({4-{[4-(propylsulfonyl)-1-piperazinyl]methyl}-2-[4-(trifluoromethyl)phenyl]-1,3-thiazol-5-yl}methyl)sulfanyl]phenoxy}propanoic acid ¹H NMR (CD₃OD) 400MHz δ 8.07(d, 2H, J=8.20Hz), 7.75(d, 2H, J=8.20Hz), 7.19(s, 1H), 7.13(d, 1H, J=8.20Hz), 6.66(d, 1H, J=8.20Hz), 4.70(q, 1H, J=6.67Hz), 4.26(s, 2H), 3.40(s, 2H), 3.22(br s, 4H), 2.95(t, 2H, J=7.43Hz), 2.54(br s, 4H), 2.17(s, 3H), 1.76(m, 2H), 1.57(d, 3H, J=6.67Hz), 1.02(t, 3H, J=7.43Hz),
MS(ES⁻) M−H=656.0

2-{4-[({4-{[4-(Ethylsulfonyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 400MHz δ 8.07(d, 2H, J=8.03Hz), 7.74(d, 2H, J=8.03Hz), 7.19(s, 1H), 7.11(d, 1H, J=8.03Hz), 6.65(d, 1H, J=8.03Hz), 4.64(q, 1H, J=6.49Hz), 4.26(s, 2H), 3.39(s, 2H), 3.23(br s, 4H), 2.99(q, 2H, J=7.41Hz), 2.51(br s, 4H), 2.16(s, 3H), 1.55(d, 3H, J=6.49Hz), 1.27(t, 3H, J=7.41Hz),
MS(ES⁻) M−H=642.0

2-{2-Methyl-4-[({4-{[4-(methylsulfonyl)-1-piperazinyl]methyl}-2-[4-(trifluoromethyl)phenyl]-1,3-thiazol-5-yl}methyl)sulfanyl]phenoxy}propanoic acid ¹H NMR (CD₃OD) 400MHz δ 8.06(d, 2H, J=8.03Hz), 7.74(d, 2H, J=8.03Hz), 7.19(s, 1H), 7.13(dd, 1H, J=8.03, 2.22Hz), 6.66(d, 1H, J=8.03Hz), 4.65(q, 1H, J=6.84Hz), 4.27(s, 2H), 3.40(s, 2H), 3.17(t, 4H, J=4.19Hz), 2.80(s, 3H), 2.53(t, 4H, J=4.19Hz), 2.17(s, 3H), 1.56(d, 3H, J=6.84Hz),
MS(ES⁻) M−H=628.0

2-{4-[({4-{[4-(4-Fluorobenzoyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 300MHz δ 8.09(d, 2H, J=8.28Hz), 7.76(d, 2H, J=8.28Hz), 7.52(M, 2H), 7.22(M, 3H), 7.13(dd, 1H, J=8.28, 2.20Hz), 6.68(d, 1H, J=8.28Hz), 4.67(q, 1H, J=6.81Hz), 4.32(s, 2H), 3.79(br s, 4H), 3.66(s, 2H), 2.90(br s, 4H), 2.17(s, 3H), 1.59(d, 3H, J=6.81Hz),
MS(ES⁻) M−H=671.9

2-{4-[({4-[(4-{[4-(Acetylamino)phenyl]sulfonyl}-1-piperazinyl)methyl]-2-[4-(trifluoromethyl)phenyl]-1,3-thiazol-5-yl}methyl)sulfanyl]-2-methylphenoxy}Propanoic acid ¹H NMR (CD₃OD) 400MHz δ 8.07(d, 2H, J=8.28Hz), 7.83(d, 2H, J=8.83Hz), 7.77(d, 2H, J=8.28Hz), 7.71(d, 2H, J=8.83Hz), 7.18(d, 1H, J=2.20Hz), 7.10(dd, 1H, J=8.28, 2.20Hz), 6.68(d, 1H, J=8.28Hz), 4.71(q, 1H, J=6.53Hz), 4.26(s, 2H), 3.42(s, 2H), 3.03(br s, 4H), 2.56(t, 4H, J=4.83Hz), 2.20(m, 6H), 1.63(d, 3H, J=6.53Hz),
MS(ES⁻) M−H=747.0

2-{4-[({4-({4-[(4-Fluoroanilino)carbonyl]-1-piperazinyl}methyl)-2-[4-(trifluoromethyl)phenyl]-1,3-thiazol-5-yl}methyl)sulfanyl]-2-methylphenoxy}propanoic acid

MS(ES⁻) M−H=687.5

2-{4-[({4-{[4-(4-Methoxybenzoyl)-1-piperazinyl]methyl}-2-[4trifluoromethyl)phenyl]-1,3-thiazol-5-yl}methyl)sulfanyl]-2-methylphenoxy}propanoic acid ¹H NMR (CD₃OD) 300MHz δ 8.02(d, 2H, J=8.20Hz), 7.69(d, 2H, J=8.20Hz), 7.38(d, 2H, J=8.79Hz), 7.12(d, 1H, J=2.24Hz), 7.06(dd, 1H, J=8.28, 2.24Hz), 6.95(d, 2H, J=8.79Hz), 6.61(d, 1H, J=8.28Hz), 4.58(q, 1H, J=6.78Hz), 4.25(s, 2H), 3.78(s, 3H), 3.71(br s, 4H), 3.64(s, 2H), 2.88(br s, 4H), 2.10(s, 3H), 1.52(d, 3H, J=6.78Hz),
MS(ES⁻) M−H=683.6

2-{4-[({4-({4-[(3-Methoxyanilino)carbonyl]-1-piperazinyl}methyl)-2-[4-(trifluoromethyl)phenyl]-1,3-thiazol-5-yl}methyl)sulfanyl]-2-methylphenoxy}propanoic acid ¹H NMR (CDCl₃) 300MHz δ 8.04(d, 2H, J=8.28Hz), 7.69(d, 2H, J=8.28Hz), 7.31(d, 1H, J=2.21Hz), 7.16(m, 2H), 6.89(m, 2H), 6.59(dd, 1H, J=8.28, 2.21Hz), 6.53(d, 1H, J=8.28Hz), 4.73(q, 1H, J=6.90Hz), 4.33(d, 1H, J=63Hz), 4.23(d, 1H, J=63Hz), 3.79(s, 3H), 3.45(m, 6H), 2.36(t, 4H, J=4.69Hz), 2.24(s, 3H), 1.64(d, 3H, J=6.90Hz),
MS(ES⁻) M−H=699.6

2-{4-[({4-{[4-(Aminocarbonyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 400MHz δ 8.15(d, 2H, J=8.28Hz), 7.83(d, 2H, J=8.28Hz), 7.27(d, 1H, J=2.48Hz), 7.19(dd, 1H, J=8.55, 2.48Hz), 6.74(d, 1H, J=8.55Hz), 4.65(br s, 1H), 4.36(s, 2H), 3.57(s, 2H), 3.48(br s, 4H), 2.64(br s, 4H), 2.24(s, 3H), 1.62(d, 3H, J=6.62Hz),
MS(ES⁻) M−H=593.1

2-{4-[({4-({4-[(Cyclohexylamino)carbonyl]-1-piperazinyl}methyl)-2-[4-(trifluoromethyl)phenyl]-1,3-thiazol-5-yl}methyl)sulfanyl]-2-methylphenoxy}propanoic acid ¹H NMR (CD₃OD) 400MHz δ 8.15(d, 2H, J=8.28Hz), 7.81(d, 2H, J=8.28Hz), 7.24(br s, 1H), 7.13(br s, 1H), 6.73(br s, 1H), 4.75(br s, 1H), 4.30(s, 2H), 3.52(m, 7H), 2.68(br s, 4H), 2.24(s, 3H), 1.75(m, 7H), 1.26(m, 6H),
MS(ES⁻) M−H=675.0

2-{2-Methyl-4-[({4-({4-[(propylamino)carbonyl]-1-piperazinyl}methyl)-2-[4-(trifluoromethyl)phenyl]-1,3-thiazol-5-yl}methyl)sulfanyl]phenoxy}propanoic acid ¹H NMR (CD₃OD) 400MHz δ 8.15(d, 2H, J=8.00Hz), 7.81(d, 2H, J=8.00Hz), 7.25(d, 1H, J=2.21Hz), 7.15(dd, 1H, J=8.55, 2.21Hz), 6.70(d, 1H, J=8.55Hz), 4.68(q, 1H, J=6.53Hz), 4.30(s, 2H), 3.60(s, 2H), 3.48(br s, 4H), 3.14(t, 2H, J=7.45Hz), 2.73(t, 4H, J=5.10Hz), 2.22(s, 3H), 1.63(d, 3H, J=6.53Hz), 1.52(s, 2H), 0.93(t, 3H, J=7.45Hz),
MS(ES⁻) M−H=635.3

2-{4-[({4-({4-[(Ethylamino)carbonyl]-1-piperazinyl}methyl)-2-[4-(trifluoromethyl)phenyl]-1,3-thiazol-5-yl}methyl)sulfanyl]-2-methylphenoxy}propanoic acid ¹H NMR (CD₃OD) 400MHz δ 8.15(d, 2H, J=8.28Hz), 7.81(d, 2H, J=8.28Hz), 7.25(d, 1H, J=2.48Hz), 7.14(dd, 1H, J=8.28, 2.48Hz), 6.70(d, 1H, J=8.28Hz), 4.67(br s, 1H), 4.29(s, 2H), 3.56(s, 2H), 3.46(br s, 4H), 3.22(q, 2H, J=7.17Hz), 2.68(t, 4H, J=4.92Hz), 2.21(s, 3H), 1.61(d, 3H, J=6.35Hz), 1.14(t, 3H, J=7.17Hz),
MS(ES⁻) M−H=621.1

2-{2-Methyl-4-[({4-({4-[(methylamino)carbonyl]-1-piperazinyl}methyl)-2-[4-(trifluoromethyl)phenyl]-1,3-thiazol-5-yl}methyl)sulfanyl]phenoxy}propanoic acid ¹H NMR (CD₃OD) 400MHz δ 8.05(d, 2H, J=8.20Hz), 7.72(d, 2H, J=8.20Hz), 7.17(d, 1H, J=2.22Hz), 7.09(dd, 1H, J=8.37, 2.22Hz), 6.61(d, 1H, J=8.37Hz), 4.66(q, 1H, J=6.75Hz), 4.20(s, 2H), 3.56(s, 2H), 3.42(br s, 4H), 2.69(m, 7H), 2.15(s, 3H), 1.58(d, 3H, J=6.75Hz),
MS(ES⁻) M−H=607.0

2-{4-[({4-({4-(Isopropylamino)carbonyl]-1-piperazinyl}methyl)-2-[4-(trifluoromethyl)phenyl]-1,3-thiazol-5-yl}methyl)sulfanyl]-2-methylphenoxy}propanoic acid ¹H NMR (CD₃OD) 400MHz δ 8.09(d, 2H, J=8.20Hz), 7.75(d, 2H, J=8.20Hz), 7.17(br s, 1H), 7.08(d, 1H, J=8.20Hz), 6.64(d, 1H, J=8.20Hz), 4.63(q, 1H, J=6.49Hz), 4.23(s, 2H), 3.84(m, 1H), 3.46(m, 6H), 2.68(br s, 4H), 2.16(s, 3H), 1.57(d, 3H, J=6.49Hz), 1.10(d, 6H, J=6.32Hz),
MS(ES⁻) M−H=635.0

2-{4-[({4-({4-[(tert-Butylamino)carbonyl]-1-piperazinyl}methyl)-2-[4-(trifluoromethyl)phenyl]-1,3-thiazol-5-yl}methyl)sulfanyl]-2-methylphenoxy}propanoic acid ¹H NMR (CD₃OD) 400MHz δ 8.08(d, 2H, J=8.20Hz), 7.75(d, 2H, J=8.20Hz), 7.16(d, 1H, J=2.22Hz), 7.07(dd, 1H, J=8.37, 2.22Hz), 6.64(d, 1H, J=8.37Hz), 4.61(q, 1H, J=6.75Hz), 4.21(s, 2H), 3.44(m, 6H), 2.71(br s, 4H), 2.16(s, 3H), 1.55(d, 3H, J=6.75Hz), 1.27(s, 9H),
MS(ES⁻) M−H=649.0

2-{2-Methyl-4-[({4-[(4-{[(2-phenylethyl)amino]carbonyl}-1-piperazinyl)methyl]-2-[4-(trifluoromethyl)phenyl]-1,3-thiazol-5-yl}methyl)sulfanyl]phenoxy}propanoic acid ¹H NMR (CD₃OD) 400MHz δ 8.08(d, 2H, J=8.03Hz), 7.75(d, 2H, J=8.03Hz), 7.17(s, 7H), 6.64(d, 1H, J=8.55Hz), 4.61(q, 1H, J=6.84Hz), 4.24(s, 2H), 3.43(m, 9H), 2.76(t, 2H, J=7.52Hz), 2.62(br s, 4H), 2.16(s, 3H), 1.56(d, 3H, J=6.67Hz),
MS(ES⁻) M−H=697.0

2-{4-[({4-[(4-Benzoyl-1-piperazinyl)methyl]-2-[4-(trifluoromethyl)phenyl]-1,3-thiazol-5-yl}methyl)sulfanyl]-2-methylphenoxy}propanoic acid ¹H NMR (CD₃OD) 300MHz δ 8.03(d, 2H, J=8.28Hz), 7.70(d, 2H, J=8.28Hz), 7.42(m, 5H), 7.13(d, 1H, J=2.24Hz), 7.07(dd, 1H, J=8.45, 2.24Hz), 6.62(d, 1H, J=8.45Hz), 4.61(q, 1H, J=6.78Hz), 4.26(s, 2H), 3.83(br s, 4H), 3.62(s, 2H), 2.86 (br s, 4H), 2.11(s, 3H), 1.53(d, 3H, J=6.78Hz),
MS(ES⁻) M−H=653.7

2-{2-Methyl-4-[({4-{[4-(4-propoxyphenyl)-1-piperazinyl]methyl}-2-[4-(trifluoromethyl)phenyl]-1,3-thiazol-5-yl}methyl)sulfanyl]phenoxy}propanoic acid ¹H NMR (CD₃OD) 400MHz δ 8.11(d, 2H, J=7.69Hz), 7.77(d, 2H, J=7.69Hz), 7.15(s, 1H), 7.08(dd, 1H, J=8.61, 2.20Hz), 6.93(d, 2H, J=8.97Hz), 6.82(d, 2H, J=8.97Hz), 6.67(d, 1H, J=8.61Hz), 4.57(q, 1H, J=6.78Hz), 4.24(s, 2H), 3.85(t, 2H, J=7.01Hz), 3.55(s, 2H), 3.18(br s, 4H), 3.03(br s, 4H), 2.16(s, 3H), 1.73(m, 2H), 1.54(d, 3H, J=6.78Hz), 100(t, 3H, J=7.01Hz),
MS(ES⁻) M−H=684.0

2-{4-[({4-{[4-(4-Ethoxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CD₃OD) 400MHz δ 8.11(d, 2H, J=8.06Hz), 7.77(d, 2H, J=8.06Hz), 7.15(s, 1H), 7.08(dd, 1H, J=8.42, 2.20Hz), 6.92(d, 2H, J=8.97Hz), 6.81(d, 2H, J=8.97Hz), 6.67(d, 1H, J=8.42Hz), 4.59(q, 1H, J=6.78Hz), 4.24(s, 2H), 3.95(q, 2H, J=6.78Hz), 3.54(s, 2H), 3.17(br s, 4H), 3.04(br s, 4H), 2.17(s, 3H), 1.55(d, 3H, J=6.78Hz), 1.32(t, 3H, J=6.78Hz),
MS(ES⁻) M−H=671.0

2-{2-Methyl-4-[({4-({4-[4-(trifluoromethoxy)phenyl]-1-piperazinyl}methyl)-2-[4-(trifluoromethyl)phenyl]-1,3-thiazol-5-yl}methyl)sulfanyl]phenoxy}propanoic acid ¹H NMR (CD₃OD) 400MHz δ 8.10(d, 2H, J=8.28Hz), 7.75(d, 2H, J=8.28Hz), 7.15(d, 1H, J=2.24Hz), 7.12(d, 2H, J=9.14Hz), 7.08(dd, 1H, J=8.45, 2.24Hz), 7.00(d, 2H, J=9.31Hz), 6.66(d, 1H, J=8.45Hz), 4.59(q, 1H, J=6.72Hz), 4.24(s, 2H), 3.54(s, 2H), 3.27(m, 4H), 2.97(t, 4H, J=4.83Hz), 2.16(s, 3H), 1.54(d, 3H, J=6.72Hz),
MS(ES⁻) M−H=710.0

2-{4-[({4-{[4-(3,4-Dimethoxyphenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 300MHz δ 8.17(d, 2H, J=8.28Hz), 7.82(d, 2H, J=8.28Hz), 7.20(br s, 1H), 7.12(br s, 1H), 6.89(d, 1H, J=8.83Hz), 6.72(m, 2H), 6.55(dd, 1H, J=8.83, 2.76Hz), 4.66(br s, 1H), 4.29(s, 2H), 3.84(s, 3H), 3.80(s, 3H), 3.57(s, 2H), 3.25(br s, 4H), 3.07(br s, 4H), 2.23(s, 3H), 1.61(br s, 3H),
MS(ES$^-$) M−H=686.0

2-{4-[({4-{[4-(4-Hydroxyphenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 300MHz δ 8.14(br s, 2H), 7.80(br s, 2H), 7.24(br s, 1H), 7.12(br s, 1H), 6.92(br s, 2H), 6.76(br s, 2H), 6.63(sbr, 1H), 4.54(br s, 1H), 4.31(br s, 2H), 3.67(br s, 2H), 3.06(br s, 8H), 2.23(br s, 3H), 1.60(br s, 3H),
MS(ES$^-$) M−H=642.3

2-{4-[({4-{[4-(3-Hydroxyphenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 300MHz δ 8.15(d, 2H, J=8.28Hz), 7.81(d, 2H, J=8.28Hz), 7.22(d, 1H, J=2.21Hz), 7.15(dd, 1H, J=8.28, 2.21Hz), 7.08(t, 1H, J=8.14Hz), 6.71(d, 1H, J=8.28Hz), 6.49(dd, 1H, J=4, 2.21Hz), 6.45(t, 1H, J=2.21Hz), 6.39(dd, 1H, J=8.14, 2.21Hz), 4.74(q, 1H, J=6.81Hz), 4.30(s, 2H), 3.85(s, 2H), 3.36(m, 4H), 3.24(m, 4H), 2.21(s, 3H), 1.61(d, 3H, J=6.81Hz),
MS(ES$^-$) M−H=642.0

2-{4-[({4-{[4-(2-Hydroxyphenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 300MHz δ 8.20(d, 2H, J=8.00Hz), 7.80(d, 2H, J=8.00Hz), 7.23(br s, 1H), 7.01(m, 3H), 6.82(m, 2H), 6.66(br s, 1H), 4.74(br s, 1H), 4.26(s, 2H), 3.56(s, 2H), 3.12(m, 8H), 2.19(s, 3H), 1.58(br s, 3H),
MS(ES$^-$) M−H=642.1

2-{4-[({4-[(4-Butyryl-1-piperazinyl)methyl]-2-[4-(trifluoromethyl)phenyl]-1,3-thiazol-5-yl}methyl)sulfanyl]-2-methylphenoxy}propanoic acid $^1$H NMR (CD$_3$OD) 400MHz δ 8.05(d, 2H, J=8.55Hz), 7.72(d, 2H, J=8.55Hz), 7.17(d, 1H, J=2.22Hz), 7.08(d, 1H, J=8.55Hz), 6.64(s, 1H), 4.56(q, 1H, J=6.55Hz), 4.26(s, 2H), 3.54(br s, 4H), 3.38(s, 2H), 2.46(br s, 4H), 2.33(t, 2H, J=7.43Hz), 2.16(s, 3H), 1.58(m, 5H), 0.93(t, 3H, J=7.43Hz),
MS(ES$^-$) M−H=620.0

2-{2-Methyl-4-[({4-[(4-pentanoyl-1-piperazinyl)methyl]-2-[4-(trifluoromethyl)phenyl]-1,3-thiazol-5-yl}methyl)sulfanyl]phenoxy}propanoic acid $^1$H NMR (CD$_3$OD) 400MHz δ 8.06(d, 2H, J=8.20Hz), 7.74(d, 2H, J=8.20Hz), 7.17(d, 1H, J=2.22Hz), 7.10(dd, 1H, J=8.20, 2.22Hz), 6.65(d, 1H, J=8.20Hz), 4.68(q, 1H, J=6.75Hz), 4.25(s, 2H), 3.56(br s, 4H), 3.40(s, 2H), 2.56(br s, 4H), 2.36(t, 2H, J=7.35Hz), 2.16(s, 3H), 1.54(m, 5H), 1.34(m, 2H), 0.90(t, 3H, J=7.35Hz),
MS(ES$^-$) M−H=634.0

2-{4-[({4-{[4-(Methoxyacetyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 300MHz δ 8.07(d, 2H, J=8.37Hz), 7.75(d, 2H, J=8.37Hz), 7.18(d, 1H, J=2.20Hz), 7.11(d, 1H, J=8.37Hz), 6.65(d, 1H, J=8.37Hz), 4.68(q, 1H, J=6.72Hz), 4.26(s, 2H), 4.12(s, 2H), 3.57(br s, 2H), 3.46(br s, 2H), 3.39(s, 2H), 3.35(s, 3H), 2.53(t, 4H, J=4.79Hz), 2.16(s, 3H), 1.56(d, 3H, J=6.72Hz),
MS(ES$^-$) M−H=622.0

2-{4-[({4-[(4-Isobutyryl-1-piperazinyl)methyl]-2-[4-(trifluoromethyl)phenyl]-1,3-thiazol-5-yl}methyl)sulfanyl]-2-methylphenoxy}propanoic acid $^1$H NMR (CD$_3$OD) 300MHz δ 8.10(d, 2H, J=8.28Hz), 7.76(d, 2H, J=8.28Hz), 7.20(d, 1H, J=2.21Hz), 7.13(dd, 1H, J=8.55, 2.21Hz), 6.69(d, 1H, J=8.55Hz), 4.67(q, 1H, J=6.81Hz), 4.31(s, 2H), 3.76(br s, 4H), 3.69(s, 2H), 2.92(m, 5H), 2.20(s, 3H), 1.59(d, 3H, J=6.81Hz), 1.10(d, 6H, J=6.62Hz),
MS(ES$^-$) M−H=620.4

2-{4-[({4-{[4-(2,2-Dimethylpropanoyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 300MHz δ 8.10(d, 2H, J=8.28Hz), 7.76(d, 2H, J=8.28Hz), 7.19(d, 1H, J=2.21Hz), 7.13(dd, 1H, J=8.28, 2.21Hz), 6.69(d, 1H, J=8.28Hz), 4.68(q, 1H, J=6.71Hz), 4.32(s, 2H), 3.83(br s, 4H), 3.71(s, 2H), 2.98(t, 4H, J=4.83Hz), 2.20(s, 3H), 1.60(d, 3H, J=6.71Hz), 1.28(s, 9H),
MS(ES$^-$) M−H=634.2

2-Methyl-2-[4-({[2-[4-(trifluoromethyl)phenyl]-4-((4-[3-(trifluoromethyl)phenyl]-1-piperazinyl}methyl)-1,3-thiazol-5-yl]methyl)sulfanyl)phenoxy]propanoic acid $^1$H NMR (CD$_3$OD) 400MHz δ 8.10(d, 2H, J=8.06Hz), 7.76(d, 2H, J=8.06Hz), 7.40(t, 1H, J=7.69Hz), 7.28(d, 2H, J=8.79Hz), 7.18(s, 2H), 7.09(d, 1H, J=7.69Hz), 6.81(d, 2H, J=8.79Hz), 4.31(s, 2H), 3,59(s, 2H), 3.31(t, 4H, J=4.94Hz), 2.88(t, 4H, J=4.94Hz), 1.54(s, 6H),
MS(ES$^-$)M−H=694.5
CHN Analysis (Theoretical % C=56.97; % H=4.49; % N=6.04; Found % C=56.69; % H=4.66; % N=5.77)

{4-[({4-{[4-(tert-Butoxycarbonyl)-1-piperazinyl]methyl}-2-[4-(trifluoromethyl)phenyl]-1,3-thiazol-5-yl}methyl)sulfanyl]-2-methylphenoxy}acetic acid $^1$H NMR (CD$_3$OD) 400MHz δ 8.05(d, 2H, J=8.28Hz), 7.73(d, 2H, J=8.28Hz), 7.18(s, 1H), 7.11(br s, 1H), 6.66(br s, 1H), 4.54(s, 2H), 4.26(s, 2H), 3.42(m, 6H), 2.50(br s, 4H), 2.19(s, 3H), 1.43(s, 9H),
MS(ES$^-$) M−H=636.5

{2-Methyl-4-[({4-{[4-(2-pyrazinyl)-1-piperazinyl]methyl}-2-[4-(trifluoromethyl)phenyl]-1,3-thiazol-5-yl}methyl)sulfanyl]phenoxy}acetic acid $^1$H NMR (CD$_3$OD) 400MHz δ 8.21(s, 1H), 8.09(d, 3H, J=8.10Hz), 7.80(s, 1H), 7.75(d, 2H, J=8.28Hz), 7.19(d, 1H, J=2.07Hz), 7.13(dd, 1H, J=8.45, 2.24Hz), 6.70(d, 1H, J=8.45Hz), 4.57(s, 2H), 4.27(s, 2H), 3.66(br s, 4H), 3.53(s, 2H), 2.77(br s, 4H), 2.17(s, 3H),
MS(ES$^-$) M−H=612.4

{4-[({4-{[4-(2-Methoxyphenyl)-1-piperazinyl]methyl}-2-[4-(trifluoromethyl)phenyl]-1,3-thiazol-5-yl}methyl)sulfanyl]-2-methylphenoxy}acetic acid $^1$H NMR (CD$_3$OD) 400MHz δ 8.10(d, 2H, J=8.28Hz), 7.75(d, 2H, J=8.28Hz), 7.18(d, 1H, J=2.20Hz), 7.02(s, 2H), 6.92(dd, 2H, J=8.10, 2.20Hz), 6.86(s, 1H), 6.62(d, 1H, J=8.45Hz), 4.48(s, 2H), 4.25(s, 2H), 3.81(s, 3H), 3.55(s, 2H), 3.11(br s, 4H), 2.96(br s, 4H), 2.17(s, 3H),
MS(ES$^-$) M−H=640.5

{4-[({4-{[4-(3-Methoxyphenyl)-1-piperazinyl]methyl}-2-[4-(trifluoromethyl)phenyl]-1,3-thiazol-5-yl}methyl)sulfanyl]-2-methylphenoxy}acetic acid $^1$H NMR (CD$_3$OD) 400MHz δ 8.10(d, 2H, J=8.28Hz), 7.75(d, 2H, J=8.28Hz), 7.18(d, 1H, J=2.24Hz), 7.10(s, 2H), 6.67(d, 1H, J=8.23Hz), 6.53(dd, 1H, J=8.28, 2.24Hz), 6.47(t, 1H, J=2.24Hz), 6.43(dd, 1H, J=8.28, 2.24Hz), 4.52(s, 2H), 4.25(s, 2H), 3.72(s, 3H), 3.58(s, 2H), 3.24(t, 4H, J=5.09Hz), 2.98(t, 4H, J=5.09Hz), 2.17(s, 3H),
MS(ES$^-$) M−H=642.0

2-Methyl-2-{4-[({4-{[4-(phenoxycarbonyl)-1-piperazinyl]methyl}-2-[4-(trifluoromethyl)phenyl]-1,3-thiazol-5-yl}methyl)sulfanyl]phenoxy}propanoic acid $^1$H NMR (CD$_3$OD) 400MHz δ 8.07(d, 2H, J=8.28Hz), 7.73(d, 2H, J=8.28Hz), 7.34(t, 2H, J=7.59Hz), 7.27(d, 2H, J=8.45Hz), 7.18(t, 1H, J=7.59Hz), 7.06(d, 2H, J=7.59Hz), 6.80(d, 2H, J=8.45Hz), 4.33(s, 2H), 3.68(br s, 2H), 3.53(br s, 2H), 3.44(s, 2H), 2.56(br s, 4H), 1.52(s, 6H),
CHN Analysis 1MeOH(Theoretical % C=58.02; % H=5.16; % N=5.97; Found % C=58.33; % H=5.09; % N=5.72)

2-{4-[({4-{[4-(tert-Butoxycarbonyl)-1-piperazinyl]methyl}-2-[4-(trifluoromethyl)phenyl]-1,3-thiazol-5-yl}methyl)sulfanyl]phenoxy}-2-methylpropanoic acid $^1$H NMR (CD$_3$OD) 400MHz δ 8.04(d, 2H, J=8.28Hz), 7.71(d, 2H, J=8.28Hz), 7.22(d, 2H, J=8.10Hz), 6.78(d, 2H, J=8.10Hz), 4.27(s, 2H), 3.40(m, 6H), 2.49(br s, 4H), 1.50(s, 6H), 1.41(s, 9H),
MS(ES$^-$) M−H=650.5

2-Methyl-2-{4-[({4-{[4-(2-pyrazinyl)-1-piperazinyl]methyl}-2-[4-(trifluoromethyl)phenyl]-1,3-thiazol-5-yl}methyl)sulfanyl]phenoxy}propanoic acid $^1$H NMR (CD$_3$OD) 400MHz δ 8.21(s, 1H), 8.07(m, 3H), 7.79(s, 1H), 7.73(d, 2H, J=8.28Hz), 7.25(d, 2H, J=8.10Hz), 6.79(d, 2H, J=8.10Hz), 4.30(s, 2H), 3.65(br s, 4H), 3.53(s, 2H), 2.72(br s, 4H), 1.53(s, 6H),
MS(ES$^-$) M−H=627.6

2-{4-[({4-{[4(2-Methoxyphenyl)-1-piperazinyl]methyl}-2-[4-(trifluoromethyl)phenyl]-1,3-thiazol-5-yl}methyl)sulfanyl]phenoxy}-2-methylpropanoic acid $^1$H NMR (CD$_3$OD) 400MHz δ 8.10(d, 2H, J=8.28Hz), 7.74(d, 2H, J=8.28Hz), 7.21(d, 2H, J=8.42Hz), 7.00(m, 1H), 6.92(m, 2H), 6.86(m, 1H), 6.78(d, 2H, J=8.42Hz), 4.27(s, 2H), 3.81(s, 3H), 3.59(s, 2H), 3.14(br s, 4H), 3.01(br s, 4H), 1.51(s, 6H),
MS(ES$^-$) M−H=656.0

2-{4-[({4-{[4-(Ethoxycarbonyl)-1-piperazinyl]methyl}-2-[4-(trifluoromethyl)phenyl]-1,3-thiazol-5-yl}methyl)sulfanyl]phenoxy}-2-methylpropanoic acid $^1$H NMR (CD$_3$OD) 400MHz δ 8.05(d, 2H, J=8.10Hz), 7.72(d, 2H, J=8.10Hz), 7.24(d, 2H, J=8.42Hz), 6.79(d, 2H, J=8.42Hz), 4.30(s, 2H), 4.09(q, 2H, J=7.16Hz), 3.44(m, 6H), 2.50(s, 4H), 1.52(s, 6H), 1.21(t, 3H, J=7.16Hz),
MS(ES$^-$) M−H=621.7

2-{4-[({4-{[4-(4-Isopropoxyphenyl)-1-piperazinyl]methyl}-2-[4-(trifluoromethyl)phenyl]-1,3-thiazol-5-yl}methyl)sulfanyl]-2-methylphenoxy}propanoic acid $^1$H NMR (CD$_3$OD) 400MHz δ 8.13(d, 2H, J=8.06Hz), 7.79(d, 2H, J=8.06Hz), 7.13(m, 2H), 6.92(d, 2H, J=8.97Hz), 6.81(d, 2H, J=8.97Hz), 6.67(d, 1H, J=8.42Hz), 4.61(q, 1H, J=6.78Hz), 4.46(m, 1H), 4.25(s, 2H), 3.56(s, 2H), 3.19(br s, 4H), 3.06(br s, 4H), 2.17(s, 3H), 1.55(d, 3H, J=6.78Hz), 1.24(d, 6H, J=6.87Hz),
MS(ES$^-$) M−H=685.0

[4-({[4-([1,1'-Biphenyl]-4-ylmethyl)-2-(4-{trifluoromethyl}phenyl)-1,3-thiazol-5-yl]methyl}sulfanyl)-2-methylphenoxy]acetic acid TLC(5% MeOH/CH$_2$Cl$_2$) R$_f$=0.16
MS(ES$^-$) M−H=603

{2-Methyl-4-[({2-(4-{trifluoromethyl}phenyl)-4-[(3-thienyl)benzyl]-1,3-thiazol-5-ylmethyl}sulfanyl]phenoxy}acetic acid $^1$H NMR (CDCl$_3$) 300MHz δ 7.93(d, 2H, J=8.23Hz), 7.61(d, 2H, J=8.23Hz), 7.44(d, 2H, J=8.23Hz), 7.36(s, 1H), 7.29(m, 2H), 7.08(m, 3H), 6.54(d, 1H, J=8.23Hz), 4.52(s, 2H), 4.06(s, 2H), 3.90(s, 2H), 2.15(s, 3H),
TLC(5% MeOH/CH$_2$Cl$_2$) R$_f$=0.18
MS(ES$^-$) M−H=609

[4-({[4-Benzyl-2-(4-{trifluoromethyl}phenyl)-1,3-thiazol-5-yl]methyl}sulfanyl)phenoxy]acetic acid $^1$H NMR (CD$_3$OD) 300MHz δ 8.04(d, 2H, J=8.23Hz), 7.75(d, 2H, J=8.23Hz), 7.34(d, 2H, J=8.76Hz), 7.20(m, 5H), 6.88(d, 2H, J=9.76Hz), 4.66(s, 2H), 4.25(s, 2H), 3.93(s, 2H),
MS(ES$^-$) M−H=513.86
TLC(20% MeOH/CH$_2$Cl$_2$) R$_f$=0.37

2-[4-({[4-Benzyl-2-{4-{trifluoromethyl}phenyl)-1,3-thiazol-5-yl]methyl}sulfanyl}phenoxy]propanoic acid ¹H NMR (CDCl₃) 300MHz δ 8.02(d, 2H, J=8.23Hz), 7.69 (d, 2H, J=8.23Hz), 7.26(m, 7H), 6.83(d, 2H, J=8.76Hz), 4.80 (q, 1H, J=6.72Hz), 4.14(s, 2H), 3.90(m, 2H), 1.68(d, 3H, J=6.72Hz),
MS(ES⁻) M−H=528.43
TLC(20% MeOH/CH₂Cl₂) R$_f$=0.60

[2-Methyl-4-({[2-(4-{trifluoromethyl}phenyl)-4-(2-phenylethyl)-1,3-thiazol-5-yl]methyl}sulfanyl)phenoxy]acetic acid ¹(CDCl₃) 300MHz δ 7.99(d, 2H, J=8.79Hz), 7.67(d, 2H, J=8.93Hz), 7.18(m, 8H), 6.60(d, 1H, J=8.51Hz), 4.64(s, 2H), 3.85(s, 2H), 2.90(m, 2H), 2.80(m, 2H), 2.23(s, 3H),

[4-({[4-[(Benzyloxy)methyl]-2-(4-{trifluoromethyl}phenyl)-1,3-thiazol-5-yl]methyl}sulfanyl)-2-methylphenoxy]acetic acid ¹(CDCl₃) 300MHz δ 7.99(d, 2H, J=8.79Hz), 7.67(d, 2H, J=8.79Hz), 7.33(m, 4H), 7.28(s, 2H), 7.18(dd, 1H, J=2.33, 0.55Hz), 7.08(ddd, 1H, J=8.38, 2.33, 0.55Hz), 6.56(d, 1H, J=8.38Hz), 4.63(s, 2H), 4.53(s, 2H), 4.39(s, 2H), 4.19(s, 2H), 2.21(s, 3H),

[2-Methyl-4-({[2-(4-{trifluoromethyl}phenyl)-4-(3-phenylpropyl)-1,3-thiazol-5-yl]methyl}sulfanyl)phenoxy]acetic acid ¹H NMR (CDCl₃) 300MHz δ 7.82(m, 2H), 7.50(m, 2H), 6.94(m, 8H), 3.95(s, 2H), 2.55(m, 4H), 1.99(m, 7H),

{2-Methyl-4-[({2-(4-{trifluoromethyl}phenyl)-4-[(2-phenylethoxy)methyl]-1,3-thiazol-5-yl}methyl)sulfanyl]phenoxy}acetic acid ¹H NMR (CDCl₃) 300MHz δ 7.92(m, 2H), 7.62(m, 2H), 7.20(m, 7H), 7.05(br s, 1H), 4.55(s, 2H), 4.38(s, 2H), 4.09(s, 2H), 3.66(br s, 2H), 2.87(br s, 2H), 2.17(s, 3H),
TLC(5% MeOH/Dichloromethane) R$_f$=0.65

[4-({[4-(4-Bromobenzyl)-2-(4-{trifluoromethyl}phenyl)-1,3-thiazol-5-yl]methyl}sulfanyl)-2-methylphenoxy]acetic acid ¹H NMR (CDCl₃) 400MHz δ 7.82(d, 2H, J=8.20Hz), 7.53 (d, 2H, J=8.20Hz), 7.22(d, 2H, J=8.55Hz), 7.05(m, 1H), 6.97 (dd, 1H, J=8.37, 2.39Hz), 6.88(d, 2H, J=8.55Hz), 6.47(d, 1H, J=8.37Hz), 4.47(s, 2H), 3.72(s, 2H), 3.36(s, 2H), 2.08(s, 3H),
TLC(5% MeOH/CH₂Cl₂) R$_f$=0.16

[4-({[4-Benzyl-2-(4-{trifluoromethyl}phenyl)-1,3-thiazol-5-yl]methyl}sulfanyl)-2-methylphenoxy]acetic acid ¹H (CDCl₃) 300MHz δ 7.97(d, 2H, J=8.79Hz), 7.64(d, 2H, J=9.48Hz), 7.21(m, 8H), 6.58(d, 1H, J=8.38Hz), 4.65(s, 2H), 4.11(s, 2H), 3.93(s, 2H), 2.22(s, 3H),
MS(ES⁺) M+H=529.99

2-{4-[({4-{[3-(5-Methyl-1,2,4-oxadiazol-3-yl)phenoxy]methyl}-2-[4-(trifluoromethyl)phenyl]-1,3-thiazol-5-yl}methyl)sulfanyl]phenoxy}propanoic acid ¹H NMR (CDCl₃) 400MHz δ 8.01(d, 2H, J=8.03Hz), 7.68 (m, 3H), 7.43(m, 1H), 7.36(t, 1H, J=8.03Hz), 7.20(d, 2H, J=8.89Hz), 7.05(dd, 1H, J=8.20, 2.39Hz), 6.79(d, 2H, J=8.89Hz), 4.76(q, 1H, J=6.78Hz), 4.66(d, 1H, J=28Hz), 4.36(d, 1H, J=28Hz), 4.24(d, 1H, J=70Hz), 4.15(d, 1H, J=70Hz), 2.71(s, 3H), 1.67(m, 3H),
MS(ES⁺) M+H=628.0

2-{4-[({4-{[4-(4-Methoxyphenyl)-1-piperazinyl]methyl}-2-[4-(trifluoromethyl)phenyl]-1,3-thiazol-5-yl}methyl)sulfanyl]-2-methylphenoxy}propanoic acid ¹H NMR (CDCl₃) 400MHz δ 9.03(br s, 1H), 7.96(d, 2H, J=8.20Hz), 7.67(d, 2H, J=8.20Hz), 7.15(d, 2H, J=8.72Hz), 6.81(m, 6H), 4.12(s, 2H), 3.73(s, 3H), 3.50(s, 2H), 3.27(br s, 4H), 3.15(br s, 4H), 1.63(s, 6H),
HPLC(C-18, 3μm) 1% MeOH/0-90% CH₃CN/Water (0.1% TFA)/(50mM Et₃N/TFA) 4min run R$_t$=2.89min

2-(4-{[(4-{[4-(4-Methoxyphenyl)-1-piperazinyl]methyl}-2-Phenyl-1,3-thiazol-5-yl)methyl]sulfanyl}phenoxy)-2-methylpropanoic acid ¹H NMR (CDCl₃) 400MHz δ 7.87(m, 2H), 7.44(m, 3H), 7.15(d, 2H, J=8.55Hz), 6.82(m, 6H), 4.08(s, 2H), 3.73(s, 3H), 3.46(s, 2H), 3.31(m, 4H), 3.18(m, 4H), 1.65(s, 6H),
HPLC(C-18, 3μm) 1% MeOH/0-90% CH₃CN/Water (0.1% TFA)/(50mM Et₃N/TFA) 4min run R$_t$=2.74min

{4-[({4-{[4-(4-Methoxyphenyl)-1-piperazinyl]methyl}-2-[4-(trifluoromethyl)phenyl]-1,3-thiazol-5-yl}methyl)sulfanyl]phenoxy}acetic acid ¹H NMR (CDCl₃) 400MHz δ 10.00(s, 1H), 7.96(d, 2H, J=8.20Hz), 7.66(d, 2H, J=8.20Hz), 7.27(d, 2H, J=8.72Hz), 6.82(m, 6H), 4.51(s, 2H), 4.22(s, 2H), 3.80(s, 2H), 3.72(s, 3H), 3.21(m, 8H),
HPLC(C-18, 3μm) 1% MeOH/0-90% CH₃CN/Water (0.1% TFA)/(50mM Et₃N/TFA) 4min run R$_t$=2.74min

(4-{[(4-{[4-(4-Methoxyphenyl)-1-piperazinyl]methyl}-2-phenyl-1,3-thiazol-5-yl)methyl]sulfanyl}phenoxy)acetic acid ¹H NMR (CDCl₃) 400MHz δ 9.49(br s, 1H), 7.86(m, 2H), 7.42(m, 3H), 7.24(d, 2H, J=8.55Hz), 6.80(m, 6H), 4.50(s, 2H), 4.22(s, 2H), 3.81(s, 2H), 3.71(s, 3H), 3.24(m, 8H),
HPLC(C-18, 3μm) 1% MeOH/0-90% CH₃CN/Water (0.1% TFA)/(50mM Et₃N/TFA) 4min run R$_t$=2.55min

2-{4-[({4-{[4-4-Methoxyphenyl)-1-piperazinyl]methyl}-2-[4-(trifluoromethyl)phenyl]-1,3-thiazol-5-yl}methyl)sulfanyl]phenoxy}propanoic acid ¹H NMR (CDCl₃) 400MHz δ 9.31(s, 1H), 7.96(d, 2H, J=8.20Hz), 7.68(d, 2H, J=8.20Hz), 7.18(d, 2H, J=8.55Hz), 6.82(m, 6H), 4.73(q, 1H, J=6.67Hz), 4.16(d, 1H, J=87Hz), 4.10(d, 1H, J=87Hz), 3.72(s, 3H), 3.58(d, 1H, J=53Hz), 3.51 (d, 1H, J=53Hz), 3.24(m, 8H), 1.59(d, 3H, J=6.67Hz),
HPLC(C-18, 3μm) 1% MeOH/0-90% CH₃CN/Water (0.1% TFA)/(50mM Et₃N/TFA) 4min run R$_t$=2.80min

2-(4-{[(4-{[4-(4-Methoxyphenyl)-1-piperazinyl]methyl}-2-phenyl-1,3-thiazol-5-yl)methyl]sulfanyl}phenoxy)propanoic acid ¹H NMR (CDCl₃) 400MHz δ 8.42(s, 1H), 7.84(m, 2H), 7.40(m, 3H), 7.17(d, 2H, J=8.72Hz), 6.81(m, 6H), 4.69(q, 1H, J=6.67Hz), 4.11(d, 1H, J=18Hz), 4.07(d, 1H, J=18Hz), 3.73(s, 3H), 3.57(d, 1H, J=87Hz), 3.49(d, 1H, J=87Hz), 3.18 (m, 8H), 1.59(d, 3H, J=6.67Hz), HPLC(C-18, 3μm) 1% MeOH/0-90% CH₃CN/Water (0.1% TFA)/(50mM Et₃N/TFA) 4min run R$_f$=2.63min

{4-[({4-{[3-(5-Methyl-1,2,4-oxadiazol-3-yl)phenoxy]methyl}-2-[4-(trifluoromethyl)phenyl]-1,3-thiazol-5-yl}methyl)sulfanyl]phenoxy}acetic acid ¹H NMR (CDCl₃) 400MHz δ 10.17(s, 1H), 8.02(d, 2H, J=8.20Hz), 7.67(m, 3H), 7.46(m, 1H), 7.36(t, 1H, J=7.95Hz), 7.22(d, 2H, J=8.72Hz), 7.06(dd, 1H, J=8.37, 2.39Hz), 6.79(d, 2H, J=8.72Hz), 4.69(s, 2H), 4.58(s, 2H), 4.22(s, 2H), 2.73(s, 3H),

MS(ES⁻) M+H=614.00

2-Methyl-2-{4-[({4-{[4-(5-methyl-1,2,4-oxadiazol-3-yl)phenoxy]methyl}-2-[4-(trifluoromethyl)phenyl]-1,3-thiazol-5-yl}methyl)sulfanyl]phenoxy}propanoic acid ¹H (CDCl₃) 400MHz δ 7.98(d, 2H, J=8.03Hz), 7.92(d, 2H, J=9.06Hz), 7.67(d, 2H, J=8.03Hz), 7.18(d, 2H, J=9.06Hz), 6.96(d, 2H, J=8.75Hz), 6.74(d, 2H, J=8.75Hz), 4.98(s, 2H), 4.29(s, 2H), 2.66(s, 3H), 1.57(s, 6H)

MS(ES⁻) M−H=640.00

2-Methyl-2-(4-{[(4-{[4-(5-methyl-1,2,4-oxadiazol-3-yl)phenoxy]methyl}-2-phenyl-1,3-thiazol-5-yl)methyl]sulfanyl}phenoxy)propanoic acid ¹H NMR (CDCl₃) 400MHz δ 7.93(d, 2H, J=9.06Hz), 7.86 (m, 2H), 7.42(m, 3H), 7.17(d, 2H, J=8.72Hz), 6.96(d, 2H, J=9.06Hz), 6.73(d, 2H, J=8.72Hz), 4.92(s, 2H), 4.27(s, 2H), 2.66(s, 3H), 1.57(s, 6H),

MS(ES⁻) M−H=571.50

{4-[({4-{[4-(5-Methyl-1,2,4-oxadiazol-3-yl)phenoxy]methyl}-2-[4-(trifluoromethyl)phenyl]-1,3-thiazol-5-yl}methyl)sulfanyl]phenoxy}acetic acid ¹H NMR (CDCl₃) 400MHz δ 7.98(d, 2H, J=8.20Hz), 7.93 (d, 2H, J=9.06Hz), 7.66(d, 2H, J=8.20Hz), 7.28(d, 2H, J=8.89Hz), 6.96(d, 2H, J=9.06Hz), 6.76(d, 2H, J=8.89Hz), 4.86(s, 2H), 4.60(s, 2H), 4.25(s, 2H), 2.62(s, 3H),

MS(ES⁻) M−H=611.80

(4-{[(4-{[4-(5-Methyl-1,2,4-oxadiazol-3-yl)phenoxy]methyl}-2-phenyl-1,3-thiazol-5-yl)methyl]sulfanyl}phenoxy)acetic acid ¹H NMR (CDCl₃) 400MHz δ 7.92(d, 2H, J=9.06Hz), 7.83 (m, 2K), 7.39(m, 3H), 7.23(d, 2H, J=8.90Hz), 6.95(d, 2H, J=9.06Hz), 6.76(d, 2H, J=8.90Hz), 4.70(s, 2H), 4.54(s, 2H), 4.18(s, 2H), 2.60(s, 3H),

MS(ES⁺) M+H=546.20

2-{4-[({4-{[4-(5-Methyl-1,2,4-oxadiazol-3-yl)phenoxy]methyl}-2-[4-(trifluoromethyl)phenyl]-1,3-thiazol-5-yl}methyl)sulfanyl]phenoxy}propanoic acid ¹H NMR (CDCl₃) 400MHz δ 7.97(d, 2H, J=8.20Hz), 7.92 (d, 2H, J=8.89Hz), 7.65(d, 2H, J=8.20Hz), 7.22(d, 2H, J=8.89Hz), 6.94(d, 2H, J=8.89Hz), 6.73(d, 2H, J=8.89Hz), 4.86(d, 1H, J=79Hz), 4.80(d, 1H, J=96Hz), 4.66(q, 1H, J=6.89Hz), 4.26(d, 1H, J=87Hz), 4.20(d, 1H, J=87Hz), 2.62 (s, 3H), 1.58(d, 3H, J=6.89Hz),

MS(ES⁻) M−H=626.00

2-(4-{[(4-{[4-(5-Methyl-1,2,4-oxadiazol-3-yl)phenoxy]methyl}-2-phenyl-1,3-thiazol-5-yl)methyl]sulfanyl}phenoxy)propanoic acid ¹H NMR (CDCl₃) 400MHz δ 7.93(d, 2H, J=9.06Hz), 7.85 (m, 2H), 7.41(m, 3H), 7.24(d, 2H, J=8.89Hz), 6.95(d, 2H, J=9.06Hz), 6.74(d, 2H, J=8.89Hz), 4.82(s, 2H), 4.68(q, 1H, J=6.89Hz), 4.25(d, 1H, J=87Hz), 4.19(d, 1H, J=87Hz), 2.64 (s, 3H), 1.61(d, 3H, J=6.89Hz),

MS(ES⁻) M−H=558.30

2-{4-[({4-{[4-(4-Acetylphenyl)-1-piperazinyl]methyl}-2-[4-(trifluoromethyl)phenyl]-1,3-thiazol-5-yl}methyl)sulfanyl]phenoxy}-2-methylpropanoic acid ¹H NMR (CD₃OD) 400MHz δ 8.04(d, 2H, J=8.10Hz), 7.85(d, 2H, J=9.14Hz), 7.72(d, 2H, J=8.10Hz), 7.25(d, 2H, J=8.79Hz), 6.93(d, 2H, J=9.14Hz), 6.81(d, 2H, J=8.79Hz), 4.32(s, 2H), 3.47(s, 2H), 3.35(t, 4H, J=4.91Hz), 2.59(t, 4H, J=4.91Hz), 2.47(s, 3H), 1.47(s, 6H),

MS(ES⁻) M−H=668.1

2-{4-[({4-{[4-(4-Chlorophenyl)-1-piperazinyl]methyl}-2-[4-(trifluoromethyl)phenyl]-1,3-thiazol-5-yl}methyl)sulfanyl]phenoxy}-2-methylpropanoic acid ¹H NMR (CD₃OD) 400MHz δ 8.05(d, 2H, J=8.10Hz), 7.73(d, 2H, J=8.10Hz), 7.24(d, 2H, J=8.79Hz), 7.15(d, 2H, J=8.97Hz), 6.90(d, 2H, J=8.97Hz), 6.80(d, 2H, J=8.79Hz), 4.30(s, 2H), 3.57(s, 2H), 3.18(t, 4H, J=5.00Hz), 2.77(t, 4H, J=5.00Hz), 1.49(s, 6H), CHN Analysis: Theory (C, 58.04%; H, 4.72%; N, 6.35%) Found (C, 57.65%; H, 4.80%; N, 6.13%)

2-{4-[f{4-{[4-(3-Methoxyphenyl)-1-piperazinyl]methyl}-2-[4-(trifluoromethyl)phenyl]-1,3-thiazol-5-yl}methyl)sulfanyl]phenoxy}-2-methylpropanoic acid ¹H NMR (CD₃OD) 400MHz δ 7.98(d, 2H, J=7.93Hz), 7.63(d, 2H, J=7.93Hz), 7.12(m, 3H), 6.73(m, 2H), 6.47(m, 1H), 6.38(m, 2H), 4.18(s, 2H), 3.70(s, 3H), 3.50(s, 2H), 3.14 (br s, 4H), 2.76(sbr, 4H), 1.49(s, 6H), CHN Analysis: Theory (C, 60.26%; H, 5.21%; N, 6.39%) Found (C, 59.83%; H, 5.29%; N, 6.32%)

2-(4-{[(2-(4-Fluorophenyl)-4-{[4-phenoxycarbonyl)-1-piperazinyl]methyl}-1,3-thiazol-5-yl)methyl]sulfanyl}-2-methyl phenoxy)-2-methylpropanoic acid ¹H NMR (CDCl₃) 400MHz δ 7.93(m, 2H), 7.35(m, 3H), 7.19(m, 4H), 7.08(m, 2H), 6.69(br s, 1H), 4.27(s, 2H), 3.60(br s, 4H), 3.39(s, 2H), 2.54(br s, 4H), 2.14(s, 3H), 1.55(s, 6H), MS(ES⁻) M−H=634.1

2-{4-[({4-{[4-(4-Methoxyphenyl)-1-piperazinyl]methyl}-2-[4-(trifluoromethyl)phenyl]-1,3-thiazol-5-yl}methyl)sulfanyl]-2-methylphenoxy}-2-methylpropanoic acid ¹H NMR (CD₃OD) 400MHz δ 8.05(br s, 2H), 7.66(d, 2H, J=8.28Hz), 7.15(s, 1H), 6.84(m, 6H), 4.19(s, 2H), 3.44(s, 2H) 3.69(s, 3H), 3.10(m, 4H), 2.82(br s, 4H), 2.10(s, 3H), 1.52(s, 6H),
MS(ES⁺) M+H=672.2

2-{4-[({4-{[4-(4-Acetylphenyl)-1-piperazinyl]methyl}-2-[4-(trifluoromethyl)phenyl]-1,3-thiazol-5-yl}methyl)sulfanyl]-2-methylphenoxy}-2-methylpropanoic acid ¹H NMR (CD₃OD) 400MHz δ 7.97(d, 2H, J=8.10Hz), 7.80(d, 2H, J=8.42Hz), 7.65(d, 2H, J=8.10Hz), 7.16(br s, 1H), 7.01(br s, 1H), 6.84(d, 2H, J=8.42Hz), 6.60(br s, 1H), 4.23(s, 2H), 3.44(s, 2H), 3.27(br s, 4H), 2.55(br s, 4H), 2.44(s, 3H), 2.11(s, 3H), 1.52(s, 6H),
MS(ES⁺) M+H=684.2

2-{4-[({4-{[4-(3-Methoxyphenyl)-1-piperazinyl]methyl}-2-[4-(trifluoromethyl)phenyl]-1,3-thiazol-5-yl}methyl)sulfanyl]-2-methylphenoxy}-2-methylpropanoic acid ¹H NMR (CD₃OD) 400MHz δ 7.96(d, 2H, J=8.10Hz), 7.61(d, 2H, J=8.10Hz), 7.03(m, 3H), 6.38(m, 4H), 4.18(s, 2H), 3.69(s, 3H), 3.33(s, 2H), 3.11(m, 4H), 2.66(br s, 4H), 2.09(s, 3H), 1.50(s, 6H),
MS(ES⁻) M−H=670.0

2-{4-[({4-{[4-(4-Fluorophenyl)-1-piperazinyl]methyl}-2-[4-(trifluoromethyl)phenyl]-1,3-thiazol-5-yl}methyl)sulfanyl]-2-methylphenoxy}-2-methylpropanoic acid ¹H NMR (CD₃OD) 400MHz δ 8.08(d, 2H, J=8.24Hz), 7.73(d, 2H, J=8.24Hz), 7.18(br s, 1H), 7.04(br s, 1H), 6.92(m, 4H), 6.72(br s, 1H), 4.26(s, 2H), 3.58(s, 2H), 3.14(br s, 4H), 2.84(br s, 4H), 2.10(s, 3H), 1.60(s, 6H),
MS(ES⁻) M−H=658.4

2-Methyl-2-{2-methyl-4-[({4-{[4-(phenoxycarbonyl)-1-piperazinyl]methyl}-2-[4-(trifluoromethyl)phenyl]-1,3-thiazol-5-yl}methyl)sulfanyl]phenoxy}propanoic acid ¹H NMR (CD₃OD) 400MHz δ 8.04(br s, 2H), 7.71(br s, 2H), 7.34(m, 2H), 7.19(m, 3H), 7.04(m, 3H), 4.28(s, 2H), 3.65(s, 2H), 3.45(br s, 4H), 2.47(br s, 4H), 2.12(s, 3H), 1.61(s, 6H),
MS(ES⁻) M−H=684.0

2-[4-({[4-{[4-(4-Acetylphenyl)-1-piperazinyl]methyl}-2-(4-fluorophenyl)-1,3-thiazol-5-yl]methyl}sulfanyl)-2-methylphenoxy]-2-methylpropanoic acid ¹H NMR (CD₃OD) 400MHz δ 7.93(m, 2H), 7.86(d, 2H, J=9.16Hz), 7.18(m, 3H), 7.07(br s, 1H), 6.95(d, 2H, J=9.16Hz), 6.69(br s, 1H), 4.23(s, 2H), 3.42(m, 6H), 2.69(br s, 4H), 2.49(s, 3H), 2.13(s, 3H), 1.56(s, 6H),
MS(ES⁻) M−H=632.3

2-{4-{[(2-(4-Fluorophenyl)-4-{[4-(3-methoxyphenyl)-1-piperazinyl]methyl}-1,3-thiazol-5-yl}methyl]sulfanyl}-2-methylphenoxy)-2-methylpropanoic acid ¹H NMR (CD₃OD) 400MHz δ 7.96(m, 2H), 7.19(m, 3H), 7.12(t, 1H, J=8.24Hz), 7.01(br s, 1H), 6.66(br s, 1H), 6.54(dd, 1H, J=8.24, 2.20Hz), 6.47(t, 1H, J=2.20Hz), 6.43(dd, 1H, J=8.24, 2.20Hz), 4.20(s, 2H), 3.73(5, 3H), 3.55(s, 2H), 3.24 (br s, 4H), 2.91(br s, 4H), 2.13(s, 3H), 1.56(s, 6H),
MS(ES⁻) M−H=620.0

2-[4-({[4-{[4-(Ethoxycarbonyl)-1-piperazinyl]methyl}-2-(4-fluorophenyl)-1,3-thiazol-5-yl]methyl}sulfanyl)-2-methylphenoxy]-2-methylpropanoic acid ¹H NMR (CD₃OD) 400MHz δ 7.94(m, 2H), 7.19(m, 3H), 7.00(br s, 1H), 6.66(br s, 1H), 4.23(s, 2H), 4.09(q, 2H, J=7.05Hz), 3.48(m, 6H), 2.49(br s, 4H), 2.13(s, 3H), 1.56(s, 6H), 1.23(t, 3H, J=7.05Hz),
MS(ES⁻) M−H=586.2

2-(4-{[(2-(4-Fluorophenyl)-4-{[4-(isopropoxycarbonyl)-1-piperazinyl]methyl}-1,3-thiazol-5-yl)methyl]sulfanyl}-2-methylphenoxy)-2-methylpropanoic acid ¹H NMR (CDCl₃) 400MHz δ 7.90(m, 2H), 7.18(m, 3H), 7.07(br s, 1H), 6.74(br s, 1H), 4.64(m, 1H), 4.26(s, 2H), 3.44(t, 4H, J=4.58Hz), 3.36(s, 2H), 2.43(br s, 4H), 2.13(s, 3H), 1.55(s, 6H), 1.22(d, 6H, J=6.23Hz),
MS(ES⁻) M−H=600.0

2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoic acid From ethyl 2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoate (0.167g, 0.25mmol), 2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoic acid (0.066g, 41%) was obtained as a white solid.

¹H NMR (CD₃OD): δ 8.05(d, 2H), 7.77(d, 2H), 7.20(m, 6H), 6.71(d, 1H), 4.80(q, 1H), 4.25(s, 2H), 3.93(s, 2H), 2.20 (s, 3H), 1.60(d, 3H); ¹⁹F NMR (CD₃OD): δ −59.87(s) −64.72 (s);. MS m/z 628(M+1); Anal. Calcd. for $C_{29}H_{23}FNOS_2$: C, 55.5; H, 3.69; N, 2.23%. found: C, 55.27; H, 3.80; N, 2.21%.

{2-methyl-4-[({4-[4-(trifluoromethoxy)benzyl]-2-[4-(trifluoromethyl)phenyl]-1,3-thiazol-5-yl}methyl)sulfanyl]phenoxy}acetic acid From methyl {2-methyl-4-[({4-[4-(trifluoromethoxy)benzyl]-2-[4-(trifluoromethyl)phenyl]-1,3-thiazol-5-yl}methyl)sulfanyl]phenoxy}acetate (0.15g, 0.24mmol), {2-methyl-4-

[({4-[4-(trifluoromethoxy)benzyl]-2-[4-(trifluoromethyl) phenyl]-1,3-thiazol-5-yl}methyl)sulfanyl]phenoxy}acetic acid (0.053g, 36%) was obtained as a white solid.

$^1$H NMR (CD$_3$OD): δ 8.05(d, 2H), 7.77(d, 2H), 7.20(m, 6H), 6.71(d, 1H), 4.70(s, 2H), 4.27(s, 2H), 3.94(s, 2H), 2.20 (s, 3H); $^{19}$F NMR (CD$_3$OD): 6-59.88(s) 64.72(s); MS m/z 614(M+1); Anal. Calcd. for C$_{28}$H$_{21}$F$_6$NO$_4$S$_2$: C, 54.81; H, 3.45; N, 2.28%. found: C, 54.64; H, 3.46; N, 2.23%.

2-{2-methyl-4-[({4-(3-thienylmethyl)-2-[4-(trifluoromethyl)phenyl]-1,3-thiazol-5-yl}methyl)sulfanyl] phenoxy}propanoic acid From ethyl 2-{2-methyl-4-[({4-(3-thienylmethyl)-2-[4-(trifluoromethyl)phenyl]-1,3-thiazol-5-yl}methyl)sulfanyl] phenoxy}propanoate (0.255g, 0.44mmol), 2-{2-methyl-4-[({4-(3-thienylmethyl)-2-[4-(trifluoromethyl)phenyl]-1,3-thiazol-5-yl}methyl)sulfanyl]phenoxy}propanoic acid (0.058g, 24%) was obtained as a white solid.

$^1$H NMR (CD$_3$OD): δ 8.05(d, 2H), 7.77(d, 2H), 7.33(t, 1H), 7.18(m, 2H), 6.95(m, 2H), 6.69(d, 1H), 4.80(q, 1H), 4.22(s, 2H), 3.95(s, 2H), 2.20(s, 3H), 1.61(d, 3H); MS m/z 550(M+1); HPLC RT 4.056(C18 4.2×100mm, 0-100% ACN/ H$_2$O (0.1% TFA), 6min @ 2ml/min @254/220nm). Anal. Calcd. for C$_{26}$H$_{22}$F$_3$NO$_3$S$_3$: C, 56.82; H, 4.03; N, 2.55%. found: C, 56.84; H, 4.16; N, 2.53%.

{2-methyl-4-[({4-(3-thienylmethyl)-2-[4-(trifluoromethyl)phenyl]-1,3-thiazol-5-yl}methyl)sulfanyl] phenoxy}acetic acid From methyl {2-methyl-4-[({4-(3-thienylmethyl)-2-[4-(trifluoromethyl)phenyl]-1,3-thiazol-5-yl}methyl)sulfanyl] phenoxy}acetate (0.259g, 0.47mmol), {2-methyl-4-[({4-(3-thienylmethyl)-2-[4-(trifluoromethyl)phenyl]-1,3-thiazol-5-yl}methyl)sulfanyl]phenoxy}acetic acid (0.138g, 55%) was obtained as a white solid.

$^1$H NMR (CD$_3$OD): δ 8.05(d, 2H), 7.77(d, 2H), 7.33(t, 1H), 7.18(m, 2H), 6.95(m, 2H), 6.69(d, 1H), 4.70(s, 2H), 4.24(s, 2H), 3.95(s, 2H), 2.21(s, 3H); MS m/z 536(M+1); HPLC RT 3.979(C18 4.2×100mm, 0-100% ACN/H$_2$O (0.1% TFA), 6min @ 2ml/min @254/220nm). Anal. Calcd. for C$_{25}$H$_{20}$F$_3$NO$_3$S$_3$: C, 56.06; H, 3.76; N, 2.61%. found: C, 55.90; H, 3.88; N, 2.62%.

2-{4-[({4-(2-furylmethyl)-2-[4-(trifluoromethyl phenyl]-1,3-thiazol-5-yl}methyl)sulfanyl]-2-methylphenoxy}propanoic acid From ethyl 2-{4-[({4-(2-furylmethyl)-2-[4-(trifluoromethyl)phenyl]-1,3-thiazol-5-yl}methyl)sulfanyl]-2-methylphenoxy}propanoate (0.091g, 0.16mmol), 2-{4-[({4-(2-furylmethyl)-2-[4-(trifluoromethyl)phenyl]-1,3-thiazol-5-yl}methyl)sulfanyl]-2-methylphenoxy}propanoic acid (0.019g, 22%) was obtained as a white solid.

$^1$H NMR (CD$_3$OD): δ 8.05(d, 2H), 7.77(d, 2H), 7.37(s, 1H), 7.21(s, 1H), 7.17(d, 1H), 6.72(d, 1H), 6.31(s, 1H), 5.99 (s, 1H), 4.80(q, 1H), 4.22(s, 2H), 3.97(s, 2H), 2.22(s, 3H), 1.63(d, 3H); MS m/z 534(M+1); HPLC RT 3.929(C18 4.2× 100mm, 0-100% ACN/H$_2$O (0.1% TFA), 6min @ 2ml/min @254/220nm). Anal. Calcd. for C$_{26}$H$_{22}$F$_3$NO$_4$S$_2$: C, 58.53; H, 4.16; N, 2.62%. found: C, 58.04; H, 4.76; N, 2.47%

2-{4-[({4-(3-furylmethyl)-2-[4-(trifluoromethyl) phenyl]-1,3-thiazol-5-yl}methyl)sulfanyl]-2-methylphenoxy}propanoic acid From ethyl 2-{4-[({4-(3-furylmethyl)-2-[4-(trifluoromethyl)phenyl]-1,3-thiazol-5-yl}methyl)sulfanyl]-2-methylphenoxy}propanoate (0.177g, 0.32mmol), 2-{4-[({4-(3-furylmethyl)-2-[4-(trifluoromethyl)phenyl]-1,3-thiazol-5-yl}methyl)sulfanyl]-2-methylphenoxy}propanoic acid (0.030g, 18%) was obtained as a white solid.

$^1$H NMR (CD$_3$OD): δ 8.05(d, 2H), 7.77(d, 2H), 7.39(s, 1H), 7.20(m, 3H), 6.70(d, 1H), 6.29(s, 1H), 4.80(q, 1H), 4.22(s, 2H), 3.70(s, 2H), 2.20(s, 3H), 1.62(d, 3H); MS m/z 534(M+1); HPLC RT 3.966(C18 4.2×100mm, 0-100% ACN/ H$_2$O (0.1% TFA), 6min @ 2ml/min @254/220nm). Anal. Calcd. for C$_{26}$H$_{22}$F$_3$NO$_4$S$_2$: C, 58.53; H, 4.16; N, 2.62%. found: C, 58.38; H, 4.30; N, 2.54%

2-{2-methyl-4-[({4-(2-thienylmethyl)-2-[4-(trifluoromethyl)phenyl]-1,3-thiazol-5-yl}methyl)sulfanyl] phenoxy}propanoic acid From ethyl 2-{4-[({4-(2-thienylmethyl)-2-[4-(trifluoromethyl)phenyl]-1,3-thiazol-5-yl}methyl)sulfanyl]-2-methylphenoxy}propanoate (0.21g, 0.36mmol), 2-{2-methyl-4-[({4-(2-thienylmethyl)-2-[4-(trifluoromethyl) phenyl]-1,3-thiazol-5-yl}methyl)sulfanyl] phenoxy}propanoic acid (0.019g, 10%) was obtained as a white solid.

$^1$H NMR (CD$_3$OD): δ 8.05(d, 2H), 7.77(d, 2H), 7.20(m, 3H), 6.91(t, 1H), 6.79(s, 1H), 6.69(d, 1H), 4.80(q, 1H), 4.24 (s, 2H), 4.09(s, 2H), 2.20(s, 3H), 1.62(d, 3H); MS m/z 550 (M+1); HPLC RT 4.074(C18 4.2×100mm, 0-100% ACN/ H$_2$O (0.1% TFA), 6min @ 2ml/min @254/220nm).

2-methyl-2-{4-[({4-[4-(trifluoromethoxy)benzyl]-2-[4-(trifluoromethyl)phenyl]-1,3-thiazol-5-yl}methyl) sulfanyl]phenoxy}propanoic acid From ethyl 2-methyl-2-{4-[({4-[4-(trifluoromethoxy)benzyl]-2-[4-(trifluoromethyl)phenyl]-1,3-thiazol-5-yl}methyl) sulfanyl]phenoxy}propanoate (0.210g, 0.32mmol), 2-methyl-2-{4-[({4-[4-(trifluoromethoxy)benzyl]-2-[4-(trifluoromethyl)phenyl]-1,3-thiazol-5-yl}methyl)sulfanyl] phenoxy}propanoic acid (0.035g, 17%) was obtained as a cream solid.

$^1$H NMR (CD$_3$Cl$_3$); 6 8.05(d, 2H), 7.77(d, 2H), 7.28(d, 2H), 7.22(d, 2H), 7.13(d, 2H), 6.86(d, 2H), 4.19(s, 2H), 3.96 (s, 2H), 1.63(s, 6H); $^{19}$F NMR (CD$_3$Cl$_3$); δ −58.26(s) −63.16 (s), MS m/z 628(M+1); HPLC RT 4.526(C18 4.2×100mm, 0-100% ACN/H$_2$O (0.1% TFA), 6min @ 2ml/min @254/ 220nm). Anal. Calcd. for C$_{29}$H$_{23}$F$_6$NO$_4$S$_2$: C, 55.5; H, 3.69; N, 2.23%. found: C, 55.78; H, 3.83; N, 2.10%

{2-Methyl1-4-[({4-[(4-methyl-2-thienyl)methyl]-2-[4-(trifluoromethyl)phenyl]-1,3-thiazol-5-yl}methyl) sulfanyl]phenoxy}acetic acid From ethyl {2-methyl-4-[({4-[(4-methyl-2-thienyl)methyl]-2-[4-(trifluoromethyl)phenyl]-1,3-thiazol-5-yl}methyl)sulfanyl]phenoxy}acetate (0.13g, 0.23mmol), {2-methyl-4-[({4-[(4-methyl-2-thienyl)methyl]-2-[4-(trifluoromethyl)phenyl]-1,3-thiazol-5-yl}methyl)sulfanyl] phenoxy}acetic acid (0.011g, 9%) was obtained as a cream solid.

$^1$H NMR (CD$_3$Cl$_3$): δ 8.01(d, 2H), 7.68(d, 2H), 7.24(s, 1H), 7.15(d, 2H), 6.72(s, 1H), 6.64(d, 1H), 4.75(s, 2H), 4.19

(s, 2H), 4.05(s, 2H), 2.20(s, 3H), 2.29(s, 3H); MS m/z 550 (M+1); HPLC RT 4.366(C18 4.2×100mm, 0-100% ACN/H$_2$O (0.1% TFA), 6min @ 2ml/min @254/220nm).

{4-[({4-(2,4-difluorobenzyl)-2-[4-(trifluoromethyl) phenyl]-1,3-thiazol-5-yl}methyl)sulfanyl]-2-methylphenoxy}acetic acid From ethyl {4-[({4-(2,4-difluorobenzyl)-2-[4-(trifluoromethyl)phenyl]-1,3-thiazol-5-yl}methyl)sulfanyl]-2-methylphenoxy}acetate, (0.1g, 0.17mmol), {4-[({4-(2,4-difluorobenzyl)-2-[4-(trifluoromethyl)phenyl]-1,3-thiazol-5-yl}methyl)sulfanyl]-2-methylphenoxy}acetic acid (0.0279, 28%) was obtained as a cream solid.

$^1$H NMR (CD$_3$Cl$_3$): δ 7.99(d, 2H), 7.68(d, 2H), 7.22(s, 1H), 7.13(m, 2H), 6.79(m, 2H), 6.62(d, 1H), 4.70(s, 2H), 4.20(s, 2H), 3.86(s, 2H), 2.23(s, 3H); $^{19}$F NMR (CD$_3$Cl$_3$): δ −63.15(s) −114.03(s) −114.06(s); MS m/z 566(M+1); HPLC RT 4.356(C18 4.2×100mm, 0-100% ACN/H$_2$O (0.1% TFA), 6min © 2ml/min @254/220nm). Anal. Calcd. for C$_{27}$H$_{20}$F$_5$NO$_3$S$_2$.0.5H$_2$O: C, 56.44; H, 3.68; N, 2.44%. found: C, 56.40; H, 3.79; N, 2.20%

{4-[({4-(4-methoxybenzyl)-2-[4-(trifluoromethyl) phenyl]-1,3-thiazol-5-yl}methyl)sulfanyl]-2-methylphenoxy}acetic acid From ethyl {4-[({4-(4-methoxybenzyl)-2-[4-(trifluoromethyl)phenyl]-1,3-thiazol-5-yl}methyl)sulfanyl]-2-methylphenoxy}acetate (0.160g 0.27mmol), {4-[({4-(4-methoxybenzyl)-2-[4-(trifluoromethyl)phenyl]-1,3-thiazol-5-yl}methyl)sulfanyl]-2-methylphenoxy}acetic acid (0.005g, 3%) was obtained as a cream solid.

$^1$H NMR (CD$_3$Cl$_3$): δ 8.01(d, 2H), 7.68(d, 2H), 7.23(s, 1H), 7.11(m, 3H), 6.82(d, 2H), 6.62(d, 1H), 4.90(s, 2H), 4.17(s, 2H), 3.90(s, 2H), 3.80(s, 3H), 2.25(s, 3H); MS m/z 560.

2-Methyl1-2-{4-[({4-[(4-methyl-2-thienyl)methyl]-2-[4-(trifluoromethyl)phenyl]-1,3-thiazol-5-yl}methyl) sulfanyl]phenoxy}propanoic acid From ethyl 2-methyl-2-{4-[({4-[(4-methyl-2-thienyl)methyl]-2-[4-(trifluoromethyl)phenyl]-1,3-thiazol-5-yl}methyl)sulfanyl]phenoxy}propanoate (0.17g 0.29mmol), 2-methyl-2-{4-[({4-[(4-methyl-2-thienyl)methyl]-2-[4-(trifluoromethyl)phenyl]-1,3-thiazol-5-yl}methyl)sulfanyl]phenoxy}propanoic acid (0.002g, 1.2%) was obtained as a cream solid.

$^1$H NMR (CD$_3$Cl$_3$): d 8.01(d, 2H), 7.78(d, 2H), 7.28(d, 2H), 6.86(d 2H), 6.73(s, 1H), 6.63(s, 1H), 4.18(s, 2H), 3.99(s, 2H), 2.21(s, 3H), 1.63(s, 6H); MS m/z 564(M+1); HPLC RT 4.413(C18 4.2×100mm, 0-100% ACN/H$_2$O (0.1% TFA), 6min @ 2ml/min @254/220nm).

The following is an alternative procedure for the synthesis of Ethyl 2-{4-[({4-(hydroxymethyl)-2-[4-(trifluoromethyl) phenyl]-1,3-thiazol-5-yl}methyl)sulfanyl]phenoxy}-2-methylpropanoate

Ethyl 2-[4-(chlorosulfonyl)phenoxy]-2-methylpropanoate

Cool a solution of the ethyl 2-methyl-2-phenoxypropanoate, (1.0wt, 1.0eq), in dichloromethane (7.5vols) to 0° C. with stirring under a nitrogen atmosphere. Slowly add neat chlorosulfonic acid (0.78wt, 1.4eq) to the reaction mixture at a rate such that the reaction temperature never rises above 5.0° C. The addition typically takes 30minutes to complete. Following the completion of the addition, stir the reaction mixture at 0-1° C. Follow the course of the reaction by HPLC. The reaction is typically complete after 30minutes. At this point, slowly treat the reaction mixture with DMF (1.75L) (1.40wt, 4.0eq). The addition of DMF to the reaction mixture is very exothermic. Adjust the rate of addition so that the reaction temperature never rises above 10.0° C. The addition of DMF to the reaction mixture takes approximately 30minutes. Following the completion of the DMF addition, re-cool the reaction mixture to 0.5to 1° C. Treat the cooled reaction mixture with neat thionyl chloride (619mL, 1.01kg) (0.86wt, 1.5eq). Adjust the rate of addition so that the process temperature never reaches 5° C. The addition of thionyl chloride to the reaction mixture is not very exothermic at all. Hence, the addition of thionyl chloride is typically complete in 5minutes. Following the completion of the DMF addition, warm the reaction mixture to 20° C. with stirring. Follow the course of the reaction via HPLC. After 2.0h, the reaction is typically complete. At this point, cool the reaction mixture to 0-1° C. and carefully treat the reaction mixture with water (8.8L) (7.5vols). [Note: The addition of water may be somewhat exothermic depending upon how much unreacted thionyl chloride is left in the reaction mixture.] Separate the organic layer and wash the organic layer with aqueous 0.1N HCl solution (2×7.5vols). Separate the organic layer, concentrate the organic layer to a minimum stir volume, treat the organic layer with isopropyl acetate (1×5.0vols) and then concentrate the resulting solution via vacuum distillation to afford the titled compound as a translucent bronze colored oil.

Yield (% theory): 85-98%.

$^1$H NMR (400MHz, CDCl$_3$) δ 7.90(2H, bd), 6.90(2H, bd), 4.22(2H, q, J=7.0Hz), 1.67(6H, s), 1.20(3H, t, J=7.0Hz)

Diethyl 2-[4-(trifluoromethyl)phenyl]-1,3-thiazole-4, 5-dicarboxylate

Heat a solution of the 4-fluorobenzenecarbothioamide, (1.0wt, 1.0eq), in absolute ethanol (3vols) to 50° C. with stirring under a nitrogen atmosphere. Add diethyl 2-chloro-3-oxosuccinate (1.2wt, 1.1eq), in one portion. Some warming is seen during the addition which is typically complete in less then 30minutes. After the addition is complete, heat the reaction mixture to about 68° C. Hold the reaction mixture at 67-69° C. for 6h and then cool the reaction mixture to ambient temperature overnight. Dilute the resulting yellow hazy solution slowly with aqueous 50% ethanol solution (3vols), stir at ambient temperature for 4h, and then cool the reaction mixture to <5° C. Filter the solids. Wash the wet cake with aqueous 50% ethanol solution (3vols) and dry at 45° C. to constant weight to afford the title compound as an off-white to white colored solid.

Yield (% theory): 78-83%.

$^1$H NMR (300MHz, CDCl$_3$) δ 8.14(2H, d, J=8.2Hz), 7.76 (2H, d, J=8.2Hz), 4.52(2H, q, J=7.1Hz), 4.43(2H, q, J=7.1Hz), 1.47(3H, t, J=7.1Hz), 1.42(3H, t, J=7.1Hz).

{5-Hydroxymethyl-2-[4-(trifluoromethyl)phenyl]-1, 3-thiazol-4-yl}methanol

To a suspension of lithium aluminum hydride (0.14wt) in THF (3.4vols), add a solution of the diethyl 2-[4-(trifluoromethyl)phenyl]-1,3-thiazole-4,5-dicarboxylate (1.0wt, 1.0eq), dissolved in THF (2vols) at a rate such that the temperature of the reaction mixture is maintained at below −10° C. The addition time is 1.5-3.0hr. After the addition is complete, stir the reaction mixture at ambient temperature for 18h. Quench the reaction by adding aqueous 16% sulfuric acid (2.4vols). Charge ethyl acetate (5vols) with stirring to the reaction mixture followed with water (5vols). Filter the resulting two phase mixture through celite (0.4wt). Separate the layers and wash the organic layer with water (4×4vols) and with brine (2×4vol). Reduce the total volume of the reaction mixture via vacuum distillation to leave the solid suspended in ethyl acetate (1-1.5vols). Dilute the slurry with dichloromethane (5vols) and stir the suspension for at least 6h. Filter the tan-colored solid. Wash the wet cake with dichloromethane (2vols) and dry the wet cake at 45° C. under mild vacuum to afford the title compound as an off-white solid.

Yield (% theory); 65-85%.

$^1$H NMR (300MHz, CD$_3$OD) δ 8.15(2H, d, J=8.3Hz), 7.79 (2H, d, J=8.3Hz), 4.92(2H, s), 4.90(2H, s), 4.77(2H, s).

Ethyl 2-{4-[({4-(hydroxymethyl)-2-[4-(trifluoromethyl)phenyl]-1,3-thiazol-5-yl}methyl)sulfanyl]phenoxy}-2-methylpropanoate To a stirred suspension of zinc dust (0.75wt, 3.5eq) in isopropyl acetate (5vols), add a solution of DME (0.5vol) and water (0.5eq). Heat the resulting solution from room temperature to 40° C. Treat the reaction mixture with a solution of ethyl 2-[4-(chlorosulfonyl)phenoxy]-2-methylpropanoate (1.0wt, 1.0eq) and dichlorodimethylsilane (0.32wt, 0.75eq) in isopropyl acetate (3vols) over a period of 2h as this addition is mildly exothermic. After the addition is complete, increase the process temperature to 60° C. Treat the suspension at 60° C. slowly with neat dichlorodimethylsilane (0.95wt. 2.3eq) over a period of 1h. When the reduction of the sulfonylchloride is deemed complete (by HPLC), treat the reaction mixture with {5-Hydroxymethyl-2-[4-(trifluoromethyl)phenyl]-1,3-thiazol-4-yl}methanol (1.04wt, 1.1eq) in one portion at 60° C. After the addition is complete, increase the process temperature to 89° C. and stir the reaction mixture at this temperature for 3to 5h then cool to ambient temperature. Filter the reaction mixture to remove unreacted zinc residue, wash the filtrate with water (2×8vols) and concentrate the organic layer to about 3.5volumes via vacuum distillation at 40-45° C. Dissolve the resultant, somewhat syrupy, residue in ethanol (2vols) and treat the resulting solution with iso-octane (2vols). Cool the clear yellow-tinted solution to ambient temperature to induce crystallization of the product. Collect the solid via filtration. Wash the wet cake with iso-octane/ EtOH (9:1, 1vol) and dry under vacuum (~21Torr) at 60° C. for 12h to afford the title compound as an off-white solid.

Yield (% theory): 45-55%.

$^1$H NMR (400MHz, CDCl$_3$) δ 7.96(2H, d, J=8.5Hz), 7.66 (2H, d, J=8.5Hz), 7.24(2H, d, J=8.8Hz), 6.74(2H, d, J=8.8Hz), 4.45(2H, d, J=3.5Hz), 4.19(2H, q, J=7.2Hz), 4.16 (2H, s), 2.30(1H, br s), 1.57(6H, s), 1.20(3H, t, J=7.2Hz).

The following intermediates and ligands were prepared for the binding and transfection assays described below:

i) 2-{2-methyl-4-[({4-methyl-2-[4-(trifluoromethyl) phenyl]-1,3-thiazol-5-yl}methyl)sulfanyl] phenoxy}acetic acid This compound was used as a PPARdelta reference in the transfection assays described below and was prepared according to the following method:

Intermediate A

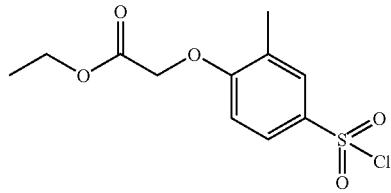

Chlorosulfonic acid (15mL) was cooled to 0° C. Then 10.0g (0.05M) of ethyl (2-methylphenoxyacetate was added over 10m. The reaction mixture was stirred at 0-5° C. for 30m, the bath was removed and stirring continued for 2h. The reaction mixture was poured into ice, forming a white solid which washed with ice water and dried under high vacuum affording the title compound (12.846g, 86%).

Intermediate B:

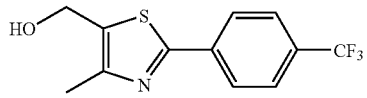

To a well stirred solution of LiAlH$_4$(1.52g, 40mmol) in dry THF (50mL) at 0° C., was slowly added a solution of ethyl 4-methyl-2-[4-(trifluoromethyl)phenyl]-thiazole-5-carboxylate (12.6g, 40mmol) in dry THF (50mL). The mixture was stirred at room temperature for 2h. The reaction was quenched by slow addition at 0° C. of water (2mL), 5N NaOH (2mL) and water (6mL). The precipitate was filtered, washed with EtOAc, MeOH, CH$_2$Cl$_2$ and THF. After evaporation, a yellow solid was obtained, that was crystallyzed from MeOH-water to afford intermediate 1depicted above (9.90g, 36mmol, 90%) as a yellow solid mp 120-122° C.

Intermediate C:

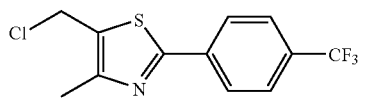

To a cold (0° C.) stirred solution of intermediate 1(8.2g, 30mmol) and Et$_3$N (6.07g, 8.36mL, 60mmol), in dry CH$_2$Cl$_2$ (120mL) was slowly added MeSO$_2$Cl (5.49g, 3.71mL, 48mmol). After 2h at 0° C. more Et$_3$N (6mmol) and MeSO$_2$Cl (4.8mmol) were added. After 2more h a tic (hexane:EtOAc, 1:1) showed complete reaction. The reaction mixture was diluted with CH$_2$Cl$_2$(120mL) and washed with NaHCO$_3$ (sat.) (2×240mL) and water (2×240mL), dried, filtered and evaporated to afford intermediate 2(8.0g, 27mmol, 90%) as a yellow solid.

2-{2-methyl-4-[({4-methyl-2-[4-(trifluoromethyl) phenyl]-1,3-thiazol-5-yl}methyl)sulfanyl] phenoxy}acetic acid

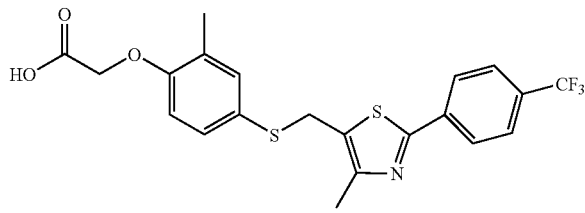

Intermediate A (4.68g, 16mM) was refluxed with 9.6g of tin powder in ethanol (20mL) and dioxane/HCl (20mL). After 3h the reaction mixture was poured into ice and $CH_2Cl_2$ (200mL) and filtered. The phases were separated and the aqueous layer was extracted 2×50mL $CH_2Cl_2$. The combined organic layers were dried ($MgSO_4$), filtered and evaporated to yield 3.5g (97%). This material readily forms disulfides and therefore was used immediately. It was dissolved in acetonitrile (50mL) with intermediate C (4.0g, 14.0mM) and $Cs_2CO_3$(10.1g, 31.0mM) and stirred for 1h then diluted with ether (200mL) and water (200mL). The phases were separated and the organic phase washed 2×NaOH 0.1N (50mL), dried ($MgSO_4$), filtered and evaporated to afford crude product (6.57g,) which was slurried in hexane:ether (1:1) and filtered to yield pure intermediate D (5.0g, 74%). This material was hydrolyzed as described below to prepare the title compound. A solution of the corresponding ester (Intermediate D) (1mmol) in THF (10mL) (in some cases few drops of MeOH were added to help solubility), was treated with 1N LiOH in water (2mL, 2mmol), and stirred 16h at room temperature (when reactions were slow, the temperature was elevated to 50° C.). The solution was neutralized with 1N HCl (2mL, 2mmol) and the organic solvent evaporated to afford an aqueous solution with an insoluble product. If the insoluble was a solid, it was filtered and dried to afford the final product. If the insoluble was an oil, it was extracted with EtOAc (30mL). The organic solution was separated, washed with water (2×30mL), dried, filtered, and evaporated to afford the final product.

Binding Assay:

Compounds were tested for their ability to bind to hPPAR gamma hPPARalpha or PPARdelta using a Scintillation Proximity Assay (SPA). The PPAR ligand binding domain (LBD) was expressed in *E. coli* as polyHis tagged fusion proteins and purified. The LBD was then labeled with biotin and immobilized on streptavidin-modified scintillation proximity beads. The beads were then incubated with a constant amount of the appropriate radioligand (3H-BRL 49653for PPARgamma, radiolabelled 2-(4-(2-(2,3-Ditritio-1-heptyl-3-(2,4-difluorophenyl)ureido)ethyl)phenoxy)-2-methylbutanoic acid for hPPAR alpha (see WO 00/08002) and labelled GW 2433(see Brown, P. J. et al. *Chem. Bol.*, 4, 909-918(1997). For the structure and synthesis of this ligand) for PPAR delta and variable concentrations of test compound, and after equilibration the radioactivity bound to the beads was measured by a scintillation counter. The amount of nonspecific binding, as assessed by control wells containing 50μM of the corresponding unlabeled ligand, was subtracted from each data point. For each compound tested, plots of ligand concentration vs. CPM of radioligand bound were constructed and apparent Ki values were estimated from nonlinear least squares fit of the data assuming simple competitive binding. The details of this assay have been reported elsewhere (see, Blanchard, S. G. et al. Development of a Scintillation Proximity Assay for Peroxisome Proliferator-Activated Receptor gamma Ligand Binding Domain. *Anal Biochem.*, 257, 112-119(1998)).

Transfection Assay:

Compounds were screened for functional potency in transient transfection assays in CV-1cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Smith-Oliver, T. A.; Wilkison, W. O.; Willson, T. M.; Kliewer, S. A., An antidiabetic thiazolidinedione is a high affinity ligand for peroxisome proliferator-activated receptor gamma (PPARgamma), *J. Biol. Chem.*, 270, 12953-6(1995). The ligand binding domains for murine and human PPAR alpha, PPAR gamma, and PPAR delta were each fused to the yeast transcription factor GAL4DNA binding domain. CV-1cells were transiently transfected with expression vectors for the respective PPAR chimera along with a reporter construct containing five copies of the GAL4DNA binding site driving expression of secreted placental alkaline phosphatase (SPAP) and beta-galactosidase. After 16h, the medium was exchanged to DME medium supplemented with 10% delipidated fetal calf serum and the test compound at the appropriate concentration. After an additional 24h, cell extracts were prepared and assayed for alkaline phosphatase and β-galactosidase activity. Alkaline phosphatase activity was corrected for transfection efficiency using the beta-galactosidase activity as an internal standard (see, for example, Kliewer, S. A., et al. Cell 83, 813-819(1995)). Rosiglitazone (BRL 49653) was used as a positive control in the hPPAR gamma assay. The positive control for PPAR delta assays was 2-{2-methyl-4-[({4-methyl-2-{trifluoromethyl}phenyl]-1, 3-thiazol-5-yl}methyl)sulfanyl]phenoxy}acetic acid.

The positive control in the hPPARalpha transfection assay was 2-[4-(2-(3-(4-fluorophenyl)-1-heptylureido)ethyl)-phenoxy]-2-methylpropionic acid, which can be prepared as described in Brown, Peter J., et al. *Synthesis Issue* 7, 778-782 (1997), or patent publication WO 9736579.

All of the above examples of this invention were agonists of at least one hPPAR subtype.

What is claimed is:

1. A compound selected from:

2-methyl-2-{2-methyl-4-[({4-(3-thienylmethyl)-2-[4-(trifluoromethyl)phenyl]-1,3-thiazol-5-yl}methyl)sulfanyl]phenoxy}propanoic acid;

2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}propanoic acid;

2-{4-[({4-(4-methoxybenzyl)-2-[4-(trifluoromethyl)phenyl]-1,3-thiazol-5-yl}methyl)sulfanyl]-2-methylphenoxy}-2-methylpropanoic acid;

2-methyl-2-{4-[({4-{[4-(2-pyrazinyl)-1-piperazinyl]methyl}-2-[4-(trifluoromethyl)phenyl]-1,3-thiazol-5-yl}methyl)sulfanyl]phenoxy}propanoic acid;

2-{4-[({4-{[4-(4-methoxyphenyl)-1-piperazinyl]methyl}-2-[4-(trifluoromethyl)phenyl]-1,3-thiazol-5-yl}methyl)sulfanyl]-2-methylphenoxy}-2-methylpropanoic acid;

2-{4-[({4-{[4-(4-methoxyphenyl)-1-piperazinyl]methyl}-2-[4-(trifluoromethyl)phenyl]-1,3-thiazol-5-yl}methyl)sulfanyl]phenoxy}-2-methylpropanoic acid;

2-methyl-2-{2-methyl-4-[({4-[4-(trifluoromethoxy)benzyl]-2-[4-(trifluoromethyl)phenyl]-1,3-thiazol-5-yl}methyl)sulfanyl]phenoxy}propanoic acid;

2-{4-[({4-{[4-(4-isopropoxyphenyl)-1-piperazinyl]methyl}-2-[4-(trifluoromethyl)phenyl]-1,3-thiazol-5-yl}methyl)sulfanyl]-2-methylphenoxy}propanoic acid;

2-{2-methyl-4-[({4-{[4-(2-pyrimidinyl)-1-piperazinyl]methyl}-2-[4-(trifluoromethyl)phenyl]-1,3-thiazol-5-yl}methyl)sulfanyl]phenoxy}propanoic acid; or a pharmaceutically acceptable salt or hydrolyzable ester thereof.

2. A compound of the structure:

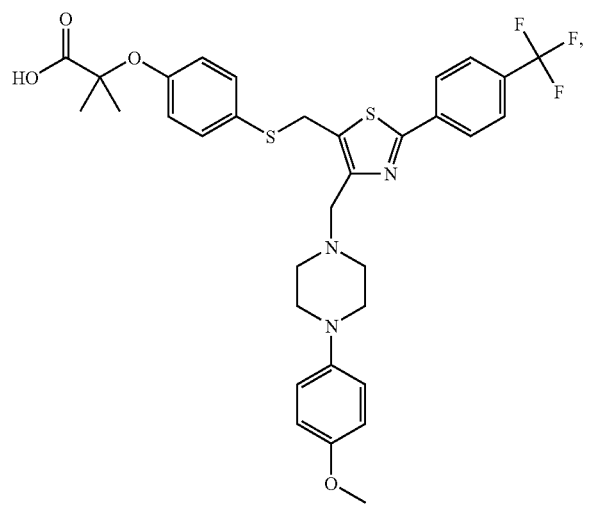

also known as 2-{4-[({4-{[4-(4-methoxyphenyl)-1-piperazinyl]methyl}-2-[4-(trifluoromethyl)phenyl]-1,3-thiazol-5-yl}methyl)sulfanyl]phenoxy}-2-methylpropanoic acid, or a pharmaceutically acceptable salt thereof.

3. A pharmaceutical composition comprising a compound according to claim 2, and a pharmaceutically acceptable diluent or carrier.

4. A method of treating a disease or condition in a patient, wherein the disease or disorder is selected from dyslipidemia, syndrome X, hypercholesteremia, type II diabetes mellitus, type I diabetes, insulin resistance, hyperlipidemia, and obesity, comprising the administration of a therapeutically effective amount of a compound according to claim 2.

5. A pharmaceutical composition comprising a compound according to claim 1, and a pharmaceutically acceptable diluent or carrier.

6. A method of treating a disease or condition in a patient, wherein the disease or disorder is selected from dyslipidemia, syndrome X, hypercholesteremia, type II diabetes mellitus, type I diabetes, insulin resistance, hyperlipidemia, and obesity, comprising the administration of a therapeutically effective amount of a compound according to claim 1.

7. A compound according to claim 2 wherein said compound is the compound of the structure:

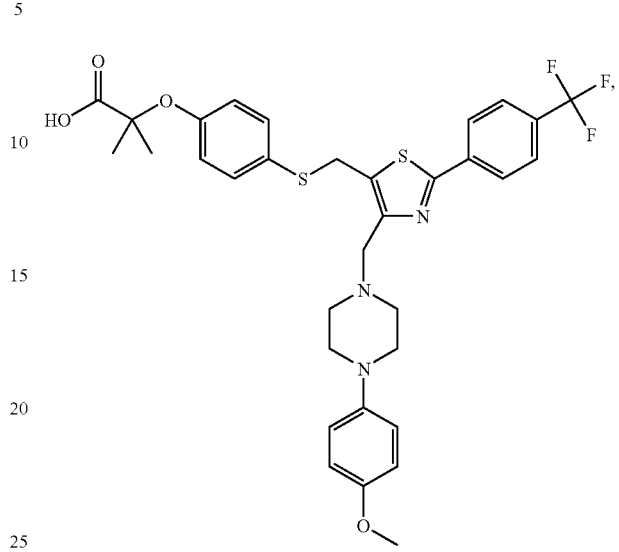

also known as 2-{4-[({4-{[4-(4-methoxyphenyl)-1-piperazinyl]methyl}-2-[4-(trifluoromethyl)phenyl]-1,3-thiazol-5-yl}methyl)sulfanyl]phenoxy}-2-methylpropanoic acid.

8. A compound according to claim 2 wherein said compound is a pharmaceutically acceptable salt of the compound of the structure:

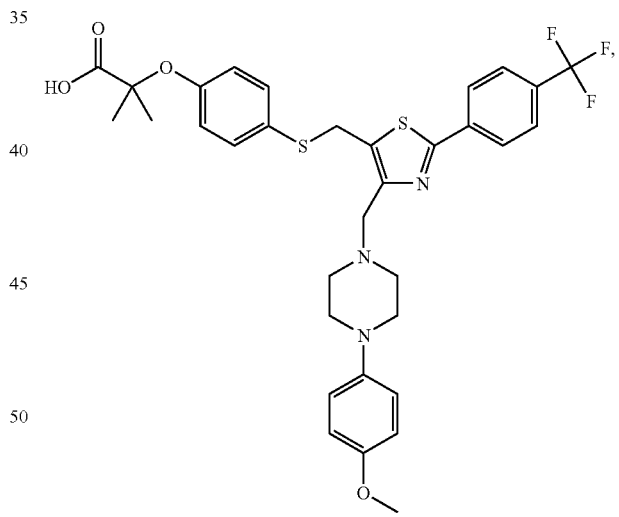

also known as 2-{4-[({4-{[4-(4-methoxyphenyl)-1-piperazinyl]methyl}-2-[4-(trifluoromethyl)phenyl]-1,3-thiazol-5-yl}methyl)sulfanyl]phenoxy}-2-methylpropanoic acid.

9. A method according to claim 4 wherein said disease or condition is type II diabetes mellitus.

* * * * *